(12) United States Patent
Asai et al.

(10) Patent No.: US 6,610,708 B1
(45) Date of Patent: Aug. 26, 2003

(54) CYCLIC AMINO COMPOUNDS

(75) Inventors: Fumitoshi Asai, Tanashi (JP); Atsuhiro Sugidachi, Kawasaki (JP); Toshihiko Ikeda, Yokohama (JP); Haruo Iwabuchi, Urawa (JP); Yoshiaki Kuroki, Ube (JP); Teruhiko Inoue, Ube (JP); Ryo Iwamura, Ube (JP); Nobuhiko Shibakawa, Ube (JP)

(73) Assignees: Sankyo Company, Limited, Tokyo (JP); Ube Industries, Ltd., Ube (JP)

( * ) Notice: Subject to any disclaimer, the term of this patent is extended or adjusted under 35 U.S.C. 154(b) by 317 days.

(21) Appl. No.: 09/622,849

(22) Filed: Aug. 24, 2000

Related U.S. Application Data

(63) Continuation of application No. PCT/JP99/00924, filed on Feb. 26, 1999.

(30) Foreign Application Priority Data

Feb. 27, 1998 (JP) .......................................... 10-046921

(51) Int. Cl.[7] ..................... A61K 31/445; C07D 211/54
(52) U.S. Cl. ..................... 514/327; 546/221; 546/216
(58) Field of Search ..................... 514/327; 546/221, 546/216

(56) References Cited

U.S. PATENT DOCUMENTS

| 3,647,796 A | 3/1972 | Elslager et al. |
| 4,051,141 A | 9/1977 | Castaigne |
| 4,740,510 A | 4/1988 | Bardorc et al. |
| 5,288,726 A | 2/1994 | Koike et al. |
| 5,436,242 A | 7/1995 | Koike et al. |
| 5,556,854 A | 9/1996 | Furrer et al. |
| 6,087,379 A | 7/2000 | Asai et al. |

FOREIGN PATENT DOCUMENTS

| EP | 0099802 A | 2/1984 |
| EP | 0542411 B | 8/1998 |
| WO | WO 93/14077 | 7/1993 |
| WO | WO 95/07691 | 3/1995 |
| WO | WO 98/08811 | 3/1998 |

*Primary Examiner*—Charanjit S. Aulakh
(74) *Attorney, Agent, or Firm*—Frishauf, Holtz, Goodman & Chick, P.C.

(57) ABSTRACT

A cyclic amino compound represented by the following formula:

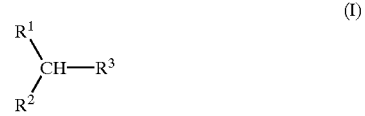

(I)

or a pharmacologically acceptable salt thereof. $R^1$ is a substitutable phenyl group. $R^2$ is a substitutable aliphatic acyl group, a substitutable benzoyl group or an alkoxycarbonyl group. $R^3$ is a substituted, saturated cyclic amino group which may optionally have a fused ring. These compounds and salts have excellent platelet aggregation inhibitory action. They are useful for the prevention and/or treatment of embolism, thrombosis or arteriosclerosis and other conditions resulting from platelet aggregation.

38 Claims, No Drawings

CYCLIC AMINO COMPOUNDS

This application is a continuation of International Application PCT/JP99/00924 filed Feb. 26, 1999, now WO 99/43648 Sep. 2, 1999.

TECHNICAL FIELD

The present invention relates to cyclic amino compounds or pharmacologically acceptable salts thereof each having excellent platelet aggregation inhibitory action and inhibitory action against the advance of arteriosclerosis, to compositions for the prevention or treatment of embolism, thrombosis or arteriosclerosis each of which comprises any one of said compounds, to use of said compounds for the preparation of a medicament for the prevention or treatment of embolism, thrombosis or arteriosclerosis, to a method for the prevention or treatment of embolism, thrombosis or arteriosclerosis, which comprises administering a pharmacologically effective amount of any one of said compounds to warm-blooded animals, and to a process for the preparation of said compounds.

BACKGROUND ART

As cyclic amino compounds having platelet aggregation inhibitory action, known are, for example, hydropyridine derivatives [ex. U.S. Pat. No. 4,051,141, Japanese Patent Application Kokai No. Sho 59-27895 (EP 99802), Japanese Patent Application Kokai No. Hei 6-41139 (EP 542411), WO 98/08811, etc.].

DISCLOSURE OF INVENTION

As a result of investigation on the pharmacological action of cyclic amino compounds for many years, the present inventors have found that specific cyclic amino compounds have excellent platelet aggregation inhibitory action and inhibitory action against the advance of arteriosclerosis (particularly, the platelet aggregation inhibitory action) and is useful as a preventive agent or remedy (particularly, as a remedy) for embolism, thrombosis and arteriosclerosis (particularly, embolism or thrombosis), leading to the completion of the present invention.

The present invention provides cyclic amino compounds or pharmacologically acceptable salts thereof having excellent platelet aggregation inhibitory action and inhibitory action against the advance of arteriosclerosis, compositions for the prevention or treatment of embolism, thrombosis or arteriosclerosis each of which comprises any one of said compounds, use of said compounds for the preparation of a medicament for the prevention or treatment of embolism, thrombosis or arteriosclerosis, a method for the prevention or treatment of embolism, thrombosis or arteriosclerosis, which comprises administering a pharmacologically effective amount of any one of said compounds to warm-blooded animals, and a process for the preparation of said compounds.

The cyclic amino compounds according to the present invention have the following formula:

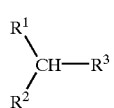
(I)

In the above-described formula, $R^1$ represents a substituted or unsubstituted phenyl group (the substituted of said group being a halogen atom, a $C_1$–$C_4$ alkyl group, a fluoro-substituted-($C_1$–$C_4$ alkyl) group, a $C_1$–$C_4$ alkoxy group, a fluoro-substituted-($C_1$–$C_4$ alkoxy) group, a cyano group or a nitro group);

$R^2$ represents a substituted or unsubstituted $C_1$–$C_8$ aliphatic acyl group (the substituent of said group being a halogen atom, a $C_1$–$C_4$ alkoxy group or a cyano group), a substituted or unsubstituted benzoyl group (the substituent of said group being a halogen atom, a $C_1$–$C_4$ alkyl group or a $C_1$–$C_4$ alkoxy group), or a ($C_1$–$C_4$ alkoxy)carbonyl group; and $R^3$ represents a substituted, 3- to 7-membered, saturated cyclic amino group which may optionally have a fused ring {said cyclic amino group is substituted with a group having the formula of —S—X—$R^4$ [wherein, $R^4$ represents a substituted or unsubstituted phenyl group (the substituent of said group being a halogen atom, a $C_1$–$C_4$ alkyl group, a $C_1$–$C_4$ alkoxy group, a nitro group or a cyano group), a substituted or unsubstituted $C_1$–$C_6$ alkyl group [the substituent of said group being an amino group, a hydroxyl group, a carboxyl group, a ($C_1$–$C_4$ alkoxy)carbonyl group, a group having the formula of —NH—$A^1$ (wherein, $A^1$ represents an α-amino acid residue) or group having the formula of —CO—$A^2$ (wherein, $A^2$ represents an α-amino acid residue)], or a $C_3$–$C_8$ cycloalkyl group, and X represents a sulfur atom, a sulfinyl group or a sulfonyl group], and said cyclic amino group may optionally be further substituted with a group having the formula of =$CR^5R^6$ [wherein, $R^5$ and $R^6$ are the same or different and each independently represents a hydrogen atom, a $C_1$–$C_4$ alkyl group, a carboxyl group, a ($C_1$–$C_4$ alkoxy)carbonyl group, a carbamoyl group, a ($C_1$–$C_4$ alkyl)carbamoyl group or a di-($C_1$–$C_4$ alkyl) carbamoyl group]}.

In the above-described definition of $R^1$, examples of the "halogen atom" serving as a substituent for the substituted phenyl group include fluorine, chlorine, bromine and iodine atoms, of which the fluorine, chlorine and bromine atoms are preferred, and the fluorine and chlorine atoms are particularly preferred.

In the definition of $R^1$, examples of the "$C_1$–$C_4$ alkyl group" serving as a substituent for the substituted phenyl group include straight or branched $C_1$–$C_4$ alkyl groups such as methyl, ethyl, propyl, isopropyl, butyl, isobutyl, s-butyl and t-butyl groups, of which the methyl and ethyl groups are preferred, and the methyl group is most preferred.

In the definition of $R^1$, examples of the "fluoro-substituted-($C_1$–$C_4$ alkyl) group" serving as a substituent for the substituted phenyl group include straight or branched fluoro-substituted-($C_1$–$C_4$ alkyl) groups such as fluoromethyl, difluoromethyl, trifluoromethyl, 2-fluoroethyl, 2-fluoropropyl, 3-fluoropropyl, 2-fluorobutyl, 3-fluorobutyl and 4-fluorobutyl groups, of which the difluoromethyl and trifluoromethyl groups are preferred, and the trifluoromethyl group is most preferred.

In the definition of $R^1$, examples of the "$C_1$–$C_4$ alkoxy group" serving as a substituent for the substituted phenyl group include straight or branched $C_1$–$C_4$ alkoxy groups such as methoxy, ethoxy, propoxy, isopropoxy, butoxy, isobutoxy, s-butoxy and t-butoxy groups, of which the methoxy and ethoxy groups are preferred, and the methoxy group is most preferred.

In the definition of $R^1$, examples of the "fluoro-substituted-$C_1$–$C_4$ alkoxy) group" serving as a substituent for the substituted phenyl group include straight or branched fluoro-substituted-($C_1$–$C_4$ alkoxy) groups such as fluoromethoxy, difluoromethoxy, trifluoromethoxy, 2-fluoroethoxy, 2-fluoropropoxy, 3-fluoropropoxy, 2-fluoroisopropoxy and 4-fluorobutoxy groups, of which the difluoromethoxy and trifluoromethoxy groups are preferred, and the trifluoromethoxy group is most preferred.

In the definition of $R^1$, preferred examples of the substituent for the substituted phenyl group include the halogen atoms, methyl group, ethyl group, difluoromethyl group, trifluoromethyl group, methoxy group, ethoxy group, difluoromethoxy group, trifluoromethoxy group, cyano group and nitro group, or which the fluorine atom, chlorine atom, bromine atom, trifluoromethyl group, difluoromethoxy group, trifluoromethoxy group, cyano group and nitro group are more preferred, and the fluorine and chlorine atoms are particularly preferred. The number of substituents preferably ranges from 1 to 3, of which 1 or 2 are more preferred, and 1 is most preferred. The position of the substituent is preferably the 2- or 4-position, of which the 2-position is most preferred.

In the definition of $R^2$, examples of the "aliphatic acyl" part of the substituted or unsubstituted $C_1$–$C_8$ aliphatic acyl group include straight or branched $C_1$–$C_8$ alkanoyl groups such as formyl, acetyl, propionyl, butyryl, isobutyryl, valeryl, isovaleryl, pivaloyl, hexanoyl, heptanoyl and octanoyl groups, and ($C_3$–$C_7$ cycloalkyl)carbonyl groups such as cyclopropylcarbonyl, cyclobutylcarbonyl, cyclopentylcarbonyl, cyclohexylcarbonyl and cycloheptylcarbonyl groups, of which $C_2$–$C_4$ alkanoyl groups and ($C_3$–$C_6$ cycloalkyl)carbonyl groups are preferred; the acetyl, propionyl, isobutyryl, cyclopropylcarbonyl and cyclobutylcarbonyl groups are more preferred; the propionyl and cyclopropylcarbonyl groups are still more preferred; and the cyclopropylcarbonyl group is most preferred.

The "halogen atom" and "$C_1$–$C_4$ alkoxy group" serving as a substituent for the aliphatic acyl group have the same meaning as that defined as the substituent for the "substituted phenyl group" in the definition of $R^1$. Preferred examples of the substituent for the aliphatic acyl group include a fluorine atom, chlorine atom, methoxy group, ethoxy group and cyano group, of which the fluorine and chlorine atoms are more preferred, and the fluorine atom is most preferred. The number of substituents preferably ranges from 1 to 3, of which 1 and 2 are more preferred, and 1 is most preferred.

Specific examples of the "substituted aliphatic acyl group" include fluoroacetyl, difluoroacetyl, trifluoroacetyl, chloroacetyl, trichloroacetyl, bromoacetyl, iodoacetyl, 3-fluoropropionyl, 3-chloropropionyl, 3-bromopropionyl, 3-iodopropionyl, 4-fluorobutyryl, 4-chlorobutyryl, 5-fluorovaleryl, methoxyacetyl, 3-methoxypropionyl, 4-methoxybutyryl, 5-methoxyvaleryl, ethoxyacetyl, 3-ethoxypropionyl, 4-ethoxybutyryl, 5-ethoxyvaleryl, cyanoacetyl, 3-cyanopropionyl, 4-cyanobutyryl, 5-cyanovaleryl, 2-fluorocyclopropylcarbonyl, 2,2-difluorocyclopropylcarbonyl, 2-chlorocyclopropylcarbonyl, 2-bromocyclopropylcarbonyl, 2-fluorocyclobutylcarbonyl, 2-chlorocyclobutylcarbonyl, 2-fluorocyclopentylcarbonyl, 2-chlorocyclopentylcarbonyl, 2-fluorocyclohexylcarbonyl, 2-chlorocyclohexylcarbonyl, 2-methoxycyclopropylcarbonyl, 2-methoxycyclobutylcarbonyl, 2-methoxycyclopentylcarbonyl, 2-methoxycyclohexylcarbonyl, 2-ethoxycyclopropylcarbonyl, 2-ethoxycyclobutylcarbonyl, 2-ethoxycyclopentylcarbonyl, 2-ethoxycyclohexylcarbonyl, 2-cyanocyclopropylcarbonyl, 2-cyanocyclobutylcarbonyl, 2-cyanocyclopentylcarbonyl and 2-cyanocyclohexylcarbonyl groups, of which the fluoroacetyl, difluoroacetyl, trifluoroacetyl, chloroacetyl, 3-fluoropropionyl, 3-chloropropionyl, methoxyacetyl, 3-methoxypropionyl, ethoxyacetyl, cyanoacetyl, 3-cyanopropionyl, 2-fluorocyclopropylcarbonyl, 2,2-difluorocyclopropylcarbonyl, 2-chlorocyclopropylcarbonyl, 2-fluorocyclobutylcarbonyl, 2-chlorocyclobutylcarbonyl, 2-fluorocyclopentylcarbonyl, 2-fluorocyclohexylcarbonyl, 2-methoxycyclopropylcarbonyl, 2-ethoxycyclopropylcarbonyl and 2-cyanocyclopropylcarbonyl groups are preferred, The fluoroacetyl, difluoroacetyl, trifluoroacetyl, chloroacetyl, 3-fluoropropionyl, 2-fluorocyclopropylcarbonyl, 2-chlorocyclopropylcarbonyl and 2-fluorocyclobutylcarbonyl groups are more preferred, and the fluoroacetyl, difluoroacetyl, trifluoroacetyl, 3-fluoropropionyl and 2-fluorocyclopropylcarbonyl groups are particularly preferred.

The "halogen atom", "$C_1$–$C_4$ alkyl group" and "$C_1$–$C_4$ alkoxy group" serving as a substituent for the substituted benzoyl group in the definition of $R^2$ have the same meaning as that defined as the substituent for the "substituted phenyl group" in the above-described definition of $R^1$. Preferred examples include the fluorine atom, chlorine atom, methyl group, ethyl group, methoxy group and ethoxy group, of which the fluorine atom and chlorine atom are more preferred and the fluorine atom is most preferred. The number of substituents preferably ranges from 1 to 3, of which 1 and 2 are more preferred and 1 is most preferred.

Examples of the "($C_1$–$C_4$ alkoxy)carbonyl group" in the definition of $R^2$ include methoxycarbonyl, ethoxycarbonyl, propoxycarbonyl, isopropoxycarbonyl, butoxycarbonyl, isobutoxycarbonyl, s-butoxycarbonyl and t-butoxycarbonyl groups, of which the methoxycarbonyl and ethoxycarbonyl groups are preferred and the methoxycarbonyl group is most preferred.

In the definition of $R^3$, the part of the "saturated cyclic amino group group which may optionally have a fused ring" of the "substituted, 3- to 7-membered, saturated cyclic amino group which may optionally have a fused ring" is a saturated cyclic amino group having in total from 2 to 8 carbon atoms in one or more rings, and which may optionally have a fused ring and may have an additional oxygen, nitrogen or sulfur atom, such as 1-aziridinyl, 1-azetidinyl, 1-pyrrolidinyl, 1-piperidinyl, 2H-hexahydroazepin-1-yl, 7-azabicyclo[3.1.1]-heptan-7-yl, 8-azabicyclo[3.2.1]octan-8-yl, 9-azabicyclo[3.3.1]nonan-9-yl, 4-morpholinyl, 4-thiomorpholinyl and 4-piperazinyl groups, of which the 1-azetidinyl, 1-pyrrolidinyl, 1-piperidinyl, 7-azabicyclo[3.1.1]heptan-7-yl, 8-azabicyclo-[3.2.1]octan-8-yl, 9-azabicyclo-[3.3.1]nonan-9-yl, 4-morpholinyl and 4-thiomorpholinyl groups are preferred; the 1-azetidinyl, 1-pyrrolidinyl, 1-piperidinyl, 8-azabicyclo[3.2.1]octan-8-yl and 9-azabicyclo[3.3.1]nonan-9-yl groups are more preferred; the 1-acetidinyl, 1-pyrrolidinyl, 1-piperidinyl and 8-azabicyclo[3.2.1]octan-8-yl groups are still more preferred; and the 1-azetidinyl, 1-pyrrolidinyl and 1-piperidinyl groups are particularly preferred. The group is attached, via a nitrogen atom of the ring thereof, to the adjacent carbon atom (the carbon atom to which $R^1$ and $R^2$ are attached).

Preferred examples of the "substituted 3- to 7-membered, saturated cyclic amino group which may be cyclocondensed" in the definition of $R^3$ include 3-(—S—X—$R^4$)-1-azetidinyl, 3-(—S—X—$R^4$)-1-pyrrolidinyl, 3- or 4-(—S—X—$R^4$)-1-piperidinyl, 4-(—S—X—$R^4$)-3-(=$CR^5R^6$)-1- piperidinyl and 8-aza-3-(—S—X—R$^4$)-bicyclo[3.2.1]octan-8-yl groups, of which 3-(—S—X—R$^4$)-1-azetidinyl, 3-(—S—X—R$^4$)-1-pyrrolidinyl, 4-(—S—X—R$^4$)-1-piperidinyl and 4-(—S—X—R$^4$)-3-(=CR$^5$R$^6$)-1-piperidinyl groups are most preferred.

The "halogen atom", "$C_1$–$C_4$ alkyl group" and "$C_1$–$C_4$ alkoxy group" serving as a substituent for the "substituted phenyl group" in the definition of R$^4$ have the same meaning as that defined in the above-described definition of R$^1$. Preferred examples of the substituent for the substituted phenyl group in R$^4$ include halogen atoms and methyl, ethyl, methoxy, ethoxy, nitro and cyano groups, of which the fluorine atom, chlorine atom, bromine atom, methyl group, methoxy group, nitro group and cyano group are more preferred, and the fluorine atom, chlorine atom, methyl group, methoxy group and nitro group are particularly preferred. The number of substituents preferably ranges from 1 to 3, or which 1 or 2 is more preferred, and 1 is most preferred.

The part of the "$C_1$–$C_6$ alkyl group" of the "substituted or unsubstituted $C_1$–$C_6$ alkyl group" in the definition of R$^4$ includes $C_1$–$C_4$ alkyl groups having the same meaning as defined above as the substituent for the "substituted phenyl group" in R$^1$, or pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups, of which the straight $C_1$–$C_6$ alkyl group such as methyl, ethyl, propyl, butyl, pentyl or hexyl is preferred, the straight $C_1$–$C_4$ alkyl group such as methyl, ethyl, propyl or butyl is more preferred, and the methyl, ethyl or propyl group is particularly preferred.

The "($C_1$–$C_4$ alkoxy)carbonyl group" serving as a substituent for the "substituted $C_1$–$C_6$ alkyl group" in the definition of R$^4$ has the same meaning as that defined above in R$^2$ and the methoxycarbonyl or ethoxycarbonyl group is preferred.

Examples of the "α-amino acid residue" of A$^1$ in the group having the formula of —NH—A$^1$ which serves as a substituent for the "substituted $C_1$–$C_6$ alkyl group" in the definition of R$^4$ include amino acid residues each having a partial structure obtained by removing a hydroxy group from the carboxyl group of an α-amino acid, such as glycyl, alanyl, valinyl, leucinyl, phenylglycyl, phenylalanyl, α-aspartyl, β-aspartyl, α-glutamyl and γ-glutamyl groups, of which the glycyl, alanyl, β-aspartyl and γ-glutamyl groups are preferred, the glycyl and γ-glutamyl groups are more preferred, and the γ-glutamyl group is most preferred.

Examples of the "α-amino acid residue" of A$^2$ in the group having the formula of —CO—A$^2$ which serves as a substituent for the "substituted $C_1$–$C_6$ alkyl group" in the definition of R$^4$ include amino acid residues each having a partial structure obtained by removing a hydrogen atom from the amino group of an α-amino acid, such as glycino, alanino, valino, leucino, phenylglycino, phenylalanino, asparto and glutamo groups, of which the glycino, alanino, valino, leucino, phenylglycino and phenylalanino groups are preferred, the glycino, alanino and valino groups are more preferred, and the glycino group is most preferred.

Preferred examples of the substituent for the "substituted $C_1$–$C_6$ alkyl group" in R$^4$ include an amino group, a hydroxy group, a carboxyl group, ($C_1$–$C_4$ alkoxy)carbonyl groups, groups having the formula —NH—A$^{1a}$ (wherein, A$^{1a}$ represents a glycyl, alanyl, β-aspartyl or γ-glutamyl group) and groups having the formula —CO—A$^{2a}$ (wherein, A$^{2a}$ represents a glycino, alanino, valino, leucino, phenylglycino or phenylalanino group), or which more preferred are:

the amino group, hydroxy group, carboxyl group, methoxycarbonyl group, ethoxycarbonyl group, groups having the formula —NH—A$^{1b}$ (wherein, A$^{1b}$ represents a glycyl or γ-glutamyl group) and groups having the formula —CO—A$^{2b}$ (wherein, A$^{2b}$ represents a glycino, alanino or valino group), of which the still more preferred groups are:

the amino group, hydroxyl group, carboxyl group, methoxycarbonyl group, ethoxycarbonyl group, groups having the formula —NH—A$^{1c}$ (wherein, A$^{1c}$ represents a γ-glutamyl group) and groups having the formula of —CO—A$^{2c}$ (wherein, A$^{2c}$ represents a glycino group), and the particularly preferred groups are:

the amino group, hydroxy group, carboxyl group, methoxycarbonyl group, ethoxycarbonyl group, groups having the formula: —NH—A$^{1c}$ (wherein, A$^{1c}$ has the same meaning as described above) and groups having the formula of —CO—A$^{2c}$ (wherein, A$^{2c}$ has the same meaning as described above)

The number of substituents for the "substituted $C_1$–$C_6$ alkyl group" in the definition of R$^4$ is preferably 1 or 2. When the number of substituents is 2, the amino group, hydroxyl group or group having the formula of —NH—A$^1$ attached to the same carbon atom as that to which the carboxyl group or group having the formula of —CO—A$^2$ is attached is particularly preferred.

Examples of the "$C_3$–$C_8$ cycloalkyl group" in the definition of R$^4$ include cyclopropyl, cyclobutyl, cyclopentyl, cyclohexyl, cycloheptyl and cyclooctyl groups, of which the cyclobutyl, cyclopentyl, cyclohexyl and cycloheptyl groups are preferred, and the cyclopentyl and cyclohexyl groups are particularly preferred.

The "$C_1$–$C_4$ alkyl group" in the definition of R$^5$ and R$^6$ has the same meaning as that defined in the above-described substituent of the "substituted phenyl group" in R$^1$.

Examples of the "($C_1$–$C_4$ alkyl)carbamoyl group" in the definition of R$^5$ and R$^6$ include methylcarbonyl, ethoxycarbamoyl, propylcarbamoyl, isopropylcarbamoyl, butylcarbamoyl, isobutylcarbamoyl, s-butylcarbamoyl and t-butylcarbamoyl groups, of which the methylcarbamoyl and ethylcarbamoyl groups are preferred and the methylcarbamoyl group is most preferred.

Examples of the "di-($C_1$–$C_4$ alkyl)carbamoyl group" in the definition of R$^5$ and R$^6$ may include N,N-dimethylcarbamoyl, N-ethyl-N-methylcarbamoyl, N,N-diethylcarbamoyl, N,N-dipropylcarbamoyl, N,N-diisopropylcarbamoyl, N,N-dibutylcarbamoyl, N,N-diisobutylcarbamoyl, N,N-di-s-butylcarbamoyl and N,N-di-t-butylcarbamoyl groups, of which the N,N-dimethylcarbamoyl group and N,N-diethylcarbamoyl groups are preferred, and the N,N-dimethylcarbamoyl group is most preferred.

The "($C_1$–$C_4$ alkoxy)carbonyl group" in the definition of R$^5$ and R$^6$ has the same meaning as that defined in R$^2$.

In the group having the formula of =CR$^5$R$^6$, it is preferred that R$^5$ and R$^6$ are the same or different and each independently represents a hydrogen atom, a methyl group, an ethyl group, a carboxyl group, a methoxycarbonyl group, an ethoxycarbonyl group, a carbamoyl group, a methylcarbamoyl group, an ethylcarbamoyl group, an N,N-dimethylcarbamoyl group or an N,N-diethylcarbamoyl group. It is more preferred that R$^5$ represents the hydrogen atom, while R$^6$ represents the hydrogen atom, methyl group, carboxyl group, methoxycarbonyl group, ethoxycarbonyl group, carbamoyl group, methylcarbamoyl group or N,N-dimethylcarbamoyl group. It is particularly preferred that $R^5$ represents the hydrogen atom, while $R^6$ represents the carboxyl, methoxycarbonyl or ethoxycarbonyl group.

X preferably represents a sulfur atom or a sulfonyl group.

In the compounds (I) of the present invention, the carbon atom to which $R^1$ is attached may be an asymmetric carbon atom. There therefore exist optical isomers based thereon. These isomers and mixtures thereof are also included in the compounds of the present invention. When, in the compound of formula (I), a double bond is contained in its molecule and/or a cycloalkyl group or a cyclic amino group contains two substituents, there exist cis/trans geometrical geometrical isomers based on them. These isomers and mixtures thereof are also embraced in the compounds of the present invention.

When the compounds (I) of the present invention contain as $R^5$ or $R^6$ a carboxyl group, they can be easily converted into their pharmacologically acceptable salts by treating it with a base. Examples of such salts include metal salts, for example, alkali metal salts such as sodium salts, potassium salts and lithium salts, alkaline earth metal salts such as calcium salts and magnesium salts, aluminum salts, iron salts, zinc salts, copper salts, nickel salts and cobalt salts; and amine salts, for example, inorganic salts such as ammonium salts and organic salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethylammonium salts and tris(hydroxymethyl)aminomethane salts, of which the alkali metal salts (particularly, the sodium or potassium salts) are preferred.

The compounds (I) of the present invention can be converted into their pharmacologically acceptable salts easily by treating with an acid. Examples of such a salt include inorganic acid salts such as hydrochlorides, sulfates, nitrates and phosphates and organic acid salts such as acetates, propionates, butyrates, benzoates, oxalates, malonates, succinates, maleates, fumarates, tartrates, citrates, methanesulfonates, ethanesulfonates, benzenesulfonates and p-toluenesulfonates, of which the hydrochlorides, sulfates, nitrates, oxalates, succinates, fumarates and methanesulfonates are preferred.

In addition, the hydrates of each of the compounds (I) or their salts are also embraced in the present invention.

Out of the compounds of the present invention having the formula (I), the following ones are preferred:

(1) compounds wherein $R^1$ represents a substituted phenyl group (the substituent being a halogen atom, methyl group, ethyl group, difluoromethyl group, trifluoromethyl group, methoxy group, ethoxy group, difluoromethoxy group, trifluoromethoxy group, cyano group or nitro group), (2) compounds wherein $R^1$ represents a substituted phenyl group (the substituent being a fluorine atom, chlorine atom, bromine atom, trifluoromethyl group, difluoromethoxy group, trifluoromethoxy group, cyano group or nitro group), (3) compounds wherein $R^1$ represents a substituted phenyl group (the substituent being a fluorine or chlorine atom), (4) compounds wherein the number of substituents for the substituted phenyl group as $R^1$ ranges from 1 to 3, (5) compounds wherein the number of substituents for the substituted phenyl group as $R^1$ is 1 or 2, (6) compounds wherein the position of the substituent on the substituted phenyl group as $R^1$ is the 2- or 4-position, (7) compounds wherein $R^2$ represents a substituted or unsubstituted $C_2$–$C_4$ alkanoyl or ($C_3$–$C_6$ cycloalkyl) carbonyl group (the substituent being a fluorine atom, chlorine atom, methoxy group, ethoxy group or cyano group), a substituted or unsubstituted benzoyl group (the substituent being a fluorine atom, chlorine atom, methyl group, ethyl group, methoxy group or ethoxy group), or a ($C_1$–$C_4$ alkoxy) carbonyl group, (8) compounds wherein $R^2$ represents a substituted or unsubstituted $C_2$–$C_4$ alkanoyl or ($C_3$–$C_6$ cycloalkyl) carbonyl group (the substituent being a fluorine or chlorine atom), a benzoyl group or a ($C_1$–$C_4$ alkoxy)carbonyl group, (9) compounds wherein $R^2$ represents a substituted or unsubstituted acetyl, propionyl, isobutyryl, cyclopropylcarbonyl, cyclobutylcarbonyl group (the substituent being a fluorine atom), methoxycarbonyl or ethoxycarbonyl group,

(10) compounds wherein $R^2$ represents a propionyl, cyclopropylcarbonyl, methoxycarbonyl or ethoxycarbonyl group,

(11) compounds wherein $R^3$ represents a 3-(—S—X—$R^4$)-1-azetidinyl, 3-(—S—X—$R^4$)-1-pyrrolidinyl, 3- or 4-(—S—X—$R^4$)-1-piperidinyl, 4-(—S—X—$R^4$)-3-(=$CR^5R^6$)-1-piperidinyl or 8-aza-3-(—S—X—$R^4$)-bicyclo[3.2.1]octan-8-yl group, $R^4$ represents a substituted or unsubstituted phenyl group (the substituent being a halogen atom, methyl group, ethyl group, methoxy group, ethoxy group, nitro group or cyano group), a substituted or unsubstituted straight $C_1$–$C_6$ alkyl group [the substituent being an amino group, hydroxyl group, carboxyl group, ($C_1$–$C_4$ alkoxy)carbonyl group, a group having the formula —NH—$A^{1a}$ (wherein, $A^{1a}$ represents a glycyl, alanyl, β-aspartyl or γ-glutamyl group) or a group having the formula —CO—$A^{2a}$ (wherein, $A^{2a}$ represents a glycino, alanino, valino, leucino, phenylglycino or phenylalanino group)], a cyclobutyl group, a cyclopentyl group, a cyclohexyl group or a cycloheptyl group, $R^5$ and $R^6$ are the same or different and each independently represents a hydrogen atom, $C_1$–$C_4$ alkyl group, carboxyl group, ($C_1$–$C_4$ alkoxy)carbonyl group, carbamoyl group, ($C_1$–$C_4$ alkyl)carbamoyl group or di-($C_1$–$C_4$ alkyl)carbamoyl group, and X represents a sulfur atom, sulfinyl group or sulfonyl group,

(12) compounds wherein $R^3$ represents a 3-(—S—X—$R^4$)-1-azetidinyl, 3-(—S—X—$R^4$)-1-pyrrolidinyl, 4-(—S—X—$R^4$)-1-piperidinyl or 4-(—S—X—$R^4$)-3-(=$CR^5R^6$)-1-piperidinyl group, $R^4$ represents a substituted or unsubstituted phenyl group (the substituent being a fluorine atom, chlorine atom, bromine atom, methyl group, methoxy group, nitro group or cyano group), a substituted or unsubstituted straight $C_1$–$C_4$ alkyl group [the substituent being an amino group, hydroxyl group, carboxyl group, methoxycarbonyl group, ethoxycarbonyl group, a group having the formula —NH—$A^{1b}$ (wherein, $A^{1b}$ represents a glycyl or γ-glutamyl group) or a group having the formula —CO—$A^{2b}$ (wherein, $A^{2b}$ represents a glycino, alanino or valino group)], a cyclopentyl group or a cyclohexyl group, $R^5$ and $R^6$ are the same or different and each independently represents a hydrogen atom, methyl group, ethyl group, carboxyl group, methoxycarbonyl group, ethoxycarbonyl group, carbamoyl group, methylcarbamoyl group, ethylcarbamoyl group, N,N-dimethylcarbamoyl group or N,N-diethylcarbamoyl group, and X represents a sulfur atom, the sulfinyl group or sulfonyl group,

(13) compounds wherein $R^3$ represents a 3-(—S—X—$R^4$)-1-azetidinyl, 3-(—S—X—$R^4$)-1-pyrrolidinyl, 4-(—S—X—$R^4$)-1-piperidinyl or 4-(—S—X—$R^4$)-3-(=$CR^5R^6$)-1-piperidinyl group, $R^4$ represents a substituted or unsubstituted phenyl group (the substituent being a fluorine atom, chlorine atom, methyl group, methoxy group or nitro group), a substituted or unsubstituted methyl, ethyl or propyl group [the substituent being an amino group, hydroxyl group, carboxyl group, methoxycarbonyl group, ethoxycarbonyl group, a group having the formula —NH—$A^{1c}$ (wherein, $A^{1c}$ represents a γ-glutamyl group) or a group having the formula —CO—$A^{2c}$ (wherein, $A^{2c}$ represents a glycino group)], a cyclopentyl group or a cyclohexyl group, $R^5$ represents a hydrogen atom, $R^6$ represents a hydrogen atom, methyl group, carboxyl group, methoxycarbonyl group, ethoxycarbonyl group, carbamoyl group, methylcarbamoyl or N,N-dimethylcarbamoyl group, and X represents a sulfur atom, sulfinyl or sulfonyl group, and

(14) compounds wherein $R^3$ represents a 3-(—S—X—$R^4$)-1-azetidinyl, 3-(—S—X—$R^4$)-1-pyrrolidinyl, 4-(—S—X—$R^4$)-1-piperidinyl or 4-(—S—X—$R^4$)-3-(=$CR^5R^6$)-1-piperidinyl group, $R^4$ represents a substituted or unsubstituted phenyl group (the substituent being a fluorine atom, chlorine atom, methyl group, methoxy group or nitro group), a substituted or unsubstituted methyl, ethyl or propyl group [the substituent being an amino group, hydroxyl group, carboxyl group, methoxycarbonyl group, ethoxycarbonyl group, a group having the formula —NH—$A^{1c}$ (wherein, $A^{1c}$ represents a γ-glutamyl group) or a group having the formula —CO—$A^{2c}$ (wherein, $A^{2c}$ represents a glycino group)], a cyclopentyl group or a cyclohexyl group, $R^5$ represents a hydrogen atom, $R^6$ represents a carboxyl, methoxycarbonyl or ethoxycarbonyl group, and X represents a sulfur atom or sulfonyl group.

Concerning $R^1$, preference for the above-described compounds increases in the order of (1) to (3) and (4) to (6), concerning $R^2$, preference for the compounds increases in the order of (7) to (10) and concerning $R^3$, preference for the compounds increases in the order of (11) to (14).

Examples of the cyclic amino group represented by the formula (I) or pharmacologically acceptable salt thereof, or medicament containing the same include any combination of 2 to 4 substituent definitions selected from the groups consisting of (1) to (3), (4) to (6), (7) to (10) and (11) to (14). The following compounds are preferred combinations:

(15) compounds wherein $R^1$ represents a substituted phenyl group (the substituent being a halogen atom, methyl group, ethyl group, difluoromethyl group, trifluoromethyl group, methoxy group, ethyl group, difluoromethoxy group, trifluoromethoxy group, cyano group or nitro group), the number of substituents for the substituted phenyl group as $R^1$ ranges from 1 to 3, $R^2$ represents a substituted or unsubstituted $C_2$–$C_4$ alkanoyl or ($C_3$–$C_6$ cycloalkyl)carbonyl group (the substituent being a fluorine atom, chlorine atom, methoxy group, ethoxy group or cyano group), a substituted or unsubstituted benzoyl group (the substituent being a fluorine atom, chlorine atom, methyl group, ethyl group, methoxy group or ethoxy group), or a ($C_1$–$C_4$ alkoxy)carbonyl group,

(16) compounds wherein $R^1$ represents a substituted phenyl group (the substituent being a fluorine atom, chlorine atom, bromine atom, trifluoromethyl group, difluoromethoxy group, trifluoromethoxy group, cyano group or nitro group), the number of substituents for the substituted phenyl group as $R^1$ is 1 or 2, $R^2$ represents a substituted or unsubstituted $C_2$–$C_4$ alkanoyl or ($C_3$–$C_6$ cycloalkyl)carbonyl group (the substituent being a fluorine or chlorine atom), a benzoyl group or a ($C_1$–$C_4$ alkoxy)carbonyl group,

(17) compounds wherein $R^1$ represents a substituted phenyl group (the substituent being a fluorine atom, chlorine atom, bromine atom, trifluoromethyl group, difluoromethoxy group, trifluoromethoxy group, cyano group or nitro group), the position of the substituent for the substituted phenyl group as $R^1$ is the 2- or 4-position, $R^2$ represents a substituted or unsubstituted $C_2$–$C_4$ alkanoyl or ($C_3$–$C_6$ cycloalkyl)carbonyl group (the substituent being a fluorine or chlorine atom), a benzoyl group or a ($C_1$–$C_4$ alkoxy)carbonyl group, $R^3$ represents a 3-(—S—X—$R^4$)-1-azetidinyl, 3-(—S—X—$R^4$)-1-pyrrolidinyl, 3- or 4-(—S—X—$R^4$)-1-piperidinyl, 4-(—S—X13 $R^4$)-3-(=$CR^5R^6$)-1-piperidinyl or 8-aza-3-(—S—X—$R^4$)-bicyclo[3.2.1]octan-8-yl group, $R^4$ represents a substituted or unsubstituted phenyl group (the substituent being a halogen atom, methyl group, ethyl group, methoxy group, ethoxy group, nitro group or cyano group), a substituted or unsubstituted straight $C_1$–$C_6$ alkyl group [the substituent being an amino group, hydroxyl group, carboxyl group, ($C_1$–$C_4$ alkoxy)carbonyl group, a group having the formula —NH—$A^{1a}$ (wherein, $A^{1a}$ represents a glycyl, alanyl, β-aspartyl or γ-glutamyl group) or a group having the formula —CO—$A^{2a}$ (wherein, $A^{2a}$ represents a glycino, alanino, valino, leucino, phenylglycino or phenylalanino group)], a cyclobutyl group, a cyclopentyl group, a cyclohexyl group or a cycloheptyl group, $R^5$ and $R^6$ are the same or different and each independently represents a hydrogen atom, $C_1$–$C_4$ alkyl group, carboxyl group, ($C_1$–$C_4$ alkoxy)carbonyl group, carbamoyl group, ($C_1$–$C_4$ alkyl)carbamoyl or di-($C_1$–$C_4$ alkyl)carbamoyl group, and X represents a sulfur atom, sulfinyl group or sulfonyl group,

(18) compounds wherein $R^1$ represents a substituted phenyl group (the substituent being a fluorine atom or chlorine atom), the position of the substituent for the substituted phenyl group as $R^1$ is the 2- or 4-position, $R^2$ represents a substituted or unsubstituted acetyl, propionyl, isobutyryl, cyclopropylcarbonyl or cyclobutylcarbonyl group (the substituent being a fluorine atom), methoxycarbonyl or ethoxycarbonyl group, $R^3$ represents a 3-(—S—X—$R^4$)-1-azetidinyl, 3-(—S—X—$R^4$)-1-pyrrolidinyl, 4-(—S—X—$R^4$)-1-piperidinyl or 4-(—S—X—$R^4$)-3-(=$CR^5R^6$)-1-piperidinyl group, $R^4$ represents a substituted or unsubstituted phenyl group (the substituent being a fluorine atom, chlorine atom, bromine atom, methyl group, methoxy group, nitro group or cyano group), a substituted or unsubstituted straight $C_1$–$C_4$ alkyl group [the substituent being an amino group, hydroxyl group, carboxyl group, methoxycarbonyl group, ethoxycarbonyl group, a group having the formula —NH—$A^{1b}$ (wherein, $A^{1b}$ represents a glycyl or γ-glutamyl group) or a group having the formula —CO—$A^{2b}$ (wherein, $A^{2b}$ represents a glycino, alanino or valino group)], a cyclopentyl group or a cyclohexyl group, $R^5$ and $R^6$ are the same or different and each independently represents a hydrogen atom, methyl group, ethyl group, carboxyl group, methoxycarbonyl group, ethoxycarbonyl group, carbamoyl group, methylcarbamoyl group, ethylcarbamoyl group, N,N-dimethylcarbamoyl group or N,N-diethylcarbamoyl group, and X represents a sulfur atom, sulfinyl group or sulfonyl group,

(19) compounds wherein $R^1$ represents a substituted phenyl group (the substituent being a fluorine atom or chlorine atom), the position of the substituent for the substituted phenyl group as $R^1$ is the 2- or 4-position, $R^2$ represents a propionyl, cyclopropylcarbonyl, methoxycarbonyl or ethoxycarbonyl group, $R^3$ represents a 3-(—S—X—$R^4$)-1-azetidinyl, 3-(—S—X—$R^4$)-1-pyrrolidinyl, 4-(—S—X—$R^4$)-1-piperidinyl or 4-(—S—X—$R^4$)-3-(=$CR^5R^6$)-1-piperidinyl group, $R^4$ represents a substituted or unsubstituted phenyl group (the substituent being a fluorine atom, chlorine atom, methyl group, methoxy group or nitro group), a substituted or unsubstituted methyl, ethyl or propyl group [the substituent being an amino group, hydroxyl group, carboxyl group, methoxycarbonyl group, ethoxycarbonyl group, a group having the formula —NH—$A^{1c}$ (wherein, $A^{1c}$ represents a γ-glutamyl group) or a group having the formula —CO—$A^{2c}$ (wherein, $A^{2c}$ represents a glycino group)], a cyclopentyl group or a cyclohexyl group, $R^5$ represents a hydrogen atom, $R^6$ represents a hydrogen atom, methyl group, carboxyl group, methoxycarbonyl group, ethoxycarbonyl group, carbamoyl group, methylcarbamoyl group or N,N-dimethylcarbamoyl group, and X represents a sulfur atom, sulfinyl group or sulfonyl group, and

(20) compounds wherein $R^1$ represents a substituted phenyl group (the substituent being a fluorine atom or chlorine atom), the position of the substituent for the substituted phenyl group as $R^1$ is the 2- or 4-position, $R^2$ represents a propionyl, cyclopropylcarbonyl, methoxycarbonyl or ethoxycarbonyl group, $R^3$ represents a 3-(—S—X—$R^4$)-1-azetidinyl, 3-(—S—X—$R^4$)-1-pyrrolidinyl, 4-(—S—X—$R^4$)-1-piperidinyl or 4-(—S—X—$R^4$)-3-(=$CR^5R^6$)-1-piperidinyl group, $R^4$ represents a substituted or unsubstituted phenyl group (the substituent being a fluorine atom, chlorine atom, methyl group, methoxy group or nitro group), a substituted or unsubstituted methyl, ethyl or propyl group [the substituent being an amino group, hydroxyl group, carboxyl group, methoxycarbonyl group, ethoxycarbonyl group, a group having the formula —NH—$A^{1c}$ (wherein, $A^{1c}$ represents a γ-glutamyl group) or group having the formula —CO—$A^{2c}$ (wherein, $A^{2c}$ represents a glycino group)], a cyclopentyl group or a cyclohexyl group, $R^5$ represents a hydrogen atom, $R^6$ represents a carboxyl, methoxycarbonyl or ethoxychloroyl group, and X represents a sulfur atom or sulfonyl group.

Preference to the above-described compounds increases in the order of (15) to (20).

As typical compounds of the present invention, the compounds shown in the below-described tables can be mentioned by way of example. It should however be borne in mind that the present invention is not limited to them.

Incidentally, the abbreviations in the tables are as follows:

| | |
|---|---|
| Ala | alanyl group |
| Asp | aspartyl group |
| Bu | butyl group |
| c-Bu | cyclobutyl group |
| Et | ethyl group |
| Glu | glutamyl group |
| gly | glycino group |
| Gly | glycyl group |
| Hx | hexyl group |
| c-Hx | cyclohexyl group |
| Me | methyl group |
| Ph | phenyl group |
| Pn | pentyl group |
| c-Pn | cyclopentyl group |
| Pr | propyl group |
| c-Pr | cyclopropyl group |
| Prop | propionyl group |

TABLE 1

(I-1)

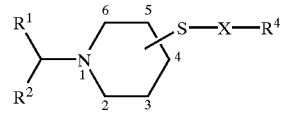

| Exemplified Compound No. | $R^1$ | $R^2$ | —S—X—$R^4$ |
|---|---|---|---|
| 1-1 | 2-F-Ph | Prop | 4-S-$SO_2$-(4-Me-Ph) |
| 1-2 | 2-Cl-Ph | c-PrCO | 4-S-$SO_2$-(4-Me-Ph) |
| 1-3 | 2-$NO_2$-Ph | c-PrCO | 4-S-$SO_2$-(4-Me-Ph) |
| 1-4 | 2-CN-Ph | c-PrCO | 4-S-$SO_2$-(4-Me-Ph) |
| 1-5 | 2-$CF_3$-Ph | c-PrCO | 4-S-$SO_2$-(4-Me-Ph) |
| 1-6 | 2-F-Ph | 2-F-c-PrCO | 4-S-$SO_2$-(4-Me-Ph) |
| 1-7 | 2-F-Ph | c-PrCO | 4-S-$SO_2$-(4-Me-Ph) |
| 1-8 | 4-F-Ph | c-PrCO | 4-S-$SO_2$-(4-Me-Ph) |
| 1-9 | 2,4-diF-Ph | c-BuCO | 4-S-$SO_2$-(4-Me-Ph) |
| 1-10 | 2-F-Ph | MeOCO | 4-S-$SO_2$-(4-Me-Ph) |
| 1-11 | 2-F-Ph | EtOCO | 4-S-$SO_2$-(4-Me-Ph) |
| 1-12 | 2-Cl-Ph | MeOCO | 4-S-$SO_2$-(4-Me-Ph) |
| 1-13 | 2-Cl-Ph | c-PrCO | 4-S-SO-(4-Me-Ph) |
| 1-14 | 2-F-Ph | c-PrCO | 4-S-SO-(4-Me-Ph) |
| 1-15 | 2-F-Ph | MeOCO | 4-S-SO-(4-Me-Ph) |
| 1-16 | 2-Cl-Ph | MeOCO | 4-S-SO-(4-Me-Ph) |
| 1-17 | 2-F-Ph | c-PrCO | 4-S-S-(4-Me-Ph) |
| 1-18 | 2-Cl-Ph | c-PrCO | 4-S-S-(4-Me-Ph) |
| 1-19 | 2-F-Ph | MeOCO | 4-S-S-(4-Me-Ph) |
| 1-20 | 2-Cl-Ph | MeOCO | 4-S-S-(4-Me-Ph) |
| 1-21 | 2-F-Ph | Prop | 4-S-$SO_2$-(4-Cl-Ph) |
| 1-22 | 2-Cl-Ph | c-PrCO | 4-S-$SO_2$-(4-Cl-Ph) |
| 1-23 | 2-$NO_2$-Ph | c-PrCO | 4-S-$SO_2$-(4-Cl-Ph) |
| 1-24 | 2-CN-Ph | c-PrCO | 4-S-$SO_2$-(4-Cl-Ph) |
| 1-25 | 2-$CF_3$-Ph | c-PrCO | 4-S-$SO_2$-(4-Cl-Ph) |
| 1-26 | 2-F-Ph | 2-F-c-PrCO | 4-S-$SO_2$-(4-Cl-Ph) |
| 1-27 | 2-F-Ph | c-PrCO | 4-S-$SO_2$-(4-Cl-Ph) |
| 1-28 | 4-F-Ph | c-PrCO | 4-S-$SO_2$-(4-Cl-Ph) |
| 1-29 | 2,4-diF-Ph | c-BuCO | 4-S-$SO_2$-(4-Cl-Ph) |
| 1-30 | 2-F-Ph | MeOCO | 4-S-$SO_2$-(4-Cl-Ph) |
| 1-31 | 2-F-Ph | EtOCO | 4-S-$SO_2$-(4-Cl-Ph) |
| 1-32 | 2-Cl-Ph | MeOCO | 4-S-$SO_2$-(4-Cl-Ph) |
| 1-33 | 2-Cl-Ph | c-PrCO | 4-S-SO-(4-Cl-Ph) |
| 1-34 | 2-F-Ph | c-PrCO | 4-S-SO-(4-Cl-Ph) |
| 1-35 | 2-F-Ph | MeOCO | 4-S-SO-(4-Cl-Ph) |

TABLE 1-continued (I-1)

$$R^1\text{-}CH(R^2)\text{-}N\text{-piperidine-}4\text{-}S\text{-}X\text{-}R^4$$

| Exemplified Compound No. | R¹ | R² | —S—X—R⁴ |
|---|---|---|---|
| 1-36 | 2-Cl-Ph | MeOCO | 4-S-SO-(4-Cl-Ph) |
| 1-37 | 2-F-Ph | c-PrCO | 4-S-S-(4-Cl-Ph) |
| 1-38 | 2-Cl-Ph | c-PrCO | 4-S-S-(4-Cl-Ph) |
| 1-39 | 2-F-Ph | MeOCO | 4-S-S-(4-Cl-Ph) |
| 1-40 | 2-Cl-Ph | MeOCO | 4-S-S-(4-Cl-Ph) |
| 1-41 | 2-F-Ph | Prop | 4-S-SO$_2$-(4-F-Ph) |
| 1-42 | 2-Cl-Ph | c-PrCO | 4-S-SO$_2$-(4-F-Ph) |
| 1-43 | 2-NO$_2$-Ph | c-PrCO | 4-S-SO$_2$-(4-F-Ph) |
| 1-44 | 2-CN-Ph | c-PrCO | 4-S-SO$_2$-(4-F-Ph) |
| 1-45 | 2-CF$_3$-Ph | c-PrCO | 4-S-SO$_2$-(4-F-Ph) |
| 1-46 | 2-F-Ph | 2-F-c-PrCO | 4-S-SO$_2$-(4-F-Ph) |
| 1-47 | 2-F-Ph | c-PrCO | 4-S-SO$_2$-(4-F-Ph) |
| 1-48 | 4-F-Ph | c-PrCO | 4-S-SO$_2$-(4-F-Ph) |
| 1-49 | 2,4-diF-Ph | c-BuCO | 4-S-SO$_2$-(4-F-Ph) |
| 1-50 | 2-F-Ph | MeOCO | 4-S-SO$_2$-(4-F-Ph) |
| 1-51 | 2-F-Ph | EtOCO | 4-S-SO$_2$-(4-F-Ph) |
| 1-52 | 2-Cl-Ph | MeOCO | 4-S-SO$_2$-(4-F-Ph) |
| 1-53 | 2-Cl-Ph | c-PrCO | 4-S-SO-(4-F-Ph) |
| 1-54 | 2-F-Ph | c-PrCO | 4-S-SO-(4-F-Ph) |
| 1-55 | 2-F-Ph | MeOCO | 4-S-SO-(4-F-Ph) |
| 1-56 | 2-Cl-Ph | MeOCO | 4-S-SO-(4-F-Ph) |
| 1-57 | 2-F-Ph | c-PrCO | 4-S-S-(4-F-Ph) |
| 1-58 | 2-Cl-Ph | c-PrCO | 4-S-S-(4-F-Ph) |
| 1-59 | 2-F-Ph | MeOCO | 4-S-S-(4-F-Ph) |
| 1-60 | 2-Cl-Ph | MeOCO | 4-S-S-(4-F-Ph) |
| 1-61 | 2-F-Ph | Prop | 4-S-SO$_2$-(4-MeO-Ph) |
| 1-62 | 2-Cl-Ph | c-PrCO | 4-S-SO$_2$-(4-MeO-Ph) |
| 1-63 | 2-NO$_2$-Ph | c-PrCO | 4-S-SO$_2$-(4-MeO-Ph) |
| 1-64 | 2-CN-Ph | c-PrCO | 4-S-SO$_2$-(4-MeO-Ph) |
| 1-65 | 2-CF$_3$-Ph | c-PrCO | 4-S-SO$_2$-(4-MeO-Ph) |
| 1-66 | 2-F-Ph | 2-F-c-PrCO | 4-S-SO$_2$-(4-MeO-Ph) |
| 1-67 | 2-F-Ph | c-PrCO | 4-S-SO$_2$-(4-MeO-Ph) |
| 1-68 | 4-F-Ph | c-PrCO | 4-S-SO$_2$-(4-MeO-Ph) |
| 1-69 | 2,4-diF-Ph | c-BuCO | 4-S-SO$_2$-(4-MeO-Ph) |
| 1-70 | 2-F-Ph | MeOCO | 4-S-SO$_2$-(4-MeO-Ph) |
| 1-71 | 2-F-Ph | EtOCO | 4-S-SO$_2$-(4-MeO-Ph) |
| 1-72 | 2-Cl-Ph | MeOCO | 4-S-SO$_2$-(4-MeO-Ph) |
| 1-73 | 2-Cl-Ph | c-PrCO | 4-S-SO-(4-MeO-Ph) |
| 1-74 | 2-F-Ph | c-PrCO | 4-S-SO-(4-MeO-Ph) |
| 1-75 | 2-F-Ph | MeOCO | 4-S-SO-(4-MeO-Ph) |
| 1-76 | 2-Cl-Ph | MeOCO | 4-S-SO-(4-MeO-Ph) |
| 1-77 | 2-F-Ph | c-PrCO | 4-S-S-(4-MeO-Ph) |
| 1-78 | 2-Cl-Ph | c-PrCO | 4-S-S-(4-MeO-Ph) |
| 1-79 | 2-F-Ph | MeOCO | 4-S-S-(4-MeO-Ph) |
| 1-80 | 2-Cl-Ph | MeOCO | 4-S-S-(4-MeO-Ph) |
| 1-81 | 2-Cl-Ph | c-PrCO | 4-S-SO$_2$-Ph |
| 1-82 | 2-F-Ph | c-PrCO | 4-S-SO$_2$-Ph |
| 1-83 | 2-F-Ph | MeOCO | 4-S-SO$_2$-Ph |
| 1-84 | 2-Cl-Ph | MeOCO | 4-S-SO$_2$-Ph |
| 1-85 | 2-Cl-Ph | c-PrCO | 4-S-SO-Ph |
| 1-86 | 2-F-Ph | c-PrCO | 4-S-SO-Ph |
| 1-87 | 2-Cl-Ph | MeOCO | 4-S-SO-Ph |
| 1-88 | 2-Cl-Ph | c-PrCO | 4-S-S-Ph |
| 1-89 | 2-F-Ph | c-PrCO | 4-S-S-Ph |
| 1-90 | 2-Cl-Ph | MeOCO | 4-S-S-Ph |
| 1-91 | 2-Cl-Ph | c-PrCO | 4-S-SO$_2$-(4-NO$_2$-Ph) |
| 1-92 | 2-F-Ph | c-PrCO | 4-S-SO$_2$-(4-NO$_2$-Ph) |
| 1-93 | 2-F-Ph | MeOCO | 4-S-SO$_2$-(4-NO$_2$-Ph) |
| 1-94 | 2-Cl-Ph | MeOCO | 4-S-SO$_2$-(4-NO$_2$-Ph) |
| 1-95 | 2-Cl-Ph | c-PrCO | 4-S-SO-(4-NO$_2$-Ph) |
| 1-96 | 2-F-Ph | c-PrCO | 4-S-SO-(4-NO$_2$-Ph) |
| 1-97 | 2-Cl-Ph | MeOCO | 4-S-SO-(4-NO$_2$-Ph) |
| 1-98 | 2-Cl-Ph | c-PrCO | 4-S-S-(4-NO$_2$-Ph) |
| 1-99 | 2-F-Ph | c-PrCO | 4-S-S-(4-NO$_2$-Ph) |
| 1-100 | 2-Cl-Ph | MeOCO | 4-S-S-(4-NO$_2$-Ph) |
| 1-101 | 2-Cl-Ph | c-PrCO | 4-S-SO$_2$-(2-NO$_2$-Ph) |
| 1-102 | 2-F-Ph | c-PrCO | 4-S-SO$_2$-(2-NO$_2$-Ph) |
| 1-103 | 2-F-Ph | MeOCO | 4-S-SO$_2$-(2-NO$_2$-Ph) |
| 1-104 | 2-Cl-Ph | MeOCO | 4-S-SO$_2$-(2-NO$_2$-Ph) |
| 1-105 | 2-Cl-Ph | c-PrCO | 4-S-SO-(2-NO$_2$-Ph) |
| 1-106 | 2-F-Ph | c-PrCO | 4-S-SO-(2-NO$_2$-Ph) |
| 1-107 | 2-Cl-Ph | MeOCO | 4-S-SO-(2-NO$_2$-Ph) |
| 1-108 | 2-Cl-Ph | c-PrCO | 4-S-S-(2-NO$_2$-Ph) |
| 1-109 | 2-F-Ph | c-PrCO | 4-S-S-(2-NO$_2$-Ph) |
| 1-110 | 2-Cl-Ph | MeOCO | 4-S-S-(2-NO$_2$-Ph) |
| 1-111 | 2-Cl-Ph | c-PrCO | 4-S-SO$_2$-(2-Cl-Ph) |
| 1-112 | 2-F-Ph | c-PrCO | 4-S-SO$_2$-(2-Cl-Ph) |
| 1-113 | 2-F-Ph | MeOCO | 4-S-SO$_2$-(2-Cl-Ph) |
| 1-114 | 2-Cl-Ph | MeOCO | 4-S-SO$_2$-(2-Cl-Ph) |
| 1-115 | 2-Cl-Ph | c-PrCO | 4-S-SO-(2-Cl-Ph) |
| 1-116 | 2-F-Ph | c-PrCO | 4-S-SO-(2-Cl-Ph) |
| 1-117 | 2-Cl-Ph | MeOCO | 4-S-SO-(2-Cl-Ph) |
| 1-118 | 2-Cl-Ph | c-PrCO | 4-S-S-(2-Cl-Ph) |
| 1-119 | 2-F-Ph | c-PrCO | 4-S-S-(2-Cl-Ph) |
| 1-120 | 2-Cl-Ph | MeOCO | 4-S-S-(2-Cl-Ph) |
| 1-121 | 2-Cl-Ph | c-PrCO | 4-S-SO$_2$-(2-F-Ph) |
| 1-122 | 2-F-Ph | c-PrCO | 4-S-SO$_2$-(2-F-Ph) |
| 1-123 | 2-F-Ph | MeOCO | 4-S-SO$_2$-(2-F-Ph) |
| 1-124 | 2-Cl-Ph | MeOCO | 4-S-SO$_2$-(2-F-Ph) |
| 1-125 | 2-Cl-Ph | c-PrCO | 4-S-SO-(2-F-Ph) |
| 1-126 | 2-F-Ph | c-PrCO | 4-S-SO-(2-F-Ph) |
| 1-127 | 2-Cl-Ph | MeOCO | 4-S-SO-(2-F-Ph) |
| 1-128 | 2-Cl-Ph | c-PrCO | 4-S-S-(2-F-Ph) |
| 1-129 | 2-F-Ph | c-PrCO | 4-S-S-(2-F-Ph) |
| 1-130 | 2-Cl-Ph | MeOCO | 4-S-S-(2-F-Ph) |
| 1-131 | 2-Cl-Ph | c-PrCO | 4-S-SO$_2$-(2,4-diNO$_2$-Ph) |
| 1-132 | 2-F-Ph | c-PrCO | 4-S-SO$_2$-(2,4-diNO$_2$-Ph) |
| 1-133 | 2-F-Ph | MeOCO | 4-S-SO$_2$-(2,4-diNO$_2$-Ph) |
| 1-134 | 2-Cl-Ph | MeOCO | 4-S-SO$_2$-(2,4-diNO$_2$-Ph) |
| 1-135 | 2-Cl-Ph | c-PrCO | 4-S-SO-(2,4-diNO$_2$-Ph) |
| 1-136 | 2-F-Ph | c-PrCO | 4-S-SO-(2,4-diNO$_2$-Ph) |
| 1-137 | 2-Cl-Ph | MeOCO | 4-S-SO-(2,4-diNO$_2$-Ph) |
| 1-138 | 2-Cl-Ph | c-PrCO | 4-S-S-(2,4-diNO$_2$-Ph) |
| 1-139 | 2-F-Ph | c-PrCO | 4-S-S-(2,4-diNO$_2$-Ph) |
| 1-140 | 2-Cl-Ph | MeOCO | 4-S-S-(2,4-diNO$_2$-Ph) |
| 1-141 | 2-Cl-Ph | c-PrCO | 4-S-SO$_2$-Me |
| 1-142 | 2-F-Ph | c-PrCO | 4-S-SO$_2$-Me |
| 1-143 | 2-F-Ph | MeOCO | 4-S-SO$_2$-Me |
| 1-144 | 2-Cl-Ph | MeOCO | 4-S-SO$_2$-Me |
| 1-145 | 2-Cl-Ph | c-PrCO | 4-S-SO-Me |
| 1-146 | 2-F-Ph | c-PrCO | 4-S-SO-Me |
| 1-147 | 2-Cl-Ph | c-PrCO | 4-S-SO-Me |
| 1-148 | 2-Cl-Ph | c-PrCO | 4-S-S-Me |
| 1-149 | 2-F-Ph | c-PrCO | 4-S-S-Me |
| 1-150 | 2-Cl-Ph | MeOCO | 4-S-S-Me |
| 1-151 | 2-Cl-Ph | c-PrCO | 4-S-SO$_2$-Et |
| 1-152 | 2-F-Ph | c-PrCO | 4-S-SO$_2$-Et |
| 1-153 | 2-F-Ph | MeOCO | 4-S-SO$_2$-Et |
| 1-154 | 2-Cl-Ph | MeOCO | 4-S-SO$_2$-Et |
| 1-155 | 2-Cl-Ph | c-PrCO | 4-S-SO-Et |
| 1-156 | 2-F-Ph | c-PrCO | 4-S-SO-Et |
| 1-157 | 2-Cl-Ph | MeOCO | 4-S-SO-Et |
| 1-158 | 2-Cl-Ph | c-PrCO | 4-S-S-Et |
| 1-159 | 2-F-Ph | c-PrCO | 4-S-S-Et |
| 1-160 | 2-Cl-Ph | MeOCO | 4-S-S-Et |
| 1-161 | 2-Cl-Ph | c-PrCO | 4-S-SO$_2$-Pr |
| 1-162 | 2-F-Ph | c-PrCO | 4-S-SO$_2$-Pr |
| 1-163 | 2-F-Ph | MeOCO | 4-S-SO$_2$-Pr |
| 1-164 | 2-Cl-Ph | MeOCO | 4-S-SO$_2$-Pr |
| 1-165 | 2-Cl-Ph | c-PrCO | 4-S-SO-Pr |
| 1-166 | 2-F-Ph | c-PrCO | 4-S-SO-Pr |
| 1-167 | 2-Cl-Ph | MeOCO | 4-S-SO-Pr |
| 1-168 | 2-Cl-Ph | c-PrCO | 4-S-S-Pr |
| 1-169 | 2-F-Ph | c-PrCO | 4-S-S-Pr |
| 1-170 | 2-Cl-Ph | MeOCO | 4-S-S-Pr |
| 1-171 | 2-Cl-Ph | c-PrCO | 4-S-SO$_2$-Bu |

TABLE 1-continued (I-1)

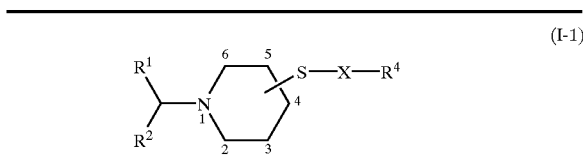

| Exemplified Compound No. | R¹ | R² | —S—X—R⁴ |
|---|---|---|---|
| 1-172 | 2-F-Ph | c-PrCO | 4-S-SO$_2$-Bu |
| 1-173 | 2-F-Ph | MeOCO | 4-S-SO$_2$-Bu |
| 1-174 | 2-Cl-Ph | MeOCO | 4-S-SO$_2$-Bu |
| 1-175 | 2-Cl-Ph | c-PrCO | 4-S-SO-Bu |
| 1-176 | 2-F-Ph | c-PrCO | 4-S-SO-Bu |
| 1-177 | 2-Cl-Ph | MeOCO | 4-S-SO-Bu |
| 1-178 | 2-Cl-Ph | c-PrCO | 4-S-S-Bu |
| 1-179 | 2-F-Ph | c-PrCO | 4-S-S-Bu |
| 1-180 | 2-Cl-Ph | MeOCO | 4-S-S-Bu |
| 1-181 | 2-Cl-Ph | c-PrCO | 4-S-SO$_2$-c-Pn |
| 1-182 | 2-F-Ph | c-PrCO | 4-S-SO$_2$-c-Pn |
| 1-183 | 2-F-Ph | MeOCO | 4-S-SO$_2$-c-Pn |
| 1-184 | 2-Cl-Ph | MeOCO | 4-S-SO$_2$-c-Pn |
| 1-185 | 2-Cl-Ph | c-PrCO | 4-S-SO-c-Pn |
| 1-186 | 2-F-Ph | c-PrCO | 4-S-SO-c-Pn |
| 1-187 | 2-Cl-Ph | MeOCO | 4-S-SO-c-Pn |
| 1-188 | 2-Cl-Ph | c-PrCO | 4-S-S-c-Pn |
| 1-189 | 2-F-Ph | c-PrCO | 4-S-S-c-Pn |
| 1-190 | 2-Cl-Ph | MeOCO | 4-S-S-c-Pn |
| 1-191 | 2-Cl-Ph | c-PrCO | 4-S-SO$_2$-c-Hx |
| 1-192 | 2-F-Ph | c-PrCO | 4-S-SO$_2$-c-Hx |
| 1-193 | 2-F-Ph | MeOCO | 4-S-SO$_2$-c-Hx |
| 1-194 | 2-Cl-Ph | MeOCO | 4-S-SO$_2$-c-Hx |
| 1-195 | 2-Cl-Ph | c-PrCO | 4-S-SO-c-Hx |
| 1-196 | 2-F-Ph | c-PrCO | 4-S-SO-c-Hx |
| 1-197 | 2-Cl-Ph | MeOCO | 4-S-SO-c-Hx |
| 1-198 | 2-Cl-Ph | c-PrCO | 4-S-S-c-Hx |
| 1-199 | 2-F-Ph | c-PrCO | 4-S-S-c-Hx |
| 1-200 | 2-Cl-Ph | MeOCO | 4-S-S-c-Hx |
| 1-201 | 2-Cl-Ph | c-PrCO | 4-S-SO$_2$—CH$_2$COOH |
| 1-202 | 2-F-Ph | c-PrCO | 4-S-S-CH$_2$COOEt |
| 1-203 | 2-F-Ph | MeOCO | 4-S-SO$_2$—CH$_2$COOH |
| 1-204 | 2-Cl-Ph | MeOCO | 4-S-S-CH$_2$COOEt |
| 1-205 | 2-Cl-Ph | c-PrCO | 4-S-SO$_2$—(CH$_2$)$_3$COOH |
| 1-206 | 2-F-Ph | c-PrCO | 4-S-S-(CH$_2$)$_2$COOH |
| 1-207 | 2-F-Ph | MeOCO | 4-S-SO$_2$—(CH$_2$)$_3$COOH |
| 1-208 | 2-Cl-Ph | MeOCO | 4-S-S-(CH$_2$)$_2$COOH |
| 1-209 | 2-Cl-Ph | c-PrCO | 4-S-SO$_2$—(CH$_2$)$_3$COOMe |
| 1-210 | 2-F-Ph | c-PrCO | 4-S-S-(CH$_2$)$_2$COOMe |
| 1-211 | 2-F-Ph | MeOCO | 4-S-SO$_2$—(CH$_2$)$_3$COOMe |
| 1-212 | 2-Cl-Ph | MeOCO | 4-S-S-(CH$_2$)$_2$COOMe |
| 1-213 | 2-Cl-Ph | c-PrCO | 4-S-SO$_2$—(CH$_2$)$_3$COOEt |
| 1-214 | 2-F-Ph | c-PrCO | 4-S-S-(CH$_2$)$_2$COOEt |
| 1-215 | 2-F-Ph | MeOCO | 4-S-SO$_2$—(CH$_2$)$_3$COOEt |
| 1-216 | 2-Cl-Ph | MeOCO | 4-S-S-(CH$_2$)$_2$COOEt |
| 1-217 | 2-Cl-Ph | c-PrCO | 4-S-SO$_2$—(CH$_2$)$_3$OH |
| 1-218 | 2-F-Ph | c-PrCO | 4-S-S-(CH$_2$)$_2$OH |
| 1-219 | 2-F-Ph | MeOCO | 4-S-SO$_2$—(CH$_2$)$_3$OH |
| 1-220 | 2-Cl-Ph | MeOCO | 4-S-S-(CH$_2$)$_2$OH |
| 1-221 | 2-Cl-Ph | c-PrCO | 4-S-SO$_2$—(CH$_2$)$_3$NH$_2$ |
| 1-222 | 2-F-Ph | c-PrCO | 4-S-S-(CH$_2$)$_2$NH$_2$ |
| 1-223 | 2-F-Ph | MeOCO | 4-S-SO$_2$—(CH$_2$)$_3$NH$_2$ |
| 1-224 | 2-Cl-Ph | MeOCO | 4-S-S-(CH$_2$)$_2$NH$_2$ |
| 1-225 | 2-Cl-Ph | c-PrCO | 4-S-S-(CH$_2$)$_2$NHGly |
| 1-226 | 2-F-Ph | c-PrCO | 4-S-S-(CH$_2$)$_2$NHAla |
| 1-227 | 2-F-Ph | MeOCO | 4-S-S-(CH$_2$)$_2$NHGly |
| 1-228 | 2-Cl-Ph | MeOCO | 4-S-S-(CH$_2$)$_2$NHAla |
| 1-229 | 2-Cl-Ph | c-PrCO | 4-S-S-(CH$_2$)$_2$NH-β-Asp |
| 1-230 | 2-F-Ph | c-PrCO | 4-S-S-(CH$_2$)$_2$NHGlu |
| 1-231 | 2-F-Ph | MeOCO | 4-S-S-(CH$_2$)$_2$NH-β-Asp |
| 1-232 | 2-Cl-Ph | MeOCO | 4-S-S-(CH$_2$)$_2$NHGlu |
| 1-233 | 2-Cl-Ph | c-PrCO | 4-S-S-CH$_2$CH(NH$_2$)COOH |
| 1-234 | 2-F-Ph | c-PrCO | 4-S-S-CH$_2$CH(NH$_2$)COOH |
| 1-235 | 2-F-Ph | MeOCO | 4-S-S-CH$_2$CH(NH$_2$)COOH |
| 1-236 | 2-Cl-Ph | MeOCO | 4-S-S-CH$_2$CH(NH$_2$)COOH |
| 1-237 | 2-Cl-Ph | c-PrCO | 4-S-S-CH$_2$CH(NHGlu)COgly |
| 1-238 | 2-F-Ph | c-PrCO | 4-S-S-CH$_2$CH(NHGlu)COgly |
| 1-239 | 2-F-Ph | MeOCO | 4-S-S-CH$_2$CH(NHGlu)COgly |

TABLE 1-continued (I-1)

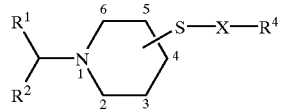

| Exemplified Compound No. | R¹ | R² | —S—X—R⁴ |
|---|---|---|---|
| 1-240 | 2-Cl-Ph | MeOCO | 4-S-S-CH$_2$CH(NHGlu)COgly |
| 1-241 | 2-Cl-Ph | c-PrCO | 3-S-SO$_2$-(4-Me-Ph) |
| 1-242 | 2-F-Ph | c-PrCO | 3-S-SO$_2$-(4-Me-Ph) |
| 1-243 | 2-F-Ph | MeOCO | 3-S-SO$_2$-(4-Me-Ph) |
| 1-244 | 2-Cl-Ph | MeOCO | 3-S-SO$_2$-(4-Me-Ph) |
| 1-245 | 2-F-Ph | c-PrCO | 3-S-SO-(4-Me-Ph) |
| 1-246 | 2-Cl-Ph | MeOCO | 3-S-SO-(4-Me-Ph) |
| 1-247 | 2-F-Ph | c-PrCO | 3-S-S-(4-Me-Ph) |
| 1-248 | 2-Cl-Ph | MeOCO | 3-S-S-(4-Me-Ph) |
| 1-249 | 2-Cl-Ph | c-PrCO | 3-S-SO$_2$-(4-Cl-Ph) |
| 1-250 | 2-F-Ph | c-PrCO | 3-S-SO$_2$-(4-Cl-Ph) |
| 1-251 | 2-F-Ph | MeOCO | 3-S-SO$_2$-(4-Cl-Ph) |
| 1-252 | 2-Cl-Ph | MeOCO | 3-S-SO$_2$-(4-Cl-Ph) |
| 1-253 | 2-F-Ph | c-PrCO | 3-S-SO-(4-Cl-Ph) |
| 1-254 | 2-Cl-Ph | MeOCO | 3-S-SO-(4-Cl-Ph) |
| 1-255 | 2-F-Ph | c-PrCO | 3-S-S-(4-Cl-Ph) |
| 1-256 | 2-Cl-Ph | MeOCO | 3-S-S-(4-Cl-Ph) |
| 1-257 | 2-Cl-Ph | c-PrCO | 3-S-SO$_2$-(4-F-Ph) |
| 1-258 | 2-F-Ph | c-PrCO | 3-S-SO$_2$-(4-F-Ph) |
| 1-259 | 2-F-Ph | MeOCO | 3-S-SO$_2$-(4-F-Ph) |
| 1-260 | 2-Cl-Ph | MeOCO | 3-S-SO$_2$-(4-F-Ph) |
| 1-261 | 2-F-Ph | c-PrCO | 3-S-SO-(4-F-Ph) |
| 1-262 | 2-Cl-Ph | MeOCO | 3-S-SO-(4-F-Ph) |
| 1-263 | 2-F-Ph | c-PrCO | 3-S-S-(4-F-Ph) |
| 1-264 | 2-Cl-Ph | MeOCO | 3-S-S-(4-F-Ph) |
| 1-265 | 2-Cl-Ph | c-PrCO | 3-S-SO$_2$-(4-MeO-Ph) |
| 1-266 | 2-F-Ph | c-PrCO | 3-S-SO$_2$-(4-MeO-Ph) |
| 1-267 | 2-F-Ph | MeOCO | 3-S-SO$_2$-(4-MeO-Ph) |
| 1-268 | 2-Cl-Ph | MeOCO | 3-S-SO$_2$-(4-MeO-Ph) |
| 1-269 | 2-F-Ph | c-PrCO | 3-S-SO-(4-MeO-Ph) |
| 1-270 | 2-Cl-Ph | MeOCO | 3-S-SO-(4-MeO-Ph) |
| 1-271 | 2-F-Ph | c-PrCO | 3-S-S-(4-MeO-Ph) |
| 1-272 | 2-Cl-Ph | MeOCO | 3-S-S-(4-MeO-Ph) |
| 1-273 | 2-Cl-Ph | c-PrCO | 3-S-SO$_2$-Ph |
| 1-274 | 2-F-Ph | c-PrCO | 3-S-SO$_2$-Ph |
| 1-275 | 2-F-Ph | MeOCO | 3-S-SO$_2$-Ph |
| 1-276 | 2-Cl-Ph | MeOCO | 3-S-SO$_2$-Ph |
| 1-277 | 2-F-Ph | c-PrCO | 3-S-SO-Ph |
| 1-278 | 2-Cl-Ph | MeOCO | 3-S-SO-Ph |
| 1-279 | 2-F-Ph | c-PrCO | 3-S-S-Ph |
| 1-280 | 2-Cl-Ph | MeOCO | 3-S-S-Ph |
| 1-281 | 2-F-Ph | c-PrCO | 3-S-SO$_2$-(4-NO$_2$-Ph) |
| 1-282 | 2-Cl-Ph | MeOCO | 3-S-SO$_2$-(4-NO$_2$-Ph) |
| 1-283 | 2-F-Ph | c-PrCO | 3-S-SO-(4-NO$_2$-Ph) |
| 1-284 | 2-F-Ph | c-PrCO | 3-S-S-(4-NO$_2$-Ph) |
| 1-285 | 2-F-Ph | c-PrCO | 3-S-SO$_2$-(2-NO$_2$-Ph) |
| 1-286 | 2-Cl-Ph | MeOCO | 3-S-SO$_2$-(2-NO$_2$-Ph) |
| 1-287 | 2-F-Ph | c-PrCO | 3-S-SO-(2-NO$_2$-Ph) |
| 1-288 | 2-F-Ph | c-PrCO | 3-S-S-(2-NO$_2$-Ph) |
| 1-289 | 2-F-Ph | c-PrCO | 3-S-SO$_2$-(2-Cl-Ph) |
| 1-290 | 2-Cl-Ph | MeOCO | 3-S-SO$_2$-(2-Cl-Ph) |
| 1-291 | 2-F-Ph | c-PrCO | 3-S-SO-(2-Cl-Ph) |
| 1-292 | 2-F-Ph | c-PrCO | 3-S-S-(2-Cl-Ph) |
| 1-293 | 2-F-Ph | c-PrCO | 3-S-SO$_2$-(2-F-Ph) |
| 1-294 | 2-Cl-Ph | MeOCO | 3-S-SO$_2$-(2-F-Ph) |
| 1-295 | 2-F-Ph | c-PrCO | 3-S-SO-(2-F-Ph) |
| 1-296 | 2-F-Ph | c-PrCO | 3-S-S-(2-F-Ph) |
| 1-297 | 2-F-Ph | c-PrCO | 3-S-SO$_2$-(2,4-diNO$_2$-Ph) |
| 1-298 | 2-Cl-Ph | MeOCO | 3-S-SO$_2$-(2,4-diNO$_2$-Ph) |
| 1-299 | 2-F-Ph | c-PrCO | 3-S-SO-(2,4-diNO$_2$-Ph) |
| 1-300 | 2-F-Ph | c-PrCO | 3-S-S-(2,4-diNO$_2$-Ph) |
| 1-301 | 2-F-Ph | c-PrCO | 3-S-SO$_2$-Me |
| 1-302 | 2-Cl-Ph | MeOCO | 3-S-SO$_2$-Me |
| 1-303 | 2-F-Ph | c-PrCO | 3-S-SO-Me |
| 1-304 | 2-F-Ph | c-PrCO | 3-S-S-Me |
| 1-305 | 2-F-Ph | c-PrCO | 3-S-SO$_2$-Et |
| 1-306 | 2-Cl-Ph | MeOCO | 3-S-SO$_2$-Et |
| 1-307 | 2-F-Ph | c-PrCO | 3-S-SO-Et |

TABLE 1-continued

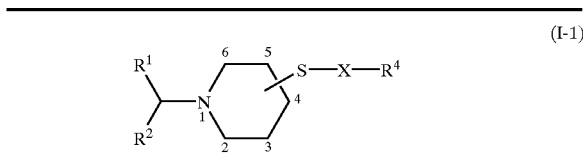

(I-1)

| Exemplified Compound No. | R¹ | R² | —S—X—R⁴ |
|---|---|---|---|
| 1-308 | 2-F-Ph | c-PrCO | 3-S-S-Et |
| 1-309 | 2-F-Ph | c-PrCO | 3-S-SO$_2$-Pr |
| 1-310 | 2-Cl-Ph | MeOCO | 3-S-SO$_2$-Pr |
| 1-311 | 2-F-Ph | c-PrCO | 3-S-S-Pr |
| 1-312 | 2-F-Ph | c-PrCO | 3-S-SO$_2$-Bu |
| 1-313 | 2-Cl-Ph | MeOCO | 3-S-SO$_2$-Bu |
| 1-314 | 2-F-Ph | c-PrCO | 3-S-S-Bu |
| 1-315 | 2-F-Ph | c-PrCO | 3-S-SO$_2$-c-Pn |
| 1-316 | 2-Cl-Ph | MeOCO | 3-S-SO$_2$-c-Pn |
| 1-317 | 2-F-Ph | c-PrCO | 3-S-S-c-Pn |
| 1-318 | 2-F-Ph | c-PrCO | 3-S-SO$_2$-c-Hx |
| 1-319 | 2-Cl-Ph | MeOCO | 3-S-SO$_2$-c-Hx |
| 1-320 | 2-F-Ph | c-PrCO | 3-S-S-c-Hx |
| 1-321 | 2-Cl-Ph | c-PrCO | 3-S-SO$_2$—CH$_2$COOH |
| 1-322 | 2-F-Ph | c-PrCO | 3-S-S-CH$_2$COOEt |
| 1-323 | 2-F-Ph | MeOCO | 3-S-SO$_2$—CH$_2$COOH |
| 1-324 | 2-Cl-Ph | MeOCO | 3-S-S-CH$_2$COOEt |
| 1-325 | 2-Cl-Ph | c-PrCO | 3-S-SO$_2$—(CH$_2$)$_3$COOH |
| 1-326 | 2-F-Ph | c-PrCO | 3-S-S-(CH$_2$)$_2$COOH |
| 1-327 | 2-F-Ph | MeOCO | 3-S-SO$_2$—(CH$_2$)$_3$COOH |
| 1-328 | 2-Cl-Ph | MeOCO | 3-S-S-(CH$_2$)$_2$COOH |
| 1-329 | 2-Cl-Ph | MeOCO | 3-S-SO$_2$—(CH$_2$)$_3$COOMe |
| 1-330 | 2-F-Ph | c-PrCO | 3-S-S-(CH$_2$)$_2$COOMe |
| 1-331 | 2-F-Ph | MeOCO | 3-S-SO$_2$—(CH$_2$)$_3$COOMe |
| 1-332 | 2-Cl-Ph | MeOCO | 3-S-S-(CH$_2$)$_2$COOMe |
| 1-333 | 2-Cl-Ph | c-PrCO | 3-S-SO$_2$—(CH$_2$)$_3$COOEt |
| 1-334 | 2-F-Ph | c-PrCO | 3-S-S-(CH$_2$)$_2$COOEt |
| 1-335 | 2-F-Ph | MeOCO | 3-S-SO$_2$—(CH$_2$)$_3$COOEt |
| 1-336 | 2-Cl-Ph | MeOCO | 3-S-S-(CH$_2$)$_2$COOEt |
| 1-337 | 2-Cl-Ph | MeOCO | 3-S-SO$_2$—(CH$_2$)$_3$OH |
| 1-338 | 2-F-Ph | c-PrCO | 3-S-S-(CH$_2$)$_2$OH |
| 1-339 | 2-F-Ph | MeOCO | 3-S-SO$_2$—(CH$_2$)$_3$OH |
| 1-340 | 2-Cl-Ph | MeOCO | 3-S-S-(CH$_2$)$_2$OH |
| 1-341 | 2-Cl-Ph | c-PrCO | 3-S-SO$_2$—(CH$_2$)$_3$NH$_2$ |
| 1-342 | 2-F-Ph | c-PrCO | 3-S-S-(CH$_2$)$_2$NH$_2$ |
| 1-343 | 2-F-Ph | MeOCO | 3-S-SO$_2$—(CH$_2$)$_3$NH$_2$ |
| 1-344 | 2-Cl-Ph | MeOCO | 3-S-S-(CH$_2$)$_2$NH$_2$ |
| 1-345 | 2-Cl-Ph | c-PrCO | 3-S-S-(CH$_2$)$_2$NHGly |
| 1-346 | 2-F-Ph | c-PrCO | 3-S-S-(CH$_2$)$_2$NHAla |
| 1-347 | 2-F-Ph | MeOCO | 3-S-S-(CH$_2$)$_2$NHGly |
| 1-348 | 2-Cl-Ph | MeOCO | 3-S-S-(CH$_2$)$_2$NHAla |
| 1-349 | 2-Cl-Ph | c-PrCO | 3-S-S-(CH$_2$)$_2$NH-β-Asp |
| 1-350 | 2-F-Ph | c-PrCO | 3-S-S-(CH$_2$)$_2$NHGlu |
| 1-351 | 2-F-Ph | MeOCO | 3-S-S-(CH$_2$)$_2$NH-β-Asp |
| 1-352 | 2-Cl-Ph | MeOCO | 3-S-S-(CH$_2$)$_2$NHGlu |
| 1-353 | 2-Cl-Ph | c-PrCO | 3-S-S-CH$_2$CH(NH$_2$)COOH |
| 1-354 | 2-F-Ph | c-PrCO | 3-S-S-CH$_2$CH(NH$_2$)COOH |
| 1-355 | 2-F-Ph | MeOCO | 3-S-S-CH$_2$CH(NH$_2$)COOH |
| 1-356 | 2-Cl-Ph | MeOCO | 3-S-S-CH$_2$CH(NH$_2$)COOH |
| 1-357 | 2-Cl-Ph | c-PrCO | 3-S-S-CH$_2$CH(NHGlu)COgly |
| 1-358 | 2-F-Ph | c-PrCO | 3-S-S-CH$_2$CH(NHGlu)COgly |
| 1-359 | 2-F-Ph | MeOCO | 3-S-S-CH$_2$CH(NHGlu)COgly |
| 1-360 | 2-Cl-Ph | MeOCO | 3-S-S-CH$_2$CH(NHGlu)COgly |
| 1-361 | 2-Cl-Ph | c-PrCO | 2-S-SO$_2$-(4-Me-Ph) |
| 1-362 | 2-F-Ph | c-PrCO | 2-S-SO$_2$-(4-Me-Ph) |
| 1-363 | 2-F-Ph | MeOCO | 2-S-SO$_2$-(4-Me-Ph) |
| 1-364 | 2-Cl-Ph | MeOCO | 2-S-SO$_2$-(4-Me-Ph) |
| 1-365 | 2-F-Ph | c-PrCO | 2-S-SO-(4-Me-Ph) |
| 1-366 | 2-Cl-Ph | MeOCO | 2-S-SO-(4-Me-Ph) |
| 1-367 | 2-F-Ph | c-PrCO | 2-S-S-(4-Me-Ph) |
| 1-368 | 2-Cl-Ph | MeOCO | 2-S-S-(4-Me-Ph) |
| 1-369 | 2-Cl-Ph | c-PrCO | 2-S-SO$_2$-(4-Cl-Ph) |
| 1-370 | 2-F-Ph | c-PrCO | 2-S-SO$_2$-(4-Cl-Ph) |
| 1-371 | 2-F-Ph | MeOCO | 2-S-SO$_2$-(4-Cl-Ph) |
| 1-372 | 2-Cl-Ph | MeOCO | 2-S-SO$_2$-(4-Cl-Ph) |
| 1-373 | 2-F-Ph | c-PrCO | 2-S-SO-(4-Cl-Ph) |
| 1-374 | 2-Cl-Ph | MeOCO | 2-S-SO-(4-Cl-Ph) |
| 1-375 | 2-F-Ph | c-PrCO | 2-S-S-(4-Cl-Ph) |

TABLE 1-continued

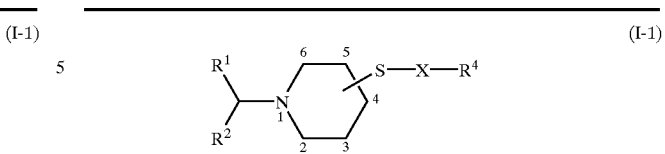

(I-1)

| Exemplified Compound No. | R¹ | R² | —S—X—R⁴ |
|---|---|---|---|
| 1-376 | 2-Cl-Ph | MeOCO | 2-S-S-(4-Cl-Ph) |
| 1-377 | 2-Cl-Ph | c-PrCO | 2-S-SO$_2$-(4-F-Ph) |
| 1-378 | 2-F-Ph | c-PrCO | 2-S-SO$_2$-(4-F-Ph) |
| 1-379 | 2-F-Ph | MeOCO | 2-S-SO$_2$-(4-F-Ph) |
| 1-380 | 2-Cl-Ph | MeOCO | 2-S-SO$_2$-(4-F-Ph) |
| 1-381 | 2-F-Ph | c-PrCO | 2-S-SO-(4-F-Ph) |
| 1-382 | 2-Cl-Ph | MeOCO | 2-S-SO-(4-F-Ph) |
| 1-383 | 2-F-Ph | c-PrCO | 2-S-S-(4-F-Ph) |
| 1-384 | 2-Cl-Ph | MeOCO | 2-S-S-(4-F-Ph) |
| 1-385 | 2-Cl-Ph | c-PrCO | 2-S-SO$_2$-(4-MeO-Ph) |
| 1-386 | 2-F-Ph | c-PrCO | 2-S-SO$_2$-(4-MeO-Ph) |
| 1-387 | 2-F-Ph | MeOCO | 2-S-SO$_2$-(4-MeO-Ph) |
| 1-388 | 2-Cl-Ph | MeOCO | 2-S-SO$_2$-(4-MeO-Ph) |
| 1-389 | 2-F-Ph | c-PrCO | 2-S-SO-(4-MeO-Ph) |
| 1-390 | 2-Cl-Ph | MeOCO | 2-S-SO-(4-MeO-Ph) |
| 1-391 | 2-F-Ph | c-PrCO | 2-S-S-(4-MeO-Ph) |
| 1-392 | 2-Cl-Ph | MeOCO | 2-S-S-(4-MeO-Ph) |
| 1-393 | 2-Cl-Ph | c-PrCO | 2-S-SO$_2$-Ph |
| 1-394 | 2-F-Ph | c-PrCO | 2-S-SO$_2$-Ph |
| 1-395 | 2-F-Ph | MeOCO | 2-S-SO$_2$-Ph |
| 1-396 | 2-Cl-Ph | MeOCO | 2-S-SO$_2$-Ph |
| 1-397 | 2-F-Ph | c-PrCO | 2-S-SO-Ph |
| 1-398 | 2-Cl-Ph | MeOCO | 2-S-SO-Ph |
| 1-399 | 2-F-Ph | c-PrCO | 2-S-S-Ph |
| 1-400 | 2-Cl-Ph | MeOCO | 2-S-S-Ph |
| 1-401 | 2-F-Ph | c-PrCO | 2-S-SO$_2$-(4-NO$_2$-Ph) |
| 1-402 | 2-Cl-Ph | MeOCO | 2-S-SO$_2$-(4-NO$_2$-Ph) |
| 1-403 | 2-F-Ph | c-PrCO | 2-S-SO-(4-NO$_2$-Ph) |
| 1-404 | 2-F-Ph | c-PrCO | 2-S-S-(4-NO$_2$-Ph) |
| 1-405 | 2-F-Ph | c-PrCO | 2-S-SO$_2$-(2-NO$_2$-Ph) |
| 1-406 | 2-Cl-Ph | MeOCO | 2-S-SO$_2$-(2-NO$_2$-Ph) |
| 1-407 | 2-F-Ph | c-PrCO | 2-S-SO-(2-NO$_2$-Ph) |
| 1-408 | 2-F-Ph | c-PrCO | 2-S-S-(2-NO$_2$-Ph) |
| 1-409 | 2-F-Ph | c-PrCO | 2-S-SO$_2$-(2-Cl-Ph) |
| 1-410 | 2-Cl-Ph | MeOCO | 2-S-SO$_2$-(2-Cl-Ph) |
| 1-411 | 2-F-Ph | c-PrCO | 2-S-SO-(2-Cl-Ph) |
| 1-412 | 2-F-Ph | c-PrCO | 2-S-S-(2-Cl-Ph) |
| 1-413 | 2-F-Ph | c-PrCO | 2-S-SO$_2$-(2-F-Ph) |
| 1-414 | 2-Cl-Ph | MeOCO | 2-S-SO$_2$-(2-F-Ph) |
| 1-415 | 2-F-Ph | c-PrCO | 2-S-SO-(2-F-Ph) |
| 1-416 | 2-F-Ph | c-PrCO | 2-S-S-(2-F-Ph) |
| 1-417 | 2-F-Ph | c-PrCO | 2-S-SO$_2$-(2,4-diNO$_2$-Ph) |
| 1-418 | 2-Cl-Ph | MeOCO | 2-S-SO$_2$-(2,4-diNO$_2$-Ph) |
| 1-419 | 2-F-Ph | c-PrCO | 2-S-SO-(2,4-diNO$_2$-Ph) |
| 1-420 | 2-F-Ph | c-PrCO | 2-S-S-(2,4-diNO$_2$-Ph) |
| 1-421 | 2-F-Ph | c-PrCO | 2-S-SO$_2$-Me |
| 1-422 | 2-Cl-Ph | MeOCO | 2-S-SO$_2$-Me |
| 1-423 | 2-F-Ph | c-PrCO | 2-S-SO-Me |
| 1-424 | 2-F-Ph | c-PrCO | 2-S-S-Me |
| 1-425 | 2-F-Ph | c-PrCO | 2-S-SO$_2$-Et |
| 1-426 | 2-Cl-Ph | MeOCO | 2-S-SO$_2$-Et |
| 1-427 | 2-F-Ph | c-PrCO | 2-S-SO-Et |
| 1-428 | 2-F-Ph | c-PrCO | 2-S-S-Et |
| 1-429 | 2-F-Ph | c-PrCO | 2-S-SO$_2$-Pr |
| 1-430 | 2-Cl-Ph | MeOCO | 2-S-SO$_2$-Pr |
| 1-431 | 2-F-Ph | c-PrCO | 2-S-S-Pr |
| 1-432 | 2-F-Ph | c-PrCO | 2-S-SO$_2$-Bu |
| 1-433 | 2-Cl-Ph | MeOCO | 2-S-SO$_2$-Bu |
| 1-434 | 2-F-Ph | c-PrCO | 2-S-S-Bu |
| 1-435 | 2-F-Ph | c-PrCO | 2-S-SO$_2$-c-Pn |
| 1-436 | 2-Cl-Ph | MeOCO | 2-S-SO$_2$-c-Pn |
| 1-437 | 2-F-Ph | c-PrCO | 2-S-S-c-Pn |
| 1-438 | 2-F-Ph | c-PrCO | 2-S-SO$_2$-c-Hx |
| 1-439 | 2-Cl-Ph | MeOCO | 2-S-SO$_2$-c-Hx |
| 1-440 | 2-F-Ph | c-PrCO | 2-S-S-c-Hx |
| 1-441 | 2-Cl-Ph | c-PrCO | 2-S-SO$_2$—CH$_2$COOH |
| 1-442 | 2-F-Ph | c-PrCO | 2-S-S-CH$_2$COOEt |
| 1-443 | 2-F-Ph | MeOCO | 2-S-SO$_2$—CH$_2$COOH |

TABLE 1-continued

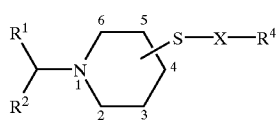

(I-1)

| Exemplified Compound No. | R¹ | R² | —S—X—R⁴ |
|---|---|---|---|
| 1-444 | 2-Cl-Ph | MeOCO | 2-S-S-CH₂COOEt |
| 1-445 | 2-Cl-Ph | c-PrCO | 2-S-SO₂—(CH₂)₃COOH |
| 1-446 | 2-F-Ph | c-PrCO | 2-S-S-(CH₂)₂COOH |
| 1-447 | 2-F-Ph | MeOCO | 2-S-SO₂—(CH₂)₃COOH |
| 1-448 | 2-Cl-Ph | MeOCO | 2-S-S-(CH₂)₂COOH |
| 1-449 | 2-Cl-Ph | c-PrCO | 2-S-SO₂—(CH₂)₃COOMe |
| 1-450 | 2-F-Ph | c-PrCO | 2-S-S-(CH₂)₂COOMe |
| 1-451 | 2-F-Ph | MeOCO | 2-S-SO₂—(CH₂)₃COOMe |
| 1-452 | 2-Cl-Ph | MeOCO | 2-S-S-(CH₂)₂COOMe |
| 1-453 | 2-Cl-Ph | c-PrCO | 2-S-SO₂—(CH₂)₃COOEt |
| 1-454 | 2-F-Ph | c-PrCO | 2-S-S-(CH₂)₂COOEt |
| 1-455 | 2-F-Ph | MeOCO | 2-S-SO₂—(CH₂)₃COOEt |
| 1-456 | 2-Cl-Ph | MeOCO | 2-S-S-(CH₂)₂COOEt |
| 1-457 | 2-Cl-Ph | c-PrCO | 2-S-SO₂—(CH₂)₃OH |
| 1-458 | 2-F-Ph | c-PrCO | 2-S-S-(CH₂)₂OH |
| 1-459 | 2-F-Ph | MeOCO | 2-S-SO₂—(CH₂)₃OH |
| 1-460 | 2-Cl-Ph | MeOCO | 2-S-S-(CH₂)₂OH |
| 1-461 | 2-Cl-Ph | c-PrCO | 2-S-SO₂—(CH₂)₃NH₂ |
| 1-462 | 2-F-Ph | c-PrCO | 2-S-S-(CH₂)₂NH₂ |
| 1-463 | 2-F-Ph | MeOCO | 2-S-SO₂—(CH₂)₃NH₂ |
| 1-464 | 2-Cl-Ph | MeOCO | 2-S-S-(CH₂)₂NH₂ |
| 1-465 | 2-Cl-Ph | c-PrCO | 2-S-S-(CH₂)₂NHGly |
| 1-466 | 2-F-Ph | c-PrCO | 2-S-S-(CH₂)₂NHAla |
| 1-467 | 2-F-Ph | MeOCO | 2-S-S-(CH₂)₂NHGly |
| 1-468 | 2-Cl-Ph | MeOCO | 2-S-S-(CH₂)₂NHAla |
| 1-469 | 2-Cl-Ph | c-PrCO | 2-S-S-(CH₂)₂NH-β-Asp |
| 1-470 | 2-F-Ph | c-PrCO | 2-S-S-(CH₂)₂NHGlu |
| 1-471 | 2-F-Ph | MeOCO | 2-S-S-(CH₂)₂NH-β-Asp |
| 1-472 | 2-Cl-Ph | MeOCO | 2-S-S-(CH₂)₂NHGlu |
| 1-473 | 2-Cl-Ph | c-PrCO | 2-S-S-CH₂CH(NH₂)COOH |
| 1-474 | 2-F-Ph | c-PrCO | 2-S-S-CH₂CH(NH₂)COOH |
| 1-475 | 2-F-Ph | MeOCO | 2-S-S-CH₂CH(NH₂)COOH |
| 1-476 | 2-Cl-Ph | MeOCO | 2-S-S-CH₂CH(NH₂)COOH |
| 1-477 | 2-Cl-Ph | c-PrCO | 2-S-S-CH₂CH(NHGlu)COgly |
| 1-478 | 2-F-Ph | c-PrCO | 2-S-S-CH₂CH(NHGlu)COgly |
| 1-479 | 2-F-Ph | MeOCO | 2-S-S-CH₂CH(NHGlu)COgly |
| 1-480 | 2-Cl-Ph | MeOCO | 2-S-S-CH₂CH(NHGlu)COgly |

TABLE 2

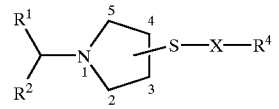

(I-2)

| Exemplified Compound No. | R¹ | R² | —S—X—R⁴ |
|---|---|---|---|
| 2-1 | 2-F-Ph | Prop | 3-S-SO₂-(4-Me-Ph) |
| 2-2 | 2-Cl-Ph | c-PrCO | 3-S-SO₂-(4-Me-Ph) |
| 2-3 | 2-NO₂-Ph | c-PrCO | 3-S-SO₂-(4-Me-Ph) |
| 2-4 | 2-CN-Ph | c-PrCO | 3-S-SO₂-(4-Me-Ph) |
| 2-5 | 2-CF₃-Ph | c-PrCO | 3-S-SO₂-(4-Me-Ph) |
| 2-6 | 2-F-Ph | 2-F-c-PrCO | 3-S-SO₂-(4-Me-Ph) |
| 2-7 | 2-F-Ph | c-PrCO | 3-S-SO₂-(4-Me-Ph) |
| 2-8 | 4-F-Ph | c-PrCO | 3-S-SO₂-(4-Me-Ph) |
| 2-9 | 2,4-diF-Ph | c-BuCO | 3-S-SO₂-(4-Me-Ph) |
| 2-10 | 2-F-Ph | MeOCO | 3-S-SO₂-(4-Me-Ph) |
| 2-11 | 2-F-Ph | EtOCO | 3-S-SO₂-(4-Me-Ph) |
| 2-12 | 2-Cl-Ph | MeOCO | 3-S-SO₂-(4-Me-Ph) |
| 2-13 | 2-Cl-Ph | c-PrCO | 3-S-SO-(4-Me-Ph) |
| 2-14 | 2-F-Ph | c-PrCO | 3-S-SO-(4-Me-Ph) |
| 2-15 | 2-F-Ph | MeOCO | 3-S-SO-(4-Me-Ph) |

TABLE 2-continued

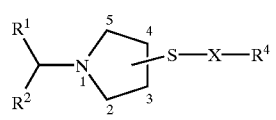

(I-2)

| Exemplified Compound No. | R¹ | R² | —S—X—R⁴ |
|---|---|---|---|
| 2-16 | 2-Cl-Ph | MeOCO | 3-S-SO-(4-Me-Ph) |
| 2-17 | 2-F-Ph | c-PrCO | 3-S-S-(4-Me-Ph) |
| 2-18 | 2-Cl-Ph | c-PrCO | 3-S-S-(4-Me-Ph) |
| 2-19 | 2-F-Ph | MeOCO | 3-S-S-(4-Me-Ph) |
| 2-20 | 2-Cl-Ph | MeOCO | 3-S-S-(4-Me-Ph) |
| 2-21 | 2-F-Ph | Prop | 3-S-SO₂-(4-Cl-Ph) |
| 2-22 | 2-Cl-Ph | c-PrCO | 3-S-SO₂-(4-Cl-Ph) |
| 2-23 | 2-NO₂-Ph | c-PrCO | 3-S-SO₂-(4-Cl-Ph) |
| 2-24 | 2-CN-Ph | c-PrCO | 3-S-SO₂-(4-Cl-Ph) |
| 2-25 | 2-CF₃-Ph | c-PrCO | 3-S-SO₂-(4-Cl-Ph) |
| 2-26 | 2-F-Ph | 2-F-c-PrCO | 3-S-SO₂-(4-Cl-Ph) |
| 2-27 | 2-F-Ph | c-PrCO | 3-S-SO₂-(4-Cl-Ph) |
| 2-28 | 4-F-Ph | c-PrCO | 3-S-SO₂-(4-Cl-Ph) |
| 2-29 | 2,4-diF-Ph | c-BuCO | 3-S-SO₂-(4-Cl-Ph) |
| 2-30 | 2-F-Ph | MeOCO | 3-S-SO₂-(4-Cl-Ph) |
| 2-31 | 2-F-Ph | EtOCO | 3-S-SO₂-(4-Cl-Ph) |
| 2-32 | 2-Cl-Ph | MeOCO | 3-S-SO₂-(4-Cl-Ph) |
| 2-33 | 2-Cl-Ph | c-PrCO | 3-S-SO-(4-Cl-Ph) |
| 2-34 | 2-F-Ph | c-PrCO | 3-S-SO-(4-Cl-Ph) |
| 2-35 | 2-F-Ph | MeOCO | 3-S-SO-(4-Cl-Ph) |
| 2-36 | 2-Cl-Ph | MeOCO | 3-S-SO-(4-Cl-Ph) |
| 2-37 | 2-F-Ph | c-PrCO | 3-S-S-(4-Cl-Ph) |
| 2-38 | 2-Cl-Ph | c-PrCO | 3-S-S-(4-Cl-Ph) |
| 2-39 | 2-F-Ph | MeOCO | 3-S-S-(4-Cl-Ph) |
| 2-40 | 2-Cl-Ph | MeOCO | 3-S-S-(4-Cl-Ph) |
| 2-41 | 2-F-Ph | Prop | 3-S-SO₂-(4-F-Ph) |
| 2-42 | 2-Cl-Ph | c-PrCO | 3-S-SO₂-(4-F-Ph) |
| 2-43 | 2-NO₂-Ph | c-PrCO | 3-S-SO₂-(4-F-Ph) |
| 2-44 | 2-CN-Ph | c-PrCO | 3-S-SO₂-(4-F-Ph) |
| 2-45 | 2-CF₃-Ph | c-PrCO | 3-S-SO₂-(4-F-Ph) |
| 2-46 | 2-F-Ph | 2-F-c-PrCO | 3-S-SO₂-(4-F-Ph) |
| 2-47 | 2-F-Ph | c-PrCO | 3-S-SO₂-(4-F-Ph) |
| 2-48 | 4-F-Ph | c-PrCO | 3-S-SO₂-(4-F-Ph) |
| 2-49 | 2,4-diF-Ph | c-BuCO | 3-S-SO₂-(4-F-Ph) |
| 2-50 | 2-F-Ph | MeOCO | 3-S-SO₂-(4-F-Ph) |
| 2-51 | 2-F-Ph | EtOCO | 3-S-SO₂-(4-F-Ph) |
| 2-52 | 2-Cl-Ph | MeOCO | 3-S-SO₂-(4-F-Ph) |
| 2-53 | 2-Cl-Ph | c-PrCO | 3-S-SO-(4-F-Ph) |
| 2-54 | 2-F-Ph | c-PrCO | 3-S-SO-(4-F-Ph) |
| 2-55 | 2-F-Ph | MeOCO | 3-S-SO-(4-F-Ph) |
| 2-56 | 2-Cl-Ph | MeOCO | 3-S-SO-(4-F-Ph) |
| 2-57 | 2-F-Ph | c-PrCO | 3-S-S-(4-F-Ph) |
| 2-58 | 2-Cl-Ph | c-PrCO | 3-S-S-(4-F-Ph) |
| 2-59 | 2-F-Ph | MeOCO | 3-S-S-(4-F-Ph) |
| 2-60 | 2-Cl-Ph | MeOCO | 3-S-S-(4-F-Ph) |
| 2-61 | 2-F-Ph | Prop | 3-S-SO₂-(4-MeO-Ph) |
| 2-62 | 2-Cl-Ph | c-PrCO | 3-S-SO₂-(4-MeO-Ph) |
| 2-63 | 2-NO₂-Ph | c-PrCO | 3-S-SO₂-(4-MeO-Ph) |
| 2-64 | 2-CN-Ph | c-PrCO | 3-S-SO₂-(4-MeO-Ph) |
| 2-65 | 2-CF₃-Ph | c-PrCO | 3-S-SO₂-(4-MeO-Ph) |
| 2-66 | 2-F-Ph | 2-F-c-PrCO | 3-S-SO₂-(4-MeO-Ph) |
| 2-67 | 2-F-Ph | c-PrCO | 3-S-SO₂-(4-MeO-Ph) |
| 2-68 | 4-F-Ph | c-PrCO | 3-S-SO₂-(4-MeO-Ph) |
| 2-69 | 2,4-diF-Ph | c-BuCO | 3-S-SO₂-(4-MeO-Ph) |
| 2-70 | 2-F-Ph | MeOCO | 3-S-SO₂-(4-MeO-Ph) |
| 2-71 | 2-F-Ph | EtOCO | 3-S-SO₂-(4-MeO-Ph) |
| 2-72 | 2-Cl-Ph | MeOCO | 3-S-SO₂-(4-MeO-Ph) |
| 2-73 | 2-Cl-Ph | c-PrCO | 3-S-SO-(4-MeO-Ph) |
| 2-74 | 2-F-Ph | c-PrCO | 3-S-SO-(4-MeO-Ph) |
| 2-75 | 2-F-Ph | MeOCO | 3-S-SO-(4-MeO-Ph) |
| 2-76 | 2-Cl-Ph | MeOCO | 3-S-SO-(4-MeO-Ph) |
| 2-77 | 2-F-Ph | c-PrCO | 3-S-S-(4-MeO-Ph) |
| 2-78 | 2-Cl-Ph | c-PrCO | 3-S-S-(4-MeO-Ph) |
| 2-79 | 2-F-Ph | MeOCO | 3-S-S-(4-MeO-Ph) |
| 2-80 | 2-Cl-Ph | MeOCO | 3-S-S-(4-MeO-Ph) |
| 2-81 | 2-Cl-Ph | c-PrCO | 3-S-SO₂-Ph |
| 2-82 | 2-F-Ph | c-PrCO | 3-S-SO₂-Ph |
| 2-83 | 2-F-Ph | MeOCO | 3-S-SO₂-Ph |

TABLE 2-continued (I-2)

R¹–CH(R²)–N(pyrrolidine ring positions 1,2,3,4,5)–S–X–R⁴

| Exemplified Compound No. | R¹ | R² | —S—X—R⁴ |
|---|---|---|---|
| 2-84 | 2-Cl-Ph | MeOCO | 3-S-SO$_2$-Ph |
| 2-85 | 2-Cl-Ph | c-PrCO | 3-S-SO-Ph |
| 2-86 | 2-F-Ph | c-PrCO | 3-S-SO-Ph |
| 2-87 | 2-F-Ph | MeOCO | 3-S-SO-Ph |
| 2-88 | 2-Cl-Ph | c-PrCO | 3-S-S-Ph |
| 2-89 | 2-F-Ph | c-PrCO | 3-S-S-Ph |
| 2-90 | 2-Cl-Ph | MeOCO | 3-S-S-Ph |
| 2-91 | 2-Cl-Ph | c-PrCO | 3-S-SO$_2$-(4-NO$_2$-Ph) |
| 2-92 | 2-F-Ph | c-PrCO | 3-S-SO$_2$-(4-NO$_2$-Ph) |
| 2-93 | 2-F-Ph | MeOCO | 3-S-SO$_2$-(4-NO$_2$-Ph) |
| 2-94 | 2-Cl-Ph | MeOCO | 3-S-SO$_2$-(4-NO$_2$-Ph) |
| 2-95 | 2-Cl-Ph | c-PrCO | 3-S-SO-(4-NO$_2$-Ph) |
| 2-96 | 2-F-Ph | c-PrCO | 3-S-SO-(4-NO$_2$-Ph) |
| 2-97 | 2-Cl-Ph | MeOCO | 3-S-SO-(4-NO$_2$-Ph) |
| 2-98 | 2-Cl-Ph | c-PrCO | 3-S-S-(4-NO$_2$-Ph) |
| 2-99 | 2-F-Ph | c-PrCO | 3-S-S-(4-NO$_2$-Ph) |
| 2-100 | 2-Cl-Ph | MeOCO | 3-S-S-(4-NO$_2$-Ph) |
| 2-101 | 2-Cl-Ph | c-PrCO | 3-S-SO$_2$-(2-NO$_2$-Ph) |
| 2-102 | 2-F-Ph | c-PrCO | 3-S-SO$_2$-(2-NO$_2$-Ph) |
| 2-103 | 2-F-Ph | MeOCO | 3-S-SO$_2$-(2-NO$_2$-Ph) |
| 2-104 | 2-Cl-Ph | MeOCO | 3-S-SO$_2$-(2-NO$_2$-Ph) |
| 2-105 | 2-Cl-Ph | c-PrCO | 3-S-SO-(2-NO$_2$-Ph) |
| 2-106 | 2-F-Ph | c-PrCO | 3-S-SO-(2-NO$_2$-Ph) |
| 2-107 | 2-Cl-Ph | MeOCO | 3-S-SO-(2-NO$_2$-Ph) |
| 2-108 | 2-Cl-Ph | c-PrCO | 3-S-S-(2-NO$_2$-Ph) |
| 2-109 | 2-F-Ph | c-PrCO | 3-S-S-(2-NO$_2$-Ph) |
| 2-110 | 2-Cl-Ph | MeOCO | 3-S-S-(2-NO$_2$-Ph) |
| 2-111 | 2-Cl-Ph | c-PrCO | 3-S-SO$_2$-(2-Cl-Ph) |
| 2-112 | 2-F-Ph | c-PrCO | 3-S-SO$_2$-(2-Cl-Ph) |
| 2-113 | 2-F-Ph | MeOCO | 3-S-SO$_2$-(2-Cl-Ph) |
| 2-114 | 2-Cl-Ph | MeOCO | 3-S-SO$_2$-(2-Cl-Ph) |
| 2-115 | 2-Cl-Ph | c-PrCO | 3-S-SO-(2-Cl-Ph) |
| 2-116 | 2-F-Ph | c-PrCO | 3-S-SO-(2-Cl-Ph) |
| 2-117 | 2-Cl-Ph | MeOCO | 3-S-SO-(2-Cl-Ph) |
| 2-118 | 2-Cl-Ph | c-PrCO | 3-S-S-(2-Cl-Ph) |
| 2-119 | 2-F-Ph | c-PrCO | 3-S-S-(2-Cl-Ph) |
| 2-120 | 2-Cl-Ph | MeOCO | 3-S-S-(2-Cl-Ph) |
| 2-121 | 2-Cl-Ph | c-PrCO | 3-S-SO$_2$-(2-F-Ph) |
| 2-122 | 2-F-Ph | c-PrCO | 3-S-SO$_2$-(2-F-Ph) |
| 2-123 | 2-F-Ph | MeOCO | 3-S-SO$_2$-(2-F-Ph) |
| 2-124 | 2-Cl-Ph | MeOCO | 3-S-SO$_2$-(2-F-Ph) |
| 2-125 | 2-Cl-Ph | c-PrCO | 3-S-SO-(2-F-Ph) |
| 2-126 | 2-F-Ph | c-PrCO | 3-S-SO-(2-F-Ph) |
| 2-127 | 2-F-Ph | MeOCO | 3-S-SO-(2-F-Ph) |
| 2-128 | 2-Cl-Ph | c-PrCO | 3-S-S-(2-F-Ph) |
| 2-129 | 2-F-Ph | c-PrCO | 3-S-S-(2-F-Ph) |
| 2-130 | 2-Cl-Ph | MeOCO | 3-S-S-(2-F-Ph) |
| 2-131 | 2-Cl-Ph | c-PrCO | 3-S-SO$_2$-(2,4-diNO$_2$-Ph) |
| 2-132 | 2-F-Ph | c-PrCO | 3-S-SO$_2$-(2,4-diNO$_2$-Ph) |
| 2-133 | 2-F-Ph | MeOCO | 3-S-SO$_2$-(2,4-diNO$_2$-Ph) |
| 2-134 | 2-Cl-Ph | MeOCO | 3-S-SO$_2$-(2,4-diNO$_2$-Ph) |
| 2-135 | 2-Cl-Ph | c-PrCO | 3-S-SO-(2,4-diNO$_2$-Ph) |
| 2-136 | 2-F-Ph | c-PrCO | 3-S-SO-(2,4-diNO$_2$-Ph) |
| 2-137 | 2-Cl-Ph | MeOCO | 3-S-SO-(2,4-diNO$_2$-Ph) |
| 2-138 | 2-Cl-Ph | c-PrCO | 3-S-S-(2,4-diNO$_2$-Ph) |
| 2-139 | 2-F-Ph | c-PrCO | 3-S-S-(2,4-diNO$_2$-Ph) |
| 2-140 | 2-F-Ph | MeOCO | 3-S-S-(2,4-diNO$_2$-Ph) |
| 2-141 | 2-Cl-Ph | c-PrCO | 3-S-SO$_2$-Me |
| 2-142 | 2-F-Ph | c-PrCO | 3-S-SO$_2$-Me |
| 2-143 | 2-F-Ph | MeOCO | 3-S-SO$_2$-Me |
| 2-144 | 2-Cl-Ph | MeOCO | 3-S-SO$_2$-Me |
| 2-145 | 2-Cl-Ph | c-PrCO | 3-S-SO-Me |
| 2-146 | 2-F-Ph | c-PrCO | 3-S-SO-Me |
| 2-147 | 2-Cl-Ph | MeOCO | 3-S-SO-Me |
| 2-148 | 2-Cl-Ph | c-PrCO | 3-S-S-Me |
| 2-149 | 2-F-Ph | c-PrCO | 3-S-S-Me |
| 2-150 | 2-Cl-Ph | MeOCO | 3-S-S-Me |
| 2-151 | 2-Cl-Ph | c-PrCO | 3-S-SO$_2$-Et |
| 2-152 | 2-F-Ph | c-PrCO | 3-S-SO$_2$-Et |
| 2-153 | 2-F-Ph | MeOCO | 3-S-SO$_2$-Et |
| 2-154 | 2-Cl-Ph | MeOCO | 3-S-SO$_2$-Et |
| 2-155 | 2-Cl-Ph | c-PrCO | 3-S-SO-Et |
| 2-156 | 2-F-Ph | c-PrCO | 3-S-SO-Et |
| 2-157 | 2-Cl-Ph | MeOCO | 3-S-SO-Et |
| 2-158 | 2-Cl-Ph | c-PrCO | 3-S-S-Et |
| 2-159 | 2-F-Ph | c-PrCO | 3-S-S-Et |
| 2-160 | 2-Cl-Ph | MeOCO | 3-S-S-Et |
| 2-161 | 2-Cl-Ph | c-PrCO | 3-S-SO$_2$-Pr |
| 2-162 | 2-F-Ph | c-PrCO | 3-S-SO$_2$-Pr |
| 2-163 | 2-F-Ph | MeOCO | 3-S-SO$_2$-Pr |
| 2-164 | 2-Cl-Ph | MeOCO | 3-S-SO$_2$-Pr |
| 2-165 | 2-Cl-Ph | c-PrCO | 3-S-SO-Pr |
| 2-166 | 2-F-Ph | c-PrCO | 3-S-SO-Pr |
| 2-167 | 2-Cl-Ph | MeOCO | 3-S-SO-Pr |
| 2-168 | 2-Cl-Ph | c-PrCO | 3-S-S-Pr |
| 2-169 | 2-F-Ph | c-PrCO | 3-S-S-Pr |
| 2-170 | 2-Cl-Ph | MeOCO | 3-S-S-Pr |
| 2-171 | 2-Cl-Ph | c-PrCO | 3-S-SO$_2$-Bu |
| 2-172 | 2-F-Ph | c-PrCO | 3-S-SO$_2$-Bu |
| 2-173 | 2-F-Ph | MeOCO | 3-S-SO$_2$-Bu |
| 2-174 | 2-Cl-Ph | MeOCO | 3-S-SO$_2$-Bu |
| 2-175 | 2-Cl-Ph | c-PrCO | 3-S-SO-Bu |
| 2-176 | 2-F-Ph | c-PrCO | 3-S-SO-Bu |
| 2-177 | 2-Cl-Ph | MeOCO | 3-S-SO-Bu |
| 2-178 | 2-Cl-Ph | c-PrCO | 3-S-S-Bu |
| 2-179 | 2-F-Ph | c-PrCO | 3-S-S-Bu |
| 2-180 | 2-Cl-Ph | MeOCO | 3-S-S-Bu |
| 2-181 | 2-Cl-Ph | c-PrCO | 3-S-SO$_2$-c-Pn |
| 2-182 | 2-F-Ph | c-PrCO | 3-S-SO$_2$-c-Pn |
| 2-183 | 2-F-Ph | MeOCO | 3-S-SO$_2$-c-Pn |
| 2-184 | 2-Cl-Ph | MeOCO | 3-S-SO$_2$-c-Pn |
| 2-185 | 2-Cl-Ph | c-PrCO | 3-S-SO-c-Pn |
| 2-186 | 2-F-Ph | c-PrCO | 3-S-SO-c-Pn |
| 2-187 | 2-Cl-Ph | MeOCO | 3-S-SO-c-Pn |
| 2-188 | 2-Cl-Ph | c-PrCO | 3-S-S-c-Pn |
| 2-189 | 2-F-Ph | c-PrCO | 3-S-S-c-Pn |
| 2-190 | 2-Cl-Ph | MeOCO | 3-S-S-c-Pn |
| 2-191 | 2-Cl-Ph | c-PrCO | 3-S-SO$_2$-c-Hx |
| 2-192 | 2-F-Ph | c-PrCO | 3-S-SO$_2$-c-Hx |
| 2-193 | 2-F-Ph | MeOCO | 3-S-SO$_2$-c-Hx |
| 2-194 | 2-Cl-Ph | MeOCO | 3-S-SO$_2$-c-Hx |
| 2-195 | 2-Cl-Ph | c-PrCO | 3-S-SO-c-Hx |
| 2-196 | 2-F-Ph | c-PrCO | 3-S-SO-c-Hx |
| 2-197 | 2-Cl-Ph | MeOCO | 3-S-SO-c-Hx |
| 2-198 | 2-Cl-Ph | c-PrCO | 3-S-S-c-Hx |
| 2-199 | 2-F-Ph | c-PrCO | 3-S-S-c-Hx |
| 2-200 | 2-Cl-Ph | MeOCO | 3-S-S-c-Hx |
| 2-201 | 2-Cl-Ph | c-PrCO | 3-S-SO$_2$—CH$_2$COOH |
| 2-202 | 2-F-Ph | c-PrCO | 3-S-S-CH$_2$COOEt |
| 2-203 | 2-F-Ph | MeOCO | 3-S-SO$_2$—CH$_2$COOH |
| 2-204 | 2-Cl-Ph | MeOCO | 3-S-S-CH$_2$COOEt |
| 2-205 | 2-Cl-Ph | c-PrCO | 3-S-SO$_2$—(CH$_2$)$_3$COOH |
| 2-206 | 2-F-Ph | c-PrCO | 3-S-S-(CH$_2$)$_2$COOH |
| 2-207 | 2-F-Ph | MeOCO | 3-S-SO$_2$—(CH$_2$)$_3$COOH |
| 2-208 | 2-Cl-Ph | MeOCO | 3-S-S-(CH$_2$)$_2$COOH |
| 2-209 | 2-Cl-Ph | c-PrCO | 3-S-SO$_2$—(CH$_2$)$_3$COOMe |
| 2-210 | 2-F-Ph | c-PrCO | 3-S-S-(CH$_2$)$_2$COOMe |
| 2-211 | 2-F-Ph | MeOCO | 3-S-SO$_2$—(CH$_2$)$_3$COOMe |
| 2-212 | 2-Cl-Ph | MeOCO | 3-S-S-(CH$_2$)$_2$COOMe |
| 2-213 | 2-Cl-Ph | c-PrCO | 3-S-SO$_2$—(CH$_2$)$_3$COOEt |
| 2-214 | 2-F-Ph | c-PrCO | 3-S-S-(CH$_2$)$_2$COOEt |
| 2-215 | 2-F-Ph | MeOCO | 3-S-SO$_2$—(CH$_2$)$_3$COOEt |
| 2-216 | 2-Cl-Ph | MeOCO | 3-S-S-(CH$_2$)$_2$COOEt |
| 2-217 | 2-Cl-Ph | c-PrCO | 3-S-SO$_2$—(CH$_2$)$_3$OH |
| 2-218 | 2-F-Ph | c-PrCO | 3-S-S-(CH$_2$)$_2$OH |
| 2-219 | 2-F-Ph | MeOCO | 3-S-SO$_2$—(CH$_2$)$_3$OH |

TABLE 2-continued (I-2)

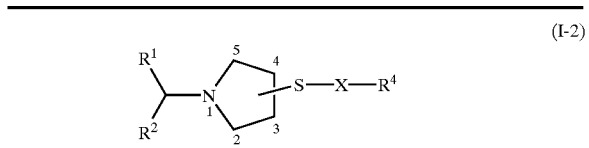

| Exemplified Compound No. | R¹ | R² | —S—X—R⁴ |
|---|---|---|---|
| 2-220 | 2-Cl-Ph | MeOCO | 3-S-S-(CH₂)₂OH |
| 2-221 | 2-Cl-Ph | c-PrCO | 3-S-SO₂—(CH₂)₃NH₂ |
| 2-222 | 2-F-Ph | c-PrCO | 3-S-S-(CH₂)₂NH₂ |
| 2-223 | 2-F-Ph | MeOCO | 3-S-SO₂—(CH₂)₃NH₂ |
| 2-224 | 2-Cl-Ph | MeOCO | 3-S-S-(CH₂)₂NH₂ |
| 2-225 | 2-Cl-Ph | c-PrCO | 3-S-S-(CH₂)₂NHGly |
| 2-226 | 2-F-Ph | c-PrCO | 3-S-S-(CH₂)₂NHAla |
| 2-227 | 2-F-Ph | MeOCO | 3-S-S-(CH₂)₂NHGly |
| 2-228 | 2-Cl-Ph | MeOCO | 3-S-S-(CH₂)₂NHAla |
| 2-229 | 2-Cl-Ph | c-PrCO | 3-S-S-(CH₂)₂NH-β-Asp |
| 2-230 | 2-F-Ph | c-PrCO | 3-S-S-(CH₂)₂NHGlu |
| 2-231 | 2-F-Ph | MeOCO | 3-S-S-(CH₂)₂NH-β-Asp |
| 2-232 | 2-Cl-Ph | MeOCO | 3-S-S-(CH₂)₂NHGlu |
| 2-233 | 2-Cl-Ph | c-PrCO | 3-S-S-CH₂CH(NH₂)COOH |
| 2-234 | 2-F-Ph | c-PrCO | 3-S-S-CH₂CH(NH₂)COOH |
| 2-235 | 2-F-Ph | MeOCO | 3-S-S-CH₂CH(NH₂)COOH |
| 2-236 | 2-Cl-Ph | MeOCO | 3-S-S-CH₂CH(NH₂)COOH |
| 2-237 | 2-Cl-Ph | c-PrCO | 3-S-S-CH₂CH(NHGlu)COgly |
| 2-238 | 2-F-Ph | c-PrCO | 3-S-S-CH₂CH(NHGlu)COgly |
| 2-239 | 2-F-Ph | MeOCO | 3-S-S-CH₂CH(NHGlu)COgly |
| 2-240 | 2-Cl-Ph | MeOCO | 3-S-S-CH₂CH(NHGlu)COgly |
| 2-241 | 2-Cl-Ph | c-PrCO | 2-S-SO₂-(4-Me-Ph) |
| 2-242 | 2-F-Ph | c-PrCO | 2-S-SO₂-(4-Me-Ph) |
| 2-243 | 2-F-Ph | MeOCO | 2-S-SO₂-(4-Me-Ph) |
| 2-244 | 2-Cl-Ph | MeOCO | 2-S-SO₂-(4-Me-Ph) |
| 2-245 | 2-F-Ph | c-PrCO | 2-S-SO-(4-Me-Ph) |
| 2-246 | 2-Cl-Ph | MeOCO | 2-S-SO-(4-Me-Ph) |
| 2-247 | 2-F-Ph | c-PrCO | 2-S-S-(4-Me-Ph) |
| 2-248 | 2-Cl-Ph | MeOCO | 2-S-S-(4-Me-Ph) |
| 2-249 | 2-Cl-Ph | c-PrCO | 2-S-SO₂-(4-Cl-Ph) |
| 2-250 | 2-F-Ph | c-PrCO | 2-S-SO₂-(4-Cl-Ph) |
| 2-251 | 2-F-Ph | MeOCO | 2-S-SO₂-(4-Cl-Ph) |
| 2-252 | 2-Cl-Ph | MeOCO | 2-S-SO₂-(4-Cl-Ph) |
| 2-253 | 2-F-Ph | c-PrCO | 2-S-SO-(4-Cl-Ph) |
| 2-254 | 2-Cl-Ph | MeOCO | 2-S-SO-(4-Cl-Ph) |
| 2-255 | 2-F-Ph | c-PrCO | 2-S-S-(4-Cl-Ph) |
| 2-256 | 2-Cl-Ph | MeOCO | 2-S-S-(4-Cl-Ph) |
| 2-257 | 2-Cl-Ph | c-PrCO | 2-S-SO₂-(4-F-Ph) |
| 2-258 | 2-F-Ph | c-PrCO | 2-S-SO₂-(4-F-Ph) |
| 2-259 | 2-F-Ph | MeOCO | 2-S-SO₂-(4-F-Ph) |
| 2-260 | 2-Cl-Ph | MeOCO | 2-S-SO₂-(4-F-Ph) |
| 2-261 | 2-F-Ph | c-PrCO | 2-S-SO-(4-F-Ph) |
| 2-262 | 2-Cl-Ph | MeOCO | 2-S-SO-(4-F-Ph) |
| 2-263 | 2-F-Ph | c-PrCO | 2-S-S-(4-F-Ph) |
| 2-264 | 2-Cl-Ph | MeOCO | 2-S-S-(4-F-Ph) |
| 2-265 | 2-Cl-Ph | c-PrCO | 2-S-SO₂-(4-MeO-Ph) |
| 2-266 | 2-F-Ph | c-PrCO | 2-S-SO₂-(4-MeO-Ph) |
| 2-267 | 2-F-Ph | MeOCO | 2-S-SO₂-(4-MeO-Ph) |
| 2-268 | 2-Cl-Ph | MeOCO | 2-S-SO₂-(4-MeO-Ph) |
| 2-269 | 2-F-Ph | c-PrCO | 2-S-SO-(4-MeO-Ph) |
| 2-270 | 2-Cl-Ph | MeOCO | 2-S-SO-(4-MeO-Ph) |
| 2-271 | 2-F-Ph | c-PrCO | 2-S-S-(4-MeO-Ph) |
| 2-272 | 2-Cl-Ph | MeOCO | 2-S-S-(4-MeO-Ph) |
| 2-273 | 2-Cl-Ph | c-PrCO | 2-S-SO₂-Ph |
| 2-274 | 2-F-Ph | c-PrCO | 2-S-SO₂-Ph |
| 2-275 | 2-F-Ph | MeOCO | 2-S-SO₂-Ph |
| 2-276 | 2-Cl-Ph | MeOCO | 2-S-SO₂-Ph |
| 2-277 | 2-F-Ph | c-PrCO | 2-S-SO-Ph |
| 2-278 | 2-Cl-Ph | MeOCO | 2-S-SO-Ph |
| 2-279 | 2-F-Ph | c-PrCO | 2-S-S-Ph |
| 2-280 | 2-Cl-Ph | MeOCO | 2-S-S-Ph |
| 2-281 | 2-F-Ph | c-PrCO | 2-S-SO₂-(4-NO₂-Ph) |
| 2-282 | 2-Cl-Ph | MeOCO | 2-S-SO₂-(4-NO₂-Ph) |
| 2-283 | 2-F-Ph | c-PrCO | 2-S-SO-(4-NO₂-Ph) |
| 2-284 | 2-F-Ph | c-PrCO | 2-S-S-(4-NO₂-Ph) |
| 2-285 | 2-F-Ph | c-PrCO | 2-S-SO₂-(2-NO₂-Ph) |
| 2-286 | 2-Cl-Ph | MeOCO | 2-S-SO₂-(2-NO₂-Ph) |
| 2-287 | 2-F-Ph | c-PrCO | 2-S-SO-(2-NO₂-Ph) |

(I-2)

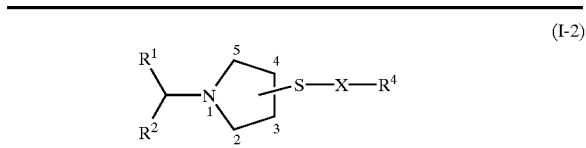

| Exemplified Compound No. | R¹ | R² | —S—X—R⁴ |
|---|---|---|---|
| 2-288 | 2-F-Ph | c-PrCO | 2-S-S-(2-NO₂-Ph) |
| 2-289 | 2-F-Ph | c-PrCO | 2-S-SO₂-(2-Cl-Ph) |
| 2-290 | 2-Cl-Ph | MeOCO | 2-S-SO₂-(2-Cl-Ph) |
| 2-291 | 2-F-Ph | c-PrCO | 2-S-SO-(2-Cl-Ph) |
| 2-292 | 2-F-Ph | c-PrCO | 2-S-S-(2-Cl-Ph) |
| 2-293 | 2-F-Ph | c-PrCO | 2-S-SO₂-(2-F-Ph) |
| 2-294 | 2-Cl-Ph | MeOCO | 2-S-SO₂-(2-F-Ph) |
| 2-295 | 2-F-Ph | c-PrCO | 2-S-SO-(2-F-Ph) |
| 2-296 | 2-F-Ph | c-PrCO | 2-S-S-(2-F-Ph) |
| 2-297 | 2-F-Ph | c-PrCO | 2-S-SO₂-(2,4-diNO₂-Ph) |
| 2-298 | 2-Cl-Ph | MeOCO | 2-S-SO₂-(2,4-diNO₂-Ph) |
| 2-299 | 2-F-Ph | c-PrCO | 2-S-SO-(2,4-diNO₂-Ph) |
| 2-300 | 2-F-Ph | c-PrCO | 2-S-S-(2,4-diNO₂-Ph) |
| 2-301 | 2-F-Ph | c-PrCO | 2-S-SO₂-Me |
| 2-302 | 2-Cl-Ph | MeOCO | 2-S-SO₂-Me |
| 2-303 | 2-F-Ph | c-PrCO | 2-S-SO-Me |
| 2-304 | 2-F-Ph | c-PrCO | 2-S-S-Me |
| 2-305 | 2-F-Ph | c-PrCO | 2-S-SO₂-Et |
| 2-306 | 2-Cl-Ph | MeOCO | 2-S-SO₂-Et |
| 2-307 | 2-F-Ph | c-PrCO | 2-S-SO-Et |
| 2-308 | 2-F-Ph | c-PrCO | 2-S-S-Et |
| 2-309 | 2-F-Ph | c-PrCO | 2-S-SO₂-Pr |
| 2-310 | 2-Cl-Ph | MeOCO | 2-S-SO₂-Pr |
| 2-311 | 2-F-Ph | c-PrCO | 2-S-S-Pr |
| 2-312 | 2-F-Ph | c-PrCO | 2-S-SO₂-Bu |
| 2-313 | 2-Cl-Ph | MeOCO | 2-S-SO₂-Bu |
| 2-314 | 2-F-Ph | c-PrCO | 2-S-S-Bu |
| 2-315 | 2-F-Ph | c-PrCO | 2-S-SO₂-c-Pn |
| 2-316 | 2-Cl-Ph | MeOCO | 2-S-SO₂-c-Pn |
| 2-317 | 2-F-Ph | c-PrCO | 2-S-S-c-Pn |
| 2-318 | 2-F-Ph | c-PrCO | 2-S-SO₂-c-Hx |
| 2-319 | 2-Cl-Ph | MeOCO | 2-S-SO₂-c-Hx |
| 2-320 | 2-F-Ph | c-PrCO | 2-S-S-c-Hx |
| 2-321 | 2-Cl-Ph | c-PrCO | 2-S-SO₂—CH₂COOH |
| 2-322 | 2-F-Ph | c-PrCO | 2-S-S-CH₂COOEt |
| 2-323 | 2-F-Ph | MeOCO | 2-S-SO₂—CH₂COOH |
| 2-324 | 2-Cl-Ph | MeOCO | 2-S-S-CH₂COOEt |
| 2-325 | 2-Cl-Ph | c-PrCO | 2-S-SO₂—(CH₂)₃COOH |
| 2-326 | 2-F-Ph | c-PrCO | 2-S-S-(CH₂)₂COOH |
| 2-327 | 2-F-Ph | MeOCO | 2-S-SO₂—(CH₂)₃COOH |
| 2-328 | 2-Cl-Ph | MeOCO | 2-S-S-(CH₂)₂COOH |
| 2-329 | 2-Cl-Ph | c-PrCO | 2-S-SO₂—(CH₂)₃COOMe |
| 2-330 | 2-F-Ph | c-PrCO | 2-S-S-(CH₂)₂COOMe |
| 2-331 | 2-F-Ph | MeOCO | 2-S-SO₂—(CH₂)₃COOMe |
| 2-332 | 2-Cl-Ph | MeOCO | 2-S-S-(CH₂)₂COOMe |
| 2-333 | 2-Cl-Ph | c-PrCO | 2-S-SO₂—(CH₂)₃COOEt |
| 2-334 | 2-F-Ph | c-PrCO | 2-S-S-(CH₂)₂COOEt |
| 2-335 | 2-F-Ph | MeOCO | 2-S-SO₂—(CH₂)₃COOEt |
| 2-336 | 2-Cl-Ph | MeOCO | 2-S-S-(CH₂)₂COOEt |
| 2-337 | 2-Cl-Ph | c-PrCO | 2-S-SO₂—(CH₂)₃OH |
| 2-338 | 2-F-Ph | c-PrCO | 2-S-S-(CH₂)₂OH |
| 2-339 | 2-F-Ph | MeOCO | 2-S-SO₂—(CH₂)₃OH |
| 2-340 | 2-Cl-Ph | MeOCO | 2-S-S-(CH₂)₂OH |
| 2-341 | 2-Cl-Ph | c-PrCO | 2-S-SO₂—(CH₂)₃NH₂ |
| 2-342 | 2-F-Ph | c-PrCO | 2-S-S-(CH₂)₂NH₂ |
| 2-343 | 2-F-Ph | MeOCO | 2-S-SO₂—(CH₂)₃NH₂ |
| 2-344 | 2-Cl-Ph | MeOCO | 2-S-S-(CH₂)₂NH₂ |
| 2-345 | 2-Cl-Ph | c-PrCO | 2-S-S-(CH₂)₂NHGly |
| 2-346 | 2-F-Ph | c-PrCO | 2-S-S-(CH₂)₂NHAla |
| 2-347 | 2-F-Ph | MeOCO | 2-S-S-(CH₂)₂NHGly |
| 2-348 | 2-Cl-Ph | MeOCO | 2-S-S-(CH₂)₂NHAla |
| 2-349 | 2-Cl-Ph | c-PrCO | 2-S-S-(CH₂)₂NH-β-Asp |
| 2-350 | 2-F-Ph | c-PrCO | 2-S-S-(CH₂)₂NHGlu |
| 2-351 | 2-F-Ph | MeOCO | 2-S-S-(CH₂)₂NH-β-Asp |
| 2-352 | 2-Cl-Ph | MeOCO | 2-S-S-(CH₂)₂NHGlu |
| 2-353 | 2-Cl-Ph | c-PrCO | 2-S-S-CH₂CH(NH₂)COOH |
| 2-354 | 2-F-Ph | c-PrCO | 2-S-S-CH₂CH(NH₂)COOH |
| 2-355 | 2-F-Ph | MeOCO | 2-S-S-CH₂CH(NH₂)COOH |

TABLE 2-continued (I-2)

R¹R²CH–N(1)–(pyrrolidine ring positions 5,4,3,2)–S–X–R⁴

| Exemplified Compound No. | R¹ | R² | —S—X—R⁴ |
|---|---|---|---|
| 2-356 | 2-Cl-Ph | MeOCO | 2-S-S-CH₂CH(NH₂)COOH |
| 2-357 | 2-Cl-Ph | c-PrCO | 2-S-S-CH₂CH(NHGlu)COgly |
| 2-358 | 2-F-Ph | c-PrCO | 2-S-S-CH₂CH(NHGlu)COgly |
| 2-359 | 2-F-Ph | MeOCO | 2-S-S-CH₂CH(NHGlu)COgly |
| 2-360 | 2-Cl-Ph | MeOCO | 2-S-S-CH₂CH(NHGlu)COgly |

TABLE 3

(I-3)

R¹R²CH–N(1)–(azetidine ring positions 4,3,2)–S–X–R⁴

| Exemplified Compound No. | R¹ | R² | —S—X—R⁴ |
|---|---|---|---|
| 3-1 | 2-F—Ph | Prop | 3-S—SO₂-(4-Me—Ph) |
| 3-2 | 2-Cl—Ph | c-PrCO | 3-S—SO₂-(4-Me—Ph) |
| 3-3 | 2-NO₂—Ph | c-PrCO | 3-S—SO₂-(4-Me—Ph) |
| 3-4 | 2-CN—Ph | c-PrCO | 3-S—SO₂-(4-Me—Ph) |
| 3-5 | 2-CF₃—Ph | c-PrCO | 3-S—SO₂-(4-Me—Ph) |
| 3-6 | 2-F—Ph | 2-F-c-PrCO | 3-S—SO₂-(4-Me—Ph) |
| 3-7 | 2-F—Ph | c-PrCO | 3-S—SO₂-(4-Me—Ph) |
| 3-8 | 4-F—Ph | c-PrCO | 3-S—SO₂-(4-Me—Ph) |
| 3-9 | 2,4-diF—Ph | c-BuCO | 3-S—SO₂-(4-Me—Ph) |
| 3-10 | 2-F—Ph | MeOCO | 3-S—SO₂-(4-Me—Ph) |
| 3-11 | 2-F—Ph | EtOCO | 3-S—SO₂-(4-Me—Ph) |
| 3-12 | 2-Cl—Ph | MeOCO | 3-S—SO₂-(4-Me—Ph) |
| 3-13 | 2-Cl—Ph | c-PrCO | 3-S—SO-(4-Me—Ph) |
| 3-14 | 2-F—Ph | c-PrCO | 3-S—SO-(4-Me—Ph) |
| 3-15 | 2-F—Ph | MeOCO | 3-S—SO-(4-Me—Ph) |
| 3-16 | 2-Cl—Ph | MeOCO | 3-S—SO-(4-Me—Ph) |
| 3-17 | 2-F—Ph | c-PrCO | 3-S—S-(4-Me—Ph) |
| 3-18 | 2-Cl—Ph | c-PrCO | 3-S—S-(4-Me—Ph) |
| 3-19 | 2-F—Ph | MeOCO | 3-S—S-(4-Me—Ph) |
| 3-20 | 2-Cl—Ph | MeOCO | 3-S—S-(4-Me—Ph) |
| 3-21 | 2-F—Ph | Prop | 3-S—SO₂-(4-Cl—Ph) |
| 3-22 | 2-Cl—Ph | c-PrCO | 3-S—SO₂-(4-Cl—Ph) |
| 3-23 | 2-NO₂—Ph | c-PrCO | 3-S—SO₂-(4-Cl—Ph) |
| 3-24 | 2-CN—Ph | c-PrCO | 3-S—SO₂-(4-Cl—Ph) |
| 3-25 | 2-CF₃—Ph | c-PrCO | 3-S—SO₂-(4-Cl—Ph) |
| 3-26 | 2-F—Ph | 2-F-c-PrCO | 3-S—SO₂-(4-Cl—Ph) |
| 3-27 | 2-F—Ph | c-PrCO | 3-S—SO₂-(4-Cl—Ph) |
| 3-28 | 4-F—Ph | c-PrCO | 3-S—SO₂-(4-Cl—Ph) |
| 3-29 | 2,4-diF—Ph | c-BuCO | 3-S—SO₂-(4-Cl—Ph) |
| 3-30 | 2-F—Ph | MeOCO | 3-S—SO₂-(4-Cl—Ph) |
| 3-31 | 2-F—Ph | EtOCO | 3-S—SO₂-(4-Cl—Ph) |
| 3-32 | 2-Cl—Ph | MeOCO | 3-S—SO₂-(4-Cl—Ph) |
| 3-33 | 2-Cl—Ph | c-PrCO | 3-S—SO-(4-Cl—Ph) |
| 3-34 | 2-F—Ph | c-PrCO | 3-S—SO-(4-Cl—Ph) |
| 3-35 | 2-F—Ph | MeOCO | 3-S—SO-(4-Cl—Ph) |
| 3-36 | 2-Cl—Ph | MeOCO | 3-S—SO-(4-Cl—Ph) |
| 3-37 | 2-F—Ph | c-PrCO | 3-S—S-(4-Cl—Ph) |
| 3-38 | 2-Cl—Ph | c-PrCO | 3-S—S-(4-Cl—Ph) |
| 3-39 | 2-F—Ph | MeOCO | 3-S—S-(4-Cl—Ph) |
| 3-40 | 2-Cl—Ph | MeOCO | 3-S—S-(4-Cl—Ph) |
| 3-41 | 2-F—Ph | Prop | 3-S—SO₂-(4-F—Ph) |
| 3-42 | 2-Cl—Ph | c-PrCO | 3-S—SO₂-(4-F—Ph) |
| 3-43 | 2-NO₂—Ph | c-PrCO | 3-S—SO₂-(4-F—Ph) |
| 3-44 | 2-CN—Ph | c-PrCO | 3-S—SO₂-(4-F—Ph) |
| 3-45 | 2-CF₃—Ph | c-PrCO | 3-S—SO₂-(4-F—Ph) |
| 3-46 | 2-F—Ph | 2-F-c-PrCO | 3-S—SO₂-(4-F—Ph) |
| 3-47 | 2-F—Ph | c-PrCO | 3-S—SO₂-(4-F—Ph) |
| 3-48 | 4-F—Ph | c-PrCO | 3-S—SO₂-(4-F—Ph) |
| 3-49 | 2,4-diF—Ph | c-BuCO | 3-S—SO₂-(4-F—Ph) |
| 3-50 | 2-F—Ph | MeOCO | 3-S—SO₂-(4-F—Ph) |
| 3-51 | 2-F—Ph | EtOCO | 3-S—SO₂-(4-F—Ph) |
| 3-52 | 2-Cl—Ph | MeOCO | 3-S—SO₂-(4-F—Ph) |
| 3-53 | 2-Cl—Ph | c-PrCO | 3-S—SO-(4-F—Ph) |
| 3-54 | 2-F—Ph | c-PrCO | 3-S—SO-(4-F—Ph) |
| 3-55 | 2-F—Ph | MeOCO | 3-S—SO-(4-F—Ph) |
| 3-56 | 2-Cl—Ph | MeOCO | 3-S—SO-(4-F—Ph) |
| 3-57 | 2-F—Ph | c-PrCO | 3-S—S-(4-F—Ph) |
| 3-58 | 2-Cl—Ph | c-PrCO | 3-S—S-(4-F—Ph) |
| 3-59 | 2-F—Ph | MeOCO | 3-S—S-(4-F—Ph) |
| 3-60 | 2-Cl—Ph | MeOCO | 3-S—S-(4-F—Ph) |
| 3-61 | 2-F—Ph | Prop | 3-S—SO₂-(4-MeO—Ph) |
| 3-62 | 2-Cl—Ph | c-PrCO | 3-S—SO₂-(4-MeO—Ph) |
| 3-63 | 2-NO₂—Ph | c-PrCO | 3-S—SO₂-(4-MeO—Ph) |
| 3-64 | 2-CN—Ph | c-PrCO | 3-S—SO₂-(4-MeO—Ph) |
| 3-65 | 2-CF₃—Ph | c-PrCO | 3-S—SO₂-(4-MeO—Ph) |
| 3-66 | 2-F—Ph | 2-F-c-PrCO | 3-S—SO₂-(4-MeO—Ph) |
| 3-67 | 2-F—Ph | c-PrCO | 3-S—SO₂-(4-MeO—Ph) |
| 3-68 | 4-F—Ph | c-PrCO | 3-S—SO₂-(4-MeO—Ph) |
| 3-69 | 2,4-diF—Ph | c-BuCO | 3-S—SO₂-(4-MeO—Ph) |
| 3-70 | 2-F—Ph | MeOCO | 3-S—SO₂-(4-MeO—Ph) |
| 3-71 | 2-F—Ph | EtOCO | 3-S—SO₂-(4-MeO—Ph) |
| 3-72 | 2-Cl—Ph | MeOCO | 3-S—SO₂-(4-MeO—Ph) |
| 3-73 | 2-Cl—Ph | c-PrCO | 3-S—SO-(4-MeO—Ph) |
| 3-74 | 2-F—Ph | c-PrCO | 3-S—SO-(4-MeO—Ph) |
| 3-75 | 2-F—Ph | MeOCO | 3-S—SO-(4-MeO—Ph) |
| 3-76 | 2-Cl—Ph | MeOCO | 3-S—SO-(4-MeO—Ph) |
| 3-77 | 2-F—Ph | c-PrCO | 3-S—S-(4-MeO—Ph) |
| 3-78 | 2-Cl—Ph | c-PrCO | 3-S—S-(4-MeO—Ph) |
| 3-79 | 2-F—Ph | MeOCO | 3-S—S-(4-MeO—Ph) |
| 3-80 | 2-Cl—Ph | MeOCO | 3-S—S-(4-MeO—Ph) |
| 3-81 | 2-Cl—Ph | c-PrCO | 3-S—SO₂—Ph |
| 3-82 | 2-F—Ph | c-PrCO | 3-S—SO₂—Ph |
| 3-83 | 2-F—Ph | MeOCO | 3-S—SO₂—Ph |
| 3-84 | 2-Cl—Ph | MeOCO | 3-S—SO₂—Ph |
| 3-85 | 2-Cl—Ph | c-PrCO | 3-S—SO—Ph |
| 3-86 | 2-F—Ph | c-PrCO | 3-S—SO—Ph |
| 3-87 | 2-Cl—Ph | MeOCO | 3-S—SO—Ph |
| 3-88 | 2-Cl—Ph | c-PrCO | 3-S—S—Ph |
| 3-89 | 2-F—Ph | c-PrCO | 3-S—S—Ph |
| 3-90 | 2-Cl—Ph | MeOCO | 3-S—S—Ph |
| 3-91 | 2-Cl—Ph | c-PrCO | 3-S—SO₂-(4-NO₂—Ph) |
| 3-92 | 2-F—Ph | c-PrCO | 3-S—SO₂-(4-NO₂—Ph) |
| 3-93 | 2-F—Ph | MeOCO | 3-S—SO₂-(4-NO₂—Ph) |
| 3-94 | 2-Cl—Ph | MeOCO | 3-S—SO₂-(4-NO₂—Ph) |
| 3-95 | 2-Cl—Ph | c-PrCO | 3-S—SO-(4-NO₂—Ph) |
| 3-96 | 2-F—Ph | c-PrCO | 3-S—SO-(4-NO₂—Ph) |
| 3-97 | 2-Cl—Ph | MeOCO | 3-S—SO-(4-NO₂—Ph) |
| 3-98 | 2-Cl—Ph | c-PrCO | 3-S—S-(4-NO₂—Ph) |
| 3-99 | 2-F—Ph | c-PrCO | 3-S—S-(4-NO₂—Ph) |
| 3-100 | 2-Cl—Ph | MeOCO | 3-S—S-(4-NO₂—Ph) |
| 3-101 | 2-Cl—Ph | c-PrCO | 3-S—SO₂-(2-NO₂—Ph) |
| 3-102 | 2-F—Ph | c-PrCO | 3-S—SO₂-(2-NO₂—Ph) |
| 3-103 | 2-F—Ph | MeOCO | 3-S—SO₂-(2-NO₂—Ph) |
| 3-104 | 2-Cl—Ph | MeOCO | 3-S—SO₂-(2-NO₂—Ph) |
| 3-105 | 2-Cl—Ph | c-PrCO | 3-S—SO-(2-NO₂—Ph) |
| 3-106 | 2-F—Ph | c-PrCO | 3-S—SO-(2-NO₂—Ph) |
| 3-107 | 2-Cl—Ph | MeOCO | 3-S—SO-(2-NO₂—Ph) |
| 3-108 | 2-Cl—Ph | c-PrCO | 3-S—S-(2-NO₂—Ph) |
| 3-109 | 2-F—Ph | c-PrCO | 3-S—S-(2-NO₂—Ph) |
| 3-110 | 2-Cl—Ph | MeOCO | 3-S—S-(2-NO₂—Ph) |
| 3-111 | 2-Cl—Ph | c-PrCO | 3-S—SO₂-(2-Cl—Ph) |
| 3-112 | 2-F—Ph | c-PrCO | 3-S—SO₂-(2-Cl—Ph) |
| 3-113 | 2-F—Ph | MeOCO | 3-S—SO₂-(2-Cl—Ph) |

TABLE 3-continued (I-3)

$$R^1R^2CH-N\underset{2}{\overset{4}{\underset{1}{\square}}}\overset{S-X-R^4}{\underset{3}{}}$$

| Exemplified Compound No. | R¹ | R² | —S—X—R⁴ |
|---|---|---|---|
| 3-114 | 2-Cl—Ph | MeOCO | 3-S—SO₂-(2-Cl—Ph) |
| 3-115 | 2-Cl—Ph | c-PrCO | 3-S—SO-(2-Cl—Ph) |
| 3-116 | 2-F—Ph | c-PrCO | 3-S—SO-(2-Cl—Ph) |
| 3-117 | 2-Cl—Ph | MeOCO | 3-S—SO-(2-Cl—Ph) |
| 3-118 | 2-Cl—Ph | c-PrCO | 3-S—S-(2-Cl—Ph) |
| 3-119 | 2-F—Ph | c-PrCO | 3-S—S-(2-Cl—Ph) |
| 3-120 | 2-Cl—Ph | MeOCO | 3-S—S-(2-Cl—Ph) |
| 3-121 | 2-Cl—Ph | c-PrCO | 3-S—SO₂-(2-F—Ph) |
| 3-122 | 2-F—Ph | c-PrCO | 3-S—SO₂-(2-F—Ph) |
| 3-123 | 2-F—Ph | MeOCO | 3-S—SO₂-(2-F—Ph) |
| 3-124 | 2-Cl—Ph | MeOCO | 3-S—SO₂-(2-F—Ph) |
| 3-125 | 2-Cl—Ph | c-PrCO | 3-S—SO-(2-F—Ph) |
| 3-126 | 2-F—Ph | c-PrCO | 3-S—SO-(2-F—Ph) |
| 3-127 | 2-Cl—Ph | MeOCO | 3-S—SO-(2-F—Ph) |
| 3-128 | 2-Cl—Ph | c-PrCO | 3-S—S-(2-F—Ph) |
| 3-129 | 2-F—Ph | c-PrCO | 3-S—S-(2-F—Ph) |
| 3-130 | 2-Cl—Ph | MeOCO | 3-S—S-(2-F—Ph) |
| 3-131 | 2-Cl—Ph | c-PrCO | 3-S—SO₂-(2,4-diNO₂—Ph) |
| 3-132 | 2-F—Ph | c-PrCO | 3-S—SO₂-(2,4-diNO₂—Ph) |
| 3-133 | 2-F—Ph | MeOCO | 3-S—SO₂-(2,4-diNO₂—Ph) |
| 3-134 | 2-Cl—Ph | MeOCO | 3-S—SO₂-(2,4-diNO₂—Ph) |
| 3-135 | 2-Cl—Ph | c-PrCO | 3-S—SO-(2,4-diNO₂—Ph) |
| 3-136 | 2-F—Ph | c-PrCO | 3-S—SO-(2,4-diNO₂—Ph) |
| 3-137 | 2-Cl—Ph | MeOCO | 3-S—SO-(2,4-diNO₂—Ph) |
| 3-138 | 2-Cl—Ph | c-PrCO | 3-S—S-(2,4-diNO₂—Ph) |
| 3-139 | 2-F—Ph | c-PrCO | 3-S—S-(2,4-diNO₂—Ph) |
| 3-140 | 2-Cl—Ph | MeOCO | 3-S—S-(2,4-diNO₂—Ph) |
| 3-141 | 2-Cl—Ph | c-PrCO | 3-S—SO₂—Me |
| 3-142 | 2-F—Ph | c-PrCO | 3-S—SO₂—Me |
| 3-143 | 2-F—Ph | MeOCO | 3-S—SO₂—Me |
| 3-144 | 2-Cl—Ph | MeOCO | 3-S—SO₂—Me |
| 3-145 | 2-Cl—Ph | c-PrCO | 3-S—SO—Me |
| 3-146 | 2-F—Ph | c-PrCO | 3-S—SO—Me |
| 3-147 | 2-Cl—Ph | MeOCO | 3-S—SO—Me |
| 3-148 | 2-Cl—Ph | c-PrCO | 3-S—S—Me |
| 3-149 | 2-F—Ph | c-PrCO | 3-S—S—Me |
| 3-150 | 2-Cl—Ph | MeOCO | 3-S—S—Me |
| 3-151 | 2-Cl—Ph | c-PrCO | 3-S—SO₂—Et |
| 3-152 | 2-F—Ph | c-PrCO | 3-S—SO₂—Et |
| 3-153 | 2-F—Ph | MeOCO | 3-S—SO₂—Et |
| 3-154 | 2-Cl—Ph | MeOCO | 3-S—SO₂—Et |
| 3-155 | 2-Cl—Ph | c-PrCO | 3-S—SO—Et |
| 3-156 | 2-F—Ph | c-PrCO | 3-S—SO—Et |
| 3-157 | 2-Cl—Ph | MeOCO | 3-S—SO—Et |
| 3-158 | 2-Cl—Ph | c-PrCO | 3-S—S—Et |
| 3-159 | 2-F—Ph | c-PrCO | 3-S—S—Et |
| 3-160 | 2-Cl—Ph | MeOCO | 3-S—S—Et |
| 3-161 | 2-Cl—Ph | c-PrCO | 3-S—SO₂—Pr |
| 3-162 | 2-F—Ph | c-PrCO | 3-S—SO₂—Pr |
| 3-163 | 2-F—Ph | MeOCO | 3-S—SO₂—Pr |
| 3-164 | 2-Cl—Ph | MeOCO | 3-S—SO₂—Pr |
| 3-165 | 2-Cl—Ph | c-PrCO | 3-S—SO—Pr |
| 3-166 | 2-F—Ph | c-PrCO | 3-S—SO—Pr |
| 3-167 | 2-Cl—Ph | MeOCO | 3-S—SO—Pr |
| 3-168 | 2-Cl—Ph | c-PrCO | 3-S—S—Pr |
| 3-169 | 2-F—Ph | c-PrCO | 3-S—S—Pr |
| 3-170 | 2-Cl—Ph | MeOCO | 3-S—S—Pr |
| 3-171 | 2-Cl—Ph | c-PrCO | 3-S—SO₂—Bu |
| 3-172 | 2-F—Ph | c-PrCO | 3-S—SO₂—Bu |
| 3-173 | 2-F—Ph | MeOCO | 3-S—SO₂—Bu |
| 3-174 | 2-Cl—Ph | MeOCO | 3-S—SO₂—Bu |
| 3-175 | 2-Cl—Ph | c-PrCO | 3-S—SO—Bu |
| 3-176 | 2-F—Ph | c-PrCO | 3-S—SO—Bu |
| 3-177 | 2-Cl—Ph | MeOCO | 3-S—SO—Bu |
| 3-178 | 2-Cl—Ph | c-PrCO | 3-S—S—Bu |
| 3-179 | 2-F—Ph | c-PrCO | 3-S—S—Bu |
| 3-180 | 2-Cl—Ph | MeOCO | 3-S—S—Bu |
| 3-181 | 2-Cl—Ph | c-PrCO | 3-S—SO₂-c-Pn |
| 3-182 | 2-F—Ph | c-PrCO | 3-S—SO₂-c-Pn |
| 3-183 | 2-F—Ph | MeOCO | 3-S—SO₂-c-Pn |
| 3-184 | 2-Cl—Ph | MeOCO | 3-S—SO₂-c-Pn |
| 3-185 | 2-Cl—Ph | c-PrCO | 3-S—SO-c-Pn |
| 3-186 | 2-F—Ph | c-PrCO | 3-S—SO-c-Pn |
| 3-187 | 2-Cl—Ph | MeOCO | 3-S—SO-c-Pn |
| 3-188 | 2-Cl—Ph | c-PrCO | 3-S—S-c-Pn |
| 3-189 | 2-F—Ph | c-PrCO | 3-S—S-c-Pn |
| 3-190 | 2-Cl—Ph | MeOCO | 3-S—S-c-Pn |
| 3-191 | 2-Cl—Ph | c-PrCO | 3-S—SO₂-c-Hx |
| 3-192 | 2-F—Ph | c-PrCO | 3-S—SO₂-c-Hx |
| 3-193 | 2-F—Ph | MeOCO | 3-S—SO₂-c-Hx |
| 3-194 | 2-Cl—Ph | MeOCO | 3-S—SO₂-c-Hx |
| 3-195 | 2-Cl—Ph | c-PrCO | 3-S—SO-c-Hx |
| 3-196 | 2-F—Ph | c-PrCO | 3-S—SO-c-Hx |
| 3-197 | 2-Cl—Ph | MeOCO | 3-S—SO-c-Hx |
| 3-198 | 2-Cl—Ph | c-PrCO | 3-S—S-c-Hx |
| 3-199 | 2-F—Ph | c-PrCO | 3-S—S-c-Hx |
| 3-200 | 2-Cl—Ph | MeOCO | 3-S—S-c-Hx |
| 3-201 | 2-Cl—Ph | c-PrCO | 3-S—SO₂—CH₂COOH |
| 3-202 | 2-F—Ph | c-PrCO | 3-S—S—CH₂COOEt |
| 3-203 | 2-F—Ph | MeOCO | 3-S—SO₂—CH₂COOH |
| 3-204 | 2-Cl—Ph | MeOCO | 3-S—S—CH₂COOEt |
| 3-205 | 2-Cl—Ph | c-PrCO | 3-S—SO₂—(CH₂)₃COOH |
| 3-206 | 2-F—Ph | c-PrCO | 3-S—S—(CH₂)₂COOH |
| 3-207 | 2-F—Ph | MeOCO | 3-S—SO₂—(CH₂)₃COOH |
| 3-208 | 2-Cl—Ph | MeOCO | 3-S—S—(CH₂)₂COOH |
| 3-209 | 2-Cl—Ph | c-PrCO | 3-S—SO₂—(CH₂)₃COOMe |
| 3-210 | 2-F—Ph | c-PrCO | 3-S—S—(CH₂)₂COOMe |
| 3-211 | 2-F—Ph | MeOCO | 3-S—SO₂—(CH₂)₃COOMe |
| 3-212 | 2-Cl—Ph | MeOCO | 3-S—S—(CH₂)₂COOMe |
| 3-213 | 2-Cl—Ph | c-PrCO | 3-S—SO₂—(CH₂)₃COOEt |
| 3-214 | 2-F—Ph | c-PrCO | 3-S—S—(CH₂)₂COOEt |
| 3-215 | 2-F—Ph | MeOCO | 3-S—SO₂—(CH₂)₃COOEt |
| 3-216 | 2-Cl—Ph | MeOCO | 3-S—S—(CH₂)₂COOEt |
| 3-217 | 2-Cl—Ph | c-PrCO | 3-S—SO₂—(CH₂)₃OH |
| 3-218 | 2-F—Ph | c-PrCO | 3-S—S—(CH₂)₂OH |
| 3-219 | 2-F—Ph | MeOCO | 3-S—SO₂—(CH₂)₃OH |
| 3-220 | 2-Cl—Ph | MeOCO | 3-S—S—(CH₂)₂OH |
| 3-221 | 2-Cl—Ph | c-PrCO | 3-S—SO₂—(CH₂)₃NH₂ |
| 3-222 | 2-F—Ph | c-PrCO | 3-S—S—(CH₂)₂NH₂ |
| 3-223 | 2-F—Ph | MeOCO | 3-S—SO₂—(CH₂)₃NH₂ |
| 3-224 | 2-Cl—Ph | MeOCO | 3-S—S—(CH₂)₂NH₂ |
| 3-225 | 2-Cl—Ph | c-PrCO | 3-S—S—(CH₂)₂NHGly |
| 3-226 | 2-F—Ph | c-PrCO | 3-S—S—(CH₂)₂NHAla |
| 3-227 | 2-F—Ph | MeOCO | 3-S—S—(CH₂)₂NHGly |
| 3-228 | 2-Cl—Ph | MeOCO | 3-S—S—(CH₂)₂NHAla |
| 3-229 | 2-Cl—Ph | c-PrCO | 3-S—S—(CH₂)₂NH-β-Asp |
| 3-230 | 2-F—Ph | c-PrCO | 3-S—S—(CH₂)₂NHGlu |
| 3-231 | 2-F—Ph | MeOCO | 3-S—S—(CH₂)₂NH-β-Asp |
| 3-232 | 2-Cl—Ph | MeOCO | 3-S—S—(CH₂)₂NHGlu |
| 3-233 | 2-Cl—Ph | c-PrCO | 3-S—S—CH₂CH(NH₂)COOH |
| 3-234 | 2-F—Ph | c-PrCO | 3-S—S—CH₂CH(NH₂)COOH |
| 3-235 | 2-F—Ph | MeOCO | 3-S—S—CH₂CH(NH₂)COOH |
| 3-236 | 2-Cl—Ph | MeOCO | 3-S—S—CH₂CH(NH₂)COOH |
| 3-237 | 2-Cl—Ph | c-PrCO | 3-S—S—CH₂CH(NHGlu)COgly |
| 3-238 | 2-F—Ph | c-PrCO | 3-S—S—CH₂CH(NHGlu)COgly |
| 3-239 | 2-F—Ph | MeOCO | 3-S—S—CH₂CH(NHGlu)COgly |
| 3-240 | 2-Cl—Ph | MeOCO | 3-S—S—CH₂CH(NHGlu)COgly |
| 3-241 | 2-Cl—Ph | c-PrCO | 2-S—SO₂-(4-Me—Ph) |
| 3-242 | 2-F—Ph | c-PrCO | 2-S—SO₂-(4-Me—Ph) |
| 3-243 | 2-F—Ph | MeOCO | 2-S—SO₂-(4-Me—Ph) |
| 3-244 | 2-Cl—Ph | MeOCO | 2-S—SO₂-(4-Me—Ph) |
| 3-245 | 2-F—Ph | c-PrCO | 2-S—SO-(4-Me—Ph) |
| 3-246 | 2-Cl—Ph | MeOCO | 2-S—SO-(4-Me—Ph) |
| 3-247 | 2-F—Ph | c-PrCO | 2-S—S-(4-Me—Ph) |

TABLE 3-continued (I-3)

R¹R²CH-N(1)-[azetidine ring with positions 2,3,4]-S-X-R⁴

| Exemplified Compound No. | R¹ | R² | —S—X—R⁴ |
|---|---|---|---|
| 3-248 | 2-Cl—Ph | MeOCO | 2-S—S-(4-Me—Ph) |
| 3-249 | 2-Cl—Ph | c-PrCO | 2-S—SO$_2$-(4-Cl—Ph) |
| 3-250 | 2-F—Ph | c-PrCO | 2-S—SO$_2$-(4-Cl—Ph) |
| 3-251 | 2-F—Ph | MeOCO | 2-S—SO$_2$-(4-Cl—Ph) |
| 3-252 | 2-Cl—Ph | MeOCO | 2-S—SO$_2$-(4-Cl—Ph) |
| 3-253 | 2-F—Ph | c-PrCO | 2-S—SO-(4-Cl—Ph) |
| 3-254 | 2-Cl—Ph | MeOCO | 2-S—SO-(4-Cl—Ph) |
| 3-255 | 2-F—Ph | c-PrCO | 2-S—S-(4-Cl—Ph) |
| 3-256 | 2-Cl—Ph | MeOCO | 2-S—S-(4-Cl—Ph) |
| 3-257 | 2-Cl—Ph | c-PrCO | 2-S—SO$_2$-(4-F—Ph) |
| 3-258 | 2-F—Ph | c-PrCO | 2-S—SO$_2$-(4-F—Ph) |
| 3-259 | 2-F—Ph | MeOCO | 2-S—SO$_2$-(4-F—Ph) |
| 3-260 | 2-Cl—Ph | MeOCO | 2-S—SO$_2$-(4-F—Ph) |
| 3-261 | 2-F—Ph | c-PrCO | 2-S—SO-(4-F—Ph) |
| 3-262 | 2-Cl—Ph | MeOCO | 2-S—SO-(4-F—Ph) |
| 3-263 | 2-F—Ph | c-PrCO | 2-S—S-(4-F—Ph) |
| 3-264 | 2-Cl—Ph | MeOCO | 2-S—S-(4-F—Ph) |
| 3-265 | 2-Cl—Ph | c-PrCO | 2-S—SO$_2$-(4-MeO—Ph) |
| 3-266 | 2-F—Ph | c-PrCO | 2-S—SO$_2$-(4-MeO—Ph) |
| 3-267 | 2-F—Ph | MeOCO | 2-S—SO$_2$-(4-MeO—Ph) |
| 3-268 | 2-Cl—Ph | MeOCO | 2-S—SO$_2$-(4-MeO—Ph) |
| 3-269 | 2-F—Ph | c-PrCO | 2-S—SO-(4-MeO—Ph) |
| 3-270 | 2-Cl—Ph | MeOCO | 2-S—SO-(4-MeO—Ph) |
| 3-271 | 2-F—Ph | c-PrCO | 2-S—S-(4-MeO—Ph) |
| 3-272 | 2-Cl—Ph | MeOCO | 2-S—S-(4-MeO—Ph) |
| 3-273 | 2-Cl—Ph | c-PrCO | 2-S—SO$_2$—Ph |
| 3-274 | 2-F—Ph | c-PrCO | 2-S—SO$_2$—Ph |
| 3-275 | 2-F—Ph | MeOCO | 2-S—SO$_2$—Ph |
| 3-276 | 2-Cl—Ph | MeOCO | 2-S—SO$_2$—Ph |
| 3-277 | 2-F—Ph | c-PrCO | 2-S—SO—Ph |
| 3-278 | 2-Cl—Ph | MeOCO | 2-S—SO—Ph |
| 3-279 | 2-F—Ph | c-PrCO | 2-S—S—Ph |
| 3-280 | 2-Cl—Ph | MeOCO | 2-S—S—Ph |
| 3-281 | 2-F—Ph | c-PrCO | 2-S—SO$_2$-(4-NO$_2$—Ph) |
| 3-282 | 2-Cl—Ph | MeOCO | 2-S—SO$_2$-(4-NO$_2$—Ph) |
| 3-283 | 2-F—Ph | c-PrCO | 2-S—SO-(4-NO$_2$—Ph) |
| 3-284 | 2-F—Ph | c-PrCO | 2-S—S-(4-NO$_2$—Ph) |
| 3-285 | 2-F—Ph | c-PrCO | 2-S—SO$_2$-(2-NO$_2$—Ph) |
| 3-286 | 2-Cl—Ph | MeOCO | 2-S—SO$_2$-(2-NO$_2$—Ph) |
| 3-287 | 2-F—Ph | c-PrCO | 2-S—SO-(2-NO$_2$—Ph) |
| 3-288 | 2-F—Ph | c-PrCO | 2-S—S-(2-NO$_2$—Ph) |
| 3-289 | 2-F—Ph | c-PrCO | 2-S—SO$_2$-(2-Cl—Ph) |
| 3-290 | 2-Cl—Ph | MeOCO | 2-S—SO$_2$-(2-Cl—Ph) |
| 3-291 | 2-F—Ph | c-PrCO | 2-S—SO-(2-Cl—Ph) |
| 3-292 | 2-F—Ph | c-PrCO | 2-S—S-(2-Cl—Ph) |
| 3-293 | 2-F—Ph | c-PrCO | 2-S—SO$_2$-(2-F—Ph) |
| 3-294 | 2-Cl—Ph | MeOCO | 2-S—SO$_2$-(2-F—Ph) |
| 3-295 | 2-F—Ph | c-PrCO | 2-S—SO-(2-F—Ph) |
| 3-296 | 2-F—Ph | c-PrCO | 2-S—S-(2-F—Ph) |
| 3-297 | 2-F—Ph | c-PrCO | 2-S—SO$_2$-(2,4-diNO$_2$—Ph) |
| 3-298 | 2-Cl—Ph | MeOCO | 2-S—SO$_2$-(2,4-diNO$_2$—Ph) |
| 3-299 | 2-F—Ph | c-PrCO | 2-S—SO-(2,4-diNO$_2$—Ph) |
| 3-300 | 2-F—Ph | c-PrCO | 2-S—S-(2,4-diNO$_2$—Ph) |
| 3-301 | 2-F—Ph | c-PrCO | 2-S—SO$_2$—Me |
| 3-302 | 2-Cl—Ph | MeOCO | 2-S—SO$_2$—Me |
| 3-303 | 2-F—Ph | c-PrCO | 2-S—SO—Me |
| 3-304 | 2-F—Ph | c-PrCO | 2-S—S—Me |
| 3-305 | 2-F—Ph | c-PrCO | 2-S—SO$_2$—Et |
| 3-306 | 2-Cl—Ph | MeOCO | 2-S—SO$_2$—Et |
| 3-307 | 2-F—Ph | c-PrCO | 2-S—SO—Et |
| 3-308 | 2-F—Ph | c-PrCO | 2-S—S—Et |
| 3-309 | 2-F—Ph | c-PrCO | 2-S—SO$_2$—Pr |
| 3-310 | 2-Cl—Ph | MeOCO | 2-S—SO$_2$—Pr |
| 3-311 | 2-F—Ph | c-PrCO | 2-S—S—Pr |
| 3-312 | 2-F—Ph | c-PrCO | 2-S—SO$_2$—Bu |
| 3-313 | 2-Cl—Ph | MeOCO | 2-S—SO$_2$—Bu |
| 3-314 | 2-F—Ph | c-PrCO | 2-S—S—Bu |
| 3-315 | 2-F—Ph | c-PrCO | 2-S—SO$_2$-c-Pn |
| 3-316 | 2-Cl—Ph | MeOCO | 2-S—SO$_2$-c-Pn |
| 3-317 | 2-F—Ph | c-PrCO | 2-S—S-c-Pn |
| 3-318 | 2-F—Ph | c-PrCO | 2-S—SO$_2$-c-Hx |
| 3-319 | 2-Cl—Ph | MeOCO | 2-S—SO$_2$-c-Hx |
| 3-320 | 2-F—Ph | c-PrCO | 2-S—S-c-Hx |
| 3-321 | 2-Cl—Ph | c-PrCO | 2-S—SO$_2$—CH$_2$COOH |
| 3-322 | 2-F—Ph | c-PrCO | 2-S—S—CH$_2$COOEt |
| 3-323 | 2-F—Ph | MeOCO | 2-S—SO$_2$—CH$_2$COOH |
| 3-324 | 2-Cl—Ph | MeOCO | 2-S—S—CH$_2$COOEt |
| 3-325 | 2-Cl—Ph | c-PrCO | 2-S—SO$_2$—(CH$_2$)$_3$COOH |
| 3-326 | 2-F—Ph | c-PrCO | 2-S—S—(CH$_2$)$_2$COOH |
| 3-327 | 2-F—Ph | MeOCO | 2-S—SO$_2$—(CH$_2$)$_3$COOH |
| 3-328 | 2-Cl—Ph | MeOCO | 2-S—S—(CH$_2$)$_2$COOH |
| 3-329 | 2-Cl—Ph | c-PrCO | 2-S—SO$_2$—(CH$_2$)$_3$COOMe |
| 3-330 | 2-F—Ph | c-PrCO | 2-S—S—(CH$_2$)$_2$COOMe |
| 3-331 | 2-F—Ph | MeOCO | 2-S—SO$_2$—(CH$_2$)$_3$COOMe |
| 3-332 | 2-Cl—Ph | MeOCO | 2-S—S—(CH$_2$)$_2$COOMe |
| 3-333 | 2-Cl—Ph | c-PrCO | 2-S—SO$_2$—(CH$_2$)$_3$COOEt |
| 3-334 | 2-F—Ph | c-PrCO | 2-S—S—(CH$_2$)$_2$COOEt |
| 3-335 | 2-F—Ph | MeOCO | 2-S—SO$_2$—(CH$_2$)$_3$COOEt |
| 3-336 | 2-Cl—Ph | MeOCO | 2-S—S—(CH$_2$)$_2$COOEt |
| 3-337 | 2-Cl—Ph | c-PrCO | 2-S—SO$_2$—(CH$_2$)$_3$OH |
| 3-338 | 2-F—Ph | c-PrCO | 2-S—S—(CH$_2$)$_2$OH |
| 3-339 | 2-F—Ph | MeOCO | 2-S—SO$_2$—(CH$_2$)$_3$OH |
| 3-340 | 2-Cl—Ph | MeOCO | 2-S—S—(CH$_2$)$_2$OH |
| 3-341 | 2-Cl—Ph | c-PrCO | 2-S—SO$_2$—(CH$_2$)$_3$NH$_2$ |
| 3-342 | 2-F—Ph | c-PrCO | 2-S—S—(CH$_2$)$_2$NH$_2$ |
| 3-343 | 2-F—Ph | MeOCO | 2-S—SO$_2$—(CH$_2$)$_3$NH$_2$ |
| 3-344 | 2-Cl—Ph | MeOCO | 2-S—S—(CH$_2$)$_2$NH$_2$ |
| 3-345 | 2-Cl—Ph | c-PrCO | 2-S—S—(CH$_2$)$_2$NHGly |
| 3-346 | 2-F—Ph | c-PrCO | 2-S—S—(CH$_2$)$_2$NHAla |
| 3-347 | 2-F—Ph | MeOCO | 2-S—S—(CH$_2$)$_2$NHGly |
| 3-348 | 2-Cl—Ph | MeOCO | 2-S—S—(CH$_2$)$_2$NHAla |
| 3-349 | 2-Cl—Ph | c-PrCO | 2-S—S—(CH$_2$)$_2$NH-β-Asp |
| 3-350 | 2-F—Ph | c-PrCO | 2-S—S—(CH$_2$)$_2$NHGlu |
| 3-351 | 2-F—Ph | MeOCO | 2-S—S—(CH$_2$)$_2$NH-β-Asp |
| 3-352 | 2-Cl—Ph | MeOCO | 2-S—S—(CH$_2$)$_2$NHGlu |
| 3-353 | 2-Cl—Ph | c-PrCO | 2-S—S—CH$_2$CH(NH$_2$)COOH |
| 3-354 | 2-F—Ph | c-PrCO | 2-S—S—CH$_2$CH(NH$_2$)COOH |
| 3-355 | 2-F—Ph | MeOCO | 2-S—S—CH$_2$CH(NH$_2$)COOH |
| 3-356 | 2-Cl—Ph | MeOCO | 2-S—S—CH$_2$CH(NH$_2$)COOH |
| 3-357 | 2-Cl—Ph | c-PrCO | 2-S—S—CH$_2$CH(NHGlu)COgly |
| 3-358 | 2-F—Ph | c-PrCO | 2-S—S—CH$_2$CH(NHGlu)COgly |
| 3-359 | 2-F—Ph | MeOCO | 2-S—S—CH$_2$CH(NHGlu)COgly |
| 3-360 | 2-Cl—Ph | MeOCO | 2-S—S—CH$_2$CH(NHGlu)COgly |

TABLE 4

(I-4)

R¹R²CH-N(8)-[bicyclic ring with positions 1,2,3,4,5,6,7]-S-X-R⁴

| Exemplified Compound No. | R¹ | R² | —S—X—R⁴ |
|---|---|---|---|
| 4-1 | 2-Cl—Ph | c-PrCO | 2-S—SO$_2$-(4-Me—Ph) |
| 4-2 | 2-F—Ph | c-PrCO | 2-S—SO$_2$-(4-Me—Ph) |
| 4-3 | 2-F—Ph | MeOCO | 2-S—SO$_2$-(4-Me—Ph) |
| 4-4 | 2-Cl—Ph | MeOCO | 2-S—SO$_2$-(4-Me—Ph) |
| 4-5 | 2-F—Ph | c-PrCO | 2-S—SO-(4-Me—Ph) |

TABLE 4-continued (I-4)

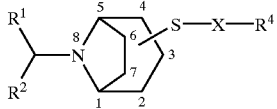

| Exemplified Compound No. | R¹ | R² | —S—X—R⁴ |
|---|---|---|---|
| 4-6 | 2-Cl—Ph | MeOCO | 2-S—SO-(4-Me—Ph) |
| 4-7 | 2-F—Ph | c-PrCO | 2-S—S-(4-Me—Ph) |
| 4-8 | 2-Cl—Ph | MeOCO | 2-S—S-(4-Me—Ph) |
| 4-9 | 2-Cl—Ph | c-PrCO | 2-S—SO$_2$-(4-Cl—Ph) |
| 4-10 | 2-F—Ph | c-PrCO | 2-S—SO$_2$-(4-Cl—Ph) |
| 4-11 | 2-F—Ph | MeOCO | 2-S—SO$_2$-(4-Cl—Ph) |
| 4-12 | 2-Cl—Ph | MeOCO | 2-S—SO$_2$-(4-Cl—Ph) |
| 4-13 | 2-F—Ph | c-PrCO | 2-S—SO-(4-Cl—Ph) |
| 4-14 | 2-Cl—Ph | MeOCO | 2-S—SO-(4-Cl—Ph) |
| 4-15 | 2-F—Ph | c-PrCO | 2-S—S-(4-Cl—Ph) |
| 4-16 | 2-Cl—Ph | MeOCO | 2-S—S-(4-Cl—Ph) |
| 4-17 | 2-Cl—Ph | c-PrCO | 2-S—SO$_2$-(4-F—Ph) |
| 4-18 | 2-F—Ph | c-PrCO | 2-S—SO$_2$-(4-F—Ph) |
| 4-19 | 2-F—Ph | MeOCO | 2-S—SO$_2$-(4-F—Ph) |
| 4-20 | 2-Cl—Ph | MeOCO | 2-S—SO$_2$-(4-F—Ph) |
| 4-21 | 2-F—Ph | c-PrCO | 2-S—SO-(4-F—Ph) |
| 4-22 | 2-Cl—Ph | MeOCO | 2-S—SO-(4-F—Ph) |
| 4-23 | 2-F—Ph | c-PrCO | 2-S—S-(4-F—Ph) |
| 4-24 | 2-Cl—Ph | MeOCO | 2-S—S-(4-F—Ph) |
| 4-25 | 2-Cl—Ph | c-PrCO | 2-S—SO$_2$-(4-MeO—Ph) |
| 4-26 | 2-F—Ph | c-PrCO | 2-S—SO$_2$-(4-MeO—Ph) |
| 4-27 | 2-F—Ph | MeOCO | 2-S—SO$_2$-(4-MeO—Ph) |
| 4-28 | 2-Cl—Ph | MeOCO | 2-S—SO$_2$-(4-MeO—Ph) |
| 4-29 | 2-F—Ph | c-PrCO | 2-S—SO-(4-MeO—Ph) |
| 4-30 | 2-Cl—Ph | MeOCO | 2-S—SO-(4-MeO—Ph) |
| 4-31 | 2-F—Ph | c-PrCO | 2-S—S-(4-MeO—Ph) |
| 4-32 | 2-Cl—Ph | MeOCO | 2-S—S-(4-MeO—Ph) |
| 4-33 | 2-Cl—Ph | c-PrCO | 2-S—SO$_2$—Ph |
| 4-34 | 2-F—Ph | c-PrCO | 2-S—SO$_2$—Ph |
| 4-35 | 2-F—Ph | MeOCO | 2-S—SO$_2$—Ph |
| 4-36 | 2-Cl—Ph | MeOCO | 2-S—SO$_2$—Ph |
| 4-37 | 2-F—Ph | c-PrCO | 2-S—SO—Ph |
| 4-38 | 2-Cl—Ph | MeOCO | 2-S—SO—Ph |
| 4-39 | 2-F—Ph | c-PrCO | 2-S—S—Ph |
| 4-40 | 2-Cl—Ph | MeOCO | 2-S—S—Ph |
| 4-41 | 2-F—Ph | c-PrCO | 2-S—SO$_2$-(4-NO$_2$—Ph) |
| 4-42 | 2-Cl—Ph | MeOCO | 2-S—SO$_2$-(4-NO$_2$—Ph) |
| 4-43 | 2-F—Ph | c-PrCO | 2-S—SO-(4-NO$_2$—Ph) |
| 4-44 | 2-F—Ph | c-PrCO | 2-S—S-(4-NO$_2$—Ph) |
| 4-45 | 2-F—Ph | c-PrCO | 2-S—SO$_2$-(2-NO$_2$—Ph) |
| 4-46 | 2-Cl—Ph | MeOCO | 2-S—SO$_2$-(2-NO$_2$—Ph) |
| 4-47 | 2-F—Ph | c-PrCO | 2-S—SO-(2-NO$_2$—Ph) |
| 4-48 | 2-F—Ph | c-PrCO | 2-S—S-(2-NO$_2$—Ph) |
| 4-49 | 2-F—Ph | c-PrCO | 2-S—SO$_2$-(2-Cl—Ph) |
| 4-50 | 2-Cl—Ph | MeOCO | 2-S—SO$_2$-(2-Cl—Ph) |
| 4-51 | 2-F—Ph | c-PrCO | 2-S—SO-(2-Cl—Ph) |
| 4-52 | 2-F—Ph | c-PrCO | 2-S—S-(2-Cl—Ph) |
| 4-53 | 2-F—Ph | c-PrCO | 2-S—SO$_2$-(2-F—Ph) |
| 4-54 | 2-Cl—Ph | MeOCO | 2-S—SO$_2$-(2-F—Ph) |
| 4-55 | 2-F—Ph | c-PrCO | 2-S—SO-(2-F—Ph) |
| 4-56 | 2-F—Ph | c-PrCO | 2-S—S-(2-F—Ph) |
| 4-57 | 2-F—Ph | c-PrCO | 2-S—SO$_2$-(2,4-diNO$_2$—Ph) |
| 4-58 | 2-Cl—Ph | MeOCO | 2-S—SO$_2$-(2,4-diNO$_2$—Ph) |
| 4-59 | 2-F—Ph | c-PrCO | 2-S—SO-(2,4-diNO$_2$—Ph) |
| 4-60 | 2-F—Ph | c-PrCO | 2-S—S-(2,4-diNO$_2$—Ph) |
| 4-61 | 2-F—Ph | c-PrCO | 2-S—SO$_2$—Me |
| 4-62 | 2-Cl—Ph | MeOCO | 2-S—SO$_2$—Me |
| 4-63 | 2-F—Ph | c-PrCO | 2-S—SO—Me |
| 4-64 | 2-F—Ph | c-PrCO | 2-S—S—Me |
| 4-65 | 2-F—Ph | c-PrCO | 2-S—SO$_2$—Et |
| 4-66 | 2-Cl—Ph | MeOCO | 2-S—SO$_2$—Et |
| 4-67 | 2-F—Ph | c-PrCO | 2-S—SO—Et |
| 4-68 | 2-F—Ph | c-PrCO | 2-S—S—Et |
| 4-69 | 2-F—Ph | c-PrCO | 2-S—SO$_2$—Pr |
| 4-70 | 2-Cl—Ph | MeOCO | 2-S—SO$_2$—Pr |
| 4-71 | 2-F—Ph | c-PrCO | 2-S—S—Pr |
| 4-72 | 2-F—Ph | c-PrCO | 2-S—SO$_2$—Bu |
| 4-73 | 2-Cl—Ph | MeOCO | 2-S—SO$_2$—Bu |
| 4-74 | 2-F—Ph | c-PrCO | 2-S—S—Bu |
| 4-75 | 2-F—Ph | c-PrCO | 2-S—SO$_2$-c-Pn |
| 4-76 | 2-Cl—Ph | MeOCO | 2-S—SO$_2$-c-Pn |
| 4-77 | 2-F—Ph | c-PrCO | 2-S—S-c-Pn |
| 4-78 | 2-F—Ph | c-PrCO | 2-S—SO$_2$-c-Hx |
| 4-79 | 2-Cl—Ph | MeOCO | 2-S—SO$_2$-c-Hx |
| 4-80 | 2-F—Ph | c-PrCO | 2-S—S-c-Hx |
| 4-81 | 2-Cl—Ph | c-PrCO | 2-S—SO$_2$—CH$_2$COOH |
| 4-82 | 2-F—Ph | c-PrCO | 2-S—S—CH$_2$COOEt |
| 4-83 | 2-F—Ph | MeOCO | 2-S—SO$_2$—CH$_2$COOH |
| 4-84 | 2-Cl—Ph | MeOCO | 2-S—S—CH$_2$COOEt |
| 4-85 | 2-Cl—Ph | c-PrCO | 2-S—SO$_2$—(CH$_2$)$_3$COOH |
| 4-86 | 2-F—Ph | c-PrCO | 2-S—S—(CH$_2$)$_2$COOH |
| 4-87 | 2-F—Ph | MeOCO | 2-S—SO$_2$—(CH$_2$)$_3$COOH |
| 4-88 | 2-Cl—Ph | MeOCO | 2-S—S—(CH$_2$)$_2$COOH |
| 4-89 | 2-Cl—Ph | c-PrCO | 2-S—SO$_2$—(CH$_2$)$_3$COOMe |
| 4-90 | 2-F—Ph | c-PrCO | 2-S—S—(CH$_2$)$_2$COOMe |
| 4-91 | 2-F—Ph | MeOCO | 2-S—SO$_2$—(CH$_2$)$_3$COOMe |
| 4-92 | 2-Cl—Ph | MeOCO | 2-S—S—(CH$_2$)$_2$COOMe |
| 4-93 | 2-Cl—Ph | c-PrCO | 2-S—SO$_2$—(CH$_2$)$_3$COOEt |
| 4-94 | 2-F—Ph | c-PrCO | 2-S—S—(CH$_2$)$_2$COOEt |
| 4-95 | 2-F—Ph | MeOCO | 2-S—SO$_2$—(CH$_2$)$_3$COOEt |
| 4-96 | 2-Cl—Ph | MeOCO | 2-S—S—(CH$_2$)$_2$COOEt |
| 4-97 | 2-Cl—Ph | c-PrCO | 2-S—SO$_2$—(CH$_2$)$_3$OH |
| 4-98 | 2-F—Ph | c-PrCO | 2-S—S—(CH$_2$)$_2$OH |
| 4-99 | 2-F—Ph | MeOCO | 2-S—SO$_2$—(CH$_2$)$_3$OH |
| 4-100 | 2-Cl—Ph | MeOCO | 2-S—S—(CH$_2$)$_2$OH |
| 4-101 | 2-Cl—Ph | c-PrCO | 2-S—SO$_2$—(CH$_2$)$_3$NH$_2$ |
| 4-102 | 2-F—Ph | c-PrCO | 2-S—S—(CH$_2$)$_2$NH$_2$ |
| 4-103 | 2-F—Ph | MeOCO | 2-S—SO$_2$—(CH$_2$)$_3$NH$_2$ |
| 4-104 | 2-Cl—Ph | MeOCO | 2-S—S—(CH$_2$)$_2$NH$_2$ |
| 4-105 | 2-Cl—Ph | c-PrCO | 2-S—S—(CH$_2$)$_2$NHGly |
| 4-106 | 2-F—Ph | c-PrCO | 2-S—S—(CH$_2$)$_2$NHAla |
| 4-107 | 2-F—Ph | MeOCO | 2-S—S—(CH$_2$)$_2$NHGly |
| 4-108 | 2-Cl—Ph | MeOCO | 2-S—S—(CH$_2$)$_2$NHAla |
| 4-109 | 2-Cl—Ph | c-PrCO | 2-S—S—(CH$_2$)$_2$NH-β-Asp |
| 4-110 | 2-F—Ph | c-PrCO | 2-S—S—(CH$_2$)$_2$NHGlu |
| 4-111 | 2-F—Ph | MeOCO | 2-S—S—(CH$_2$)$_2$NH-β-Asp |
| 4-112 | 2-Cl—Ph | MeOCO | 2-S—S—(CH$_2$)$_2$NHGlu |
| 4-113 | 2-Cl—Ph | c-PrCO | 2-S—S—CH$_2$CH(NH$_2$)COOH |
| 4-114 | 2-F—Ph | c-PrCO | 2-S—S—CH$_2$CH(NH$_2$)COOH |
| 4-115 | 2-F—Ph | MeOCO | 2-S—S—CH$_2$CH(NH$_2$)COOH |
| 4-116 | 2-Cl—Ph | MeOCO | 2-S—S—CH$_2$CH(NH$_2$)COOH |
| 4-117 | 2-Cl—Ph | c-PrCO | 2-S—S—CH$_2$CH(NHGlu)COgly |
| 4-118 | 2-F—Ph | c-PrCO | 2-S—S—CH$_2$CH(NHGlu)COgly |
| 4-119 | 2-F—Ph | MeOCO | 2-S—S—CH$_2$CH(NHGlu)COgly |
| 4-120 | 2-Cl—Ph | MeOCO | 2-S—S—CH$_2$CH(NHGlu)COgly |
| 4-121 | 2-Cl—Ph | c-PrCO | 3-S—SO$_2$-(4-Me—Ph) |
| 4-122 | 2-F—Ph | c-PrCO | 3-S—SO$_2$-(4-Me—Ph) |
| 4-123 | 2-F—Ph | MeOCO | 3-S—SO$_2$-(4-Me—Ph) |
| 4-124 | 2-Cl—Ph | MeOCO | 3-S—SO$_2$-(4-Me—Ph) |
| 4-125 | 2-F—Ph | c-PrCO | 3-S—SO-(4-Me—Ph) |
| 4-126 | 2-Cl—Ph | MeOCO | 3-S—SO-(4-Me—Ph) |
| 4-127 | 2-F—Ph | c-PrCO | 3-S—S-(4-Me—Ph) |
| 4-128 | 2-Cl—Ph | MeOCO | 3-S—S-(4-Me—Ph) |
| 4-129 | 2-Cl—Ph | c-PrCO | 3-S—SO$_2$-(4-Cl—Ph) |
| 4-130 | 2-F—Ph | c-PrCO | 3-S—SO$_2$-(4-Cl—Ph) |
| 4-131 | 2-F—Ph | MeOCO | 3-S—SO$_2$-(4-Cl—Ph) |
| 4-132 | 2-Cl—Ph | MeOCO | 3-S—SO$_2$-(4-Cl—Ph) |
| 4-133 | 2-F—Ph | c-PrCO | 3-S—SO-(4-Cl—Ph) |
| 4-134 | 2-Cl—Ph | MeOCO | 3-S—SO-(4-Cl—Ph) |
| 4-135 | 2-F—Ph | c-PrCO | 3-S—S-(4-Cl—Ph) |
| 4-136 | 2-Cl—Ph | MeOCO | 3-S—S-(4-Cl—Ph) |
| 4-137 | 2-Cl—Ph | c-PrCO | 3-S—SO$_2$-(4-F—Ph) |
| 4-138 | 2-F—Ph | c-PrCO | 3-S—SO$_2$-(4-F—Ph) |
| 4-139 | 2-F—Ph | MeOCO | 3-S—SO$_2$-(4-F—Ph) |
| 4-140 | 2-Cl—Ph | MeOCO | 3-S—SO$_2$-(4-F—Ph) |
| 4-141 | 2-F—Ph | c-PrCO | 3-S—SO-(4-F—Ph) |

TABLE 4-continued (I-4)

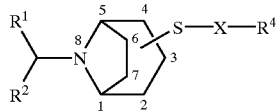

| Exemplified Compound No. | R$^1$ | R$^2$ | —S—X—R$^4$ |
|---|---|---|---|
| 4-142 | 2-Cl—Ph | MeOCO | 3-S—SO-(4-F—Ph) |
| 4-143 | 2-F—Ph | c-PrCO | 3-S—S-(4-F—Ph) |
| 4-144 | 2-Cl—Ph | MeOCO | 3-S—S-(4-F—Ph) |
| 4-145 | 2-Cl—Ph | c-PrCO | 3-S—SO$_2$-(4-MeO—Ph) |
| 4-146 | 2-F—Ph | c-PrCO | 3-S—SO$_2$-(4-MeO—Ph) |
| 4-147 | 2-F—Ph | MeOCO | 3-S—SO$_2$-(4-MeO—Ph) |
| 4-148 | 2-Cl—Ph | MeOCO | 3-S—SO$_2$-(4-MeO—Ph) |
| 4-149 | 2-F—Ph | c-PrCO | 3-S—SO-(4-MeO—Ph) |
| 4-150 | 2-Cl—Ph | MeOCO | 3-S—SO-(4-MeO—Ph) |
| 4-151 | 2-F—Ph | c-PrCO | 3-S—S-(4-MeO—Ph) |
| 4-152 | 2-Cl—Ph | MeOCO | 3-S—S-(4-MeO—Ph) |
| 4-153 | 2-Cl—Ph | c-PrCO | 3-S—SO$_2$—Ph |
| 4-154 | 2-F—Ph | c-PrCO | 3-S—SO$_2$—Ph |
| 4-155 | 2-F—Ph | MeOCO | 3-S—SO$_2$—Ph |
| 4-156 | 2-Cl—Ph | MeOCO | 3-S—SO$_2$—Ph |
| 4-157 | 2-F—Ph | c-PrCO | 3-S—SO—Ph |
| 4-158 | 2-Cl—Ph | MeOCO | 3-S—SO—Ph |
| 4-159 | 2-F—Ph | c-PrCO | 3-S—S—Ph |
| 4-160 | 2-Cl—Ph | MeOCO | 3-S—S—Ph |
| 4-161 | 2-F—Ph | c-PrCO | 3-S—SO$_2$-(4-NO$_2$—Ph) |
| 4-162 | 2-Cl—Ph | MeOCO | 3-S—SO$_2$-(4-NO$_2$—Ph) |
| 4-163 | 2-F—Ph | c-PrCO | 3-S—SO-(4-NO$_2$—Ph) |
| 4-164 | 2-F—Ph | c-PrCO | 3-S—S-(4-NO$_2$—Ph) |
| 4-165 | 2-F—Ph | c-PrCO | 3-S—SO$_2$-(2-NO$_2$—Ph) |
| 4-166 | 2-Cl—Ph | MeOCO | 3-S—SO$_2$-(2-NO$_2$—Ph) |
| 4-167 | 2-F—Ph | c-PrCO | 3-S—SO-(2-NO$_2$—Ph) |
| 4-168 | 2-F—Ph | c-PrCO | 3-S—S-(2-NO$_2$—Ph) |
| 4-169 | 2-F—Ph | c-PrCO | 3-S—SO$_2$-(2-Cl—Ph) |
| 4-170 | 2-Cl—Ph | MeOCO | 3-S—SO$_2$-(2-Cl—Ph) |
| 4-171 | 2-F—Ph | c-PrCO | 3-S—SO-(2-Cl—Ph) |
| 4-172 | 2-F—Ph | c-PrCO | 3-S—S-(2-Cl—Ph) |
| 4-173 | 2-F—Ph | c-PrCO | 3-S—SO$_2$-(2-F—Ph) |
| 4-174 | 2-Cl—Ph | MeOCO | 3-S—SO$_2$-(2-F—Ph) |
| 4-175 | 2-F—Ph | c-PrCO | 3-S—SO-(2-F—Ph) |
| 4-176 | 2-F—Ph | c-PrCO | 3-S—S-(2-F—Ph) |
| 4-177 | 2-F—Ph | c-PrCO | 3-S—SO$_2$-(2,4-diNO$_2$—Ph) |
| 4-178 | 2-Cl—Ph | MeOCO | 3-S—SO$_2$-(2,4-diNO$_2$—Ph) |
| 4-179 | 2-F—Ph | c-PrCO | 3-S—SO-(2,4-diNO$_2$—Ph) |
| 4-180 | 2-F—Ph | c-PrCO | 3-S—S-(2,4-diNO$_2$—Ph) |
| 4-181 | 2-F—Ph | c-PrCO | 3-S—SO$_2$—Me |
| 4-182 | 2-Cl—Ph | MeOCO | 3-S—SO$_2$—Me |
| 4-183 | 2-F—Ph | c-PrCO | 3-S—SO—Me |
| 4-184 | 2-F—Ph | c-PrCO | 3-S—S—Me |
| 4-185 | 2-F—Ph | c-PrCO | 3-S—SO$_2$—Et |
| 4-186 | 2-Cl—Ph | MeOCO | 3-S—SO$_2$—Et |
| 4-187 | 2-F—Ph | c-PrCO | 3-S—SO—Et |
| 4-188 | 2-F—Ph | c-PrCO | 3-S—S—Et |
| 4-189 | 2-F—Ph | c-PrCO | 3-S—SO$_2$—Pr |
| 4-190 | 2-Cl—Ph | MeOCO | 3-S—SO$_2$—Pr |
| 4-191 | 2-F—Ph | c-PrCO | 3-S—S—Pr |
| 4-192 | 2-F—Ph | c-PrCO | 3-S—SO$_2$—Bu |
| 4-193 | 2-Cl—Ph | MeOCO | 3-S—SO$_2$—Bu |
| 4-194 | 2-F—Ph | c-PrCO | 3-S—S—Bu |
| 4-195 | 2-F—Ph | c-PrCO | 3-S—SO$_2$-c-Pn |
| 4-196 | 2-Cl—Ph | MeOCO | 3-S—SO$_2$-c-Pn |
| 4-197 | 2-F—Ph | c-PrCO | 3-S—S-c-Pn |
| 4-198 | 2-F—Ph | c-PrCO | 3-S—SO$_2$-c-Hx |
| 4-199 | 2-Cl—Ph | MeOCO | 3-S—SO$_2$-c-Hx |
| 4-200 | 2-F—Ph | c-PrCO | 3-S—S-c-Hx |
| 4-201 | 2-Cl—Ph | c-PrCO | 3-S—SO$_2$—CH$_2$COOH |
| 4-202 | 2-F—Ph | c-PrCO | 3-S—S—CH$_2$COOEt |
| 4-203 | 2-F—Ph | MeOCO | 3-S—SO$_2$—CH$_2$COOH |
| 4-204 | 2-Cl—Ph | MeOCO | 3-S—S—CH$_2$COOEt |
| 4-205 | 2-Cl—Ph | c-PrCO | 3-S—SO$_2$—(CH$_2$)$_3$COOH |
| 4-206 | 2-F—Ph | c-PrCO | 3-S—S—(CH$_2$)$_2$COOH |
| 4-207 | 2-F—Ph | MeOCO | 3-S—SO$_2$—(CH$_2$)$_3$COOH |
| 4-208 | 2-Cl—Ph | MeOCO | 3-S—S—(CH$_2$)$_2$COOH |
| 4-209 | 2-Cl—Ph | c-PrCO | 3-S—SO$_2$—(CH$_2$)$_3$COOMe |
| 4-210 | 2-F—Ph | c-PrCO | 3-S—S—(CH$_2$)$_2$COOMe |
| 4-211 | 2-F—Ph | MeOCO | 3-S—SO$_2$—(CH$_2$)$_3$COOMe |
| 4-212 | 2-Cl—Ph | MeOCO | 3-S—S—(CH$_2$)$_2$COOMe |
| 4-213 | 2-Cl—Ph | c-PrCO | 3-S—SO$_2$—(CH$_2$)$_3$COOEt |
| 4-214 | 2-F—Ph | c-PrCO | 3-S—S—(CH$_2$)$_2$COOEt |
| 4-215 | 2-F—Ph | MeOCO | 3-S—SO$_2$—(CH$_2$)$_3$COOEt |
| 4-216 | 2-Cl—Ph | MeOCO | 3-S—S—(CH$_2$)$_2$COOEt |
| 4-217 | 2-Cl—Ph | c-PrCO | 3-S—SO$_2$—(CH$_2$)$_3$OH |
| 4-218 | 2-F—Ph | c-PrCO | 3-S—S—(CH$_2$)$_2$OH |
| 4-219 | 2-F—Ph | MeOCO | 3-S—SO$_2$—(CH$_2$)$_3$OH |
| 4-220 | 2-Cl—Ph | MeOCO | 3-S—S—(CH$_2$)$_2$OH |
| 4-221 | 2-Cl—Ph | c-PrCO | 3-S—SO$_2$—(CH$_2$)$_3$NH$_2$ |
| 4-222 | 2-F—Ph | c-PrCO | 3-S—S—(CH$_2$)$_2$NH$_2$ |
| 4-223 | 2-F—Ph | MeOCO | 3-S—SO$_2$—(CH$_2$)$_3$NH$_2$ |
| 4-224 | 2-Cl—Ph | MeOCO | 3-S—S—(CH$_2$)$_2$NH$_2$ |
| 4-225 | 2-Cl—Ph | c-PrCO | 3-S—S—(CH$_2$)$_2$NHGly |
| 4-226 | 2-F—Ph | c-PrCO | 3-S—S—(CH$_2$)$_2$NHAla |
| 4-227 | 2-F—Ph | MeOCO | 3-S—S—(CH$_2$)$_2$NHGly |
| 4-228 | 2-Cl—Ph | MeOCO | 3-S—S—(CH$_2$)$_2$NHAla |
| 4-229 | 2-Cl—Ph | c-PrCO | 3-S—S—(CH$_2$)$_2$NH-β-Asp |
| 4-230 | 2-F—Ph | c-PrCO | 3-S—S—(CH$_2$)$_2$NHGlu |
| 4-231 | 2-F—Ph | MeOCO | 3-S—S—(CH$_2$)$_2$NH-β-Asp |
| 4-232 | 2-Cl—Ph | MeOCO | 3-S—S—(CH$_2$)$_2$NHGlu |
| 4-233 | 2-Cl—Ph | c-PrCO | 3-S—S—CH$_2$CH(NH$_2$)COOH |
| 4-234 | 2-F—Ph | c-PrCO | 3-S—S—CH$_2$CH(NH$_2$)COOH |
| 4-235 | 2-F—Ph | MeOCO | 3-S—S—CH$_2$CH(NH$_2$)COOH |
| 4-236 | 2-Cl—Ph | MeOCO | 3-S—S—CH$_2$CH(NH$_2$)COOH |
| 4-237 | 2-Cl—Ph | c-PrCO | 3-S—S—CH$_2$CH(NHGlu)COgly |
| 4-238 | 2-F—Ph | c-PrCO | 3-S—S—CH$_2$CH(NHGlu)COgly |
| 4-239 | 2-F—Ph | MeOCO | 3-S—S—CH$_2$CH(NHGlu)COgly |
| 4-240 | 2-Cl—Ph | MeOCO | 3-S—S—CH$_2$CH(NHGlu)COgly |
| 4-241 | 2-Cl—Ph | c-PrCO | 6-S—SO$_2$-(4-Me—Ph) |
| 4-242 | 2-F—Ph | c-PrCO | 6-S—SO$_2$-(4-Me—Ph) |
| 4-243 | 2-F—Ph | MeOCO | 6-S—SO$_2$-(4-Me—Ph) |
| 4-244 | 2-Cl—Ph | MeOCO | 6-S—SO$_2$-(4-Me—Ph) |
| 4-245 | 2-F—Ph | c-PrCO | 6-S—SO-(4-Me—Ph) |
| 4-246 | 2-Cl—Ph | MeOCO | 6-S—SO-(4-Me—Ph) |
| 4-247 | 2-F—Ph | c-PrCO | 6-S—S-(4-Me—Ph) |
| 4-248 | 2-Cl—Ph | MeOCO | 6-S—S-(4-Me—Ph) |
| 4-249 | 2-Cl—Ph | c-PrCO | 6-S—SO$_2$-(4-Cl—Ph) |
| 4-250 | 2-F—Ph | c-PrCO | 6-S—SO$_2$-(4-Cl—Ph) |
| 4-251 | 2-F—Ph | MeOCO | 6-S—SO$_2$-(4-Cl—Ph) |
| 4-252 | 2-Cl—Ph | MeOCO | 6-S—SO$_2$-(4-Cl—Ph) |
| 4-253 | 2-F—Ph | c-PrCO | 6-S—SO-(4-Cl—Ph) |
| 4-254 | 2-Cl—Ph | MeOCO | 6-S—SO-(4-Cl—Ph) |
| 4-255 | 2-F—Ph | c-PrCO | 6-S—S-(4-Cl—Ph) |
| 4-256 | 2-Cl—Ph | MeOCO | 6-S—S-(4-Cl—Ph) |
| 4-257 | 2-Cl—Ph | c-PrCO | 6-S—SO$_2$-(4-F—Ph) |
| 4-258 | 2-F—Ph | c-PrCO | 6-S—SO$_2$-(4-F—Ph) |
| 4-259 | 2-F—Ph | MeOCO | 6-S—SO$_2$-(4-F—Ph) |
| 4-260 | 2-Cl—Ph | MeOCO | 6-S—SO$_2$-(4-F—Ph) |
| 4-261 | 2-F—Ph | c-PrCO | 6-S—SO-(4-F—Ph) |
| 4-262 | 2-Cl—Ph | MeOCO | 6-S—SO-(4-F—Ph) |
| 4-263 | 2-F—Ph | c-PrCO | 6-S—S-(4-F—Ph) |
| 4-264 | 2-Cl—Ph | MeOCO | 6-S—S-(4-F—Ph) |
| 4-265 | 2-Cl—Ph | c-PrCO | 6-S—SO$_2$-(4-MeO—Ph) |
| 4-266 | 2-F—Ph | c-PrCO | 6-S—SO$_2$-(4-MeO—Ph) |
| 4-267 | 2-F—Ph | MeOCO | 6-S—SO$_2$-(4-MeO—Ph) |
| 4-268 | 2-Cl—Ph | MeOCO | 6-S—SO$_2$-(4-MeO—Ph) |
| 4-269 | 2-F—Ph | c-PrCO | 6-S—SO-(4-MeO—Ph) |
| 4-270 | 2-Cl—Ph | MeOCO | 6-S—SO-(4-MeO—Ph) |
| 4-271 | 2-F—Ph | c-PrCO | 6-S—S-(4-MeO—Ph) |
| 4-272 | 2-Cl—Ph | MeOCO | 6-S—S-(4-MeO—Ph) |
| 4-273 | 2-Cl—Ph | c-PrCO | 6-S—SO$_2$—Ph |
| 4-274 | 2-F—Ph | c-PrCO | 6-S—SO$_2$—Ph |
| 4-275 | 2-F—Ph | MeOCO | 6-S—SO$_2$—Ph |
| 4-276 | 2-Cl—Ph | MeOCO | 6-S—SO$_2$—Ph |
| 4-277 | 2-F—Ph | c-PrCO | 6-S—SO—Ph |

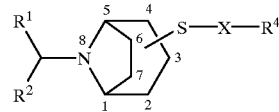

TABLE 4-continued

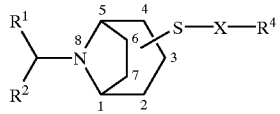

(I-4)

| Exemplified Compound No. | R¹ | R² | —S—X—R⁴ |
|---|---|---|---|
| 4-278 | 2-Cl—Ph | MeOCO | 6-S—SO—Ph |
| 4-279 | 2-F—Ph | c-PrCO | 6-S—S—Ph |
| 4-280 | 2-Cl—Ph | MeOCO | 6-S—S—Ph |
| 4-281 | 2-F—Ph | c-PrCO | 6-S—SO$_2$-(4-NO$_2$—Ph) |
| 4-282 | 2-Cl—Ph | MeOCO | 6-S—SO$_2$-(4-NO$_2$—Ph) |
| 4-283 | 2-F—Ph | c-PrCO | 6-S—SO-(4-NO$_2$—Ph) |
| 4-284 | 2-F—Ph | c-PrCO | 6-S—S-(4-NO$_2$—Ph) |
| 4-285 | 2-F—Ph | c-PrCO | 6-S—SO$_2$-(2-NO$_2$—Ph) |
| 4-286 | 2-Cl—Ph | MeOCO | 6-S—SO$_2$-(2-NO$_2$—Ph) |
| 4-287 | 2-F—Ph | c-PrCO | 6-S—SO-(2-NO$_2$—Ph) |
| 4-288 | 2-F—Ph | c-PrCO | 6-S—S-(2-NO$_2$—Ph) |
| 4-289 | 2-F—Ph | c-PrCO | 6-S—SO$_2$-(2-Cl—Ph) |
| 4-290 | 2-Cl—Ph | MeOCO | 6-S—SO$_2$-(2-Cl—Ph) |
| 4-291 | 2-F—Ph | c-PrCO | 6-S—SO-(2-Cl—Ph) |
| 4-292 | 2-F—Ph | c-PrCO | 6-S—S-(2-Cl—Ph) |
| 4-293 | 2-F—Ph | c-PrCO | 6-S—SO$_2$-(2-F—Ph) |
| 4-294 | 2-Cl—Ph | MeOCO | 6-S—SO$_2$-(2-F—Ph) |
| 4-295 | 2-F—Ph | c-PrCO | 6-S—SO-(2-F—Ph) |
| 4-296 | 2-F—Ph | c-PrCO | 6-S—S-(2-F—Ph) |
| 4-297 | 2-F—Ph | c-PrCO | 6-S—SO$_2$-(2,4-diNO$_2$—Ph) |
| 4-298 | 2-Cl—Ph | MeOCO | 6-S—SO$_2$-(2,4-diNO$_2$—Ph) |
| 4-299 | 2-F—Ph | c-PrCO | 6-S—SO-(2,4-diNO$_2$—Ph) |
| 4-300 | 2-F—Ph | c-PrCO | 6-S—S-(2,4-diNO$_2$—Ph) |
| 4-301 | 2-F—Ph | c-PrCO | 6-S—SO$_2$—Me |
| 4-302 | 2-Cl—Ph | MeOCO | 6-S—SO$_2$—Me |
| 4-303 | 2-F—Ph | c-PrCO | 6-S—SO—Me |
| 4-304 | 2-F—Ph | c-PrCO | 6-S—S—Me |
| 4-305 | 2-F—Ph | c-PrCO | 6-S—SO$_2$—Et |
| 4-306 | 2-Cl—Ph | MeOCO | 6-S—SO$_2$—Et |
| 4-307 | 2-F—Ph | c-PrCO | 6-S—SO—Et |
| 4-308 | 2-F—Ph | c-PrCO | 6-S—S—Et |
| 4-309 | 2-F—Ph | c-PrCO | 6-S—SO$_2$—Pr |
| 4-310 | 2-Cl—Ph | MeOCO | 6-S—SO$_2$—Pr |
| 4-311 | 2-F—Ph | c-PrCO | 6-S—S—Pr |
| 4-312 | 2-F—Ph | c-PrCO | 6-S—SO$_2$—Bu |
| 4-313 | 2-Cl—Ph | MeOCO | 6-S—SO$_2$—Bu |
| 4-314 | 2-F—Ph | c-PrCO | 6-S—S—Bu |
| 4-315 | 2-F—Ph | c-PrCO | 6-S—SO$_2$-c-Pn |
| 4-316 | 2-Cl—Ph | MeOCO | 6-S—SO$_2$-c-Pn |
| 4-317 | 2-F—Ph | c-PrCO | 6-S—S-c-Pn |
| 4-318 | 2-F—Ph | c-PrCO | 6-S—SO$_2$-c-Hx |
| 4-319 | 2-Cl—Ph | MeOCO | 6-S—SO$_2$-c-Hx |
| 4-320 | 2-F—Ph | c-PrCO | 6-S—S-c-Hx |
| 4-321 | 2-Cl—Ph | c-PrCO | 6-S—SO$_2$—CH$_2$COOH |
| 4-322 | 2-F—Ph | c-PrCO | 6-S—S—CH$_2$COOEt |
| 4-323 | 2-F—Ph | MeOCO | 6-S—SO$_2$—CH$_2$COOH |
| 4-324 | 2-Cl—Ph | MeOCO | 6-S—S—CH$_2$COOEt |
| 4-325 | 2-Cl—Ph | c-PrCO | 6-S—SO$_2$—(CH$_2$)$_3$COOH |
| 4-326 | 2-F—Ph | c-PrCO | 6-S—S—(CH$_2$)$_2$COOH |
| 4-327 | 2-F—Ph | MeOCO | 6-S—SO$_2$—(CH$_2$)$_3$COOH |
| 4-328 | 2-Cl—Ph | MeOCO | 6-S—S—(CH$_2$)$_2$COOH |
| 4-329 | 2-Cl—Ph | c-PrCO | 6-S—SO$_2$—(CH$_2$)$_3$COOMe |
| 4-330 | 2-F—Ph | c-PrCO | 6-S—S—(CH$_2$)$_2$COOMe |
| 4-331 | 2-F—Ph | MeOCO | 6-S—SO$_2$—(CH$_2$)$_3$COOMe |
| 4-332 | 2-Cl—Ph | MeOCO | 6-S—S—(CH$_2$)$_2$COOMe |
| 4-333 | 2-Cl—Ph | c-PrCO | 6-S—SO$_2$—(CH$_2$)$_3$COOEt |
| 4-334 | 2-F—Ph | c-PrCO | 6-S—S—(CH$_2$)$_2$COOEt |
| 4-335 | 2-F—Ph | MeOCO | 6-S—SO$_2$—(CH$_2$)$_3$COOEt |
| 4-336 | 2-Cl—Ph | MeOCO | 6-S—S—(CH$_2$)$_2$COOEt |
| 4-337 | 2-Cl—Ph | c-PrCO | 6-S—SO$_2$—(CH$_2$)$_3$OH |
| 4-338 | 2-F—Ph | c-PrCO | 6-S—S—(CH$_2$)$_2$OH |
| 4-339 | 2-F—Ph | MeOCO | 6-S—SO$_2$—(CH$_2$)$_3$OH |
| 4-340 | 2-Cl—Ph | MeOCO | 6-S—S—(CH$_2$)$_2$OH |
| 4-341 | 2-Cl—Ph | c-PrCO | 6-S—SO$_2$—(CH$_2$)$_3$NH$_2$ |
| 4-342 | 2-F—Ph | c-PrCO | 6-S—S—(CH$_2$)$_2$NH$_2$ |
| 4-343 | 2-F—Ph | MeOCO | 6-S—SO$_2$—(CH$_2$)$_3$NH$_2$ |
| 4-344 | 2-Cl—Ph | MeOCO | 6-S—S—(CH$_2$)$_2$NH$_2$ |
| 4-345 | 2-Cl—Ph | c-PrCO | 6-S—S—(CH$_2$)$_2$NHGly |
| 4-346 | 2-F—Ph | c-PrCO | 6-S—S—(CH$_2$)$_2$NHAla |
| 4-347 | 2-F—Ph | MeOCO | 6-S—S—(CH$_2$)$_2$NHGly |
| 4-348 | 2-Cl—Ph | MeOCO | 6-S—S—(CH$_2$)$_2$NHAla |
| 4-349 | 2-Cl—Ph | c-PrCO | 6-S—S—(CH$_2$)$_2$NH-β-Asp |
| 4-350 | 2-F—Ph | c-PrCO | 6-S—S—(CH$_2$)$_2$NHGlu |
| 4-351 | 2-F—Ph | MeOCO | 6-S—S—(CH$_2$)$_2$NH-β-Asp |
| 4-352 | 2-Cl—Ph | MeOCO | 6-S—S—(CH$_2$)$_2$NHGlu |
| 4-353 | 2-Cl—Ph | c-PrCO | 6-S—S—CH$_2$CH(NH$_2$)COOH |
| 4-354 | 2-F—Ph | c-PrCO | 6-S—S—CH$_2$CH(NH$_2$)COOH |
| 4-355 | 2-F—Ph | MeOCO | 6-S—S—CH$_2$CH(NH$_2$)COOH |
| 4-356 | 2-Cl—Ph | MeOCO | 6-S—S—CH$_2$CH(NH$_2$)COOH |
| 4-357 | 2-Cl—Ph | c-PrCO | 6-S—S—CH$_2$CH(NHGlu)COgly |
| 4-358 | 2-F—Ph | c-PrCO | 6-S—S—CH$_2$CH(NHGlu)COgly |
| 4-359 | 2-F—Ph | MeOCO | 6-S—S—CH$_2$CH(NHGlu)COgly |
| 4-360 | 2-Cl—Ph | MeOCO | 6-S—S—CH$_2$CH(NHGlu)COgly |

TABLE 5

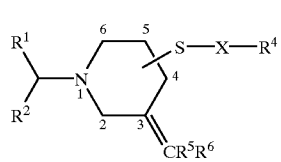

(I-5)

| Exemplified Compound No. | R¹ | R² | —S—X—R⁴ | =CR⁵R⁶ |
|---|---|---|---|---|
| 5-1 | 2-F—Ph | c-PrCO | 4-S—SO$_2$-(4-Me—Ph) | =CHCOOMe |
| 5-2 | 2-Cl—Ph | MeOCO | 4-S—SO$_2$-(4-Me—Ph) | =CHCOOMe |

TABLE 5-continued

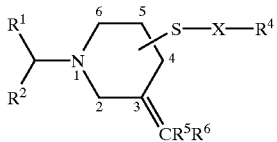

(I-5)

| Exemplified Compound No. | R¹ | R² | —S—X—R⁴ | =CR⁵R⁶ |
|---|---|---|---|---|
| 5-3 | 2-F—Ph | c-PrCO | 4-S—S-(4-Me—Ph) | =CHCOOMe |
| 5-4 | 2-Cl—Ph | MeOCO | 4-S—S-(4-Me—Ph) | =CHCOOMe |
| 5-5 | 2-F—Ph | c-PrCO | 4-S—SO₂-(4-Cl—Ph) | =CHCOOMe |
| 5-6 | 2-Cl—Ph | MeOCO | 4-S—SO₂-(4-Cl—Ph) | =CHCOOMe |
| 5-7 | 2-F—Ph | c-PrCO | 4-S—S-(4-Cl—Ph) | =CHCOOMe |
| 5-8 | 2-Cl—Ph | MeOCO | 4-S—S-(4-Cl—Ph) | =CHCOOMe |
| 5-9 | 2-F—Ph | c-PrCO | 4-S—SO₂-(4-F—Ph) | =CHCOOMe |
| 5-10 | 2-Cl—Ph | MeOCO | 4-S—SO₂-(4-F—Ph) | =CHCOOMe |
| 5-11 | 2-F—Ph | c-PrCO | 4-S—S-(4-F—Ph) | =CHCOOMe |
| 5-12 | 2-Cl—Ph | MeOCO | 4-S—S-(4-F—Ph) | =CHCOOMe |
| 5-13 | 2-F—Ph | c-PrCO | 4-S—SO₂-(4-MeO—Ph) | =CHCOOMe |
| 5-14 | 2-Cl—Ph | MeOCO | 4-S—SO₂-(4-MeO—Ph) | =CHCOOMe |
| 5-15 | 2-F—Ph | c-PrCO | 4-S—S-(4-MeO—Ph) | =CHCOOMe |
| 5-16 | 2-Cl—Ph | MeOCO | 4-S—S-(4-MeO—Ph) | =CHCOOMe |
| 5-17 | 2-F—Ph | c-PrCO | 4-S—SO₂—Ph | =CHCOOMe |
| 5-18 | 2-Cl—Ph | MeOCO | 4-S—SO₂—Ph | =CHCOOMe |
| 5-19 | 2-F—Ph | c-PrCO | 4-S—S—Ph | =CHCOOMe |
| 5-20 | 2-Cl—Ph | MeOCO | 4-S—S—Ph | =CHCOOMe |
| 5-21 | 2-F—Ph | c-PrCO | 4-S—SO₂-(4-NO₂—Ph) | =CHCOOMe |
| 5-22 | 2-Cl—Ph | MeOCO | 4-S—SO₂-(4-NO₂—Ph) | =CHCOOMe |
| 5-23 | 2-F—Ph | c-PrCO | 4-S—S-(4-NO₂—Ph) | =CHCOOMe |
| 5-24 | 2-Cl—Ph | MeOCO | 4-S—S-(4-NO₂—Ph) | =CHCOOMe |
| 5-25 | 2-F—Ph | c-PrCO | 4-S—SO₂—Me | =CHCOOMe |
| 5-26 | 2-Cl—Ph | MeOCO | 4-S—SO₂—Me | =CHCOOMe |
| 5-27 | 2-F—Ph | c-PrCO | 4-S—S—Me | =CHCOOMe |
| 5-28 | 2-F—Ph | c-PrCO | 4-S—SO₂—Et | =CHCOOMe |
| 5-29 | 2-Cl—Ph | MeOCO | 4-S—SO₂—Et | =CHCOOMe |
| 5-30 | 2-F—Ph | c-PrCO | 4-S—S—Et | =CHCOOMe |
| 5-31 | 2-F—Ph | c-PrCO | 4-S—SO₂—Pr | =CHCOOMe |
| 5-32 | 2-Cl—Ph | MeOCO | 4-S—SO₂—Pr | =CHCOOMe |
| 5-33 | 2-F—Ph | c-PrCO | 4-S—SO₂-c-Ph | =CHCOOMe |
| 5-34 | 2-F—Ph | c-PrCO | 4-S—SO₂-c-Hx | =CHCOOMe |
| 5-35 | 2-F—Ph | c-PrCO | 4-S—S—(CH₂)₂COOMe | =CHCOOMe |
| 5-36 | 2-Cl—Ph | MeOCO | 4-S—S—(CH₂)₂COOMe | =CHCOOMe |
| 5-37 | 2-F—Ph | c-PrCO | 4-S—S—CH₂CH(NH₂)COOH | =CHCOOMe |
| 5-38 | 2-Cl—Ph | MeOCO | 4-S—S—CH₂CH(NH₂)COOH | =CHCOOMe |
| 5-39 | 2-F—Ph | c-PrCO | 4-S—S—CH₂CH(NHGlu)COgly | =CHCOOMe |
| 5-40 | 2-Cl—Ph | MeOCO | 4-S—S—CH₂CH(NHGlu)COgly | =CHCOOMe |
| 5-41 | 2-F—Ph | c-PrCO | 4-S—SO₂-(4-Me—Ph) | =CHCOOEt |
| 5-42 | 2-Cl—Ph | MeOCO | 4-S—SO₂-(4-Me—Ph) | =CHCOOEt |
| 5-43 | 2-F—Ph | c-PrCO | 4-S—S-(4-Me—Ph) | =CHCOOEt |
| 5-44 | 2-Cl—Ph | MeOCO | 4-S—S-(4-Me—Ph) | =CHCOOEt |
| 5-45 | 2-F—Ph | c-PrCO | 4-S—SO₂-(4-Cl—Ph) | =CHCOOEt |
| 5-46 | 2-Cl—Ph | MeOCO | 4-S—SO₂-(4-Cl—Ph) | =CHCOOEt |
| 5-47 | 2-F—Ph | c-PrCO | 4-S—S-(4-Cl—Ph) | =CHCOOEt |
| 5-48 | 2-Cl—Ph | MeOCO | 4-S—S-(4-Cl—Ph) | =CHCOOEt |
| 5-49 | 2-F—Ph | c-PrCO | 4-S—SO₂-(4-F—Ph) | =CHCOOEt |
| 5-50 | 2-Cl—Ph | MeOCO | 4-S—SO₂-(4-F—Ph) | =CHCOOEt |
| 5-51 | 2-F—Ph | c-PrCO | 4-S—S-(4-F—Ph) | =CHCOOEt |
| 5-52 | 2-Cl—Ph | MeOCO | 4-S—S-(4-F—Ph) | =CHCOOEt |
| 5-53 | 2-F—Ph | c-PrCO | 4-S—SO₂-(4-MeO—Ph) | =CHCOOEt |
| 5-54 | 2-Cl—Ph | MeOCO | 4-S—SO₂-(4-MeO—Ph) | =CHCOOEt |
| 5-55 | 2-F—Ph | c-PrCO | 4-S—S-(4-MeO—Ph) | =CHCOOEt |
| 5-56 | 2-Cl—Ph | MeOCO | 4-S—S-(4-MeO—Ph) | =CHCOOEt |
| 5-57 | 2-F—Ph | c-PrCO | 4-S—SO₂—Ph | =CHCOOEt |
| 5-58 | 2-Cl—Ph | MeOCO | 4-S—SO₂—Ph | =CHCOOEt |
| 5-59 | 2-F—Ph | c-PrCO | 4-S—S—Ph | =CHCOOEt |
| 5-60 | 2-Cl—Ph | MeOCO | 4-S—S—Ph | =CHCOOEt |
| 5-61 | 2-F—Ph | c-PrCO | 4-S—SO₂-(4-NO₂—Ph) | =CHCOOEt |
| 5-62 | 2-Cl—Ph | MeOCO | 4-S—SO₂-(4-NO₂—Ph) | =CHCOOEt |
| 5-63 | 2-F—Ph | c-PrCO | 4-S—S-(4-NO₂—Ph) | =CHCOOEt |
| 5-64 | 2-Cl—Ph | MeOCO | 4-S—S-(4-NO₂—Ph) | =CHCOOEt |
| 5-65 | 2-F—Ph | c-PrCO | 4-S—SO₂—Me | =CHCOOEt |

TABLE 5-continued (I-5)

$$\text{Structure with piperidine ring: R}^1\text{R}^2\text{CH-N(1), positions 2,3,4,5,6; S-X-R}^4 \text{ at position 4; =CR}^5\text{R}^6 \text{ at position 3}$$

| Exemplified Compound No. | R¹ | R² | —S—X—R⁴ | =CR⁵R⁶ |
|---|---|---|---|---|
| 5-66 | 2-Cl—Ph | MeOCO | 4-S—SO₂—Me | =CHCOOEt |
| 5-67 | 2-F—Ph | c-PrCO | 4-S—S—Me | =CHCOOEt |
| 5-68 | 2-F—Ph | c-PrCO | 4-S—SO₂—Et | =CHCOOEt |
| 5-69 | 2-Cl—Ph | MeOCO | 4-S—SO₂—Et | =CHCOOEt |
| 5-70 | 2-F—Ph | c-PrCO | 4-S—S—Et | =CHCOOEt |
| 5-71 | 2-F—Ph | c-PrCO | 4-S—SO₂—Pr | =CHCOOEt |
| 5-72 | 2-Cl—Ph | MeOCO | 4-S—SO₂—Pr | =CHCOOEt |
| 5-73 | 2-F—Ph | c-PrCO | 4-S—SO₂-c-Pn | =CHCOOEt |
| 5-74 | 2-F—Ph | c-PrCO | 4-S—SO₂-c-Hx | =CHCOOEt |
| 5-75 | 2-F—Ph | c-PrCO | 4-S—S—CH₂CHCOOMe | =CHCOOEt |
| 5-76 | 2-Cl—Ph | MeOCO | 4-S—S—CH₂CHCOOMe | =CHCOOEt |
| 5-77 | 2-F—Ph | c-PrCO | 4-S—S—CH₂CH(NH₂)COOH | =CHCOOEt |
| 5-78 | 2-Cl—Ph | MeOCO | 4-S—S—CH₂CH(NH₂)COOH | =CHCOOEt |
| 5-79 | 2-F—Ph | c-PrCO | 4-S—S—CH₂CH(NHGlu)COgly | =CHCOOEt |
| 5-80 | 2-Cl—Ph | MeOCO | 4-S—S—CH₂CH(NHGlu)COgly | =CHCOOEt |
| 5-81 | 2-F—Ph | c-PrCO | 4-S—SO₂-(4-Me—Ph) | =CHCOOH |
| 5-82 | 2-Cl—Ph | MeOCO | 4-S—SO₂-(4-Me—Ph) | =CHCOOH |
| 5-83 | 2-F—Ph | c-PrCO | 4-S—S-(4-Me—Ph) | =CHCOOH |
| 5-84 | 2-Cl—Ph | MeOCO | 4-S—S-(4-Me—Ph) | =CHCOOH |
| 5-85 | 2-F—Ph | c-PrCO | 4-S—SO₂-(4-Cl—Ph) | =CHCOOH |
| 5-86 | 2-Cl—Ph | MeOCO | 4-S—SO₂-(4-Cl—Ph) | =CHCOOH |
| 5-87 | 2-F—Ph | c-PrCO | 4-S—S-(4-Cl—Ph) | =CHCOOH |
| 5-88 | 2-Cl—Ph | MeOCO | 4-S—S-(4-Cl—Ph) | =CHCOOH |
| 5-89 | 2-F—Ph | c-PrCO | 4-S—SO₂-(4-F—Ph) | =CHCOOH |
| 5-90 | 2-Cl—Ph | MeOCO | 4-S—SO₂-(4-F—Ph) | =CHCOOH |
| 5-91 | 2-F—Ph | c-PrCO | 4-S—S-(4-F—Ph) | =CHCOOH |
| 5-92 | 2-Cl—Ph | MeOCO | 4-S—S-(4-F—Ph) | =CHCOOH |
| 5-93 | 2-F—Ph | c-PrCO | 4-S—SO₂-(4-MeO—Ph) | =CHCOOH |
| 5-94 | 2-Cl—Ph | MeOCO | 4-S—SO₂-(4-MeO—Ph) | =CHCOOH |
| 5-95 | 2-F—Ph | c-PrCO | 4-S—S-(4-MeO—Ph) | =CHCOOH |
| 5-96 | 2-Cl—Ph | MeOCO | 4-S—S-(4-MeO—Ph) | =CHCOOH |
| 5-97 | 2-F—Ph | c-PrCO | 4-S—SO₂—Ph | =CHCOOH |
| 5-98 | 2-Cl—Ph | MeOCO | 4-S—SO₂—Ph | =CHCOOH |
| 5-99 | 2-F—Ph | c-PrCO | 4-S—S—Ph | =CHCOOH |
| 5-100 | 2-Cl—Ph | MeOCO | 4-S—S—Ph | =CHCOOH |
| 5-101 | 2-F—Ph | c-PrCO | 4-S—SO₂-(4-NO₂—Ph) | =CHCOOH |
| 5-102 | 2-Cl—Ph | MeOCO | 4-S—SO₂-(4-NO₂—Ph) | =CHCOOH |
| 5-103 | 2-F—Ph | c-PrCO | 4-S—S-(4-NO₂—Ph) | =CHCOOH |
| 5-104 | 2-Cl—Ph | MeOCO | 4-S—S-(4-NO₂—Ph) | =CHCOOH |
| 5-105 | 2-F—Ph | c-PrCO | 4-S—SO₂—Me | =CHCOOH |
| 5-106 | 2-Cl—Ph | MeOCO | 4-S—SO₂—Me | =CHCOOH |
| 5-107 | 2-F—Ph | c-PrCO | 4-S—S—Me | =CHCOOH |
| 5-108 | 2-F—Ph | c-PrCO | 4-S—SO₂—Et | =CHCOOH |
| 5-109 | 2-Cl—Ph | MeOCO | 4-S—SO₂—Et | =CHCOOH |
| 5-110 | 2-F—Ph | c-PrCO | 4-S—S—Et | =CHCOOH |
| 5-111 | 2-F—Ph | c-PrCO | 4-S—SO₂—Pr | =CHCOOH |
| 5-112 | 2-Cl—Ph | MeOCO | 4-S—SO₂—Pr | =CHCOOH |
| 5-113 | 2-F—Ph | c-PrCO | 4-S—SO₂-c-Pn | =CHCOOH |
| 5-114 | 2-F—Ph | c-PrCO | 4-S—SO₂-c-Hx | =CHCOOH |
| 5-115 | 2-F—Ph | c-PrCO | 4-S—S—(CH₂)₂COOMe | =CHCOOH |
| 5-116 | 2-Cl—Ph | MeOCO | 4-S—S—(CH₂)₂COOMe | =CHCOOH |
| 5-117 | 2-F—Ph | c-PrCO | 4-S—S—CH₂CH(NH₂)COOH | =CHCOOH |
| 5-118 | 2-Cl—Ph | MeOCO | 4-S—S—CH₂CH(NH₂)COOH | =CHCOOH |
| 5-119 | 2-F—Ph | c-PrCO | 4-S—S—CH₂CH(NHGlu)COgly | =CHCOOH |
| 5-120 | 2-Cl—Ph | MeOCO | 4-S—S—CH₂CH(NHGlu)COgly | =CHCOOH |
| 5-121 | 2-F—Ph | c-PrCO | 4-S—SO₂-(4-Me—Ph) | =CHCONH₂ |
| 5-122 | 2-F—Ph | c-PrCO | 4-S—SO₂-(4-Cl—Ph) | =CHCONH₂ |
| 5-123 | 2-F—Ph | c-PrCO | 4-S—SO₂-(4-F—Ph) | =CHCONH₂ |
| 5-124 | 2-F—Ph | c-PrCO | 4-S—SO₂-(4-MeO—Ph) | =CHCONH₂ |

TABLE 5-continued (I-5)

R¹—CH(R²)—N piperidine ring with 4-S—X—R⁴ and 3-=CR⁵R⁶

| Exemplified Compound No. | R¹ | R² | —S—X—R⁴ | =CR⁵R⁶ |
|---|---|---|---|---|
| 5-125 | 2-F—Ph | c-PrCO | 4-S—SO₂—Ph | =CHCONH₂ |
| 5-126 | 2-F—Ph | c-PrCO | 4-S—SO₂—Me | =CHCONH₂ |
| 5-127 | 2-F—Ph | c-PrCO | 4-S—S—(CH₂)₂COOMe | =CHCONH₂ |
| 5-128 | 2-F—Ph | c-PrCO | 4-S—S—CH₂CH(NH₂)COOH | =CHCONH₂ |
| 5-129 | 2-F—Ph | c-PrCO | 4-S—SO₂-(4-Me—Ph) | =CHCONHMe |
| 5-130 | 2-F—Ph | c-PrCO | 4-S—SO₂-(4-Cl—Ph) | =CHCONHMe |
| 5-131 | 2-F—Ph | c-PrCO | 4-S—SO₂-(4-F—Ph) | =CHCONHMe |
| 5-132 | 2-F—Ph | c-PrCO | 4-S—SO₂-(4-MeO—Ph) | =CHCONHMe |
| 5-133 | 2-F—Ph | c-PrCO | 4-S—SO₂—Ph | =CHCONHMe |
| 5-134 | 2-F—Ph | c-PrCO | 4-S—SO₂—Me | =CHCONHMe |
| 5-135 | 2-F—Ph | c-PrCO | 4-S—S—(CH₂)₂COOMe | =CHCONHMe |
| 5-136 | 2-F—Ph | c-PrCO | 4-S—S—CH₂CH(NH₂)COOH | =CHCONHMe |
| 5-137 | 2-F—Ph | c-PrCO | 4-S—SO₂-(4-Me—Ph) | =CHCONHEt |
| 5-138 | 2-F—Ph | c-PrCO | 4-S—SO₂-(4-Cl—Ph) | =CHCONHEt |
| 5-139 | 2-F—Ph | c-PrCO | 4-S—SO₂-(4-F—Ph) | =CHCONHEt |
| 5-140 | 2-F—Ph | c-PrCO | 4-S—SO₂-(4-MeO—Ph) | =CHCONHEt |
| 5-141 | 2-F—Ph | c-PrCO | 4-S—SO₂—Ph | =CHCONHEt |
| 5-142 | 2-F—Ph | c-PrCO | 4-S—SO₂—Me | =CHCONHEt |
| 5-143 | 2-F—Ph | c-PrCO | 4-S—S—(CH₂)₂COOMe | =CHCONHEt |
| 5-144 | 2-F—Ph | c-PrCO | 4-S—S—CH₂CH(NH₂)COOH | =CHCONHEt |
| 5-145 | 2-F—Ph | c-PrCO | 4-S—SO₂-(4-Me—Ph) | =CHCONMe₂ |
| 5-146 | 2-F—Ph | c-PrCO | 4-S—SO₂-(4-Cl—Ph) | =CHCONMe₂ |
| 5-147 | 2-F—Ph | c-PrCO | 4-S—SO₂-(4-F—Ph) | =CHCONMe₂ |
| 5-148 | 2-F—Ph | c-PrCO | 4-S—SO₂-(4-MeO—Ph) | =CHCONMe₂ |
| 5-149 | 2-F—Ph | c-PrCO | 4-S—SO₂—Ph | =CHCONMe₂ |
| 5-150 | 2-F—Ph | c-PrCO | 4-S—SO₂—Me | =CHCONMe₂ |
| 5-151 | 2-F—Ph | c-PrCO | 4-S—S—(CH₂)₂COOMe | =CHCONMe₂ |
| 5-152 | 2-F—Ph | c-PrCO | 4-S—S—CH₂CH(NH₂)COOH | =CHCONMe₂ |
| 5-153 | 2-F—Ph | c-PrCO | 4-S—SO₂-(4-Me—Ph) | =CHMe |
| 5-154 | 2-F—Ph | c-PrCO | 4-S—SO₂-(4-Cl—Ph) | =CHMe |
| 5-155 | 2-F—Ph | c-PrCO | 4-S—SO₂-(4-F—Ph) | =CHMe |
| 5-156 | 2-F—Ph | c-PrCO | 4-S—SO₂-(4-MeO—Ph) | =CHMe |
| 5-157 | 2-F—Ph | c-PrCO | 4-S—SO₂—Ph | =CHMe |
| 5-158 | 2-F—Ph | c-PrCO | 4-S—SO₂—Me | =CHMe |
| 5-159 | 2-F—Ph | c-PrCO | 4-S—S—(CH₂)₂COOMe | =CHMe |
| 5-160 | 2-F—Ph | c-PrCO | 4-S—S—CH₂CH(NH₂)COOH | =CHMe |
| 5-161 | 2-F—Ph | c-PrCO | 4-S—SO₂-(4-Me—Ph) | =CHCOOPr |
| 5-162 | 2-Cl—Ph | MeOCO | 4-S—SO₂-(4-Me—Ph) | =CHCOOPr |
| 5-163 | 2-F—Ph | c-PrCO | 4-S—SO₂-(4-Cl—Ph) | =CHCOOPr |
| 5-164 | 2-Cl—Ph | MeOCO | 4-S—SO₂-(4-Cl—Ph) | =CHCOOPr |
| 5-165 | 2-F—Ph | c-PrCO | 4-S—SO₂-(4-F—Ph) | =CHCOOPr |
| 5-166 | 2-Cl—Ph | MeOCO | 4-S—SO₂-(4-F—Ph) | =CHCOOPr |
| 5-167 | 2-F—Ph | c-PrCO | 4-S—SO₂-(4-MeO—Ph) | =CHCOOPr |
| 5-168 | 2-Cl—Ph | MeOCO | 4-S—SO₂-(4-MeO—Ph) | =CHCOOPr |
| 5-169 | 2-F—Ph | c-PrCO | 4-S—SO₂—Ph | =CHCOOPr |
| 5-170 | 2-Cl—Ph | MeOCO | 4-S—SO₂—Ph | =CHCOOPr |
| 5-171 | 2-F—Ph | c-PrCO | 4-S—SO₂-(4-Me—Ph) | =CHCOOBu |
| 5-172 | 2-Cl—Ph | MeOCO | 4-S—SO₂-(4-Me—Ph) | =CHCOOBu |
| 5-173 | 2-F—Ph | c-PrCO | 4-S—SO₂-(4-Cl—Ph) | =CHCOOBu |
| 5-174 | 2-Cl—Ph | MeOCO | 4-S—SO₂-(4-Cl—Ph) | =CHCOOBu |
| 5-175 | 2-F—Ph | c-PrCO | 4-S—SO₂-(4-F—Ph) | =CHCOOBu |
| 5-176 | 2-Cl—Ph | MeOCO | 4-S—SO₂-(4-F—Ph) | =CHCOOBu |
| 5-177 | 2-F—Ph | c-PrCO | 4-S—SO₂-(4-MeO—Ph) | =CHCOOBu |
| 5-178 | 2-Cl—Ph | MeOCO | 4-S—SO₂-(4-MeO—Ph) | =CHCOOBu |
| 5-179 | 2-F—Ph | c-PrCO | 4-S—SO₂—Ph | =CHCOOBu |
| 5-180 | 2-Cl—Ph | MeOCO | 4-S—SO₂—Ph | =CHCOOBu |
| 5-181 | 2-Cl—Ph | MeOCO | 4-S—SO₂-(4-Me—Ph) | =CHCONHMe |
| 5-182 | 2-Cl—Ph | MeOCO | 4-S—SO₂-(4-Cl—Ph) | =CHCONHMe |
| 5-183 | 2-Cl—Ph | MeOCO | 4-S—SO₂-(4-F—Ph) | =CHCONHMe |
| 5-184 | 2-Cl—Ph | MeOCO | 4-S—SO₂-(4-MeO—Ph) | =CHCONHMe |
| 5-185 | 2-Cl—Ph | MeOCO | 4-S—SO₂—Ph | =CHCONHMe |
| 5-186 | 2-Cl—Ph | MeOCO | 4-S—SO₂—Me | =CHCONHMe |

TABLE 5-continued

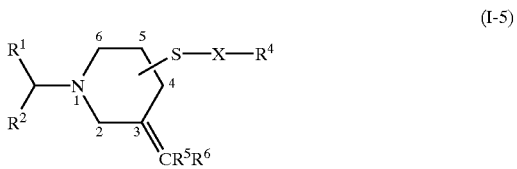

(I-5)

| Exemplified Compound No. | R¹ | R² | —S—X—R⁴ | =CR⁵R⁶ |
|---|---|---|---|---|
| 5-187 | 2-Cl—Ph | MeOCO | 4-S—SO₂—(CH₂)₂COOMe | =CHCONHMe |
| 5-188 | 2-Cl—Ph | MeOCO | 4-S—SO₂—CH₂CH(NH₂)COOH | =CHCONHMe |
| 5-189 | 2-Cl—Ph | MeOCO | 4-S—SO₂-(4-Me—Ph) | =CHCONMe₂ |
| 5-190 | 2-Cl—Ph | MeOCO | 4-S—SO₂-(4-Cl—Ph) | =CHCONMe₂ |
| 5-191 | 2-Cl—Ph | MeOCO | 4-S—SO₂-(4-F—Ph) | =CHCONMe₂ |
| 5-192 | 2-Cl—Ph | MeOCO | 4-S—SO₂-(4-MeO—Ph) | =CHCONMe₂ |
| 5-193 | 2-Cl—Ph | MeOCO | 4-S—SO₂—Ph | =CHCONMe₂ |
| 5-194 | 2-Cl—Ph | MeOCO | 4-S—SO₂—Me | =CHCONMe₂ |
| 5-195 | 2-Cl—Ph | MeOCO | 4-S—SO₂—(CH₂)₂COOMe | =CHCONMe₂ |
| 5-196 | 2-Cl—Ph | MeOCO | 4-S—SO₂—CH₂CH(NH₂)COOH | =CHCONMe₂ |
| 5-197 | 2-Cl—Ph | MeOCO | 4-S—S—(CH₂)₂COOMe | =CHCONHMe |
| 5-198 | 2-Cl—Ph | MeOCO | 4-S—S—CH₂CH(NH₂)COOH | =CHCONHMe |
| 5-199 | 2-Cl—Ph | MeOCO | 4-S—S—(CH₂)₂COOMe | =CHCONMe₂ |
| 5-200 | 2-Cl—Ph | MeOCO | 4-S—S—CH₂CH(NH₂)COOH | =CHCONMe₂ |

In the Tables, preferred compounds are exemplified compounds numbers 1-2, 1-6, 1-7, 1-10, 1-12, 1-13, 1-14, 1-16, 1-17, 1-20, 1-22, 1-27, 1-30, 1-32, 1-34, 1-36, 1-37, 1-40, 1-42, 1-47, 1-50, 1-52, 1-54, 1-56, 1-57, 1-60, 1-62, 1-67, 1-70, 1-72, 1-74, 1-76, 1-77, 1-80, 1-81, 1-82, 1-83, 1-84, 1-86, 1-87, 1-89, 1-90, 1-109, 1-110, 1-112, 1-114, 1-122, 1-124, 1-139, 1-140, 1-142, 1-144, 1-145, 1-146, 1-152, 1-154, 1-182, 1-184, 1-189, 1-192, 1-194, 1-199, 1-202, 1-204, 1-206, 1-210, 1-214, 1-216, 1-222, 1-225, 1-230, 1-234, 1-236, 1-238, 1-242, 1-244, 1-250, 1-252, 1-258, 1-260, 1-266, 1-268, 1-274, 1-276, 1-301, 1-305, 1-315, 1-318, 1-354, 1-356, 2-2, 2-7, 2-10, 2-12, 2-14, 2-16, 2-17, 2-20, 2-22, 2-27, 2-30, 2-32, 2-34, 2-36, 2-37, 2-40, 2-42, 2-47, 2-50, 2-52, 2-54, 2-56, 2-57, 2-60, 2-62, 2-67, 2-70, 2-72, 2-74, 2-76, 2-77, 2-80, 2-82, 2-84, 2-86, 2-89, 2-109, 2-112, 2-114, 2-122, 2-124, 2-139, 2-140, 2-142, 2-144, 2-145, 2-152, 2-154, 2-182, 2-192, 2-202, 2-206, 2-210, 2-214, 2-222, 2-230, 2-234, 2-236, 2-238, 3-7, 3-12, 3-17, 3-20, 3-27, 3-32, 3-37, 3-40, 3-47, 3-52, 3-57, 3-60, 3-67, 3-72, 3-77, 3-80, 3-82, 3-84, 3-86, 3-89, 3-109, 3-122, 3-124, 3-139, 3-142, 3-144, 3-145, 3-152, 3-182, 3-192, 3-202, 3-206, 3-210, 3-214, 3-234, 3-236, 3-238, 4-2, 4-4, 4-10, 4-12, 4-18, 4-20, 4-26, 4-28, 4-36, 4-61, 4-65, 4-75, 4-78, 4-114, 4-116, 5-1, 5-2, 5-5, 5-6, 5-9, 5-10, 5-13, 5-14, 5-17, 5-25, 5-35, 5-37, 5-39, 5-41, 5-42, 5-45, 5-46, 5-49, 5-50, 5-53, 5-54, 5-57, 5-65, 5-75, 5-77, 5-79, 5-81, 5-82, 5-85, 5-86, 5-89, 5-90, 5-93, 5-94, 5-97, 5-105, 5-115, 5-117, 5-119, 5-121, 5-125, 5-126, 5-129, 5-133, 5-134, 5-137, 5-141, 5-145, 5-149, 5-150, 5-153, 5-157, 5-158, 5-161, 5-162, 5-169, 5-170, 5-171, 5-172, 5-179, 5-180, 5-181, 5-185, 5-186, 5-189, 5-193 and 5-194.

More preferred compounds are exemplified compounds numbers 1-2, 1-7, 1-10, 1-12, 1-14, 1-16, 1-17, 1-20, 1-22, 1-27, 1-30, 1-32, 1-34, 1-36, 1-37, 1-40, 1-42, 1-47, 1-50, 1-52, 1-54, 1-56, 1-57, 1-60, 1-62, 1-67, 1-70, 1-72, 1-74, 1-76, 1-77, 1-80, 1-81, 1-82, 1-83, 1-84, 1-86, 1-87, 1-89, 1-90, 1-109, 1-110, 1-122, 1-124, 1-139, 1-140, 1-142, 1-144, 1-145, 1-146, 1-182, 1-189, 1-192, 1-199, 1-202, 1-206, 1-210, 1-214, 1-216, 1-234, 2-7, 2-14, 2-17, 2-20, 2-27, 2-32, 2-37, 2-40, 2-47, 2-52, 2-57, 2-60, 2-67, 2-72, 2-77, 2-80, 2-82, 2-84, 2-86, 2-89, 2-109, 2-122, 2-124, 2-142, 2-144, 2-145, 2-202, 2-206, 2-210, 2-214, 2-234, 3-7, 3-12, 3-17, 3-20, 3-27, 3-32, 3-37, 3-40, 3-47, 3-52, 3-57, 3-60, 3-67, 3-72, 3-77, 3-80, 3-82, 3-84, 3-86, 3-89, 3-109, 3-122, 3-124, 3-142, 3-144, 3-145, 3-202, 3-206, 3-210, 3-214, 3-234, 5-1, 5-2, 5-5, 5-9, 5-13, 5-17, 5-37, 5-41, 5-42, 5-45, 5-49, 5-53, 5-57, 5-65, 5-77, 5-81, 5-82, 5-85, 5-89, 5-93, 5-97, 5-117, 5-121, 5-129, 5-137, 5-145, 5-153, 5-161, 5-162, 5-171, 5-172, 5-181 and 5-189.

Still more preferred compounds are exemplified compounds numbers 1-7, 1-10, 1-12, 1-14, 1-17, 1-27, 1-32, 1-34, 1-37, 1-47, 1-52, 1-54, 1-57, 1-67, 1-72, 1-74, 1-77, 1-82, 1-84, 1-86, 1-109, 1-139, 1-142, 1-145, 1-146, 1-189, 1-199, 1-210, 2-7, 2-14, 2-27, 2-32, 2-47, 2-52, 2-67, 2-72, 2-82, 2-142, 3-7, 3-12, 3-27, 3-32, 3-47, 3-52, 3-67, 3-72, 3-82, 3-142, 5-2, 5-5, 5-9, 5-13, 5-17, 5-41, 5-42, 5-45, 5-49, 5-53, 5-57, 5-65, 5-81, 5-82, 5-85, 5-89, 5-93, 5-97, 5-117, 5-129, 5-145, 5-171, 5-172, 5-181 and 5-189.

Of which, the following compounds are particularly preferred:

Exemplified Compound No. 1-7: 1-(α-cyclopropylcarbonyl-2-fluorobenzyl)-4-(4-methylphenylsulfonylthio)piperidine, Exemplified Compound No. 1-10: 1-(2-fluoro-α-methoxycarbonylbenzyl)-4-(4-methylphenylsulfonylthio)piperidine, Exemplified Compound No. 1-12: 1-(2-chloro-α-methoxycarbonylbenzyl)-4-(4-methylphenylsulfonylthio)piperidine, Exemplified Compound No. 1-14: 1-(α-cyclopropylcarbonyl-2-fluorobenzyl)-4-(4-methylphenylsulfinylthio)piperidine, Exemplified Compound No. 1-17: 1-(α-cyclopropylcarbonyl-2-fluorobenzyl)-4-(4-methylphenyldisulfanil)piperidine, Exemplified Compound No. 1-27: 4-(4-chlorophenylsulfonylthio)-1-(α-cyclopropylcarbonyl-2-fluorobenzyl)piperidine, Exemplified Compound No. 1-47: 1-(α-cyclopropylcarbonyl-2-fluorobenzyl)-4-(4-fluorophenylsulfonylthio)piperidine;

Exemplified Compound No. 1-67: 1-(α-cyclopropylcarbonyl-2-fluorobenzyl)-4-(4-methoxyphenylsulfonylthio)piperidine, Exemplified Compound No. 1-82: 1-(α-cyclopropylcarbonyl-2-fluorobenzyl)-4-phenylsulfonylthiopiperidine, Exemplified Compound No. 1-109: 1-(α-cyclopropylcarbonyl-2-fluorobenzyl)-4-(2-nitrophenyldisulfanil)piperidine;

Exemplified Compound No. 1-139: 1-(α-cyclopropylcarbonyl-2-fluorobenzyl)-4-(2,4-dinitrophenyldisulfanil)piperidine, Exemplified Compound No. 1-142: 1-(α-cyclopropylcarbonyl-2-fluorobenzyl)-4-methylsulfonylthiopiperidine, Exemplified Compound No. 1-146: 1-(α-cyclopropylcarbonyl-2-fluorobenzyl)-4-methylsulfinylthiopiperidine, Exemplified Compound No. 1-210: 1-(α-cyclopropylcarbonyl-2-fluorobenzyl)-4-(2-methoxycarbonylethyldisulfanil)piperidine, Exemplified Compound No. 2-7: 1-(α-cyclopropylcarbonyl-2-fluorobenzyl)-3-(4-methylphenylsulfonylthio)pyrrolidine, Exemplified Compound No. 2-14: 1-(α-cyclopropylcarbonyl-2-fluorobenzyl)-3-(4-methylphenylsulfinylthio)pyrrolidine, Exemplified Compound No. 3-7: 1-(α-cyclopropylcarbonyl-2-fluorobenzyl)-3-(4-methylphenylsulfonylthio)azetidine, Exemplified Compound No. 5-2: (E)-1-(2-chloro-α-methoxycarbonylbenzyl)-3-methoxycarbonylmethylidene-4-(4-methylphenylsulfonylthio)piperidine, Exemplified Compound No. 5-41: (E)-1-(α-cyclopropylcarbonyl-2-fluorobenzyl)-3-ethoxycarbonylmethylidene-4-(4-methylphenylsulfonylthio)piperidine, Exemplified Compound No. 5-42: (E)-1-(2-chloro-α-methoxycarbonylbenzyl)-3-ethoxycarbonylmethylidene-4-(4-methylphenylsulfonylthio)piperidine, and Exemplified Compound No. 5-117: (Z)-4-[(R)-2-amino-2-carboxyethyldisulfanil]-3-carboxymethylidene-1-(α-cyclopropylcarbonyl-2-fluorobenzyl)piperidine The compounds of the formula (I) according to the present invention are prepared by the process as described below.

Process A

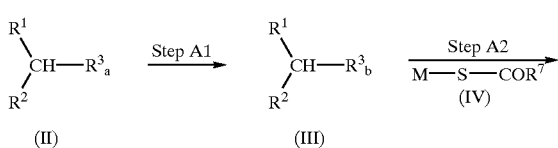

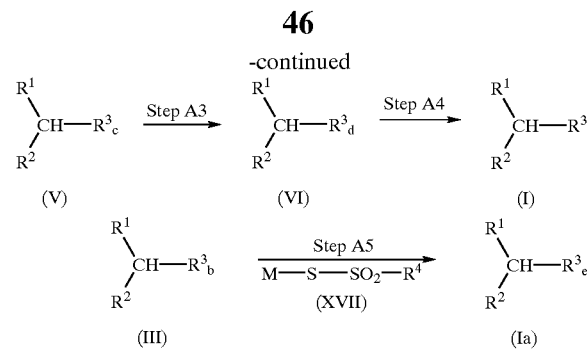

wherein, $R^1$, $R^2$, $R^3$ and $R^4$ have the same meanings as described above.

$R^3a$ represents a substituted, 3- to 7-membered, saturated cyclic amino group which may optionally have a fused ring [the essential substituent of said group being a hydroxyl group, while the optional substituent of said group being a group having the formula of $=CR^5aR^6a$ (wherein, $R^5a$ and $R^6a$ have the same meanings as $R^5$ and $R^6$, respectively, except a carboxyl group)], $R^3b$ has the same meaning as $R^3a$ except that the hydroxyl group is replaced with a halogen atom (preferably, a chlorine or bromine atom), a substituted or unsubstituted $C_1$–$C_4$ alkanesulfonyloxy group (the substituent being a halogen atom, and preferably, a methanesulfonyloxy group) or a substituted or unsubstituted benzenesulfonyloxy group (the substituent being a halogen atom, $C_1$–$C_4$ alkyl group, $C_1$–$C_4$ alkoxy group or nitro group, of which a chlorine atom, methyl group, methoxy group or nitro group is preferred and a p-methyl or p-nitro group is particularly preferred), $R^3c$ has the same meaning as $R^3a$ except that the hydroxyl group is replaced with a group having the formula of —S—COR$^7$ (wherein, $R^7$ represents a $C_1$–$C_4$ alkyl group (with a methyl group being particularly preferred)], $R^3d$ has the same meaning as $R^3$ except for the use of a mercapto group as the essential substituent, $R^3e$ represents a substituted, 3- to 7-membered, saturated cyclic amino group which may optionally have a fused ring [the essential substituent of said group being a group of the formula —S—SO$_2$—R$^4$ and the optical substituent of said group being a group of the formula $=CR^5aR^6a$ (wherein, $R^5a$ and $R^6a$ have the same meanings as described above)], and M stands for an alkali metal atom (such as lithium, sodium or potassium, of which sodium or potassium are preferred).

Process A is for the preparation of each of the compounds (I).

Step A1 is for the preparation of a compound represented by the formula (III) which step is accomplished by reacting a compound represented by the formula (II) with a halogenating agent or sulfonylating agent.

Examples of the halogenating agent usable here include thionyl halides such as thionyl chloride and thionyl bromide, phosphorus trihalides such as phosphorus trichloride and phosphorus tribromide, phosphorous pentahalides such as phosphorus pentachloride and phosphorus pentabromide, phosphorus oxyhalides such as phosphorus oxychloride and phosphorus oxybromide, and tri(phenyl which may be substituted with a $C_1$–$C_4$ alkyl)phosphine-carbon tetrahalides such as triphenylphosphine-carbon tetrachloride, tritolylphosphine-carbon tetrachloride and triphenylphosphine-carbon tetrabromide, of which thionyl chloride, phosphorus trichloride, phosphorus tribromide, phosphorus pentachloride, triphenylphosphine-carbon tetrachloride, tritolylphosphine-carbon tetrachloride and triphenylphosphine-carbon tetrabromide are preferred; and thionyl chloride, triphenylphosphine-carbon tetrachloride and triphenylphosphine-carbon tetrabromide are particularly preferred.

Examples of the sulfonylating agent usable here include substituted or unsubstituted $C_1$–$C_4$ alkanesulfonyl halides (the substituent being a halogen atom), substituted or unsubstituted $C_1$–$C_4$ alkanesulfonic anhdyrides (the substituents being a halogen atom) and benzenesulfonyl halides which may be substituted, of which the substituted or unsubstituted $C_1$–$C_4$ alkanesulfonyl chlorides (the substituent being a fluorine atom), substituted or unsubstituted $C_1$–$C_4$ alkanesulfonyl bromides (the substituent being a fluorine atom), substituted or unsubstituted $C_1$–$C_4$ alkanesulfonic anhydrides (the substituent being a fluorine atom), benzenesulfonyl chloride which may be substituted and benzenesulfonyl bromide which may be substituted are preferred; the $C_1$–$C_2$ alkanesulfonyl chlorides, trifluoromethanesulfonyl chloride, $C_1$–$C_2$ alkanesulfonic anhydrides, trifluoromethanesulfonic anhydride, benzenesulfonyl chloride, toluenesulfonyl chloride and nitrobenzenesulfonyl bromide are more preferred; and methanesulfonyl chloride, trifluoromethanesulfonyl chloride, benzenesulfonyl chloride and p-toluenesulfonyl chloride are particularly preferred.

The reaction of the compound (II) with the halogenating agent is carried out in the presence or absence (preferably, in the presence) of an inert solvent. There is no particular limitation on the nature of the inert solvent to be employed in the above-described reaction provided that it does not take part in the reaction. Examples include hydrocarbons such as hexane, benzene and toluene, halogenated hydrocarbons such as dichloromethane, chloroform, carbon tetrachloride and 1,2-dichloroethane, ethers such as diethyl ether, tetrahydrofuran and dioxane, ketones such as acetone and methyl ethyl ketone, nitriles such as acetontrile, amides such as N,N-dimethylformamide, N,N-dimethylacetamide and N-methyl-2-pyrrolidone and hexamethylphosphoramide, and sulfoxides such as dimethyl sulfoxide; and mixed solvents thereof, of which the ethers and halogenated hydrocarbons are preferred.

Although the reaction temperature depends on the nature of the raw material compound (II), halogenating agent and solvent, it usually ranges from −10° C. to 200° C. (preferably, from 0 to 100° C.). The reaction time ranges from 30 minutes to 24 hours (preferably from 1 to 12 hours), though depending on the reaction temperature and the like.

The compound (II and the sulfonylating agent are reacted in an inert solvent in the presence or absence (preferably in the presence) of a base and an inert solvent similar to those used for the above-described reaction of the compound (II) with the halogenating agent are usable here.

Examples of the base usable in this reaction include alkali metal hydroxides such as lithium hydroxide, sodium hydroxide and potassium hydroxide; alkali metal carbonates such as lithium carbonate, sodium carbonate and potassium carbonate; alkali metal bicarbonates such as sodium bicarbonate and potassium bicarbonate; alkali metal alkoxides such as lithium methoxide, sodium methoxide, sodium ethoxide and potassium t-butoxide; and organic amines such as triethylamine, tributylamine, ethyldiisopropylamine, N-methylmorpholine, pyridine, 4-dimethylaminopyridine, picoline, lutidine, collidine, 1,5-diazabicyclo[4.3.0]-5-nonene and 1,8-diazabicyclo[5.4.0]-7-undecene, of which the alkali metal carbonates and organic amines are preferred; and sodium carbonate, potassium carbonate, triethylamine, tributylamine, ethyldiisopropylamine, pyridine and lutidine are particularly preferred. When the organic amine is used in the liquid form, it can be used in a large excess for serving also as a solvent.

Although the reaction temperature depends on the nature of the raw material compound (II), sulfonylating agent and solvent, it usually ranges from −10° C. to 100° C. (preferably, from 0 to 50° C.). The reaction time ranges from 30 minutes to 24 hours (preferably from 1 to 10 hours), though depending on the reaction temperature and the like.

After completion of the reaction, the desired compound of each of the reactions is collected from the reaction mixture in a conventional manner, for example, by filtering off insoluble matter, if any, as needed, and distilling off the solvent under reduced pressure; or by distilling off the solvent under reduced pressure, adding water to the residue, extracting the mixture with a water immiscible organic solvent such as ethyl acetate, drying over anhydrous magnesium sulfate and distilling off the solvent. If necessary, the residue can be purified further in a conventional manner such as recrystallization or column chromatography.

Step A2 is a step for preparing a compound of the formula (V), which step is accomplished by reacting the compound (III) with a compound of the formula (IV) in an inert solvent.

There is no particular limitation on the nature of the inert solvent to be employed in the above-described reaction provided that it does not adversely affect the reaction. Examples include ethers such as diethyl ether, tetrahydrofuran and dioxane; ketones such as acetones and methyl ethyl ketone, esters such as ethyl acetate and butyl acetate, alcohols such as methanol, ethanol, propyl alcohol, isopropyl alcohol and butyl alcohol; nitriles such as acetonitrile; amides such as N,N-dimethylformamide, N,N-dimethylacetamide, N-methyl-2-pyrrolidone and hexamethylphosphoramide; and sulfoxides such as dimethyl sulfoxide; and mixed solvents thereof. Preferred are the alcohols, amides and sulfoxides.

Although the reaction temperature depends on the nature of the raw material compound (III), raw material compound (IV) and solvent, it usually ranges from 0 to 200° C. (preferably from 20 to 150° C.). The reaction time ranges from 30 minutes to 24 hours (preferably, from 1 to 12 hours), though depending on the reaction temperature and the like.

After completion of the reaction, the desired compound of this reaction is collected from the reaction mixture in a conventional manner, for example, by filtering off insoluble matter, if any, as needed and then distilling off the solvent under reduced pressure; or by distilling off the solvent under reduced pressure, adding water to the residue, extracting the mixture with a water immiscible organic solvent such as ethylene acetate, drying over anhydrous magnesium sulfate and distilling off the solvent. If necessary, the residue can be purified further in a conventional manner such as recrystallization or column chromatography.

Step A3 is a step for the preparation of a compound represented by the formula (IV), which step comprises:

Reaction (a) for converting the group which is contained in $R^3c$ and has the formula —S—$COR^7$ (wherein, $R^7$ has the same meaning as described above) into a mercapto group, and if necessary, Reaction (b) for converting the alkoxycarbonyl group contained in $R^3c$ into a carboxyl group or another alkoxycarbonyl group, and Reaction (c) for isomerizing the cis/trans form based on the double bond contained in $R^3c$. These reactions are conducted in the order changed as needed.

Reaction (a):

The conversion of the group having the formula of —S—$COR^7$ (wherein $R^7$ has the same meaning as described above) into a mercapto group in this Reaction (a) is attained by subjecting the corresponding compound to hydrolysis or alcoholysis by using an acid or alkali (preferably, the acid). It is carried out in a manner well known in organic synthetic chemistry.

Reaction (a) and Reaction (b) which will be described later can be conducted simultaneously by selecting the reaction conditions (temperature, nature of the acid or alkali, using amount thereof, solvent, and the like) for this hydrolysis as needed.

Examples of the acid usable for this reaction include inorganic acids such as hydrogen chloride, nitric acid, hydrochloric acid and sulfuric acid and organic acids such as acetic acid, trifluoroacetic acid, methanesulfonic acid and p-toluenesulfonic acid, of which hydrogen chloride, hydrochloride acid, sulfuric acid and trifluoroacetic acid are preferred, and hydrogen chloride and hydrochloric acid are particularly preferred.

Examples of the alkali usable for this reaction include alkali metal hydroxides such as sodium hydroxide and potassium hydroxide, alkali metal carbonates such as sodium carbonate and potassium carbonate and alkali metal bicarbonates such as sodium bicarbonate and potassium bicarbonate, of which the alkali metal hydroxides (particularly, sodium hydroxide) are preferred.

There is not particular limitation on the nature of the inert solvent to be employed in the above-described reaction provided that it does not adversely affect the reaction. Examples include hydrocarbons such as hexane, benzene and toluene, halogenated hydrocarbons such as dichloromethane, chloroform, carbon tetrachloride and 1,2-dichloroethane, ethers such as diethyl ether, tetrahydrofuran and dioxane, ketones such as acetone and methyl ethyl ketone, alcohols such as methanol, ethanol, propyl alcohol, isopropyl alcohol and butyl alcohol, carboxylic acids such as formic acid, acetic acid, propionic acid and butanoic acid, and water; and mixed solvents thereof. For hydrolysis with the acid, the alcohols, carboxylic acids and water and mixed solvents thereof are preferred, while for hydrolysis by using the alkali, the alcohols and water are preferred.

Although the reaction temperature differs with the nature of the raw material compound (V), acid, alkali and solvent, it usually ranges from −10 to 70° C. (preferably from 0 to 50° C.). The reaction time ranges from 30 minutes to 20 days (preferably from 1 hour to 12 days), though depending on the reaction temperature and the like.

After completion of the reaction, the desired compound of the reaction is collected from the reaction mixture in a conventional manner, for example, by filtering off insoluble matter, if any, as needed, neutralizing the reaction mixture as needed if it is acidic or alkaline, and distilling off the solvent under reduced pressure; or by distilling off the solvent under reduced pressure, adding water to the residue; extracting the mixture with a water immiscible organic solvent such as ethyl acetate, drying over anhydrous magnesium sulfate and then distilling off the solvent. If necessary, the residue can be purified further in a conventional manner such as recrystallization or column chromatography.

Reaction (b):

Reaction (b) for converting the alkoxycarbonyl group contained in $R^3c$ into a carboxyl group is conducted in a similar manner to Reaction (a) for converting the group having the formula of —S—$COR^7$ (wherein, $R^7$ has the same meaning as described above) into a mercapto group. When $R^3c$ and $R^2$ both contain an alkoxycarbonyl group, the alkoxycarbonyl group contained in $R^3c$ can selectively be converted into a carboxyl group after being distinguished from that contained in $R^2$ by properly selecting hydrolysis conditions or by using a compound different in the alkoxy part between $R^2$ and $R^3c$ (for example, by using a compound containing as $R^2$ a methoxycarbonyl or ethoxycarbonyl group and containing, as the alkoxycarbonyl group contained in $R^3c$, a t-butoxycarbonyl group) and conducting this reaction under acidic conditions.

The conversion of the alkoxycarbonyl group contained in $R^3c$ into another alkoxycarbonyl group is conducted easily by reacting it under the conditions similar to the above-described ones (preferably, acidic conditions, more preferably, in the presence of hydrogen chloride) in a solvent of a desired alcohol.

In general, Reaction (b) requires more severe conditions than Reaction (a) so that Reaction (a) and Reaction (b) can be conducted simultaneously by reacting the compound (V) under the conditions of Reaction (b).

After completion of the reaction, the desired compounds of this reaction are collected respectively from the reaction mixture in a conventional manner. In the reaction to convert the alkoxycarbonyl group into a carboxyl group, the desired compound is obtainable by collecting it through filtration as needed when it can be precipitated or it can be precipitated by distilling off the solvent under reduced pressure; or by distilling off the solvent under reduced pressure, adding an acid to adjust the pH of the solution to acidic, extracting with a water immiscible organic solvent such as ethyl acetate, drying over anhydrous magnesium sulfate and then distilling off the solvent. If necessary, the residue can be purified further in a conventional manner such as recrystallization or column chromatography. In the reaction to convert the alkoxycarbonyl group into another alkoxycarbonyl group, on the other hand, the desired compound is obtainable by removing insoluble matter, if any, as needed, neutralizing the reaction mixture as needed if the reaction mixture is acidic or alkaline and distilling off the solvent under reduced pressure; or by distilling off the solvent under reduced pressure, adding water to the residue, extracting the resulting mixture from a water immiscible organic solvent such as ethyl acetate, drying over anhydrous magnesium sulfate and then distilling off the solvent. If necessary, the residue can be purified further in a conventional manner such as recrystallization or column chromatography.

Reaction (c):

Reaction (c) for isomerizing the cis/trans form based on the double bond contained in $R^3c$ is conducted by exposing the corresponding compound to light in an inert solvent in the presence or absence (preferably, in the absence) of a sensitizer.

A light source for exposure is a low-pressure mercury lamp (from 20 W to 100 W, preferably 32 W) and examples of the sensitizer include benzophenone, fluorenone and anthraquinone.

The present reaction can be conducted by adding an organic sulfur compound such as dimethyl disulfide, diethyl disulfide or diphenyl disulfide for the purpose of accelerating the reaction and/or suppressing side reactions.

There is no particular limitation on the nature of the inert solvent to be employed in the above-described reaction provided that it does not adversely affect the reaction. Examples include ethers such as diethyl ether, tetrahydrofuran and dioxane, esters such as ethyl acetate and butyl acetate, alcohols such as methanol, ethanol, propyl alcohol, isopropyl alcohol and butyl alcohol, nitriles such as acetonitrile, amides such as N,N-dimethylformamide, N,N-dimethylacetamide, N-methyl-2-pyrrolidone and hexamethylphosphoramide, sulfoxides such as dimethyl sulfoxide and water; and mixed solvents thereof. Preferred are water, alcohols and nitriles, and mixed solvents thereof.

Although the reaction temperature depends on the nature of the raw material compound, light source and solvent, it usually ranges from −20 to 100° C. (preferably 0 to 50° C.). The reaction time ranges from 5 minutes to 8 hours (preferably, from 10 minutes to 3 hours), although depending on the reaction temperature and the like.

After completion of the reaction, the desired compound of the present reaction is collected from the reaction mixture in a conventional manner, for example, by removing insoluble matter, if any, by filtration as needed and distilling off the solvent under reduced pressure; or by distilling off the solvent under reduced pressure, adding water to the residue, extracting the mixture from a water immiscible organic solvent such as ethyl acetate, drying over anhydrous magnesium sulfate and then distilling off the solvent. If necessary, the residue can be purified further in a conventional manner such as recrystallization or column chromatography.

Step A4 is a step for preparing the desired compound having the formula (I), which can be roughly classified into:

Reaction (d): for sulfonylating the mercapto group contained in $R^3d$ to obtain a sulfonylthio group, Reaction (e): for sulfinylating the mercapto group contained in $R^3d$ to obtain a sulfinylthio group, and Reaction (f): for sulfenylating the mercapto group contained in $R^3d$ to obtain a disulfanyl group.

Reaction (d):

The sulfonylation in Reaction (d) is conducted by reacting the compound (VI) with a compound having the formula of $R^4SO_2Y$ [wherein, $R^4$ has the same meaning as described above, and Y represents a halogen atom (preferably, a chlorine or bromine atom)] in an inert solvent in the presence or absence (preferably, in the presence) of a base.

There is no particular limitation on the nature of the inert solvent to be employed in the above-described reaction provided that it does not adversely affect the reaction. Examples include hydrocarbons such as hexane, benzene and toluene, halogenated hydrocarbons such as dichloromethane, chloroform, carbon tetrachloride and 1,2-dichloroethane; ethers such as diethyl ether, tetrahydrofuran and dioxane; ketones such as acetone and methyl ethyl ketone; nitriles such as acetonitrile; amides such as N,N-dimethylformamide, N,N-dimethylacetamide, N-methyl-2-pyrrolidone and hexamethylphosphoramide; and sulfoxides such as dimethyl sulfoxide; and mixed solvents thereof. Preferred are the halogenated hydrocarbons, hydrocarbons and ethers.

Examples of the base usable in this reaction include alkali metal carbonates such as lithium carbonate, sodium carbonate and potassium carbonate; alkali metal alkoxides such as lithium methoxide, sodium methoxide, sodium ethoxide and potassium t-butoxide; and organic amines such as triethylamine, tributylamine, ethyldiisopropylamine, N-methylmorpholine, pyridine, 4-dimethylaminopyridine, picoline, lutidine, collidine, 1,5-diazabicyclo[4.3.0]-5-nonene, and 1,8-diazabicyclo[5.4.0]-7-undecene, of which the alkali metal alkoxides and organic amines are preferred; sodium methoxide, sodium ethoxide, triethylamine, tributylamine, ethyldiisopropylamine, N-methylmorpholine and pyridine are more preferred; and triethylamine, tributylamine and ethyldiisopropylamine are particularly preferred.

The compound $R^4SO_2Y$ is usually added in a molar amount 1 to 15 times, preferably, in a molar amount 1 to 10 times, relative to the compound (VI).

Although the reaction temperature differs with the nature of the compound $R^4SO_2Y$ and the like, it usually ranges from −10 to 100° C. (preferably from 0 to 50° C.). The reaction time ranges from 30 minutes to 24 hours (preferably, from 1 to 12 hours), though depending on the reaction temperature and the like.

After completion of the reaction, the desired compound of this reaction is collected from the reaction mixture in a conventional manner, for example, by removing insoluble matter, if any, by filtration as needed, and distilling off the solvent under reduced pressure; or by distilling off the solvent under reduced pressure, adding water to the residue, extracting the mixture with a water immiscible organic solvent such as ethyl acetate, drying over anhydrous magnesium sulfate and then distilling off the solvent. If necessary, the residue can be purified further in a conventional manner such as recrystallization or column chromatography.

Reaction (e):

The sulfinylation in Reaction (e) is conducted by reacting the compound (VI) with a compound having the formula of $R^4SO_2H$ [wherein, $R^4$ has the same meaning as described above] or an alkali metal salt thereof in an inert solvent in the presence of a condensing agent, or by reacting the compound (VI) with a compound having the formula of $R^4SOY$ [wherein, $R^4$ and Y have the same meanings as described above] in an inert solvent in the presence of a base.

The reaction between the compound (VI) with the compound $R^4SO_2H$ is usually conducted using the compound $R^4SO_2H$ in an molar amount 1 to 5 times (preferably, in a molar amount 1 to 3 times) relative to the raw material compound (VI). As the condensing agent, dicyclohexylcarbodiimide or 1-ethyl-3-(3-dimethylaminopropyl)carbodiimide is preferably employed and it is used in an equimolar amount relative to the compound $R^4SO_2H$.

There is no particular limitation on the nature of the inert solvent to be employed in the above-described reaction provided that it does not adversely affect the reaction. Examples include halogenated hydrocarbons such as dichloromethane, chloroform, carbon tetrachloride and 1,2-dichloroethane; ethers such as diethyl ether, tetrahydrofuran, dioxane, dimethoxyethane and diethoxyethane; nitriles such as acetonitrile; amides such as N,N-dimethylformamide, N,N-dimethylacetamide, N-methyl-2-pyrrolidone and hexamethylphopshoramide; and sulfoxides such as dimethyl sulfoxide; and mixed solvents thereof. Preferred are the halogenated hydrocarbons, ethers and amides.

The reaction temperature usually ranges from −10 to 100° C. (preferably from 0 to 50° C.). The reaction time ranges from 30 minutes to 24 hours (preferably, from 1 to 12 hours), although depending on the reaction temperature and the like.

The reaction between the compound (VI) and the compound $R_4SOY$ is conducted under similar reaction conditions to those of Reaction (d) except for the use of the compound $R_4SOY$ instead of the compound $R_4SO_2Y$.

After completion of the reaction, the desired compound of each of the reactions is collected from the reaction mixture in a conventional manner, for example, by removing insoluble matter, if any, by filtration as needed and distilling off the solvent under reduced pressure; or by distilling off the solvent under reduced pressure, adding water to the residue; extracting the mixture with a water immiscible organic solvent such as ethyl acetate, drying over anhydrous magnesium sulfate and then distilling off the solvent. If necessary, the residue can be purified further in a conventional manner such as recrystallization or column chromatography.

Reaction (f):

The sulfenylation in Reaction (f) is conducted selecting as needed from a process of reacting the compound (VI) with a compound having the formula of R⁴SYa [wherein, R⁴ has the same meaning as described above, Ya represents a halogen atom (preferably, a chlorine or bromine atom), alkylsulfonyl group (preferably, a methylsulfonyl group), substituted or unsubstituted phenylsulfonyl group (preferably, a phenylsulfonyl or 4-methylphenylsulfonyl group) or a nitro-substituted phenylthio group (preferably, a 2,4-dinitrophenylthio, 4-nitrophenylthio or 2-nitrophenylthio group)] in an inert solvent in the presence of a base; and a process of reacting the compound (VI) with a compound having the formula of R⁴SH [wherein, R⁴ has the same meaning as described above] in an inert solvent in the presence of an oxidizing agent.

The reaction between the compound (VI) and the compound R⁴SYa can be conducted under similar conditions to those of Reaction (d) except for the use of the compound R⁴SYa instead of the compound R⁴SO₂Y. When Ya represents a nitro-substituted phenylthio group, the sulfenylation can easily be carried out by converting the compound (VI) into a silver salt thereof and then reacting the salt with the compound R⁴SYa. The reaction conditions are selected as needed, for example, in accordance with the process as described in *Chem. Lett.*, 813(1975).

The reaction between the compound (VI) and the compound R⁴SH in the presence of an oxidizing agent is usually conducted using an excess (preferably, in a molar amount 5 to 20 times) of the compound R⁴SH.

Preferred examples of the oxidizing agent include iodine, bromine, hypochlorous acid, hypobromous acid and hydrogen peroxide, of which iodine is most preferred. The oxidizing agent is usually added in a molar amount 2 to 10 times (preferably, 5 to 10 times) relative to the compound (VI).

There is no particular limitation on the nature of the inert solvent to be employed in the above-described reaction provided that it does not adversely affect the reaction. Examples include halogenated hydrocarbons such as dichloromethane, chloroform, carbon tetrachloride and 1,2-dichloroethane; ethers such as diethyl ether, tetrahydrofuran, dioxane, dimethoxyethane and diethoxyethane; alcohols such as methanol, ethanol, propyl alcohol, isopropyl alcohol and butyl alcohol; nitriles such as acetontrile; amides such as N,N-dimethylformamide, N,N- dimethylacetamide, N-methyl-2-pyrrolidone and hexamethylphosphoramide; sulfoxides such as dimethyl sulfoxide and water; and mixed solvents thereof. Preferred are the halogenated hydrocarbons, ethers, alcohols and water, and mixed solvents thereof.

The reaction temperature usually ranges from −10 to 100° C. (preferably from 0 to 50°0 C.). The reaction time ranges from 30 minutes to 24 hours (preferably, from 1 to 12 hours), though depending on the reaction temperature and the like.

The present reaction may be conducted in the presence of a base in order to suppress side reactions. Examples of such a base include alkali metal carbonates (preferably, sodium carbonate or potassium carbonate) and organic amines (preferably, triethylamine, tributylamine and ethyldiisopropylamine).

After completion of the reaction, the desired compound of the present reaction is collected from the reaction mixture in conventional manner, for example, by removing insoluble matter, if any, by filtration as needed and distilling off the solvent under reduced pressure; or by distilling off the solvent under reduced pressure, adding water to the residue; extracting the mixture with a water immiscible organic solvent such as ethyl acetate, drying over anhydrous magnesium sulfate and then distilling off the solvent. If necessary, the residue can be purified further in a conventional manner such as recrystallization or column chromatography.

Step A5 is another method for preparing a compound having the formula (Ia), that is, a compound (I) having a sulfonyl group as X and it is accomplished by reacting the compound (III) obtainable by Step A2 with a compound represented by the formula (XVII) in an inert solvent in the presence or absence (preferably, in the presence) of a base. The above-described reaction is conducted under similar conditions to Step A2 except for the use of the compound (XVII) instead of the compound (IV).

The compounds (I) may have optical isomers or geometric isomers. In such a case, the desired optical isomer or geometric isomer of the desired compound can be obtained using a raw material compound subjected to optical resolution or separation of a geometric isomer.

It is also possible to treat the optical isomer or geometric isomer mixture in accordance with a conventional optical resolution or separation method in the desired stage of the preparation process, thereby obtaining the corresponding isomer.

The compounds (I) can be converted into a pharmacologically acceptable salt thereof by treating them with an acid in a conventional manner, for example, by reacting them with a corresponding acid in an inert solvent (preferably, ethers such as diethyl ether, tetrahydrofuran or dioxane, alcohols such as methanol or ethanol or halogenated hydrocarbons such as methylene chloride or chloroform) at room temperature for 5 minutes to 1 hour and then distilling off the solvent under reduced pressure.

The raw material compound (II) of the present invention is easily prepared by the following process:

Process B:

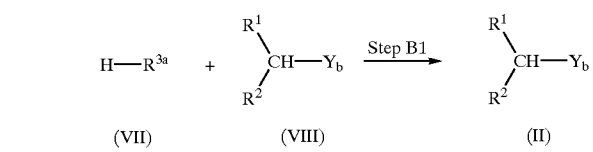

Process C:

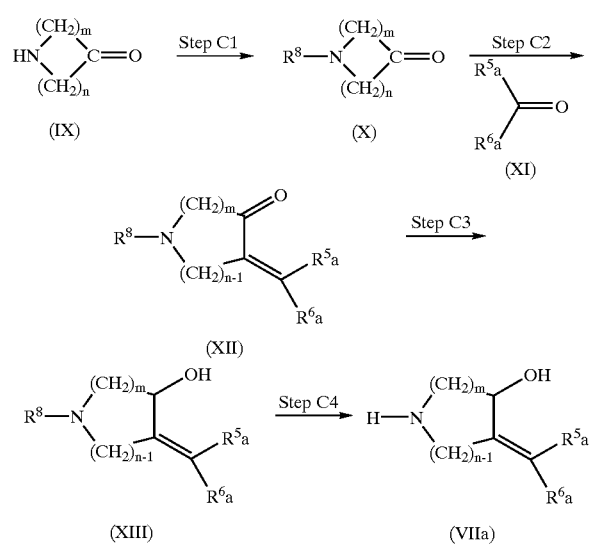

Process D:

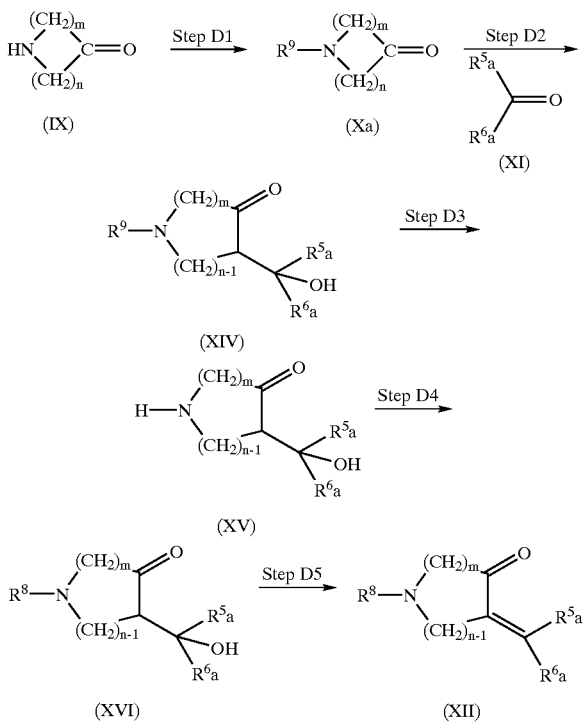

In the above-described formulae, $R^1$, $R^2$, $R^3a$, $R^5a$ and $R^6a$ have the same meanings as described above, $R^8$ represents an amino-protecting group which is removed under acidic conditions, $R^9$ represents an amino-protecting group which is removed under reducing conditions, Yb represents a halogen atom (preferably, a chlorine or bromine atom), m stands for 0 to 3 and n stands for 1 or 2.

The amino-protecting group, as $R^8$, removed under acidic conditions is, for example, a trityl group or t-butoxycarbonyl group, while the amino-protecting group, as $R^9$, removed under reducing condition is, for example, a substituted or unsubstituted benzyl or benzyloxycarbonyl group similar to the above-described hydroxyl-protecting groups and preferred examples include benzyl, p-methoxybenzyl, p-chlorobenzyl, benzyloxycarbonyl, p-methoxybenzyloxycarbonyl and p-chlorobenzyloxycarbonyl groups, of which the benzyl and p-methoxybenzyl groups are particularly preferred.

Process B is a process for preparing the compound (II).

Step B1 is a step for preparing the compound (II) by reacting a compound having the formula (VII) with a compound having the formula (VIII) in an inert solvent (preferably, an amide such as N,N-dimethylacetamide, N,N-dimethylformamide, N-methylpyrrolidone or hexamethylphosphoramide or sulfoxide such as dimethyl sulfoxide) in the presence or absence of a base (preferably, in the presence of an alkali metal carbonate such as sodium carbonate or potassium carbonate) at 0 to 200° C. (preferably, at 20 to 150° C. for 1 to 24 hours (preferably, for 2 to 15 hours).

The compound (II) containing an alkoxycarbonyl group in $R^3a$ is hydrolyzed similar to Reaction (b) of Step A3 of Process A to prepare the corresponding carboxylic acid derivative. The resulting carboxylic acid derivative is then reacted with a $C_1$–$C_4$ alkyl halogencarbonate such as methyl chlorocarbonate, ethyl chlorocarbonate, ethyl bromocarbonate, propyl chlorocarbonate, butyl chlorocarbonate or isobutyl chlorocarbonate in the presence of a base such as triethylamine or ethyldiisopropylamine, whereby the corresponding active ester derivative is prepared. The resulting ester derivative is then reacted with ammonia or a mono- or di-($C_1$–$C_4$ alkyl)amine in an inert solvent (preferably, a halogenated hydrocarbon such as dichloromethane, chloroform, carbon tetrachloride or 1,2-dichloroethane) at −10 to 100° C. (preferably, at 10 to 50° C.) for 1 to 24 hours (preferably, for 2 to 10 hours), whereby the corresponding amide derivative can be prepared.

After completion of reaction, the desired compound of the present reaction is collected from the reaction mixture in a conventional manner, for example, by removing insoluble matter, if any, by filtration as needed, neutralizing the reaction mixture as needed if it is acidic or alkaline, and distilling off the solvent under reduced pressure; or by distilling off the solvent under reduced pressure, adding water to the residue, extracting the mixture with a water immiscible organic solvent such as ethyl acetate, drying over anhydrous magnesium sulfate and then distilling off the solvent. If necessary, the residue can be purified further in a conventional manner such as recrystallization or column chromatography.

Process C is a process for preparing a compound (VIIa) which is one of the raw material compounds (VII) in Process B and contains a substituent having the formula =$CR^5aR^6a$ (wherein, $R^5a$ and $R^6a$ have the same meanings as described above).

Step C1 is a step for preparing a compound represented by the formula (X) and is conducted by reacting a compound having the formula (IX) with a trityl halide such as trityl chloride or trityl bromide, a t-butoxycarbonyl halide such as t-butoxcarbonyl chloride or t-butoxycarbonyl bromide, or di-t-butyl dicarbonate in an inert solvent (preferably, a halogenated hydrocarbon such as dichloromethane, chloroform, carbon tetrachloride or 1,2-dichloroethane, amide such as N,N-dimethylacetamide, N,N-dimethylformamide, N-methylpyrrolidone or hexamethylphosphoramide, or a sulfoxide such as dimethyl sulfoxide) in the presence or absence of a base (preferably, in the presence of an alkali metal carbonate such as lithium carbonate, sodium carbonate or potassium carbonate or an organic amine such as triethylamine or ethyldiisopropylamine) at 0 to 150° C. (preferably, at 20 to 100° C. for 1 to 24 hours (preferably, for 2 to 10 hours).

Step C2 is a step for preparing a compound represented by the formula (XII) and is conducted by reacting the compound (X) with a di-($C_1$–$C_4$ alkyl)amine or a 3- to 6-membered cyclic amine (preferably, dimethylamine, diethylamine, pyrrolidine, piperidine or morpholine, with pyrrolidine, piperidine or morpholine being particularly preferred) in an inert solvent (preferably, an aromatic hydrocarbon such as benzene, toluene or xylene) at 60 to 200° C. (preferably, at 80 to 150° C.) for 30 minutes to 15 hours (preferably, for 1 to 10 hours) under azeotropic dehydration to prepare the corresponding enamine derivative and then reacting the enamine derivative with a compound having the formula (XI) in an inert solvent (preferably, an aromatic hydrocarbon such as benzene, toluene or xylene) at 60 to 200° C. (preferably, at 80 to 150° C.) for 30 minutes to 10 hours (preferably, for 1 to 5 hours) under azeotropic dehydration.

Step C3 is a step for preparing a compound represented by the formula (XIII) and is conducted by reacting the compound (XII) with a reducing agent (preferably, a borohydride compound such as sodium borohydride or sodium cyanoborohydride) in an inert solvent (preferably, an alcohol such as methanol or ethanol) at 0 to 100° C. (preferably, at 5 to 50° C.) for 10 minutes to 6 hours (preferably, for 30 minutes to 3 hours).

Step C4 is a step for preparing the compound (VIIa) which is accomplished by removing amino-protecting group from the compound (XIII). This step is carried out in accordance with the process described in "Protective Groups in Organic Synthesis, 2nd edition, 309, T. W. Greene & P. G. M. Wuts; John Wiley & Sons, Inc." in which process an acid (preferably, p-toluenesulfonic acid or trifluoroacetic acid) is employed.

After completion of the each reaction, the desired compound of this reaction is collected from the reaction mixture in a conventional manner, for example, by removing insoluble matter, if any, by filtration as needed, neutralizing the reaction mixture as needed if it is acidic or alkaline, and distilling off the solvent under reduced pressure; or by distilling off the solvent under reduced pressure, adding water to the residue, extracting the mixture with a water immiscible organic solvent such as ethyl acetate, drying over anhydrous magnesium sulfate and then distilling off the solvent. If necessary, the residue can be purified further in a conventional manner such as recrystallization or column chromatography.

Process D is another method for preparing the intermediate (XII) employed in Process C.

Step D1 is a step for preparing a compound represented by the formula (Xa) and is conducted by reacting the compound (IX) with a substituted or unsubstituted benzyl halide or a substituted or unsubstituted benzyloxycarbonyl halide (preferably, the chloride) in a manner similar to Step C1 of Process C.

Step D2 is a step for preparing a compound represented by the formula (XIV) and is conducted by reacting the compound (Xa) with a di($C_1$–$C_4$ alkyl)amine or a 3- to 6-membered cyclic amine (preferably, dimethylamine, diethylamine, pyrrolidone, piperidine or morpholine, with pyrrolidine, piperidine or morpholine being particularly preferred) in a similar manner to the first stage of Step C2 of Process C to prepare the corresponding enamine derivative and then reacting the resulting enamine derivative with a compound represented by the formula (XI) in an inert solvent (preferably, halogenated hydrocarbons such as dichloromethane, chloroform, carbon tetrachloride or 1,2-dichloroethane) in the presence of an acid catalyst (preferably, a Lewis acid such as boron trifluoride—ether complex, aluminum chloride, titanium tetrachloride or tin tetrachloride) at −10 to 100° C. (preferably, at 10 to 50° C.) for 1 to 24 hours (preferably, for 2 to 20 hours).

Step D3 is a step for preparing a compound represented by the formula (XV) and it is accomplished by removing the amino-protecting group from the compound (XIV). This step is conducted in accordance with the reduction method with hydrogen as described in the above-described "Protective Groups in Organic Synthesis, 2nd edition".

Step D4 is a step for preparing a compound represented by the formula (XVI) and is accomplished by protecting the amino group of the compound (XV). This step is conducted in a similar manner to Step C1 of Process C.

Step D5 is a step for preparing the compound (XII) which comprises sulfonylating the compound (XVI) as in Step A1 of Process A and then reacting the resulting sulfonyloxy derivative with a base (preferably, an organic amine such as triethylamine, N-methylmorpholine, pyridine, 4-dimethylaminopyridine, 1,5-diazabicyclo[4.3.0]-5-nonene or 1,8-diazabicyclo[5.4.0]-7-undecene) in an inert solvent (preferably, a halogenated hydrocarbon such as dichloromethane, chloroform, carbon tetrachloride or 1,2-dichloroethane) at −10 to 100° C. (preferably, at 10 to 50° C.) for 30 minutes to 10 hours (preferably, for 1 to 5 hours).

After completion of the reaction, the desired compound of the present reaction is collected from the reaction mixture in a conventional manner, for example, by removing an insoluble matter, if any, by filtration as needed, neutralizing the reaction mixture as needed if it is acidic or alkaline, and distilling off the solvent under reduced pressure; or by distilling off the solvent under reduced pressure, adding water to the residue, extracting the mixture with a water immiscible organic solvent such as ethyl acetate, drying over anhydrous magnesium sulfate and then distilling off the solvent. If necessary, the residue can be purified further in a conventional manner such as recrystallization or column chromatography.

The raw material compound (VIII) is known or prepared in a known manner [e.g. Japanese Patent Application Kokai No. Sho 59-27895 (EP99802), Japanese Patent Application kokai No. Hei 6-41139 (EP542411), or the like]. The raw material compound (VII) is known or prepared in a known manner [e.g. The Journal of Organic Chemistry: J. Org. Chem., 37, 3953(1972)].

The present invention will hereinafter be described in further detail by Examples, Referential Examples, Tests and Formulation Examples. It should however be borne in mind that the scope of the present invention is not limited to or by them.

EXAMPLE 1

1-(α-Cyclopropylcarbonyl-2-fluorobenzyl)-4-(4-methylphenylsulfonylthio)-piperidine (Exemplified Compound No. 1-7)

(a) 8.0 g (28.9 mmol) of 1-(α-cyclopropylcarbonyl-2-fluorobenzyl)-4-hydroxypiperidine were dissolved in 50 ml of dichloromethane, followed by the addition of 2.92 g (28.9 mmol) of triethylamine. A 10 ml dichloromethane solution of 3.31 g (28.9 mmol) of methanesulfonyl chloride was added dropwise under ice cooling and the resulting mixture was stirred at room temperature for 1 hour. The solvent was then distilled off under reduced pressure. Ethyl acetate was added to the residue and the triethylamine hydrochloride thus precipitated was filtered off. The filtrate was concentrated under reduced pressure, whereby crude 1-(α-cyclopropylcarbonyl-2-fluorobenzyl)-4-methylsulfonyloxypiperidine was obtained. To the resulting crude product were added 50 ml of dimethyl sulfoxide (DMSO) and 19.8 g (170 mmol) of potassium thioacetate and the resulting mixture was stirred at 50° C. for 4 hours. Water was added to the reaction mixture. The resulting mixture was extracted with ethyl acetate, dried over anhydrous sodium sulfate and distilled under reduced pressure to remove the solvent. The residue was subjected to chromatography on a silica gel column (eluting solvent: toluene/ethyl acetate=19/1), whereby a reddish brown oil was obtained. The oil was then crystallized from hexane, whereby 3.6 g of 4-acetylthio-1-(α-cyclopropylcarbonyl-2-fluorobenzyl)piperidine were obtained as pale brown crystals (yield: 37%).

Melting point: 78 to 80° C.;

NMR spectrum (CDCl$_3$, δ): 0.79–0.87 (2H, m), 0.98–1.04 (2H, m), 1.66–1.80 (2H, m), 1.90–2.00 (2H, m), 2.16–2.22 (2H, m), 2.28 (3H, s), 2.32–2.35 (1H, m), 2.70–2.78 (1H, m), 2.80–2.88 (1H, m), 3.38–3.47 (1H, m), 4.62 (1H, s), 7.08–7.38 (4H, m);

Mass spectrum (CI, m/z): 336 (M$^+$+1);

IR spectrum (KBr, $v_{max}$ cm$^{-1}$): 1689.

(b) 2.00 g (5.97 mmol) of the 4-acetylthio-1-(α-cyclopropylcarbonyl-2-fluorobenzyl)piperidine obtained in the above-described step (a) were dissolved in 50 ml of ethanol. An appropriate amount of a hydrogen chloride gas was blown through the resulting solution and the resulting mixture was allowed to stand overnight at room temperature. The solvent was then distilled off under reduced pressure. The residue was crystallized from diethyl ether, whereby 1.95 g of 1-(α-cyclopropylcarbonyl-2-fluorobenzyl)-4-mercaptopiperidine hydrochloride were obtained as faintly brown crystals (yield: 99%).

Melting point: 135 to 140° C.;

Anal. Calcd for $C_{16}H_{20}FNOS·HCl·¼H_2O$: C, 57.48; H, 6.48; N, 4.19 Found: C, 57:33; H, 6.43; N, 4.15;

Mass spectrum (CI, m/z): 294 (M$^+$+1).

(c) 0.92 g (3.9 mmol) of (4-methylphenyl)sulfonyl bromide were dissolved in 50 ml of carbon tetrachloride, followed by the dropwise addition of 0.395 g (3.91 mmol) of triethylamine under ice cooling. Then, 30 ml of a carbon tetrachloride suspension containing 1.29 g (3.91 mmol) of the 1-(α-cyclopropylcarbonyl-2-fluorobenzyl)-4-mercaptopiperidine hydrochloride obtained in the above-described step (b) and 0.49 g (4.85 mmol) of triethylamine were added dropwise over 60 minutes. After stirring for 2 hours under ice cooling, 50 ml of water were added and the resulting mixture was extracted with chloroform. The organic layer was dried over anhydrous magnesium sulfate and distilled under reduced pressure to remove the solvent. The residue was subjected to chromatography on a silica gel column (eluting solvent: toluene/ethyl acetate=9/1), whereby 0.96 g of a pale yellow oil were obtained. The oil was crystallized from diisopropyl ether, whereby 0.85 g of the title compound were obtained as a white solid (yield: 49%).

Melting point: 63 to 69° C.;

NMR spectrum (CDCl$_3$, δ): 0.70–0.93 (2H, m), 0.93–1.10 (2H, m), 1.45–2.38 (9H, m), 2.44 (3H, s), 2.57–2.85 (2H, m), 3.20–3.38 (1H, m), 4.61 (1H, s), 7.03–7.43 (6H, m), 7.78 (2H, d, J=8.1 Hz);

Mass spectrum (CI, m/z): 448 (M$^+$+1);

IR spectrum (KBr, $v_{max}$ cm$^{-1}$): 1701, 1326, 1142.

EXAMPLE 2

1-(2-Chloro-α-methoxycarbonylbenzyl)-4-(4-methylphenylsulfonylthio)-piperidine (Exemplified Compound No. 1-12)

(a) In a similar manner to Example 1(a) except for the use of 1-(2-chloro-α-methoxycarbonylbenzyl)-4-hydroxypiperidine instead of 1-(α-cyclopropylcarbonyl-2-fluorobenzyl)-4-hydroxypiperidine, the reaction was conducted, whereby 4-acetylthio-1-(2-chloro-α-methoxycarbonylbenzyl)piperidine was obtained as a reddish brown oil in a yield of 37%.

NMR spectrum (CDCl$_3$, δ): 1.60–1.80 (2H, m), 1.85–2.00 (2H, m), 2.10–2.25 (1H, m), 2.30 (3H, s), 2.32–2.48 (1H, m), 2.55–2.75 (1H, m), 2.80–2.90 (1H, m), 3.40–3.60 (1H, m), 3.70 (3H, s), 4.70 (1H, s), 7.20–7.65 (4H, m);

Mass spectrum (CI, m/z): 342 (M$^+$+1).

(b) In a similar manner to Example 1(b) except for the use of the 4-acetylthio-1-(2-chloro-α-methoxycarbonylbenzyl) piperidine obtained in the above-described step (a) instead of 4-acetylthio-1-(α-cyclopropylcarbonyl-2-fluorobenzyl) piperidine, the reaction was conducted, whereby 1-(2-chloro-α-methoxycarbonylbenzyl)-4-mercaptopiperidine hydrochloride was obtained in quantitative yield as faintly brown crystals.

Melting point: 134 to 140° C.;

Mass spectrum (CI, m/z): 300 (M$^+$+1).

(c) In a similar manner to Example 1(c) except for the use of the 1-(2-chloro-α-methoxycarbonylbenzyl)-4-mercaptopiperidine hydrochloride obtained in the above-described step (b) instead of 1-(α-cyclopropylcarbonyl-2-fluorobenzyl)-4-mercaptopiperidine hydrochloride, the reaction was conducted, whereby the title compound was obtained as a pale yellow oil (yield: 62%).

NMR spectrum (CDCl$_3$, δ): 1.59–1.80 (2H, m), 1.85–2.00 (2H, m), 2.22–2.41 (2H, m), 2.44 (3H, s), 2.57–2.69 (1H, m), 2.72–2.85 (1H, m), 3.28–3.42 (1H, m), 3.67 (3H, s), 4.67 (1H, s), 7.21–7.55 (6H, m), 7.78–7.82 (2H, m);

Mass spectrum (CI, m/z): 454 (M$^+$+1);

IR spectrum (Liquid membrane method, $v_{max}$ cm$^{-1}$): 1743, 1326, 1142.

(d) The pale yellow oil obtained in the above-described step (c) was dissolved in anhydrous diethyl ether, followed by the addition of a diethyl ether solution of hydrogen chloride while stirring in a water bath. The crystals thus precipitated were collected by filtration, washed with diethyl ether and hexane and thus dried under reduced pressure, whereby the hydrochloride of the title compound was obtained as a white solid.

Melting point: 100 to 115° C.;

Mass spectrum (CI, m/z): 454 (M$^+$+1).

EXAMPLE 3

1-(2-Fluoro-α-methoxycarbonylbenzyl)-4-(4-methylphenylsulfonylthio)-piperidine (Exemplified Compound No. 1-10)

(a) In a similar manner to Example 1(a) except for the use of the 1-(2-fluoro-α-methoxycarbonylbenzyl)-4-hydroxypiperidine instead of 1-(α-cyclopropylcarbonyl-2-fluorobenzyl)-4-hydroxypiperidine, the reaction was conducted, whereby 4-acetylthio-1-(2-fluoro-α-methoxycarbonylbenzyl)-piperidine was obtained as a pale yellow solid (amorphous) in a yield of 45.6%.

NMR spectrum (CDCl$_3$, δ): 1.65–1.78 (2H, m), 1.88–1.99 (2H, m), 2.20–2.33 (4H, m), 2.39 (1H, t, J=9.6 Hz), 2.75–2.86 (2H, m), 3.40–3.50 (1H, m), 3.71 (3H, s), 4.53 (1H, s), 7.04–7.49 (4H, m);

Mass spectrum (CI, m/z): 326 (M$^+$+1).

(b) In a similar manner to Example 1(b) except for the use of the 4-acetylthio-1-(2-fluoro-α-methoxycarbonylbenzyl) piperidine obtained in the above-described step (a) instead of 4-acetylthio-1-(α-cyclopropylcarbonyl-2-fluorobenzyl) piperidine, the reaction was conducted, whereby 1-(2-fluoro-α-methoxycarbonylbenzyl)-4-mercaptopiperidine hydrochloride was obtained as a pale yellow solid (amorphous) in a yield of 97.1%.

NMR spectrum (CDCl$_3$, δ): 1.70–2.24 (3H, m), 2.47–3.13 (3.5H, m), 3.21–3.36 (0.5H, m), 3.38–3.72 (2.5H, m), 3.83, 3.84 (total 3H, each s), 3.92–4.02 (0.5H, m), 5.21, 5.24 (total 1H, each s), 7.20–7.93 (4H, m), 12.91–13.34 (1H, m);

Mass spectrum (CI, m/z): 284 (M$^+$+1).

(c) In a similar manner to Example 1(c) except for the use of the 1-(2-fluoro-α-methoxycarbonylbenzyl)-4-mercaptopiperidine hydrochloride obtained in the above-described step (b) instead of 1-(α-cyclopropylcarbonyl-2-fluorobenzyl)-4-mercaptopiperidine hydrochloride, the reaction was conducted in methylene chloride, whereby the title compound was obtained as a colorless oil (yield: 38%).

NMR spectrum (CDCl$_3$, δ): 1.62–1.82 (2H, m), 1.85–2.04 (2H, m), 2.20–2.50 (2H, m), 2.44 (3H, s), 2.66–2.83 (2H, m), 3.25–3.38 (2H, m), 3.25–3.38 (1H, m), 3.68 (3H, s), 4.50 (1H, s), 7.01–7.45 (6H, m), 7.80 (2H, d, J=8.1 Hz);

Mass spectrum (CI, m/z): 438 (M$^+$+1);

IR spectrum (Liquid membrane method, $v_{max}$ cm$^{-1}$): 1747, 1326, 1142.

(d) Reaction was conducted in a similar manner to Example 2(d) except for the use of the 1-(2-fluoro-α-methoxycarbonylbenzyl)-4-(4-methylphenylsulfonylthio)piperidine obtained in the above-described step (c), whereby the hydrochloride of the title compound was obtained as a white solid.

Melting point: 106 to 109° C.;

Mass spectrum (CI, m/z): 438 (M$^+$+1).

EXAMPLE 4

1-(α-Cyclopropylcarbonyl-2-fluorobenzyl)-3-(4-methylphenylsulfonylthio)-pyrrolidine (Exemplified Compound No. 2-7)

(a) In a similar manner to Example 1(a) except for the use of 1-(α-cyclopropylcarbonyl-2-fluorobenzyl)-3-hydroxypyrrolidine instead of 1-(α-cyclopropylcarbonyl-2-fluorobenzyl)-4-hydroxypiperidine, the reaction was conducted, whereby 3-acetylthio-1-(α-cyclopropylcarbonyl-2-fluorobenzyl)-pyrrolidine as a brown oil in a yield of 51%.

NMR spectrum (CDCl$_3$, δ): 0.78–0.85 (2H, m), 0.97–1.02 (2H, m), 1.75–1.78 (1H, m), 2.09–2.15 (1H, m), 2.28 (3H, s), 2.32–3.39 (1H, m), 2.48–2.61 (2H, m), 2.72–2.80 (1H, m), 2.97–3.10 (1H, m), 3.91–3.97 (1H, m), 4.63, 4.65 (total 1H, each s), 7.06–7.48 (4H, m);

Mass spectrum (CI, m/z): 321 (M$^+$+1);

IR spectrum (Liquid membrane, $v_{max}$ cm$^{-1}$): 1692.

(b) In a similar manner to Example 1(b) except for the use of the 3-acetylthio-1-(α-cyclopropylcarbonyl-2-fluorobenzyl)pyrrolidine obtained in the above-described step (a) instead of 4-acetylthio-1-(α-cyclopropylcarbonyl-2-fluorobenzyl)piperidine, the reaction was conducted, whereby 1-(α-cyclopropylcarbonyl-2-fluorobenzyl)-3-mercaptopyrrolidine hydrochloride was obtained as a faintly brown solid (amorphous) in a yield of 74%.

Mass spectrum (CI, m/z): 280 (M$^+$+1);

IR spectrum (KBr, $v_{max}$ cm$^{-1}$): 1710.

(c) In a similar manner to Example 1(c) except for the use of the 1-(α-cyclopropylcarbonyl-2-fluorobenzyl)-3-mercaptopyrrolidine hydrochloride obtained in the above-described step (b) instead of 1-(α-cyclopropylcarbonyl-2-fluorobenzyl)-4-mercaptopiperidine hydrochloride, the reaction was conducted, whereby the title compound was obtained as a pale yellow oil (yield: 46%).

NMR spectrum (CDCl$_3$, δ): 0.71–0.88 (2H, m), 0.92–1.01 (2H, m), 1.72–1.82 (1H, m), 1.99–2.09 (1H, m), 2.25–2.60 (6H, m), 2.69–2.78 (1H, m), 2.87–3.07 (1H, m), 3.70–3.79 (1H, m), 4.59–4.65 (1H, m), 7.05–7.39 (6H, m), 7.75–7.79 (2H, m);

Mass spectrum (CI, m/z): 434 (M$^+$+1);

IR spectrum (Liquid membrane method, $v_{max}$ cm$^{-1}$): 1705, 1326, 1142.

(d) Reaction was conducted in a similar manner to Example 2(d) by using the 1-(α-cyclopropylcarbonyl-2-fluorobenzyl)-3-(4-methylphenylsulfonylthio)pyrrolidine obtained in the above-described step (c), whereby the hydrochloride of the title compound was obtained as a faintly beige solid.

Melting point: 98 to 106° C.;

Mass spectrum (CI, m/z): 434 (M$^+$+1).

EXAMPLE 5

1-(α-Cyclopropylcarbonyl-2-fluorobenzyl)-3-(4-methylphenylsulfonylthiol)-azetidine (Exemplified Compound No. 3-7)

(a) In a similar manner to Example 1(a) except for the use of 1-(α-cyclopropylcarbonyl-2-fluorobenzyl)-3-hydroxyazetidine instead of 1-(α-cyclopropylcarbonyl-2-fluorobenzyl)-4-hydroxypiperidine, the reaction was conducted, whereby 3-acetylthio-1-(α-cyclopropylcarbonyl-2-fluorobenzyl)-azetidine was obtained as pale yellow crystals in a yield of 54%.

Melting point: 49 to 52° C.;

NMR spectrum (CDCl$_3$, δ): 0.74–0.87 (2H, m), 0.94–1.01 (2H, m), 1.92–1.98 (1H, m), 2.28 (3H, s), 3.06–3.19 (2H, m), 3.62 (1H, dd, J=7.3 Hz, 7.9 Hz), 3.91 (1H, dd, J=7.3 Hz, 7.9 Hz), 4.13–4.21 (1H, m), 4.62 (1H, s), 7.07–7.42 (4H, m);

Mass spectrum (CI, m/z): 308 (M$^+$+1);

IR spectrum (KBr, $v_{max}$ cm$^{-1}$): 1695.

(b) In a similar manner to Example 1(b) except for the use of the 3-acetylthio-1-(α-cyclopropylcarbonyl-2-fluorobenzyl)azetidine obtained in the above-described step (a) instead of 4-acetylthio-1-(α-cyclopropylcarbonyl-2-fluorobenzyl)piperidine, the reaction was conducted, whereby 1-(α-cyclopropylcarbonyl-2-fluorobenzyl)-3-mercaptoazetidine hydrochloride was obtained as a white solid (amorphous) in a yield of 83%.

Mass spectrum (CI, m/z): 266 (M$^+$+1);

IR spectrum (KBr, $v_{max}$ cm$^{-1}$): 1709;

Anal Calcd for $C_{14}H_{16}FNOS \cdot HCl \cdot \frac{1}{2}H_2O$: C, 54.10; H, 5.84; N, 4.51 Found: C, 53.95; H, 5.68; N, 4.45.

(c) In a similar manner to Example 1(c) except for the use of the 1-(α-cyclopropylcarbonyl-2-fluorobenzyl)-3-mercaptoazetidine hydrochloride obtained in the above-described step (b) instead of 1-(α-cyclopropylcarbonyl-2-fluorobenzyl)-4-mercaptopiperidine hydrochloride, the reaction was conducted, whereby the title compound was obtained as a pale yellow oil.

NMR spectrum (CDCl$_3$, δ): 0.70–1.00 (4H, m), 1.81–1.88 (1H, m), 2.44 (3H, s), 3.03–3.14 (2H, m), 3.46–3.53 (1H, m), 3.86–3.90 (1H, m), 3.96–4.03 (1H, m), 4.59 (1H, s), 7.07–7.17 (2H, m), 7.27–7.33 (4H, m), 7.74–7.77 (2H, m);

Mass spectrum (CI, m/z): 420 (M$^+$+1);

IR spectrum (Liquid membrane method, $v_{max}$ cm$^{-1}$): 1706, 1329, 1144.

(d) Reaction was conducted in a similar manner to Example 2(d) by using the 1-(α-cyclopropylcarbonyl-2-fluorobenzyl)-3-(4-methylphenylsulfonylthio)azetidine obtained in the above-described step (c), whereby the hydrochloride of the title compound was obtained as a white solid.

Melting point: 80 to 86° C.;

Mass spectrum (CI, m/z): 420 (M$^+$+1).

EXAMPLE 6

(E)-1-(α-Cyclopropylcarbonyl-2-fluorobenzyl)-3-ethoxycarbonylmethylidene-4-(4-methylphenylsulfonylthio)piperidine (Exemplified Compound No. 5-41)

(a) 3.28 g (9.1 mmol) of (E)-1-(α-cyclopropylcarbonyl-2-fluorobenzyl)-3-ethoxycarbonyl-methylidene-4-hydroxypiperidine were dissolved in 50 ml of anhydrous methylene chloride, followed by the addition of 6.02 g (18.2 mmol) of carbon tetrabromide at room temperature. Then, 2.62 g (9.9 mmol) of triphenylphosphine were added in one portion and the mixture was stirred at room temperature for 1 hours. The reaction mixture was concentrated and the concentrate was purified by chromatography on a silica gel column (eluting solvent: toluene/ethyl acetate=19/1), whereby 2.00 g (yield: 52.1%) of (E)-4-bromo-1-(α-cyclopropylcarbonyl-2-fluorobenzyl)-3-ethoxycarbonylmethylidene-piperidine were obtained as a pale yellow oil.

NMR spectrum (CDCl$_3$, δ): 0.75–0.88 (2H, m), 0.97–1.11 (2H, m), 1.22, 1.25 (total 3H, each t, J=6.8 Hz, J=7.3 Hz), 2.05–3.00 (6H, m), 4.11, 4.13 (total 2H, each q, J=6.8 Hz, J=7.3 Hz), 4.45, 4.60 (total 1H, each d, J=13.6 Hz, J=14.1 Hz), 4.77, 4.78 (total 1H, each s), 5.90 (1H, s), 7.05–7.43 (4H, m);

Mass spectrum (CI, m/z): 424 (M$^+$+1).

2.14 g (18.7 mmol) of potassium thioacetate and 1.98 g (4.7 mmol) of the (E)-4-bromo-1-(α-cyclopropylcarbonyl-2-fluorobenzyl)-3-ethoxycarbonylmethylidenepiperidine obtained above were added to 30 ml of absolute ethanol, followed by stirring at room temperature for 1 hour and at 50° C. for 5 hours. The reaction mixture was filtered to remove the salt thus precipitate, followed by concentration. The concentrate was purified by chromatography on a silica gel column (eluting solvent: toluene/ethyl acetate=19/1), whereby 0.95 g (yield: 48.2%) of (E)-4-acetylthio-1-(α-cyclopropylcarbonyl-2-fluorobenzyl)-3-ethoxycarbonylmethylidenepiperidine were obtained as a pale yellow oil.

NMR spectrum (CDCl$_3$, δ): 0.78–0.90 (2H, m), 0.99–1.10 (2H, m), 1.22, 1.25 (total 3H, each t, J=6.8 Hz, J=7.3 Hz), 1.82–1.94 (1H, m), 2.13–2.28 (2H, m), 2.30, 2.31 (total 3H, each s), 2.35–2.90 (3H, m), 3.40 (1H, br.s), 4.11, 4.13 (total 2H, each q, J=6.8 Hz, J=7.3 Hz), 4.25–4.40 (1H, m), 4.75, 4.77 (total 1H, each s), 5.93 (1H, s), 7.08–7.38 (4H, m);

Mass spectrum (CI, m/z): 420 (M$^+$+1), 350.

(b) In a similar manner to Example 1(b), the reaction was conducted using 0.57 g (1.3 mmol) of the (E)-4-acetylthio-1-(α-cyclopropylcarbonyl-2-fluorobenzyl)-3-ethoxycarbonylmethylidenepiperidine obtained in the above-described step (a), whereby 0.52 g (yield: 92%) of (E)-1-(α-cyclopropylcarbonyl-2-fluorobenzyl)-3-ethoxycarbonylmethylidene-4-mercaptopiperidine hydrochloride were obtained as pale yellowish white crystals.

Melting point: 120 to 125° C.;

NMR spectrum (CDCl$_3$, δ): 0.80–0.93 (1H, m), 0.94–1.06 (1H, m), 1.23 (3H, t, J=7.3 Hz), 1.70–2.20 (5H, m), 2.80–3.06, 3.11–3.39 (total 1H, each m), 3.45–3.80 (1H, m), 3.90–4.25 (2H, m), 4.20 (2H, q, J=7.3 Hz), 4.85, 5.05 (total 1H, each m), 5.49 (1H, s), 6.25 (1H, s), 7.15–8.10 (4H, m);

Mass spectrum (CI, m/z): 378 (M$^+$+1), 308;

IR spectrum (KBr, ν$_{max}$ cm$^{-1}$): 1712.

(c) In a similar manner to Example 1(c) except for the use of the (E)-1-(α-cyclopropylcarbonyl-2-fluorobenzyl)-3-ethoxycarbonylmethylidene-4-mercaptopiperidine hydrochloride obtained in the above-described step (b) instead of 1-(α-cyclopropylcarbonyl-2-fluorobenzyl)-4-mercaptopiperidine hydrochloride, the reaction was conducted, whereby the title compound was obtained as a pale yellow oil (yield: 74%).

NMR spectrum (CDCl$_3$, δ): 0.75–0.92 (2H, m), 0.94–1.10 (2H, m), 1.13–1.28 (3H, m), 2.01–2.78 (5H, m), 2.42 (3H, s), 3.30 (0.5H, d, J=13.5 Hz), 3.35 (0.5H, d, J=13.5 Hz), 3.92–4.15 (4H, m), 4.69, 4.72 (total 1H, each s), 5.51 (1H, s), 7.05–7.45 (6H, m), 7.75 (2H, d, J=8.1 Hz);

Mass spectrum (CI, m/z): 532 (M$^+$+1);

IR spectrum (Liquid membrane method, ν$_{max}$ cm$^{-1}$): 1712, 1327, 1142.

(d) The reaction was conducted in a similar manner to Example 2(d) by using the (E)-1-(α-cyclopropylcarbonyl-2-fluorobenzyl)-3-ethoxycarbonylmethylidene-4-(4-methylphenylsulfonylthio)piperidine) obtained in the above-described step (c), whereby the hydrochloride of the title compound was obtained as a white solid.

Melting point: 94 to 103° C.;

Mass spectrum (CI, m/z): 532 (M$^+$+1).

EXAMPLE 7

(i) (E)-1-(2-Chloro-α-methoxycarbonylbenzyl)-3-ethoxycarbonylmethylidene-4-(4-methylphenylsulfonylthio)piperidine (Exemplified Compound No. 5-42), and (ii) (E)-1-(2-Chloro-α-methoxycarbonylbenzyl)-3-methoxycarbonylmethylidene-4-(4-methylphenylsulfonylthio)piperidine (Exemplified Compound No. 5-2)

(a) In a similar manner to Example 6(a) except for the use of (E)-1-(2-chloro-α-methoxycarbonylbenzyl)-3-ethoxycarbonylmethylidene-4-hydroxypiperidine instead of (E)-1-(α-cyclopropylcarbonyl-2-fluorobenzyl)-3-ethoxycarbonylmethylidene-4-hydroxypiperidine, the reaction was conducted, whereby (E)-4-acetylthio-1-(2-chloro-α-methoxycarbonylbenzyl)-3-ethoxycarbonylmethylidenepiperidine was obtained as a pale reddish brown oil in a yield of 35.3%.

NMR spectrum (CDCl$_3$, δ): 1.21, 1.23 (total 3H, each t, J=7.3 Hz), 1.75–1.92 (1H, m), 2.15–2.30 (1H, m), 2.32 (3H, s), 2.52–2.85 (2H, m), 3.48 (0.5 H, d, J=13.9 Hz), 3.60 (0.5H, d, J=13.9 Hz), 3.71, 3.72 (total 3H, each s), 4.05–4.14 (2.5 H, m), 4.25 (0.5H, d, J=13.9 Hz), 4.31–4.44 (1H, m), 4.83, 4.85 (total 1H, each s), 5.96 (1H, s), 7.15–7.70 (4H, m);

Mass spectrum (CI, m/z): 426 (M$^+$+1).

(b) 1.22 g of the (E)-4-acetylthio-1-(2-chloro-α-methoxycarbonylbenzyl)-3-ethoxycarbonylmethylidenepiperidine obtained in the above-described step (a) were dissolved in 50 ml of methanol was dissolved. An appropriate amount of hydrogen chloride gas was blown through the resulting solution and the resulting mixture was allowed to stand overnight at room temperature. The residue after the removal of the solvent under reduced pressure was crystallized from diethyl ether, whereby 1.25 g of a mixture of (E)-1-(2-chloro-α-methoxycarbonylbenzyl)-3-ethoxycrbonylmethylidene-4-mercaptopiperidine hydrochloride and (E)-1-(2-chloro-α-methoxycarbonylbenzyl)-4-mercapto-3-methoxycarbonylmethylidene-piperidine hydrochloride was obtained.

(c) In a similar manner to Example 1(c) except for the use of 1.25 g of the mixture of (E)-1-(2-chloro-α-methoxycarbonylbenzyl)-3-ethoxycarbonylmethylidene-4-mercaptopiperidine hydrochloride and (E)-1-(2-chloro-α-methoxycarbonylbenzyl)-4-mercapto-3-methoxycarbonylmethylidenepiperidine hydrochloride obtained in the above-described step (b) instead of 1-(α-cyclopropylcarbonyl-2-fluorobenzyl)-4-mercaptopiperidine hydrochloride, the reaction was conducted, followed by separation of the product by chromatography on a silica gel column, whereby 0.22 g (pale yellow oil, yield: 13%) of (E)-1-(2-chloro-α-methoxycarbonylbenzyl)-3-ethoxycarbonylmethylidene-4-(4-methylphenylsulfonylthio)piperidine and 0.81 g (white solid, yield: 48%) of (E)-1-(2-chloro-α-methoxycarbonylbenzyl)-3-methoxycarbonylmethylidene-4-(4-methylphenylsulfonylthio)piperidine were obtained.

(i) (E)-1-(2-chloro-α-methoxycarbonylbenzyl)-3-ethoxycarbonylmethylidene-4-(4-methylphenylsulfonylthio)piperidine NMR spectrum (CDCl$_3$, δ): 1.16–1.28 (2H, m), 2.00–2.06 (1H, m), 2.14–2.20 (1H, m), 2.42 (3H, s), 2.60–2.71 (2H, m), 3.34 (0.5H, d, J=14.8 Hz), 3.44 (0.5H, d, J=14.8 Hz), 3.68 (3H, s), 4.02–4.10 (3.5H, m), 4.17 (0.5H, d, J=14.8 Hz), 4.78, 4.79 (total 1H, each s), 5.52 (1H, s), 7.13–7.55 (6H, m), 7.75 (2H, d, J=8.0 Hz);

Mass spectrum (CI, m/z): 538 (M$^+$+1);

IR spectrum (Liquid membrane method, $v_{max}$ cm$^{-1}$): 1715, 1326, 1141.

(ii) (E)-1-(2-chloro-α-methoxycarbonylbenzyl)-3-methoxycarbonylmethylidene-4-(4-methylphenylsulfonylthio)piperidine Melting point: 144 to 146° C.;

NMR spectrum (CDCl$_3$, δ): 2.00–2.07 (2H, m), 2.15–2.23 (2H, m), 2.42 (3H, s), 2.60–2.70 (2H, m), 3.34 (0.5H, d, J=15.2 Hz), 3.45 (0.5H, d, J=15.2 Hz), 3.59 (3H, s), 3.70 (3H, s), 4.07–4.15 (1.5H, m), 4.18 (0.5H, d, J=15.2 Hz), 4.78, 4.79 (total 1H, each s), 5.52 (1H, s), 7.16–7.55 (6H, m), 7.75 (2H, d, J=8.3 Hz);

Mass spectrum (CI, m/z): 524 (M$^+$+1);

IR spectrum (KBr, $v_{max}$ cm$^{-1}$): 1720, 1326, 1141.

(d) The reaction was conducted in similar manner to Example 2(d) by using the (E)-1-(2-chloro-α-methoxycarbonylbenzyl)-3-ethoxycarbonylmethylidene-4-(4-methylphenylsulfonylthio)piperidine obtained in the above-described step (c)(i), whereby (E)-1-(2-chloro-α-methoxycarbonylbenzyl)-3-ethoxycarbonylmethylidene-4-(4-methylphenylsulfonylthio)piperidine hydrochloride was obtained as a pale yellowish white solid.

Melting point: 73 to 78° C.;

Mass spectrum (CI, m/z): 538 (M$^+$+1).

EXAMPLE 8

1-(α-Cyclopropylcarbonyl-2-fluorobenzyl)-4-methylsulfonylthiopiperidine (Exemplified Compound No. 1-142)

In a similar manner to Example 1(c) except that methanesulfonyl chloride was used instead of 4-methylphenylsulfonyl bromide, the reaction was conducted in methylene chloride, whereby the title compound was obtained as white crystals in a yield of 26.2%.

Melting point: 89 to 91° C.;

NMR spectrum (CDCl$_3$, δ): 0.73–0.95 (2H, m), 0.98–1.11 (2H, m), 1.43–2.45 (9H, m), 2.75–2.98 (2H, m), 3.31 (3H, s), 3.37–3.53 (1H, m), 4.68 (1H, s), 7.05–7.40 (4H, m);

Mass spectrum (CI, m/z): 372 (M$^+$+1);

IR spectrum (KBr, $v_{max}$ cm$^{-1}$): 1701, 1322, 1131.

EXAMPLE 9

1-(α-Cyclopropylcarbonyl-2-fluorobenzyl)-4-phenylsulfonylthiopiperidine (Exemplified Compound No. 1-82)

(a) In a similar manner to Example 1(c) except that benezenesulfonyl bromide was used instead of 4-methylphenylsulfonyl bromide, the reaction was conducted in methylene chloride, whereby the title compound was obtained as a pale yellow oil in a yield of 51%.

NMR spectrum (CDCl$_3$, δ): 0.73–1.06 (4H, m), 1.60–2.32 (7H, m), 2.55–2.80 (2H, m), 3.25–3.39 (1H, m), 4.61 (1H, s), 7.04–7.17 (2H, m), 7.21–7.35 (2H, m), 7.38–7.65 (3H, m), 7.86–7.94 (2H, m);

Mass spectrum (CI, m/z): 434 (M$^+$+1);

IR spectrum (Liquid membrane method, $v_{max}$ cm$^{-1}$): 1701, 1325, 1144.

(b) In a similar manner to Example 2(d) by using the 1-(α-cyclopropylcarbonyl-2-fluorobenzyl)-4-phenylsulfonylthiopiperidine obtained in the above-described step (a), the reaction was conducted, whereby the hydrochloride of the title compound was obtained as a faintly yellowish white solid.

Melting point: 105 to 116° C.;

Mass spectrum (CI, m/z): 434 (M$^+$+1).

EXAMPLE 10

4-(4-Chlorophenylsulfonylthio)-1-(α-cyclopropylcarbonyl-2-fluorobenzyl)-piperidine (Exemplified Compound No. 1-27)

(a) In a similar manner to Example 1(c) except that 4-chlorobenzenesulfonyl bromide was used instead of 4-methylphenylsulfonyl bromide, the reaction was conducted in methylene chloride, whereby the title compound was obtained as a pale yellow oil in a yield of 54%.

NMR spectrum (CDCl$_3$, δ): 0.72–1.09 (4H, m), 1.66–2.38 (7H, m), 2.63–2.82 (2H, m), 3.25–3.36 (1H, m), 4.62 (1H, s), 7.05–7.36 (4H, m), 7.45–7.55 (2H, m), 7.79–7.89 (2H, m);

Mass spectrum (CI, m/z): 468 (M$^+$+1);

IR spectrum (Liquid membrane method, $v_{max}$ cm$^{-1}$): 1701, 1329, 1145.

(b) In a similar manner to Example 2((d) by using the 4-(4-chlorophenylsulfonylthio)-1-(α-cyclopropylcarbonyl-2-fluorobenzyl)piperidine obtained in the above-described step (a), the reaction was conducted, whereby the hydrochloride of the title compound was obtained as a white solid.

Melting point: 108 to 116° C.;

Mass spectrum (CI, m/z): 468 (M$^+$+1).

EXAMPLE 11

1-(α-Cyclopropylcarbonyl-2-fluorobenzyl)-4-(4-fluorophenylsulfonylthio)-piperidine (Exemplified Compound No. 1-47)

(a) 2.34 g (12.0 mmol) of 4-fluorophenylsulfonyl chloride were dissolved in 40 ml of methylene chloride, followed by the addition of 0.44 g (4.30 mmol) of triethylamine under ice cooling. Then, a 10 ml methylene chloride suspension containing 0.67 g (2.03 mmol) of 1-(α-cyclopropylcarbonyl-2-fluorobenzyl)-4-mercaptopiperidine hydrochloride and 0.22 g (2.17 mmol) of triethylamine was added dropwise over 1 hour and the resulting mixture was stirred for 1 hour under ice cooling. To the reaction mixture was added 30 ml of water, followed by extraction twice with 50 ml of methylene chloride. The organic layer was washed with 20 ml of saturated saline and then dried over anhydrous magnesium sulfate. The solvent was distilled off under reduced pressure. The residue was subjected to chromatography on a silica gel column (eluting solvent: toluene/ethyl acetate=19/1), whereby 0.42 g of the title compound were obtained as a faintly yellow oil (yield: 46%).

NMR spectrum (CDCl$_3$, δ): 0.71–1.07 (4H, m), 1.59–2.34 (7H, m), 2.58–2.81 (2H, m), 3.21–3.36 (1H, m), 4.62 (1H, s), 7.00–7.39 (6H, m), 7.84–7.99 (2H, m);

Mass spectrum (CI, m/z): 452 (M$^+$+1);

IR spectrum (Liquid membrane method, $v_{max}$ cm$^{-1}$): 1703, 1330, 1142.

(b) In a similar manner to Example 2(d) by using the 1-(α-cyclopropylcarbonyl-2-fluorobenzyl)-4-(4- fluorophenylsulfonylthio)piperidine obtained in the above-described step (a), the reaction was conducted, whereby the hydrochloride of the title compound was obtained as a faintly yellowish white solid.

Melting point: 110 to 121° C.;
Mass spectrum (CI, m/z): 452 (M++1).

EXAMPLE 12

1-(α-Cyclopropylcarbonyl-2-fluorobenzyl)-4-(4-methoxyphenylsulfonylthio)piperidine (Exemplified Compound No. 1-67)

(a) In a similar manner to Example 11(a) except for the use of 4-methoxybenzenesulfonyl chloride instead of 4-fluorobenzenesulfonyl chloride, the reaction was conducted, whereby the title compound was obtained as a pale yellow oil in a yield of 37%.

NMR spectrum (CDCl$_3$, δ): 0.72–1.07 (4H, m), 1.63–2.34 (7H, m), 2.60–2.80 (2H, m), 3.22–3.34 (1H, m), 3.88 (3H, s), 4.61 (1H, s), 6.92–7.35 (6H, m), 7.77–7.88 (2H, m);

Mass spectrum (CI, m/z): 464 (M++1);

IR spectrum (Liquid membrane method, ν$_{max}$ cm$^{-1}$): 1713, 1327, 1139.

(b) In a similar manner to Example 2(d) by using the 1-(α-cyclopropylcarbonyl-2-fluorobenzyl)-4-(4-methoxyphenylsulfonylthio)piperidine obtained in the above-described step (a), the reaction was conducted, whereby the hydrochloride of the title compound was obtained as a faintly yellowish white solid.

Melting point: 113 to 122° C.;
Mass spectrum (CI, m/z): 464 (M++1).

EXAMPLE 13

1-(α-Cyclopropylcarbonyl-2-fluorobenzyl)-4-(4-methylphenylsulfinylthio)-piperidine (Exemplified Compound No. 1-14)

(a) 0.48 g (3.07 mmol) of p-toluenesulfinic acid were added to 15 ml of methylene chloride, followed by the addition of 0.59 (3.08 mmol) of 1-ethyl-3-(3-dimethylaminopropyl)carbodiimide (EDC) hydrochloride under ice cooling. Then, a 20 ml methylene chloride solution containing 1.00 g (3.03 mmol) of 1-(α-cyclopropylcarbonyl-2-fluorobenzyl)-4-mercaptopiperidine hydrochloride and 0.34 g (3.37 mmol) of triethylamine was added dropwide over 20 minutes. After stirring for 1 hour under ice cooling, 25 ml of water were added and the mixture was extracted with methylene chloride. The organic layer was washed with 30 ml of saturated saline, dried over anhydrous magnesium sulfate and then distilled under reduced pressure to remove the solvent. The residue was subjected to chromatography on a silica gel column (eluting solvent: toluene/ethyl acetate=15/1), whereby 0.80 g of the title compound were obtained as a pale yellow oil (yield: 61%).

NMR spectrum (CDCl$_3$, δ): 0.78–0.90 (2H, m), 0.95–1.08 (2H, m), 1.85–2.38 (7H, m), 2.41 (3H, s), 2.79–2.99 (2H, m), 3.40–3.50 (1H, m), 4.63 (1H, s), 7.05–7.18 (3H, m), 7.22–7.39 (3H, m), 7.58–7.62 (2H, m);

Mass spectrum (FAB, m/z): 432 (M++1);

IR spectrum (Liquid membrane method, ν$_{max}$ cm$^{-1}$): 1702, 1092.

(b) In a similar manner to Example 2(d) by using the 1-(α-cyclopropylcarbonyl-2-fluorobenzyl)-4-(4-methylphenylsulfinylthio)piperidine obtained in the above-described step (a), the reaction was conducted, whereby the hydrochloride of the title compound was obtained as a faintly yellowish white solid.

Melting point: 110 to 118° C.;
Mass spectrum (FAB, m/z): 432 (M++1).

EXAMPLE 14

1-(α-Cyclopropylcarbonyl-2-fluorobenzyl)-3-(4-methylphenylsulfinylthio)-pyrrolidine (Exemplified Compound No. 2-14)

(a) In a similar manner to Example 13(a) except for the use of 1-(α-cyclopropylcarbonyl-2-fluorobenzyl)-3-mercaptopyrrolidine hydrochloride instead of 1-(α-cyclopropylcarbonyl-2-fluorobenzyl)-4-mercaptopiperidine hydrochloride, the reaction was conducted, whereby the title compound was obtained as a pale yellow oil in a yield of 62%.

NMR spectrum (CDCl$_3$, δ): 0.76–0.85 (2H, m), 0.96–1.08 (2H, m), 1.90–1.94 (1H, m), 2.02–2.17 (2H, m), 2.40, 2.41 (total 3H, each s), 2.53–2.67 (2H, m), 2.73–2.84 (1.5H, m), 2.96–3.01 (0.25H, m), 3.13–3.18 (0.5H, m), 3.25–3.28 (0.25H, m), 3.25–4.03 (1H, m), 4.62, 4.64, 4.67, 4.68 (total 1H, each s), 7.06–7.62 (4H, m);

Mass spectrum (FAB, m/z): 418 (M++1);

IR spectrum (Liquid membrane method, ν$_{max}$ cm$^{-1}$): 1710, 1090.

(b) In a similar manner to Example 2(d) by using the 1-(α-cyclopropylcarbonyl-2-fluorobenzyl)-3-(4-methylphenylsulfinylthio)pyrrolidine obtained in the above-described step (a), the reaction was conducted, whereby the hydrochloride of the title compound was obtained as a faintly yellowish white solid.

Melting point: 87 to 100° C.;
Mass spectrum (CI, m/z): 418 (M++1).

EXAMPLE 15

1-(α-Cyclopropylcarbonyl-2-fluorobenzyl)-4-methylsulfinylthiopiperidine (Exemplified Compound No. 1-146)

(a) In a similar manner to Example 13(a) except for the use of sodium methanesulfinate instead of p-toluenesulfinic acid, the reaction was conducted, whereby the title compound was obtained as a pale yellow oil in a yield of 39%.

NMR spectrum (CDCl$_3$, δ): 0.77–0.92 (2H, m), 0.95–1.09 (2H, m), 1.82–2.40 (7H, m), 2.75–3.02 (2H, m), 2.98 (3H, s), 3.30–3.46 (1H, m), 4.64 (1H, s), 7.04–7.41 (4H, m);

Mass spectrum (CI, m/z): 356 (M++1);

IR spectrum (Liquid membrane method, ν$_{max}$ cm$^{-1}$): 1700, 1085.

(b) In a similar manner to Example 2(d) by using the 1-(α-cyclopropylcarbonyl-2-fluorobenzyl)-4-methylsulfinylthiopiperidine obtained in the above-described step (a), the reaction was conducted, whereby the hydrochloride of the title compound was obtained as a white solid.

Melting point: 105 to 111° C.;
Mass spectrum (CI, m/z): 356 (M++1).

EXAMPLE 16

1-(α-Cyclopropylcarbonyl-2-fluorobenzyl)-4-(4-methylphenyldisulfanyl)-piperidine (Exemplified Compound No. 1-17)

(a) 90 ml of pyridine were added to 2.98 g (24.0 mmol) of p-thiocresol. Then, 4.01 g (24.0 mmol) of silver acetate were added and the mixture was stirred at room temperature for 60 minutes. The precipitate was collected by filtration, washed with water and then dried under reduced pressure, whereby 5.38 g (23.3 mmol, yield: 96.9) of the silver salt of p-thiocresol were obtained as a grey powder.

In a nitrogen atmosphere, 3.70 g (16.0 mmol) of the silver salt of p-thiocresol and 3.75 g (16.0 mmol) of 2,4-dinitrophenylsulfenyl chloride were stirred for 3 hours in 150 ml of acetonitrile serving as a solvent, while cooling with ice water. The reaction mixture was filtered and the residue obtained after the concentration of the filtrate under reduced pressure was subjected to chromatography on a silica gel column (eluting solvent: hexane/ethyl acetate=5/1), whereby 1.64 g (5.08 mmol, yield: 31.8%) of 2,4-dinitrophenyl p-tolyldisulfide were obtained as yellow crystals.

(b) 0.38 ml of triethylamine and 0.42 g (2.5 mmol) of silver acetate were added to a 10 ml pyridine solution of 0.83 g (2.5 mmol) of 1-(α-cyclopropylcarbonyl-2-fluorobenzyl)-4-mercaptopiperidine hydrochloride, followed by stirring at room temperature for 5 hours. To the reaction mixture was added 30 ml of water. The solid thus precipitated was collected by filtration, washed with ethyl acetate and hexane and then dried under reduced pressure, whereby 0.67 g of the silver salt of 1-(α-cyclopropylcarbonyl-2-fluorobenzyl)-4-mercaptopiperidine were obtained as a yellowish brown solid (yield: 64%).

(c) In a nitrogen atmosphere, 0.65 g (2.02 mmol) of the 2,4-dinitrophenyl-p-tolyldisulfide obtained in the above-described step (a) were dissolved in 13 ml of DMF, followed by the addition of 0.52 g (1.30 mmol) of the silver salt of 1-(α-cyclopropylcarbonyl-2-fluorobenzyl)-4-mercaptopiperidine obtained in the above-described step (b). The resulting mixture was stirred overnight at room temperature. To the reaction mixture was added 30 ml of water. After extraction with 100 ml of toluene, the organic layer was dried over anhydrous magnesium sulfate and then distilled under reduced pressure to remove the solvent. The residue was subjected to chromatography on a silica gel column (eluting solvent: toluene/ethyl acetate=15/1), whereby 0.20 g of the title compound were obtained as a pale yellow oil (yield: 30%).

NMR spectrum (CDCl$_3$, δ): 0.77–0.86 (2H, m), 0.97–1.04 (2H, m), 1.70–1.80 (2H, m), 1.94–2.05 (3H, m), 2.15–2.25 (2H, m), 2.32 (3H, m), 2.74–2.86 (2H, m), 2.87–2.98 (1H, m), 4.59 (1H, s), 7.04–7.16 (4H, m), 7.25–7.41 (4H, m);

Mass spectrum (CI, m/z): 416 (M$^+$+1);

IR spectrum (Liquid membrane method, v$_{max}$ cm$^{-1}$): 1702.

(d) In a similar manner to Example 2(d), the reaction was conducted using the 1-(α-cyclopropylcarbonyl-2-fluorobenzyl)-4-(4-methylphenyldisulfanyl)piperidine obtained in the above-described step (c), whereby the hydrochloride of the title compound was obtained as a faintly yellowish white solid.

Melting point: 96 to 103° C.;

Mass spectrum (CI, m/z): 416 (M$^+$+1).

EXAMPLE 17

1-(α-Cyclopropylcarbonyl-2-fluorobenzyl)-4-(2,4-dinitrophenyldisulfanyl)-piperidine (Exemplified Compound No. 1-139)

(a) 0.71 g (3.03 mmol) of 2,4-dinitrophenylsulfenyl chloride were dissolved in 30 ml of methylene chloride, followed by the dropwise addition of a 20 ml methylene chloride suspension containing 1.00 g (3.03 mmol) of 1-(α-cyclopropylcarbonyl-2-fluorobenzyl)-4-mercaptopiperidine hydrochloride and 0.34 g (3.36 mmol) of triethylamine over 20 minutes under ice cooling. After stirring for 3 hours under ice cooling, 30 ml of water were added and the resulting mixture was extracted thrice with 50 ml of methylene chloride. The organic layer was washed with 30 ml of saturated saline, dried over anhydrous magnesium sulfate and distilled under reduced pressure to remove the solvent. The residue was subjected to chromatography on a silica gel column (eluting solvent: toluene/ethyl acetate=20/1), whereby 0.50 g of the title compound were obtained as a yellow oil (yield: 34%).

NMR spectrum (CDCl$_3$, δ): 0.78–0.90 (2H, m), 0.95–1.05 (2H, m), 1.70–2.22 (7H, m), 2.79–3.01 (3H, m), 4.63 (1H, s), 7.05–7.19 (2H, m), 7.22–7.34 (2H, m), 8.40–8.53 (2H, m), 9.08–9.10 (1H, m);

Mass spectrum (FAB, m/z): 492 (M$^+$+1);

IR spectrum (Liquid membrane method, v$_{max}$ cm$^{-1}$): 1700, 1592, 1339, 1304.

(b) In a similar manner to Example 2(d), the reaction was conducted using the 1-(α-cyclopropylcarbonyl-2-fluorobenzyl)-4-(2,4-dinitrophenyldisulfanyl)piperidine obtained in the above-described step (a), whereby the hydrochloride of the title compound was obtained as a pale yellow solid.

Melting point: 120 to 127° C.;

Mass spectrum (FAB, m/z): 492 (M$^+$+1).

EXAMPLE 18

1-(α-Cyclopropylcarbonyl-2-fluorobenzyl)-4-(2-nitrophenyldisulfanyl)-piperidine (Exemplified Compound No. 1-109)

(a) In a similar manner to Example 17(a) except for the use of 2-nitrophenylsulfenyl chloride instead of 2,4-dinitrophenylsulfenyl chloride, the reaction was conducted, whereby the title compound was obtained as a yellow foamy solid in a yield of 59%.

NMR spectrum (CDCl$_3$, δ): 0.73–0.86 (2H, m), 0.93–1.08 (2H, m), 1.63–2.07 (5H, m) 2.08–2.23 (2H, m), 2.68–2.99 (3H, m), 4.61 (1H, s), 7.03–7.26 (2H, m), 7.27–7.36 (3H, m), 7.60–7.68 (1H, m), 8.21–8.30 (2H, m);

Mass spectrum (CI, m/z): 447 (M$^+$+1);

IR spectrum (Liquid membrane method, v$_{max}$cm$^{-1}$): 1699, 1589, 1337, 1304.

(b) In a similar manner to Example 2(d), the reaction was conducted using the 1-(α-cyclopropylcarbonyl-2-fluorobenzyl)-4-(2-nitrophenyldisulfanyl)piperidine obtained in the above-described step (a), whereby the hydrochloride of the title compound was obtained as a pale yellowish white solid.

Melting point: 110 to 116° C.;

Mass spectrum (CI, m/z): 447 (M$^+$+1).

EXAMPLE 19

(Z)-4-[(R)-2-Amino-2-carboxyethyldisulfanyl]-3-carboxymethylidene-1-(α-cyclopropylcarbonyl-2-fluorobenzyl)piperidine (Exemplified Compound No. 5-117)

(a) 0.44 g (1.1 mmol) of (E)-1-(α-cyclopropyl-carbonyl-2-fluorobenzyl)-3-ethoxycarbonylmethylidene-4-mercaptopiperidine were dissolved in a mixed solvent of 15 ml of acetic acid and 10 ml of concentrated hydrochloric acid. The resulting solution was allowed to stand in a dark place at room temperature for 12 days. The reaction mixture was concentrated to dryness, followed by crystallization from ethyl ether. The crystals collected by filtration were purified by chromatography on a silica gel column (eluting solvent: chloroform/methanol=30/1), whereby 0.12 g (yield: 27%) of (E)-3-carboxymethylidene-1-(α-cyclopropylcarbonyl-2-fluorobenzyl)-4-mercaptopiperidine hydrochloride were obtained as pale yellowish white crystals.

Melting point: 109 to 111° C.;

NMR spectrum (CDCl$_3$, δ): 0.74–0.92 (1H, m), 1.00–1.14 (1H, m), 1.62–1.75 (1H, m), 1.76–1.90 (1H, m), 1.94–2.08 (2H, m), 2.20–2.39 (1H, m), 2.50–2.70 (2H, m), 2.90–3.03, 3.08–3.18 (total 1H, each m), 3.41–3.80 (3H, m), 4.11–4.28 (1H, m), 4.90, 5.03 (total 1H, each d, J=17.6 Hz), 5.98, 6.12 (total 1H, each s), 7.10–7.55 (4H, m);

Mass spectrum (CI, m/z): 350 (M$^+$+1), 280;

IR spectrum (KBr, ν$_{max}$cm$^{-1}$): 1712.

(b) 0.50 g (1.3 mmol) of the (E)-3-carboxymethylidene-1-(α-cyclopropylcarbonyl-2-fluorobenzyl)-4-mercaptopiperidine hydrochloride obtained in the above-described step (a) and 0.05 ml of dimethyl sulfide were dissolved in 60 ml of a 1:1 mixed solvent of water and acetonitrile, followed by exposure to light under a 32W low-pressure mercury lamp for 90 minutes under cooling. After completion of the reaction, the reaction mixtures was concentrated under reduced pressure. The residue was subjected to high-performance liquid chromatography [column: TSK-GEL ODS-80TS, mobile phase: acetonitrile/water=3/7 (containing 0.016% trifluoroacetic acid), temperature: room temperature], whereby two diastereomers, that is, 14.0 mg of the A-form and 13.5 mg of the B-form, of (Z)-3-carboxymethylidene-1-(α-cyclopropylcarbonyl-2-fluorobenzyl)-4-mercaptopiperidine trifluoroacetate were obtained each as a white powder (amorphous). The retention times of these diastereomers A and B in high-performance liquid chromatography [column: Inertsil ODS-2, mobile phase: acetonitrile/water=20/80 (containing 0.02% of trifluoroacetic acid), temperature: 27° C., flow rate: 1.5 ml/min] were 16.5 minutes and 18.5 minutes respectively.

A-form

NMR spectrum (CD$_3$CN, δ): 0.80–1.10 (4H, m), 1.82–1.89 (1H, m), 1.92–2.02 (1H, m), 2.26–2.46 (2H, m), 3.11–3.29 (2H, m), 3.46 (1H, d, J=13.6 Hz), 3.81 (1H, d, J=14.2 Hz), 5.26 (1H, s), 5.38 (1H, s), 5.73 (1H, s), 7.27–7.59 (4H, m);

Mass spectrum (CI, m/z): 350 (M$^+$+1), 280.

B-form

NMR spectrum (CD$_3$CN, δ): 0.80–1.11 (4H, m), 1.79–1.88 (1H, m), 1.95–2.04 (1H, m), 2.28–2.43 (2H, m), 2.86–3.01 (1H, m), 3.03–3.12 (1H, m), 3.52 (1H, d, J=12.8 Hz), 3.87 (1H, d, J=12.8 Hz), 5.24 (1H, s), 5.29 (1H, s), 5.68 (1H, s), 7.25–7.56 (4H, m);

Mass spectrum (CI, m/z): 350 (M$^+$+1), 280.

(c) Hydrochloric acid was added to a solution of 2.57 g (6.67 mmol) of the (E)-3-carboxymethylidene-1-(α-cyclopropylcarbonyl-2-fluorobenzyl)-4-mercaptopiperidine hydrochloride obtained in the above-described step (a) in a 1:2.5 mixture of water and acetonitrile to adjust its pH to 2.9. Then, the resulting mixture was exposed to light for 120 minutes under a 32 W low-pressure mercury lamp under ice cooling. A saturated aqueous solution of sodium acetate was added to the reaction mixture to adjust its pH to 5.7, followed by concentration under reduced pressure. The residue was subjected to high-performance liquid chromatography [column: TSK-GEL ODS-80TS, mobile phase: acetonitrile/water=3/7 (containing 0.012% trifluoroacetic acid), temperature: room temperature]. The eluate thus obtained was neutralized with a saturated aqueous solution of sodium acetate, followed by concentration under reduced pressure. The residue was desalted using a solid-phase extraction cartridge and then concentrated, whereby 182 mg of a diastereomeric mixture of (Z)-3-carboxymethylidene-1-(α-cyclopropylcarbonyl-2-fluorobenzyl)-4-mercaptopiperidine was obtained as a white powder (yield: 7.8%).

NMR spectrum (D$_2$O, δ): 0.85–1.27 (4H, m), 1.80–1.94 (1H, m), 1.99–2.10 (1H, m), 2.21–2.49 (1H, m), 2.85–3.02 (1H, m), 3.10–3.30 (1.5H, m), 3.35–3.52 (0.5H, m), 3.62–3.93 (1H, m), 4.8 (1H, m), 5.35–5.58 (1H, m), 5.71, 5.80 (each 0.5H, total 1H, each s), 7.20–7.75 (4H, m).

(d) 550.6 mg (4.543 mmol) of L-cysteine were dissolved in 8.8 ml of water. A 8.8 ml methanolic solution of 117.1 mg (0.3351 mmol) of the diastereomeric mixture of the (Z)-3-carboxymethylidene-1-(α-cyclopropylcarbonyl-2-fluorobenzyl)-4-mercaptopiperidine obtained in the above-described step (c) was added to the resulting solution. Then, iodine was added until the iodine colour disappeared. The resulting mixture was stirred at room temperature for 2 hours. After completion of the reaction, the cystine thus precipitated was filtered off and the solvent was then distilled off under reduced pressure. The residue was subjected to high-performance liquid chromatography [TSK-GEL ODS-80TS, 21.5×300 mm, eluant: acetonitrile/water=⅓ (containing 0.03% trifluoroacetic acid)], whereby the desired product was isolated and purified. After acetonitrile was distilled off under reduced pressure from the eluate, the residue was retained in a solid-phase extraction cartridge (filler: C18, 500 mg). After the cartridge was washed with water to remove trifluoroacetic acid, and eluted with methanol. The methanol was distilled off under reduced pressure, whereby 60.8 mg of the title compound (mixture of Z and E isomers) were obtained as a pale yellow solid (yield: 38%).

Melting point: 135 to 138° C.

NMR spectrum (DMSO-d$_6$, δ): 0.60–0.95 (4H, m), 1.80–1.99 (1H, m), 2.00–4.20 (9H, m), 4.21–4.46 (0.5H, m), 4.52–4.75 (1H, m), 5.15–5.30 (0.5H, m), 5.65–5.90 (1H, m), 7.12–7.28 (2H, m), 7.30–7.52 (2H, m);

Mass spectrum (FAB, m/z): 469 (M$^+$+1);

IR spectrum (KBr, ν$_{max}$ cm$^{-1}$): 1700, 1642.

(e) 1.00 g, (8.25 mmol) of L-cystein were dissolved in 15 ml water, followed by the addition of a 16 ml methanolic solution of 191 mg (0.547 mmol) of (Z)-3-carboxymethylidene-1-(α-cyclopropylcarobnyl-2-fluorobenzyl)-4-mercapto-piperidine. A methanolic solution of iodine was added to the resulting mixture until the iodine colour disappeared. The resulting mxiture was stirred at room temperature for 1 hour. After completion of the reaction, cystine thus precipitated was filtered out and then the solvent was distilled off under reduced pressure. The residue was retained in solid-phase extraction cartridge (filler: C18, 10 g). After the cartridge was washed successively with water and acetonitrile, the desired produce was eluted with methanol. Methanol was distilled off under reduced pressure, whereby 219 mg of the title compound were obtained as a white foamy solid (yield: 85.4%).

NMR spectrum (CD$_3$OD, δ): 0.79–1.20 (4H, m), 1.86–2.10 (1H, m), 2.11–2.49 (2.5H, m), 2.60–2.98 (2.5H, m), 3.05–3.46 (3H, m), 3.80–3.90 (1H, m), 4.79–4.88 (1H, m), 5.35–5.44 (1H, m), 5.76, 5.78, 5.86, 5.88 (total 1H, each s), 7.10–7.29 (2H, m), 7.32–7.48 (2H, m);

Mass spectrum (FAB, m/z): 469 (M$^+$+1).

EXAMPLE 20

1-(α-Cyclopropylcarbonyl-2-fluorobenzyl)-4-(2-methoxycarbonylethyldisulfanyl)piperidine (Exemplified Compound No. 1-210)

(a) 1.03 g (8.53 mmol) of methyl 3-mercaptopropionate and 5.68 g (56.09 mmol) of triethylamine were added to a methanolic solution of 0.50 g (1.70 mmol) of 1-(α-cyclopropyl-carbonyl-2-fluorobenzyl)-4-mercaptopiperidine. A methanolic solution of iodine was then added to the resulting mixture until the iodine colour disappeared. After completion of the reaction, the solvent was distilled off under reduced pressure. Toluene was added to the residue. The triethylamine salt thus precipitated was filtered off, followed by distillation under reduced pressure to remove the toluene. The residue was subjected to chromatography on a silica gel column (eluting solvent: toluene/ethyl acetate=50/1 to 19/1), whereby 0.563 g of the title compound were obtained as a yellowish orange oil (yield: 80%).

NMR spectrum (CDCl$_3$, δ): 0.77–0.90 (2H, m), 0.93–1.08 (2H, m), 1.65–1.85 (2H, m), 1.92–2.08 (3H, m), 2.15–2.29 (2H, m), 2.64–2.75 (3H, m), 2.81–2.91 (3H, m), 2.93–3.03 (1H, m), 3.69 (3H, s), 4.61 (1H, s), 7.05–7.19 (2H, m), 7.27–7.41 (2H, m);

Mass spectrum (CI, m/z): 412 (M$^+$+1);

IR spectrum (liquid membrane method, ν$_{max}$cm$^{-1}$): 1740, 1702.

EXAMPLE 21

(E)-1-(α-Cyclopropylcarbonyl-2-fluorobenzyl)-3-ethoxycarbonyl-methylidene-4-methylsulfonylthiopiperidine (Exemplified Compound No. 5-65)

(a) In a similar manner to Example 6(c) except for the use of methanesulfonyl chloride instead of 4-methylphenylsulfonyl bromide, the reaction was conducted, whereby the title compound was obtained as a pale yellow oil (yield: 14%).

NMR spectrum (CDCl$_3$, δ): 0.75–0.92 (2H, m), 0.96–1.11 (2H, m), 1.21–1.30 (3H, m), 2.04–2.86 (5H, m), 3.21 (3H, s), 3.37–3.52 (1H, m), 4.01–4.33 (4H, m), 4.78, 4.80 (total 1H, each s), 5.98 (1H, s), 7.11–7.40 (4H, m);

Mass spectrum (Cl, m/z): 456 (M$^+$+1);

IR spectrum (liquid membrane method, ν$_{max}$cm$^{-1}$): 1711, 1324, 1133.

(b) In a similar manner to Example 2(d), the reaction was conducted using the (E)-1-(α-cyclopropylcarbonyl-2-fluorobenzyl)-3-ethoxycarbonylmethylidene-4-methylsulfonylthiopiperidine obtained in the above-described step (a), whereby the hydrochloride of the title compound was obtained as a pale yellowish white solid.

Melting point: 98 to 115° C.

Mass spectrum (CI, m/z): 456 (M$^+$+1).

EXAMPLE 22

4-Cyclohexyldisulfanyl-1-(α-cyclopropylcarbonyl-2-fluorobenzyl)piperidine (Exemplified Compound No. 1-199)

In a similar manner to Example 20(a) except for the use of cyclohexanethiol instead of methyl 3-mercaptopropionate, the reaction was conducted, whereby the title compound was obtained as an orange brown oil (yield: 86%).

NMR spectrum (CDCl$_3$, δ): 0.77–0.90 (2H, m), 0.91–1.08 (2H, m), 1.12–1.37 (5H, m), 1.52–1.85 (5H, m), 1.90–2.10 (5H, m), 2.13–2.30 (2H, m), 2.58–2.72 (2H, m), 2.80–2.90 (1H, m), 2.91–3.01 (1H, m), 4.61 (1H, s), 7.02–7.22 (2H, m), 7.25–7.41 (2H, m);

Mass spectrum (CI, m/z): 408 (M$^+$+1);

IR spectrum (Liquid membrane method, ν$_{max}$ cm$^{-1}$): 2930, 1702.

EXAMPLE 23

4-Cyclopentyldisulfanyl-1-(60-cyclopropylcarbonyl-2-fluorobenzyl)-piperidine (Exemplified Compound No. 1-189)

In a similar manner to Example 20(a) except for the use of cyclopentanethiol instead of methyl 3-mercaptopropionate, the reaction was conducted, whereby the title compound was obtained as an orange brown oil (yield: 84%).

NMR spectrum CDCl$_3$, δ): 0.75–0.90 (2H, m), 0.91–1.08 (2H, m), 1.45–1.84 (8H, m), 1.86–2.10 (5H, m), 2.12–2.30 (2H, m), 2.61–2.75 (1H, m), 2.79–2.90 (1H, m), 2.92–3.03 (1H, m), 3.18–3.29 (1H, m), 4.61 (1H, s), 7.01–7.20 (2H, m), 7.22–7.42 (2H, m);

Mass spectrum (CI, m/z): 394 (M$^+$+1);

IR spectrum (Liquid membrane method, ν$_{max}$cm$^{-1}$): 2952, 1702.

EXAMPLE 24

(E)-3-Carboxymethylidene-1-(α-cyclopropylcarbonyl-2-fluorobenzyl)-4-(4-methylphenylsulfonylthio)piperidine (Exemplified Compound No. 5-81)

(a) In a similar manner to Example 1(c) except the (E)-3-carboxymethylidene-1-(α-cyclopropylcarbonyl)-2-fluorobenzyl)-4-mercaptopiperidine hydrochloride was used instead of 1-(α-cyclopropylcarbonyl-2-fluorobenzyl)-4-mercaptopiperidine hydrochloride, the reaction was conducted in methylene chloride, whereby the title compound was obtained as a yellow foamy solid (yield: 49%).

NMR spectrum (CDCl$_3$, δ): 0.73–0.92 (2H, m), 0.95–1.09 (2H, m), 1.90–2.37 (3H, m), 2.38–2.63 (4H, m), 2.73–2.94 (1H, m), 3.05 (0.5H, d, J=14.7 Hz), 3.50 (0.5H, d, J=14.2 Hz), 3.86 (0.5H, J=15.6 Hz), 4.01–4.08 (1H, m), 4.23 (0.5H, d, J=14.7 Hz), 4.80, 4.86 (total 1H, each s), 5.55 (1H, s), 7.05–7.43 (6H, m), 7.67–7.80 (2H, m).

(b) In a similar manner to Example 2(d), the reaction was conducted using the (E)-3-carboxymethylidene-1-(α-cyclopropylcarbonyl-2-fluorobenzyl)-4-(4-methylphenylsulfonylthio)piperidine obtained in the above-described step (a), whereby the hydrochloride of the title compound was obtained as a pale yellow solid.

Mass spectrum (FAB, m/z): 504 (M$^+$1);

IR spectrum (KBr, ν$_{max}$cm$^{-1}$): 1713, 1329, 1143.

EXAMPLE 25

(E)-1-(α-Cyclopropylcarbonyl-2-fluorobenzyl)-3-(N,N-dimethylcarbonyl)-methylidene-4-(4-methylphenylsulfonylthio)piperidine (Exemplified Compound No. 5-145)

(a) In a similar manner to Example 1(a) except that (E)-1-(α-cyclopropylcarbonyl-2-fluorobenzyl)-3-(N,N-dimethylcarbamoyl)methylidene-4-hydroxypiperidine was used instead of 1-(α-cyclopropylcarbonyl-2-fluorobenzyl)-4-hydroxypiperidine, and N,N-dimethylformamide (DMF) was used instead of dimethyl sulfoxide (DMSO) as the reaction solvent, whereby (E)-4-acetylthio-1-(α-cyclopropylcarbonyl-2-fluorobenzyl)-3-(N,N-dimethylcarbamoyl)methylidene-piperidine was obtained as a reddish brown oil in a yield of 27.5%.

NMR spectrum (CDCl$_3$, δ): 0.76–0.91 (2H, m), 0.95–1.09 (2H, m), 1.70–1.94 (2H, m), 2.15–2.50 (5H, m), 2.70–3.30 (8H, m), 3.55–3.80 (1H, m), 4.28–4.40 (1H, m), 4.68, 4.75 (total 1H, each s), 6.14 (1H, s), 7.05–7.80 (4H, m);

Mass spectrum (CI, m/z): 419 (M⁺+1).

(b) In a similar manner to Example 1(b) except for the use of the (E)-4-acetylthio-1-(α-cyclopropylcarbonyl-2-fluorobenzyl)-3-(N,N-dimethylcarbamoyl)-methylidenepiperidine obtained in the above-described step (a) instead of 4-acetylthio-1-(α-cyclopropylcarbonyl-2-fluorobenzyl)piperidine, the reaction was conducted, whereby (E)-1-(α-cyclopropylcarbonyl-2-fluorobenzyl)-3-(N,N-dimethylcarbamoyl)methylidene-4-mercaptopiperidine hydrochloride was obtained as pale brown crystals in a yield of 96.3%.

Melting point: 106 to 111° C.;

NMR spectrum (CDCl$_3$, δ): 0.75–1.55 (4H, m), 1.60–2.50 (4H, m), 2.75–3.35 (7H, m), 3.40–4.80 (4H, m), 5.53 (1H, s), 6.31, 6.60 (total 1H, each s), 7.10–7.90 (4H, m), 12.9 (1H, br.s);

Mass spectrum (CI, m/z): 377 (M⁺+1).

(c) In a similar manner to Example 1(c) except for use of the (E)-1-(α-cyclopropylcarbonyl-2-fluorobenzyl)-3-(N,N-dimethylcarbamoyl)methylidene-4-mercaptopiperidine hydrochloride obtained in the above-described step (b) instead of 1-(α-cyclopropylcarbonyl-2-fluorobenzyl)-4-mercaptopiperidine hydrochloride, the reaction was conducted, whereby the title compound was obtained as white crystals in a yield 23.2%.

Melting point: 48 to 52° C.;

NMR spectrum (CDCl$_3$, δ): 0.73–0.89 (2H, m), 0.90–1.05 (2H, m), 1.94–2.04 (1H, m), 2.10–2.29 (2H, m), 2.43 (3H, s), 2.54–2.78 (2H, m), 2.83–2.97 (6H, m), 3.10–3.28 (1H, m), 3.37–3.65 (1H, m), 4.06–4.14 (1H, m), 4.63, 4.68 (total 1H, each s), 5.93 (1H, s), 7.03–7.40 (6H, m), 7.78 (2H, d, J=8.3 Hz);

Mass spectrum (FAB, m/z): 531 (M⁺+1);

IR spectrum (KBr, $v_{max}$cm⁻¹): 1699, 1629, 1324, 1141.

EXAMPLE 26

(E)-1-(α-Cyclopropylcarbonyl-2-fluorobenzyl)-3-(N-methylcarbamoyl)-methylidene-4-(4-methylphenylsulfonylthio)piperidine (Exemplified Compound No. 5-129)

(a) In a similar manner to Example 1(a) except that (E)-1-(α-cyclopropylcarbonyl-2-fluorobenzyl)-4-hydroxy-3-(N-methylcarbamoyl)-methylidenepiperidine was used instead of 1-(α-cyclopropylcarbonyl-2-fluorobenzyl)-4-hydroxypiperidine and N,N-dimethylformamide (DMF) was used instead of dimethyl sulfoxide (DMSO) as the reaction solvent, the reaction was conducted, whereby (E)-4-acetylthio-1-(α-cyclopropylcarbonyl-2-fluorobenzyl)-3-(N-methylcarbamoyl)methylidenepiperidine was obtained as pale brown crystals in a yield of 47.6%.

NMR spectrum (CDCl$_3$, δ): 0.75–0.98 (2H, m), 0.98–1.13 (2H, m), 1.50–1.72 (1H, m), 1.72–1.90 (1H, m), 1.91–2.10 (1H, m), 2.10–2.45 (5H, m), 2.55–3.05 (5H, m), 3.05–3.35 (1H, m), 3.85–4.10 (1H, m), 4.26, 4.28 (total 1H, each s), 4.79, 4.83 (total 1H, each s), 5.90 (1H, s), 6.05 (1H, br.s), 7.05–7.50 (4H, m);

Mass spectrum (CI, m/z): 405 (M⁺+1).

(b) In a similar manner to Example 1(b) except for the use of the (E)-4-acetylthio-1-(α-cyclopropylcarbonyl-2-fluorobenzyl)-3-(N-methylcarbamoyl)-methylidenepiperidine obtained in the above-described step (a) instead of 4-acetylthio-1-(α-cyclopropylcarbonyl-2-fluorobenzyl)piperidine, the reaction was conducted, whereby (E)-1-(α-cyclopropylcarbonyl-2-fluorobenzyl)-3-(N-methylcarbamoyl)methylidene-4-mercaptopiperidine hydrochloride was obtained as pale brown crystals in a yield of 93.3%.

Melting point: 133 to 141° C.;

NMR spectrum (CDCl$_3$, δ): 0.80–1.15 (2H, m), 1.13–1.40 (2H, m), 1.60–2.08 (5H, m), 2.50–3.05 (3H, m), 3.06–4.50 (5H, m), 5.41, 5.42 (total 1H, each S), 6.09, 6.18 (total 1H, each S), 7.15–7.98 (4H, m), 8.61, 8.81 (total 1H, each br.s), 12.90 (1H, br.s);

Mass spectrum (CI, m/z): 3.63 (M⁺+1).

(c) In a similar manner to Example 1(c) except for the use of The (E)-1-(α-cyclopropylcarbonyl-2-fluorobenzyl)-3-(N-methylcarbamoyl)methylidene-4-mercaptopiperidine hydrochloride obtained in the above-described step (b) instead of 1-(α-cyclopropylcarbonyl-2-fluorobenzyl)-4-mercaptopiperidine hydrochloride, the reaction was conducted, whereby the title compound was obtained as pale yellow crystals (yield: 2.2%).

Melting point: 69 to 73° C.

NMR spectrum (CDCl$_3$, δ): 0.74–0.90 (2H, m), 0.94–1.11 (2H, m), 1.90–2.11 (1H, m), 2.35–2.50 (4H, m), 2.53–3.69 (1H, m), 2.72–2.83 (3H, m), 3.03–3.27 (1H, m), 3.67–3.87 (1H, m), 3.99–4.14 (1H, m), 4.70, 4.75 (total 1H, each s), 5.57 (1H, s), 5.74, 5.90 (total 1H, each br.s), 7.03–7.40 (6H, m), 7.75 (2H, dd, J=2.1, 8.1 Hz);

Mass spectrum (FAB, m/z): 517 (M⁺+1);

IR spectrum (KBr, $v_{max}$cm⁻¹): 1700, 1670, 1324, 1140.

EXAMPLE 27

(E)-1-(2-Chloro-α-methoxycarbonylbenzyl)-3-(N,N-dimethylcarbamoyl)-methylidene-4-(4-methylphenylsulfonylthio)piperidine (Exemplified Compound No. 5-189)

(a) 4.55 g (12.4 mmol) of (E)-1-(2-chloro-α-methoxycarbonylbenzyl)-3-(N,N-dimethylcarbamoyl)methylidene-4-hydroxypiperidine were dissolved in 30 ml of dichoromethane, followed by the addition of 1.76 g (13.6 mmol) of N-ethyl-diisopropylamine. A 10 ml dichloromethane solution of 1.56 g (13.6 mmol) of methanesulfonyl chloride was added dropwise under ice cooling and the resulting mixture was stirred at room temperature for 1 hour. The solvent was distilled off under reduced pressure, whereby crude (E)-1-(2-chloro-α-methoxycarbonylbenzyl)-3-(N,N-dimethylcarbamoyl)methylidene-4-methylsulfonyloxypiperidine was obtained. To the resulting crude product were added 50 ml of N,N-dimethylformamide (DMF) and 7.02 g (31.0 mmol) of potassium p-toluenethiosulfonate and the resulting mixture was stirred at 60° C. for 4 hours. Water was added to the reaction mixture. The resulting mixture was extracted with toluene, dried over anhydrous sodium sulfate and distilled under reduced pressure to remove the solvent. The residue was subjected to chromatography on a silica gel column (eluting solvent: chloroform/methanol=100/1, and then eluting solvent: toluene/ethyl acetate=6/4), whereby 0.58 g (yield: 8.7%) of the title compound were obtained as pale yellow crystals.

NMR spectrum (CDCl$_3$, δ): 1.88–2.05 (1H, m), 2.10–2.27 (1H, m), 2.43 (3H, s), 2.55–2.75 (2H, m), 2.83, 2.85 (total 3H, each s), 2.88, 2.89 (total 3H, each s), 3.29 (0.5H, d, J=13.5 Hz), 3.31 (0.5 H, d, J=13.5 Hz), 3.57 (0.5H, d, J=13.5 Hz), 3.61 (0.5H, d, J=13.5 Hz), 3.67 (3H, s), 4.09–4.18 (1H, m), 4.75, 4.76 (total 1H, each s), 5.90 (1H, s), 7.15–7.55 (6H, m), 7.80 (2H, dd, J=2.0, 8.0 Hz);

Mass spectrum (FAB, m/z): 537 (M⁺);

IR spectrum (KBr, $v_{max}$cm⁻¹): 1741, 1630, 1325, 1140.

(b) 0.39 g (0.73 mmol) of the (E)-1-(2-chloro-α-methoxycarbonylbenzyl)-3-(N,N-dimethylcarbamoyl)methylidene-4-(4-methylphenylsulfonylthio)piperidine obtained in the above-described step (a) were dissolved in 30 ml of ethyl ether. An ethyl ester solution through which hydrogen chloride gas had been blown in advance was added to the resulting solution and the mixture was allowed to stand for 30 minutes. The crystals thus precipitated were collected by filtration, dried under vacuum, whereby 0.30 g (yield: 72%) of the hydrochloride of the title compound were obtained as a white powder.

Melting point: 89 to 93° C.

Mass spectrum: (FAB, m/z): 537 (M$^+$).

EXAMPLE 28

(E)-1-(2-Chloro-α-methoxycarbonylbenzyl)-3-(N-methylcarbamoyl)-methylidene-4-(4-methylphenylsulfonylthio)piperidine (Exemplified Compound No. 5-181)

(a) In a similar manner to Example 27(a) except for the use of (E)-1-(2-chloro-α-methoxycarbonylbenzyl)-3-(N-methylcarbamoyl)methylidene-4-hydroxypiperidine instead of (E)-1-(2-chloro-α-methoxycarbonylbenzyl)-3-(N,N-dimethylcarbamoyl)methylidene-4-hydroxypiperidine, the reaction was conducted, whereby the title compound was obtained as pale yellowish white crystals in a yield of 10%.

NMR spectrum (CDCl$_3$, δ): 1.88–2.02 (1H, m), 2.11–2.23 (1H, m), 2.44 (3H, s), 2.47–2.81 (5H, m), 3.31 (0.5H, d, J=14.4 Hz), 3.44 (0.5H, d, J=14.4 Hz), 3.68 (3H, s), 3.89–4.13 (2H, m), 4.76, 4.81 (total 1H, each s), 5.50 (1H, br.s), 5.57, 5.59 (total 1H, each s), 7.11–7.55 (6H, m), 7.77 (2H, dd, J=1.2, 8.3 Hz);

Mass spectrum (FAB m/z): 523 (M$^+$);

IR spectrum (KBr, ν$_{max}$cm$^{-1}$); 1740, 1670, 1324, 1140.

(b) In a similar manner to Example 27(b), the reaction was conducted by using the (E)-1-(2-chloro-α-methoxycarbonylbenzyl)-3-(N-methylcarbamoyl)-methylidene-4-(4-methylphenylsulfonylthio)piperidine obtained in the above-described step (a), whereby the hydrochloride of the title compound was obtained as a white solid.

Melting point: 108 to 114° C.

EXAMPLE 29

(E)-3-Butoxycarbonylmethylidene-1-(2-chloro-α-methoxycarbonylbenzyl)-4-(4-methylphenylsulfonylthio)piperidine (Exemplified Compound No. 5-172)

(a) In a similar manner to Example 27(a) except for the use of (E)-3-butoxycarbonylmethylidene-1-(2-chloro-α-methoxycarbonylbenzyl)-4-hydroxypiperidine instead of (E)-1-(2-chloro-α-methoxycarbonylbenzyl)-3-(N,N-dimethylcarbamoyl)methylidene-4-hydroxypiperidine, the reaction was conducted, whereby the title compound was obtained as a brown oil in a yield of 16%.

NMR spectrum (CDCl$_3$, δ): 0.94 (3H, t, J=7.1 Hz), 1.23–1.41 (2H, m), 1.45–1.64 (2H, m), 1.95–2.08 (1H, m), 2.14–2.28 (1H, m), 2.42, 2.44 (total 3H, each s), 2.55–2.77 (2H, m), 3.33 (0.5H, d, J=1.54 Hz), 3.45 (0.5H, d, J=15.4 Hz), 3.68, 3.69 (total 3H, each s), 3.86–4.20 (4H, m), 4.78, 4.79 (total 1H, each s), 5.35, 5.55 (total 1H, each s), 7.17–7.58 (6H, m), 7.75 (2H, dd, J=1.8, 8.1 Hz);

Mass spectrum (FAB, m/z): 566 (M$^+$);

IR spectrum (Liquid membrane method, ν$_{max}$cm$^{-1}$): 1740, 1715, 1327, 1142.

(b) In a similar manner to Example 27(b), the reaction was conducted using the (E)-3-butoxycarbonylmethylidene-1-(2-chloro-α-methoxycarbonylbenzyl)-4-(4-methylphenylsulfonylthio)piperidine obtained in the above-described step (a), whereby the hydrochloride of the title compound was obtained as a yellow solid.

Melting point: 59 to 63° C.

EXAMPLE 30

(E)-3-Butoxycarbonylmethylidene-1-(α-cyclopropylcarbonyl-2-fluorobenzyl)-4-(4-methylphenylsulfonylthio)piperidine (Exemplified Compound No. 5-171)

(a) In a similar manner to Example 27(a) except for the use of (E)-3-butoxycarbonylmethylidene-1-(α-cyclopropylcarbonyl-2-fluorobenzyl)-4-hydroxypiperidine instead of (E)-1-(2-chloro-α-methoxycarbonylbenzyl)-3-(N,N-dimethylcarbamoyl)methylene-4-hydroxypiperidine, the reaction was conducted, whereby the title compound was obtained as a brown oil in a yield of 8.3%.

NMR spectrum (CDCl$_3$, δ): 0.67–1.13 (7H, m), 1.25–1.46 (2H, m), 1.50–1.69 (2H, m), 1.96–2.82 (8H, m), 3.14 (0.5H, d, J=14.3 Hz), 3.28 (0.5H, d, J=14.3 Hz), 3.88–4.17 (4H, m), 4.68, 4.71 (total 1H, each s), 5.52 (1H, s), 7.03–7.40 (6H, m), 7.75 (2H, d, J=8.3 Hz);

Mass spectrum (FAB m/z): 560 (M$^+$1);

IR spectrum (Liquid membrane method, ν$_{max}$cm$^{-1}$): 1713, 1653, 1329, 1142.

(b) In a similar manner to Example 27(b), the reaction was conducted by using the (E)-3-butoxycarbonylmethylidene-1-(α-cyclopropylcarbonyl-2-fluorobenzyl)-4-(4-methylphenylsulfonylthio)piperidine obtained in the above-described step (a), whereby the hydrochloride of the title compound was obtained as a yellow solid.

Melting point: 84 to 87° C.

EXAMPLE 31

(E)-4-[(R)-2-Amino-2-carboxyethyldisulfanyl]-3-carboxymethylidene-1-(α-cyclopropylcarbonyl-2-fluorobenzyl)piperidine (Exemplified Compound No. 5-117)

1.00 g (8.25 mmol) of L-cysteine were dissolved in 15 ml of water. A 15 ml methanolic solution of 191 mg (0.547 mmol) of (E)-3-carboxymethylidene-1-(α-cyclopropylcarbonyl-2-fluorobenzyl)-4-mercaptopiperidine was added. Then, a methanolic solution of iodine was added until the iodine colour disappeared. The resulting mixture was stirred to room temperature for 30 minutes. After completion of the reaction, cystine thus precipitated was filtered out and methanol was then distilled off under reduced pressure. The residue was retained in a solid-phase extraction cartridge (filler: C18, 10 g). After the cartridge was washed with water to remove hydrogen iodide and impurities were eluted with acetonitrile, the desired product was eluted with methanol. The methanol was distilled off under reduced pressure, whereby 0.16 g (yield: 62%) of the title compound were obtained as a faintly yellow foamy solid.

NMR spectrum (CD$_3$OD, δ): 0.79–1.20 (4H, m), 1.89–2.10 (1H, m), 2.15–2.54 (2.5H, m), 2.65–2.88 (2H, m), 2.92–3.01 (0.5H, m), 3.10–3.42 (2H, m), 3.72–3.89 (2H, m), 4.47 (0.25H, d, J=14.2 Hz), 4.50 (0.25H, d, J=13.7 Hz), 4.56–4.65 (0.5H, m), 4.73–4.80 (1H, m), 5.83, 5.85, 5.95, 5.96 (total 1H, each s), 7.11–7.27 (2H, m), 7.33–7.50 (2H, m);

Mass spectrum (FAB, m/z): 469 (M$^+$1).

REFERENCE EXAMPLE 1

1-(α-Cyclopropylcarbonyl-2-fluorobenzyl)-4-hydroxypiperidine 3.13 g (31 mmol) of 4-hydroxypiperidine were dissolved in 30 ml of dimethylformamide (DMF), followed by the addition of 7.94 g (31 mmol) of α-cyclopropylcarbonyl-2-fluorobenzyl bromide and 4.7 g (34 mmol) of potassium carbonate. The resulting mixture was stirred at room temperature for 2 hours. Water was added to the reaction mixture and the resulting mixture was extracted with toluene. The organic layer thus obtained was dried over anhydrous sodium sulfate. The solvent was concentrated under reduced pressure. The resulting residue was purified by chromatography on a silica gel column (eluting solvent: chloroform/methanol=19/1), whereby 8.00 g of the title compound were obtained as a brown oil (yield: 93%).

NMR spectrum (CDCl$_3$, δ): 0.79–0.87 (2H, m), 0.98–1.04 (2H, m), 1.50–1.72 (2H, m), 1.82–1.98 (2H, m), 2.02–2.15 (1H, m), 2.18–2.30 (2H, m), 2.70–2.90 (2H, m), 3.60–3.74 (1H, m), 4.62 (1H, s), 7.05–7.45 (4H, m);

Mass spectrum (CI, m/z): 278 (M$^+$+1).

REFERENCE EXAMPLE 2

1-(2-Chloro-α-methoxycarbonylbenzyl)-4-hydroxypiperidine

In a similar manner to Reference Example 1 except for the use of 2-chloro-α-methoxycarbonylbenzyl bromide instead of α-cyclopropylcarbonyl-2-fluorobenzyl bromide, the reaction was conducted, whereby the title compound was obtained as a colorless oil in a yield of 95%.

NMR spectrum (CDCl$_3$, δ): 1.55–1.70 (2H, m), 1.80–2.00 (2H, m), 2.22–2.45 (2H, m), 2.64–2.82 (1H, m), 2.83–2.98 (1H, m), 3.70 (3H, s), 3.72–3.80 (1H, m), 4.70 (1H, s), 7.20–7.70 (4H, m);

Mass spectrum (CI, m/z): 283 (M$^+$+1).

REFERENCE EXAMPLE 3

1-(α-Cyclopropylcarbonyl-2-fluorobenzyl)-3-hydroxypiperidine

In a similar manner to Reference Example 1 except for the use of 3-hydroxypiperidine instead of 4-hydroxypiperidine, the reaction was conducted, whereby the title compound was obtained as a brown oil in an approximately quantitative yield.

NMR spectrum (CDCl$_3$, δ): 0.75–0.95 (2H, m), 1.00–1.10 (2H, m), 1.45–1.68 (3H, m), 1.72–1.95 (1H, m), 2.02–2.20 (1H, m), 2.30–2.70 (4H, m), 3.80–3.90 (1H, m), 4.72 (1H, s), 7.05–7.45 (4H, m);

Mass spectrum (CI, m/z): 2.78 (M$^+$+1).

REFERENCE EXAMPLE 4

1-(α-Cyclopropylcarbonyl-2-fluorobenzyl)-3-hydroxypyrrolidine

In a similar manner to Reference Example 1 except for the use of 3-hydroxypyrrolidine instead of 4-hydroxypiperidine, the reaction was conducted, whereby the title compound was obtained as a yellow oil in a yield of 97%.

NMR spectrum (CDCl$_3$, δ): 0.79–0.90 (2H, m), 1.00–1.03 (2H, m), 1.70–1.90 (1H, m), 2.02–2.20 (2H, m), 2.41–3.08 (5H, m), 4.28–4.40 (1H, m), 4.71, 4.72 (total 1H, each s), 7.07–7.46 (4H, m);

Mass spectrum (CI, m/z): 264 (M$^+$+1).

REFERENCE EXAMPLE 5

1-(α-Cyclopropylcarbonyl-2-fluorobenzyl)-3-hydroxyazetidine

In a similar manner to Reference Example 1 except for the use of 3-hydroxyazetidine instead of 4-hydroxypiperidine, the reaction was conducted, whereby the title compound was obtained as white crystals in a yield of 66%.

NMR spectrum (CDCl$_3$, δ): 0.69–0.88 (2H, m), 0.90–1.07 (2H, m), 1.87–1.96 (1H, m), 2.94–3.03 (2H, m), 3.17 (1H, br.s), 3.44 (1H, dd, J=6.1, 6.7 Hz), 3.83 (1H, dd, J=6.7, 7.3 Hz), 4.45–4.53 (1H, m), 4.62 (1H, s), 7.07–7.38 (4H, m);

Mass Spectrum (CI, m/z): 250 (m$^+$+1).

REFERENCE EXAMPLE 6

8-(α-Cyclopropylcarbonyl-2-fluorobenzyl)-3-hydroxy-8-azabicyclo-[3.2.1]octane

In a similar manner to Reference Example 1 except for the use of 3-hydroxy-8-azabicyclo[3.2.1]octane (mixture of exo and endo isomers) instead of 4-hydroxypiperidine, the reaction was conducted, followed by separation by chromatography on a silica gel column (eluting solvent: toluene/ethyl acetate=100/3), whereby two isomers A-1 and B-1 of the title compound were obtained in yields of 45.2% and 24.6%, respectively. In the high-performance liquid chromatography (column: TSK-GEL ODS 80TM, mobile phase: acetonitrile/12 mM KH$_2$PO$_4$=45/55, temperature: 35° C., flow rate: 1.0 ml/min), these isomers A-1 and B-1 exhibited retention times of 4.0 minutes and 4.3 minutes, respectively.

Isomer A-1

Appearance: Pale yellow solid

NMR spectrum (CDCl$_3$, δ): 0.68–1.06 (4H, m), 1.35 (1H, s), 1.62 (1H, d, J=13.9 Hz), 1.72 (1H, d, J=13.9 Hz), 1.82–2.32 (6H, m), 2.39–2.54 (1H, m), 3.05 (1H, s), 3.22 (1H, s), 4.13 (1H, s), 4.64 (1H, s), 6.95–7.80 (4H, m);

Mass spectrum (CI, m/z): 304 (M$^+$+1).

Isomer B-1

Appearance: Pale yellow oil

NMR spectrum (CDCl$_3$, 67): 0.68–1.08 (4H, m), 1.25 (1H, s), 1.46–2.35 (8H, m), 2.38–2.54 (1H, m), 3.18 (1H, s), 3.26 (1H, s), 3.89–4.05 (1H, m), 4.72 (1H, s), 6.96–7.95 (4H, m);

Mass spectrum (CI, m/z): 304 (M$^+$+1).

REFERENCE EXAMPLE 7

(E)-1-(α-Cyclopropylcarbonyl-2-fluorobenzyl)-3-ethoxycarbonyl-methylindene-4-hydroxypiperidine (a) (E)-3-Ethoxycarbonylmethylidene-1-triphenylmethyl-4-piperidone After the portionwise addition of 18.1 g (65.1 mmol) of chlorotriphenylmethane methane to a 150 ml dimethylformamide solution of 10.0 g (65.1 mmol) of 4-piperidone monohydrate hydrochloride and 20.0 g (198 mmol) of triethylamine at 60° C. under stirring, the resulting mixture was stirring further for 5 hours at the same temperature. The triethylamine hydrochloride precipitated by cooling was filtered out and the filtrate was concentrated under reduced pressure. To the residue was added 150 ml of water, followed by extraction with 300 ml of ethyl acetate. The organic layer was then washed with saturated saline and dried over anhydrous magnesium sulfate. The solvent was concentrated under reduced pressure, whereby 23.0 g (yield: 98.3%) of 1-triphenylmethyl-4-piperidone were obtained.

A 300 ml benzene solution of 23.0 g of the resulting produce and 4.36 g (65.0 mmol) of pyrrolidine was subjected to azetrophic dehydration for 2 hours under heating and reflux by using a water separator. Then, a 50 ml benzene solution of 6.63 g (65.0 mmol) of ethyl glyoxylate (polymer type) was added and again the resulting mixture was subjected to azeotrophic dehydration for 90 minutes under heating and reflux. After cooling, 200 ml of water were added for washing and the organic layer was dried over anhydrous magnesium sulfate. The residue obtained by concentrating the solvent under reduced pressure was purified by chromatography on a silica gel column (eluting solvent: toluene/ethyl acetate=19/1), whereby 16.6 g (yield: 60.2%) of the title compound were obtained as a pale yellow oil.

NMR spectrum (CDCl$_3$, δ): 1.15 (3H, t, J=6.3 Hz), 2.57–2.68 (2H, m), 2.72–2.81 (2H, m), 3.61–3.79 (2H, m), 4.08 (2H, q, J=6.3 Hz), 6.55 (1H, s), 7.15–7.60 (15H, m);

Mass spectrum (CI, m/z): 426 (M$^+$+1).

(b) (E)-1-(α-Cyclopropylcarbonyl-2-fluorobenzyl)-3-ethoxycarbonylmethylidene-4-hydroxypiperidine After the portionwise addition of 1.48 g (39.1 mmol) of sodium borohydride to a 150 ml methanolic solution of 16.6 g (39.1 mmol) of (E)-3-ethoxycarbonylmethylidene-1-triphenylmethyl-4-piperidone under ice cooling, the resulting mixture was stirred for 1 hour at room temperature. The reaction mixture was concentrated under reduced pressure. The concentrate was extracted with 50 ml of water and 150 ml of ethyl acetate. The organic layer was washed with saturated saline and dried over anhydrous magnesium sulfate. The solvent was then distilled off under reduced pressure, whereby 16.8 g (yield: 100%) of (E)-3-ethoxycarbonylmethylidene-4-hydroxy-1-triphenylmethylpiperidine were obtained as a brown oil. 200 ml of tetrahydrofuran and 6.70 g (35.2 mmol) of p-toluenesulfonic acid monohydrate were added to the resulting product and the resulting mixture was stirred at 50° C. for 1 hour. After completion of the reaction, the solvent was distilled off under reduced pressure. The resulting solid was washed with toluene, whereby 10.8 g (yield: 86.6%) of the p-toluenesulfonate salt of 3-ethoxycarbonylmethylidene-4-hydroxypiperidine were obtained.

Then, the resulting product was dissolved in 80 ml of dimethylformamide. After the addition of 7.84 g (30.5 mmol) of α-cyclopropylcarbonyl-2-fluorobenzyl bromide and 9.27 g (67.0 mmol) of potassium carbonate, the resulting mixture was stirred at room temperature for 1 hour and then at 50° C. for 3 hours. After completion of the reaction, 150 ml of water were added and the mixture was extracted with ethyl cetate. The organic layer was washed with saturated saline, dried over anhydrous magnesium sulfate and distilled under reduced pressure to remove the solvent. The residue thus obtained was purified by chromatography on a silica gel column (eluting solvent: tolune/ethyl acetate=9/1 to 4/1), whereby 7.63 g (yield: 69.3%) were obtained as a pale yellow oil.

NMR spectrum (CDCl$_3$, δ): 0.74–0.88 (2H, m), 0.97–1.10 (2H, m), 1.22, 1.25 (total 3H, each t, J=6.8 Hz, J=7.3 Hz), 1.75–1.87 (1H, m), 2.00–2.65 (4H, m), 2.89–3.09 (2H, m), 4.11, 4.13 (total 2H, each q, J=6.8 Hz, J=7.3 Hz), 4.46, 4.58 (total 1H, each d, J=13.6 Hz, J=14.1 Hz), 4.77, 4.78 (total 1H, each s), 6.00 (1H, s), 7.05–7.43 (4H, m);

Mass spectrum (CI, m/z): 362 (M$^+$+1), 292.

REFERENCE EXAMPLE 8

(E)-1-(2-Chloro-α-methoxycarbonylbenzyl)-3-ethoxycarbonylmethylidene-4-hydroxypiperidine In a similar manner to Reference Example 7(b) except for the use of 2-chloro-α-methoxycarbonylbenzyl bromide instead of α-cyclopropylcarbonyl-2-fluorobenzyl bromide, the reaction was conducted, whereby the title compound was obtained as a yellow oil in a yield of 62.1%.

NMR spectrum (CDCl$_3$, δ): 1.10–1.35 (3H, m), 1.70–1.89 (1H, m), 1.91–2.10 (1H, m), 2.41–2.74 (2H, m), 2.82–2.96 (1H, m), 3.14 (0.5H, d, J=13.9 Hz), 3.21 (0.5H, d, J=13.9 Hz), 3.70, 3.71 (total 3H, each s), 4.00–4.22 (2H, m), 4.52 (0.5H, d, J=13.9 Hz), 4.61 (0.5H, d, J=13.9 Hz), 4.82, 4.87 (total 1H, each s), 5.99, 6.01 (total 1H, each s), 7.1–7.7 (4H, m);

Mass spectrum (CI, m/z): 368 (M$^+$+1).

REFERENCE EXAMPLE 9

(E)-1-(α-Cyclopropylcarbonyl-2-fluorobenzyl)-3-(N,N-dimethylcarbonyl)-methylidene-4-hydroxypiperidine 9.72 g (26.9 mmol) of (E)-1-(α-cyclopropylcarbonyl-2-fluorobenzyl)-3-ethoxycarbonylmethylidene-4-hydroxypiperidine were dissolved in a mixture of 75 ml of concentrated hydrochloric acid and 180 ml of acetic acid. The resulting solution was allowed to stand at room temperature for 7 days. The reaction mixture was concentrated to dryness under reduced pressure, followed by chromatography on a silica gel column (eluting solvent: chloroform/methanol=100/3 to 2/1), whereby 5.11 g (yield: 57%) of (E)-3-carboxymethylidene-1-(α-cyclopropylcarobonyl-2-fluorobenzyl)-4-hydroxypiperidine were obtained.

50 ml of methylene chloride and 3.25 g (32.2 mmol) of triethylamine were added to the resulting product. The resulting mixture was cooled to −5 to 0° C., followed by the dropwise addition of 1.66 g (15.3 mmol) of ethyl chlorocarbonate. The reaction mixture was allowed to warm back to room temperature and then stirred for 30 minutes. After cooling to 10° C, 1.25 g (15.3 mmol) of dimethylamine hydrochloride, and then 1.54 g (15.3 mmol) of triethylamine were hours. Methylene chloride-water was added to the reaction mixture to separate the methylene chloride layer, followed by drying over anhydrous magnesium sulfate. After concentration under reduced pressure, the concentrate was purified by chromatography on a silica gel column (eluting solvent: chloroform/methanol=10/3), whereby 3.56 g (yield: 64.4%) of the title compound was obtained as a pale yellow oil.

NMR spectrum (CDCl$_3$, δ): 0.75–0.90 (2H, m), 0.93–1.06 (2H, m), 1.62–1.83 (1H, m), 1.85–2.10 (1H, m), 2.10–2.59 (2H, m), 2.75 (0.5H, d, J=13.9 Hz), 2.83 (0.5H, d, J=13.9 Hz), 2.89, 2.92, 3.04 (total 6H, each s), 3.12–3.40 (1H, m), 3.66 (0.5H, d, J=13.9 Hz), 3.84 (0.5H, d, J=13.9 Hz), 4.00–4.13 (1H, m), 4.68, 4.71 (total 1H, each s), 6.13 (1H, s), 7.00–7.48 (4H, m);

Mass spectrum (CI, m/z): 361 (M$^+$+1).

REFERENCE EXAMPLE 10

(E)-1-(α-Cyclopropylcarbonyl-2-fluorobenzyl)-3-(N-methylcarbamoyl)-methylidene-4-hydroxypiperidine In a similar manner to Reference Example 9 except for the use of methylamine hydrochloride instead of dimethylamine hydrochloride, the reaction was conducted, whereby the title compound was obtained as a white solid in a yield of 55.1%.

NMR spectrum (CDCl$_3$, δ): 0.72–0.93 (2H, m), 0.94–1.12 (2H, m), 1.65–1.85 (1H, m), 1.85–2.12 (2H, m), 2.15–2.34 (0.5H, m), 2.4–2.68 (1H, m), 2.70–3.00 (4.5H, m), 3.95–4.20 (2H, m), 4.79 (0.5H, s), 4.85 (0.5H, s), 5.96

(0.5H, s), 5.97 (0.5s), 6.60 (0.5H, br.s), 6.83 (0.5H, br.s), 7.05–7.45 (4H, m);

Mass spectrum (CI, m/z): 347 (M$^+$+1).

REFERENCE EXAMPLE 11

1-(α-Cyclopropylcarbonyl-2-fluorobenzyl)-3-ethylidene-4-hydroxypiperidine (a) 1-(t-Butoxycarbonyl)-3-ethylidene-4-piperidone A 100 ml tolune solution of 10.0 g (52.9 mmol) of 1-benzyl-4-piperidone and 4.61 g (52.9 mmol) of morpholine was subjected to azeotropic dehydration for 5 hours under heating and reflux by using a water separator. After completion of the reaction, the solvent was distilled off under reduced pressure, whereby 13.7 g of 1-benzyl-4-morpholino-1,2,5,6-tetrahydropyridine were quantitatively obtained. In an argon atmosphere, a 20 ml methylene chloride solution of 1.52 g (34.6 mmol) of acetaldehyde was cooled to −40° C., followed by the dropwise addition of 5.3 ml (43 mmol) of a boron trifluoride-ether complex and 7.44 g (28.8 mmol) of the 1-benzyl-4-morpholino-1,2,5,6-tetrahydropyridine obtained above. After completion of the dropwise addition, the temperature was gradually raised and the reaction mixture was allowed to stand overnight at room temperature. Water was added to terminate the reaction, followed by extraction with methylene chloride. The organic layer was washed with saturated saline, dried over anhydrous sodium sulfate and concentrated under reduced pressure. The residue was subjected to chromatography on a silica gel column (eluting solvent: toluene/ethyl acetate=4/1), whereby 4.68 g (yield: 69.7%) of 1-benzyl-3-(1-hydroxyethyl)-4-piperidone were obtained as a yellowish brown oil.

NMR spectrum (CDCl$_3$, δ): 1.11–1.14 (3H, d, J=6 Hz), 2.35–2.95 (7H, m), 3.54–3.70 (2H, m), 4.02–4.22 (1H, m), 7.28–7.36 (5H, m).

4.68 g (20 mmol) of the 1-benzyl-3-(1-hydroxyethyl)-4-piperidone obtained above were dissolved in 100 ml of ethanol. 0.5 g of 5% palladium-carbon were added to the resulting solution, followed by stirring at 60° C. for 8 hours in a hydrogen atmosphere. After completion of the reaction, the palladium-carbon was filtered off using Celite® and the solvent was distilled off under reduced pressure, whereby 2.98 g of 3-(1-hydroxyethyl)-4-piperidone were quantitatively obtained as a colorless oil.

The resulting product was then dissolved in 20 ml of methylene chloride and 20 ml of a 15% aqueous solution of potassium carbonate was added to the resulting solution. Under stirring, 4.6 g (21 mmol) of di-t-butyl dicarbonate were added. The mixture was stirred at room temperature for 3 hours. After completion of the reaction, the reaction mixture was extracted with methylene chloride. The organic layer was washed with saturated saline, dried over anhydrous sodium sulfate and then concentrated under reduced pressure. The residue thus obtained was subjected to chromatography on a silica gel column (eluting solution: toluene/ethyl acetate=4/1), whereby 1.86 g (yield: 38.3%) of 1-(t-butoxycarbonyl)-3-(1-hydroxyethyl)-4-piperidone were obtained as a colorless oil.

NMR spectrum (CDCl$_3$, δ): 1.21 (1.5H, d, J=7 Hz), 1.25 (1.5H, d, J=6 Hz), 1.50 (9H, s), 2.40–2.49 (3H, m), 2.98–3.08 (0.5H, m), 3.26–3.33 (1H, m), 3.40–3.90 (2.5H, m), 3.95–3.98 (0.5H, m), 4.08–4.28 (1.5H, m);

Mass spectrum (CI, m/z): 188, 144.

0.77 g (7.6 mmol) of triethylamine were added to a 20 ml methylene chloride solution of 1.86 g (7.6 mmol) of the 1-(t-butoxycarbonyl)-3-(1-hydroxyethyl)-4-piperidone obtained above. Under ice cooling, 0.88 g (7.6 mmol) of methanesulfonyl chloride were added and the resulting mxiture was stirred at room temperature for 1 hour. The solvent was distilled off under reduced pressure. Ethyl acetate was added to the residue. The solid thus precipitated was filled out, followed by concentration under reduced pressure again. The concentrate was then dissolved in 20 ml of chloroform, followed by the addition of 1.16 g (7.6 mmol) of 1,8-diazabicyclo[5.4.0]under-7-ene (DBU) at room temperature. The mixture was stirred for 2 hours at the same temperature. After completion of the reaction, the reaction mixture was concentrated under reduced pressure. The residue was subjected to chromatography on a silica gel column (eluting solvent: toluene/ethyl acetate=19/1), whereby 1.32 g (yield: 77.2%) of the title compound were obtained as a colorless oil.

NMR spectrum (CDCl$_3$,δ): 1.49 (9H, s), 1.80 (3H, d, J=7 Hz), 2.64 (2H, t, J=6 Hz), 3.71 (2H, t, J=6 Hz), 4.35 (2H, br.s), 6.86 (1H, br.q);

Mass spectrum (CI, m/z): 170.

(b) 1-(α-Cyclopropylcarbonyl-2-fluorobenzyl)-3-ethylidene-4-hydroxypiperidine 2.19 g (5.9 mmol) of cerium chloride heptahydrate and 0.22 g (5.9 mmol) of sodium borohydride were successively added to a 10 ml methanolic solution of 1.32 (5.9 mmol) of 1-(t-butoxycarbonyl)-3-ethylidene-4-piperidone under ice cooling. The resulting mixture was stirred at room temperature for 1 hour. After distillation under reduced pressure to remove the solvent, water was added and the mixture was extracted with ethyl acetate. The organic layer was dried over anhydrous sodium sulfate and concentrated under reduced pressure. The residue was subjected to chromatography on a silica gel column (eluting solvent: chloroform), whereby 1.33 g of 1-(t-butoxycarbonyl)-3-ethylidene-4-hydroxypiperidine were quantitatively obtained as a colorless oil.

NMR spectrum (CDCl$_3$, δ): 1.46 (9H, s), 1.60–1.69 (1H, m), 1.71 (3H, d, J=7 Hz), 1.80–1.90 (1H, m), 3.50–3.65 (2H, m), 4.04 (1H, br.s), 4.23 (1H, br.t), 5.54 (1H, q, J=7 Hz).

Mass spectrum (CI, m/z): 172, 154.

1.51 g (6.7 mmol) of 1-(t-butoxycarbonyl)-3-ethylene-4-hydroxypiperidine were dissolved in 20 ml of methylene chloride. After the addition of 5 ml of trifluoroacetic acid under ice cooling, the resulting mixture was stirred at room temperature for 2 hours. Under ice cooling, 11 ml of triethylamine and 1.70 g (6.7 mmol) of α-cyclopropylcarbonyl-2-fluorobenzyl bromide were added and the resulting mixture was stirred at room temperature for 2 hours. The solvent was distilled off under reduced pressure. Ethyl acetate was added to the residue. After the solid thus precipitated was filtered off, the residue was concentrated under reduced pressure. The residue was subjected to chromatography on a silica gel column (eluting solvent: chloroform/methanol=100/1), whereby 1.52 g (yield: 74.9%) of the title compound were obtained as a yellow oil.

NMR spectrum (CDCl$_3$, δ): 0.80–0.88 (2H, m), 0.96–1.06 (2H, m), 1.23 (3H, d, J=6 Hz), 2.20–2.27 (3H, m), 2.40–2.73 (2H, m), 2.98–3.17 (2H, m), 4.17–4.19 (1H, m), 4.73 (0.5H, s), 4.74 (0.5H, s), 5.75 (1H, br.s), 7.08–7.18 (2H, m), 7.28–7.33 (1H, m), 7.41–7.48 (1H, m);

Mass spectrum (CI, m/z): 304 (M$^+$+1).

REFERENCE EXAMPLE 12

1-(2-Fluoro-α-methoxycarbonylbenzyl)-4-hydroxypiperidine

In a similar manner to Reference Example 1 except for the use of 2-fluoro-α-methoxycarbonylbenzyl bromide instead of α-cyclopropylcarbonyl-2-fluorobenzyl bromide, the reaction was conducted, whereby the title compound was obtained as a colorless oil in a yield of 91.7%.

NMR spectrum (CDCl$_3$, δ): 1.54–1.74 (2H, m), 1.83–1.97 (2H, m), 2.16–2.35 (2H, m), 2.73–2.88 (2H, m), 3.55–3.78 (1H, m), 3.70 (3H, s), 4.53 (1H, s), 7.02–7.53 (4H, m);

Mass spectrum (CI, m/z): 268 (M$^+$+1).

REFERENCE EXAMPLE 13

(E)-1-(2-Chloro-α-methoxycarbonylbenzyl-3-(N,N-dimethylcarbamoyl)-methylidene-4-hydroxypiperidine (a) (E)-3-Carboxymethylidene-4-hydroxy-1-triphenylmethylpiperidine 1.0 g (2.3 mmol) of (E)-3-ethoxy-carbonylmethylidene-4-hydroxy-1-triphenylmethylpiperidine were dissolved in 15 ml of ethanol, followed by the addition of 6.0 g (25 mmol) of a 16.7% aqueous solution of sodium hydroxide. The resulting mxiture was stirred at room temperature for 15hours. After neutralization of the reaction mixture with 1.8 g (30 mmol) of acetic acid, water was added. The resulting mixture was extracted with chloroform. The extract was washed with saturated saline, dried over anhydrous sodium sulfate and distilled under reduced pressure to remove the solvent, whereby 0.92 g (yield: 98%) of (E)-3-carboxymethylidene-4-hydroxy-1-triphenylmethylpiperidine were obtained as a white powder.

NMR spectrum (CDCl$_3$, δ): 1.69–1.99 (2H, m), 2.03–2.23 (2H, m), 2H, m), 3.01 (1H, d, J=10.0 Hz), 3.93–4.05 (1H, m), 4.61 (1H, d, J=10.0 Hz), 6.11 (1H, s), 7.05–7.56 (15H, m);

IR spectrum (KBr, $v_{max}$cm$^{-1}$): 1695.

(b) (E)-3-(N,N-Dimethylcarbamoyl)methylidene-4-hydroxy-1-piperidine p-toluenesulfonate 20 ml of methylene chloride and 0.35 g (3.5 mmol) of triethylamine were added to the resulting product. After cooling to −5 to 0° C., 0.28 g (2.6 mmol) of ethyl chlorocarbonate were added dropwise. The reaction mixture was allowed to warm to room temperature. After stirring for 30 minutes, 0.21 g (2.6 mmol) of dimethylamine hydrochloride and 0.28 g (2.8 mmol) of triethylamine were added successively. The resulting mixture was stirred at room temperature for 5 hours. The organic layer separated by the addition of chloroform and water was dried over anhydrous magnesium sulfate and then distilled under reduced pressure to remove the solvent. The residue was purified by chromatography on a silica gel column (eluting solvent: chloroform/methanol=100/3), whereby 0.56 g (yield: 57%) of (E)-3-(N,N-dimethylcarbamoyl)methylidene-4-hydroxy-1-triphenylmethylpiperidine were obtained as a white powder.

NMR spectrum (CDCl$_3$, δ): 1.68–1.93 (2H, m), 1.95–2.20 (2H, m), 2.90 (3H, s), 2.91–3.03 (1H, m), 3.13 (3H, s), 3.68–3.84 (1H, m), 3.87–4.00 (1H, m), 6.18 (1H, s), 7.06–7.53 (15H, m);

IR spectrum (KBr, $v_{max}$cm$^{-1}$): 1613.

50 ml of tetrahydrofuran and 0.25 g (1.3 mmol) of p-toluenesulfonic acid monohydrate were added to the resulting product. After stirring at 50° C. for 1 hour, the reaction mixture was allowed to stand overnight. After completion of the reaction, the solvent was distilled off under reduced pressure. The residue was washed with toluene, whereby 0.55 g (yield: 100%) of (E)-3-(N,N-dimethylcarbamoyl)methylidene-4-hydroxypiperidine p-toluenesulfonate were obtained as a white solid.

NMR spectrum (CD$_3$OD, δ): 1.78–1.93 (1H, m), 2.11–2.24 (1H, m), 2.37 (3H, s), 2.98 (3H, s), 3.07 (3H, s), 3.17–3.33 (1H, m), 3.41–3.52 (1H, m), 3.81 (1H, d, J=13.8 Hz), 4.32–4.40 (2H, m), 6.59 (1H, s), 7.22 (2H, dd, J=1.8, 8.4 Hz), 7.70 (2H, dd, J=1.8, 8.4 Hz);

IR spectrum (KBr, $v_{max}$cm$^{-1}$): 1616.

(c) (E)-1-(2-Chloro-α-methoxycarbonylbenzyl)-3-(N,N-dimethylcarbamoyl)methylidene-4-hydroxypiperidine 7.95 g (23.3 mmol) of the (E)-3-(N,N-dimethylcarbamoyl)methylidene-4-hydroxypiperidine p-toluenesulfonate were dissolved in 50 ml of N,N-dimethylformamide (DMF), followed by the addition of 7.35 g (purity: 80.0%, 22.3 mmol) of 2-chloro-α-methoxycarbonylbenzyl bromide and 7.40 g (53.5 mmol) of potassium carbonate. The resulting mixture was stirred at room temperature for 15 hours. After completion of the reaction, 150 ml water were added. The resulting mixture was extracted with toluene and ethyl acetate. The extract was distilled under reduced pressure. The residue was then purified by chromatography on a silica gel column (eluting solvent: chloroform/methanol=9/1 to 4/1), whereby 6.38 g (77.9%) of the title compound were obtained as a yellowish brown oil.

NMR spectrum (CDCl$_3$, δ): 1.58–1.77 (1H, m), 1.89–2.04 (1H, m), 2.41–2.62 (1H, m), 2.77–3.06 (7H, m), 3.61–3.75 (4H, m), 3.92–4.19 (2H, m), 4.74, 4.79 (total 1H, each s), 6.06, 6.13 (total 1H, each s), 7.17–7.60 (4H, m);

Mass spectrum (CI, m/z): 367 (M$^+$+1);

IR spectrum (KBr, vhd maxcm$^{-1}$): 1743, 1667, 1612.

REFERENCE EXAMPLE 14

(E)-1-(2-Chloro-α-Methoxycarbonylbenzyl)-3-(N-Methylcarbamoyl)-Methylidene-4-Hydroxypiperidine In a similar manner to Reference Example 13 except that methylamine hydrochloride was used instead of dimethylamine hydrochloride in the step (b) of Example 13, the title compound was obtained as pale yellowish brown powder in a yield of 57.7%.

NMR spectrum (CDCl$_3$, δ): 1.58–1.81 (1H, m), 1.91–2.06 (1H, m), 2.33–2.46 (0.5H, m), 2.52–2.61 (0.5H, m), 2.77 (1.5H, d, J≦4.9Hz), 2.80 (1.5H, d, J=4.9Hz), 2.87–3.15 (2H, m), 3.70 (3H, s), 4.05–4.30 (2H, m), 4.77, 4.87 (total 1H, each s), 5.95 (1H, s), 6.22 (1H, br.s), 7.19–7.61 (4H, m);

Mass spectrum (CI, m/z): 353 (M$^+$+1);

IR spectrum (KBr, $v_{max}$ cm$^{-1}$): 1740, 1670, 1635.

REFERENCE EXAMPLE 15

(E)-3-Butoxycarbonylmethylidene-1-(2-Chloro-α-Methoxycarbonylbenzyl)-4-Hydroxypiperidine 50 ml of 1-butanol were added to 5.44 g (13.6 mmol) of (E)-3-carboxymethylidene-4-hydroxy-1-triphenylmethylpiperidine. Hydrogen chloride gas was blown through the resulting mixture, followed by stirring at 60° C. for 1 hour. After completion of the reaction, the solvent was distilled off under reduced pressure. The residue was washed with toluene, whereby 3.43 g (yield: 100%) of (E)-3-butoxycarbonylmethylidene-4-hydroxypiperidine hydrochloride were obtained as a white solid.

NMR spectrum (CD$_3$OD, δ): 0.96 (3H, t, J=7.3Hz), 1.33–1.49 (2H, m), 1.58–1.71 (2H, m), 1.81–1.95 (1H, m), 2.11–2.27 (1H, m), 3.17–3.33 (1H, m), 3.40–3.56 (1H, m), 4.05 (1H, d, J=13.9Hz), 4.16 (2H, d, J=6.6Hz), 4.30–4.43 (1H, m), 4.92 (1H, d, J=13.9Hz), 6.25 (1H, s), 7.04–7.24 (1H, m);

Mass spectrum (CI, m/z): 214 (M$^+$+1). p In a similar manner to Reference Example 13(c), the reaction was conducted using the hydrochloride obtained above, whereby the title compound was obtained as a pale yellow oil in a yield of 61.7%.

NMR spectrum (CDCl$_3$, δ): 0.92 (3H, t, J=7.3Hz), 1.29–1.43 (2H, m), 1.50–1.64 (2H, m), 1.71–1.87 (1H, m), 1.96–2.08 (1H, m), 2.48–2.69 (1H, m), 2.83–2.96 (1H, m), 3.16 (0.5H, J=13.9Hz), 3.24 (0.5H, d, J=13.9Hz), 3.70, 3.72 (total 3H, each s), 4.00–4.08 (2H, m), 4.10–4.21 (1H, m), 4.52 (0.5H, d, J=13.9Hz), 4.61 (0.5H, d, J=13.9Hz), 4.83, 4.87 (total 1H, each s), 5.99, 6.00 (total 1H, each s), 71.5–7.61 (4H, m);

Mass spectrum (CI, m/z): 396 (M$^+$+1);

IR spectrum (Liquid membrane method, $v_{max}$ cm$^{-1}$): 1741, 1715, 1662.

REFERENCE EXAMPLE 16

(E)-3-Butoxycarbonylmethylidene-1-(α-Cyclopropylcarbonyl-2-Fluorobenzyl)-4-Hydroxypiperidine 150 ml of 1-butanol were added to 3.19 g (9.58 mmol) of (E)-3-carboxymethylidene-1-(α-cyclopropyl-carbonyl-2-fluorobenzyl)-4-hydroxypiperidine. Hydrogen chloride gas was blown through the resulting mixture until the solution became acidic. After standing at room temperature for 2 hours, 100 ml of benzene were added and the mixture was subjected to azeotropic dehydration for 2 hours. After completion of the reaction, the solvent was distilled off under reduced pressure. Toluene and an aqueous solution of sodium bicarbonate were added to the residue. The toluene layer thus separated was dried over anhydrous sodium sulfate. The solvent was distilled off under reduced pressure, followed by purification by chromatography on a silica gel column (eluting solvent: toluene/ethyl acetate=4/1), whereby 2.75 g (yield: 73.7%) of the tile compound were obtained as a pale yellow oil.

NMR spectrum (CDCl$_3$, δ): 0.74–1.11 (7H, m), 1.30–1.46 (2H, m), 1.50–1.64 (2H, m), 1.74–1.90 (1H, m), 1.96–2.08 (1H, m), 2.11–2.24 (1H, m), 2.82–3.05 (2H, m), 3.98–4.16 (4H, m), 4.46 (0.5H, d, J=12.2Hz), 4.60 (0.5H, d, J=12.2Hz), 4.76, 4.77 (total 1H, each s), 6.00 (1H, s), 7.05–7.39 (4H, m);

Mass spectrum (CI, m/z): 390 (M$^+$+1);

IR spectrum (Liquid membrane method, $v_{max}$ cm$^{-1}$): 1713, 1663.

TEST EXAMPLE 1

Antiaggregatory Action in Human Platelets

Platelet aggregation was measured using an automatic platelet aggregometer (PAM-8C, Mebanix) using the method of G.V.R. Born [Nature, 194, 927–929 (1992)] with a slight modification. Blood was collected from the antecubital vein of healthy volunteers who had not taken any medications for two weeks using 3.8% sodium citrate as an anticoagulant (⅑ volumes of blood). Platelet-rich plasma (PRP) was obtained by centrifugation (CR5DL, Hitachi) at 200× g for 15 min at room temperature. Platelet-poor plasma (PPP) was obtained by centrifugation of the remaining blood at 2,000× g for 10 min at room temperature. Platelet counts in PRP were measured by an automatic hematology analyzer (K-1000, Toa Iyo Denshi), and adjusted to 3×10$^8$ /ml by adding PPP. PRP prepared as described above was used for the platelet aggregation experiment. PRP (0.24 ml) containing a test compound was added to a cuvette and set placed in the platelet aggregometer. After pre-incubation for 1.5 min at 37° C., 0.01 ml of 0.25 mM ADP were added to the cuvette to induce platelet aggregation. Platelet aggregation was monitored for 10 min.

Antiaggregatory action of the test compound was determined as a percent inhibition (%) against platelet aggregation of a control (free of the test compound). Results are shown in Table 6.

TABLE 6

| Test compound | Test 1 (% inhibition) | | |
| --- | --- | --- | --- |
| | 10 μg/ml | 30 μg/ml | 100 μg/ml |
| Example 1 (c) | 36.5 | 99.6 | 100 |
| Example 2 (d) | 32.8 | 97.1 | 98 |
| Example 3 (d) | 24.4 | 89.3 | 99.8 |
| Example 4 (d) | 30.6 | 77.6 | 99.5 |
| Example 5 (d) | 37.1 | 98.4 | 99.6 |
| Example 6 (d) | 22.5 | 53.2 | 100 |
| Example 7 (c) (ii) | 34.5 | 81.5 | — |
| Example 7 (d) | 24.6 | 60 | 99.1 |
| Example 8 | 19.5 | 88 | 100 |
| Example 9 (b) | 23.4 | 97.3 | 94 |
| Example 10 (b) | 35.2 | 96.2 | 98.8 |
| Example 11 (b) | 15.5 | 98 | 92.5 |
| Example 12 (b) | 19.2 | 93.9 | 100 |
| Example 13 (b) | 13.3 | 40 | 91.8 |
| Example 14 (b) | 28.6 | 64 | 95.8 |
| Example 15 (b) | 12.3 | 28.1 | 71.1 |

TEST EXAMPLE 2

Antiaggregatory Action in Rats

Platelet aggregation was measured using an automatic platelet aggregometer (PAM-8C, Mebanix) using the method of G.V.R. Born [Nature, 194, 927–929(1962)] with a slight modification. The experimental animals were male SD rats (Japan SLC). One hour after intravenous administration of a test compound to the rats, blood was collected from the abdominal aorta under anesthesia, using 3.8% sodium citrate as an anticoagulant (⅑ volumes of blood). Platelet-rich plasma (PRP) was obtained by centrifugation (CR5DL, Hitachi) at 230× g for 15 min at room temperature. Platelet-poor plasma (PPP) was obtained by centrifugation of the remaining blood at 2,000× g for 10 min at room temperature. Platelet counts in PRP were measured by an automatic hematology analyzer (K-1000, Toa Iyo Denshi), and adjusted to 5×10$^8$ /ml by adding PPP, and then used for the platelet aggregation experiment. PRP (0.24 ml) was added to a cuvette and placed in the platelet aggregometer. After pre-incubation for 1.5 min at 37° C., 0.01 ml of 0.75 mM ADP were added to the cuvette to induce platelet aggregation. Platelet aggregation was monitored for 8 min.

Antiaggregatory action (% inhibition) of the test compound was determined from a comparison of the maximum aggregation of the test compound-treated rat with that of control rats (free of the administration of the test compound). Results are shown in Table 7.

TABLE 7

| Test compound | Test 2 (% inhibition) 10 mg/kg |
|---|---|
| Example 6 (d) | 51.8 |
| Example 7 (d) | 59.0 |
| Example 19 (d) | 89.2 |

FORMULATION EXAMPLE 1

Hard Capsules 50 mg of the compound of Example 7(d) in the powdery form, 128.7 mg of lactose, 70 mg of cellulose and 1.3 mg of magnesium stearate were mixed together. The resulting mixture was allowed to pass through a sieve of 60 mesh and the resulting powder was used to fill No. 3 gelatin capsules, whereby capsules were obtained.

FORMULATION EXAMPLE 2

Tablets 50 mg of the compound of Example 7(d) in the powdery form, 124 mg of lactose, 25 mg of cellulose and 1 mg of magnesium stearate were mixed together. The resulting mixture was tableted using a tableting machine, whereby a tablet, containing 200 mg, was obtained. These tablets can be coated with sugar if necessary.

The compounds of the formula (I) according to the present invention have excellent platelet aggregation inhibitory action and inhibitory action against the advance of arteriosclerosis (particularly, the platelet aggregation inhibitory action) and have low toxicity. They are therefore useful as a preventive agent or remedy (particularly, as a remedy) for embolism, thrombosis or arteriosclerosis (particularly, embolism or thrombosis).

When the compounds of formula (I) of the present invention or pharmacologically acceptable salts thereof are used as a remedy or preventive agent for the above-described diseases, they can be administered orally as tablets, capsules, granules, powders or syrups or parenterally as injections or suppositories after being mixed with a carrier such as an excipient, diluent or the like.

The above-described formulations can be prepared in a known manner by using carriers. Examples of such carriers include excipients (e.g. organic excipients, for example, sugar derivatives such as lactose, sucrose, dextrose, mannitol and sorbitol, starch derivatives such as corn starch, potato starch, α-starch and dextrin, cellulose derivatives such as crystalline cellulose, gum arabic, dextran, and pullulan; and inorganic excipients, for example, silicate derivatives such as light silicic acid anhydride, synthetic aluminum silicate, calcium silicate and magnesium aluminate metasilicate, phosphates such as calcium hydrogenphosphate, carbonates such as calcium carbonate, and sulfates such as calcium sulfate), lubricants (for example, stearic acid, metal salts of stearic acid such as calcium stearate and magnesium stearate, talc, collidol silica, waxes such as bees wax and spermaceti, boric acid, adipic acid, sulfates such as sodium sulfate, glycol, fumaric acid, sodium benzoate, DL leucine, lauryl sulfates such as sodium lauryl sulfate and magnesium lauryl sulfate, silicic acids such a silicic acid anhydride and silicic acid hydrate and the above-exemplified starch derivatives), binders (for example, hydroxypropyl cellulose, hydroxypropylmethyl cellulose, polyvinyl pyrrolidone, macrogol and compounds similar to those exemplified above as excipients), disintegrators (for example, cellulose derivatives such as low-substituted hydroxypropyl cellulose, carboxymethyl cellulose, carboxymethyl cellulose calcium and internally crosslinked carboxymethyl cellulose sodium and chemically modified starches celluloses such as carboxymethyl starch, carboxymethyl starch sodium and crosslinked polyvinyl pyrrolidone), emulsifiers (for example, colloidal clay such as bentonite and bee gum, metal hydroxides such as magnesium hydroxide and aluminum hydroxide, anionic surfactants such as sodium lauryl sulfate and calcium stearate, cationic surfactants such as benzalkonium chloride, and nonionic surfactants such as polyoxyethylene alkyl ethers and polyoxyethylene sorbitan fatty acid esters and sucrose fatty acid esters), stabilizers (paraoxybenzoates such as methyl paraben and propyl paraben, alcohols such as chlorobutanol, benzyl alcohol and phenyl ethyl alcohol, benzalkonium chloride, phenols such as phenol and cresol, thimerosal, dehydroacetic acid, and sorbic acid), corrigents (ordinarily-used sweeteners, acidifiers and flavors), and diluents.

The dose of the compound of formula (I) varies with symptoms, age and the like of a patient, but is, per human adult, 1 mg/once (preferably, 10 mg/once) as the lower limit and 1000 mg/once (preferably, 500 mg/once) as the upper limit in the case of oral administration, while it is 0.5 mg/once (preferably, 5 mg/once) as the lower limit and 500 mg/once (preferably, 250 mg/once) as the upper limit in the case of intravenous administration. The dose is desirably administered 1 to 6 times a day depending on the symptom of the patient.

What is claimed is:

1. A cyclic amino compound represented by the following formula:

wherein:
- $R^1$ represents a phenyl group which may optionally be substituted by at least one substituent selected from the group consisting of halogen atoms, $C_1$–$C_4$ alkyl groups, fluoro-substituted-($C_1$–$C_4$ alkyl) groups, $C_1$–$C_4$ alkoxy groups, fluoro-substituted- ($C_1$–$C_4$ alkoxy) groups, cyano groups and nitro groups;
- $R^2$ represents a substituent selected from the group consisting of
  - $C_1$–$C_8$ aliphatic acyl groups which may optionally be substituted by at least one substituent selected from the group consisting of halogen atoms, $C_1$–$C_4$ alkoxy groups and cyano groups,
  - benzoyl groups which may optionally be substituted by at least one substituent selected from the group consisting of halogen atoms, $C_1$–$C_4$ groups and $C_1$–$C_4$ alkoxy groups, and
  - ($C_1$–$C_4$ alkoxy) carbonyl groups; and
- $R^3$ represents a saturated cyclic amino group having five carbon atoms and one ring nitrogen atom, said saturated cyclic amino group being substituted by a group having the formula —S—X— $R^4$ wherein $R^4$ and X are as defined below, said saturated cyclic amino group being attached via the ring nitrogen atom thereof to the carbon atom to which substitutents $R^1$ and $R^2$ are attached, R⁴ represents a substituent selected from the group consisting of
  phenyl groups which may optionally be substituted by at least one substituent selected from the group consisting of halogen atoms, $C_1$–$C_4$ alkyl groups, $C_1$–$C_4$ alkoxy groups, nitro groups and cyano groups,
  $C_1$–$C_4$ alkyl groups which may optionally be substituted by at least one substituent selected from the group consisting of amino groups, hydroxyl groups, carboxyl groups, ($C_1$–$C_4$ alkoxy) carbonyl groups, substituents having the formula —NH—A¹, wherein A¹ represents an α-amino acid residue, and substituents having the formula —CO—A², wherein A² represents an α-amino acid residue, and
  $C_3$–$C_8$ cycloalkyl groups; and
X represents a sulfur atom, a sulfinyl group or a sulfonyl group;
said cyclic amino group may optionally be further substituted by a group having the formula =CR⁵R⁶, wherein R⁵ and R⁶ are the same or different and each is independently selected from the group consisting of hydrogen atoms, $C_1$–$C_4$ alkyl groups, carboxyl groups, ($C_1$–$C_4$ alkoxy) carbonyl groups, carbamoyl groups, ($C_1$–$C_4$ alkyl) carbamoyl groups and di-($C_1$–$C_4$ alkyl) carbamoyl groups;
or a pharmacologically acceptable salt thereof.

2. A cyclic amino compound or a pharmacologically acceptable salt thereof according to claim 1, wherein R¹ represents a phenyl group which is substituted by at least one substituent selected from the group consisting of halogen atoms, methyl groups, ethyl groups, difluoromethyl groups, trifluoromethyl groups, methoxy groups, ethoxy groups, difluoromethoxy groups, trifluoromethoxy groups, cyano groups and nitro groups.

3. A cyclic amino compound or a pharmacologically acceptable salt thereof according to claim 1, wherein R¹ represents a phenyl group which is substituted by at least one substituent selected from the group consisting of fluorine atoms, chlorine atoms, bromine atoms, trifluoromethyl groups, difluoromethoxy groups, trifluoromethoxy groups, cyano groups and nitro groups.

4. A cyclic amino compounds or a pharmacologically acceptable salt thereof according to claim 1, wherein R¹ represents a phenyl group which is substituted by at least one fluorine or chlorine atom.

5. A cyclic amino compound or a pharmacologically acceptable salt thereof according to claim 1 wherein, where R¹ represents a substituted phenyl group, the number of substituents ranges from 1 to 3.

6. A cyclic amino compound or a pharmacologically acceptable salt thereof according to claim 1 wherein, where R¹ represents a substituted phenyl group, the number of substituents is 1 or 2.

7. A cyclic amino compound or a pharmacologically acceptable salt thereof according to claim 1 wherein, where R¹ represents a substituted phenyl group, said phenyl group is substituted at the 2- or 4-position.

8. A cyclic amino compound or a pharmacologically acceptable salt thereof according to claim 1, wherein where R² represents a substituent selected from the group consisting of
  $C_2$–$C_4$ alkanoyl groups and ($C_3$–$C_6$ cycloalkyl)carbonyl groups, said groups optionally being substituted by at least one substituent selected from the group consisting of fluorine atoms, chlorine atoms, methoxy groups, ethoxy groups and cyano groups,
  benzoyl groups which may optionally be substituted by at least one substituent selected from the group consisting of fluorine atoms, chlorine atoms, methyl groups, ethyl groups, methoxy groups and ethoxy groups, and
  ($C_1$–$C_4$ alkoxy)carbonyl groups.

9. A cyclic amino compound or a pharmacologically acceptable salt thereof according to claim 1, wherein where R² represents a substituent selected from the group consisting of
  $C_2$–$C_4$ alkanoyl groups and ($C_3$–$C_6$ cycloalkyl)carbonyl groups, said groups optionally being substituted by at least one fluorine or chlorine atom,
  benzoyl groups, and
  ($C_1$–$C_4$ alkoxy)carbonyl groups.

10. A cyclic amino compound or a pharmacologically acceptable salt thereof according to claim 1, wherein where R² represents a substituent selected from the group consisting of
  acetyl, propionyl, isobutyryl, cyclopropylcarbonyl and cyclobutylcarbonyl groups, said groups optionally being substituted by at least one fluorine atom,
  methoxylcarbony groups, and
  ethoxycarbonyl groups.

11. A cyclic amino compound or a pharmacologically acceptable salt thereof according to claim 1, wherein where R² represents a propionyl, cyclopropylcarbonyl, methoxycarbonyl or ethoxycarbonyl group.

12. A cyclic amino compound or a pharmacologically acceptable salt thereof according to claim 1, wherein
  R³ is selected from the group consisting of 3- or 4-(—S—X—R⁴)-1-piperidinyl groups and 4-(—S—X—R⁴)-3-(=CR⁵⁼ᴸ ᴿ⁶)-1-piperidinyl groups, wherein
  R⁴ is selected from the group consisting of
    phenyl groups which may optionally be substituted by at least one substituent selected from the group consisting of halogen atoms, methyl groups, ethyl groups, methoxy groups, ethoxy groups, nitro groups and cyano groups,
    straight $C_1$–$C_6$ alkyl groups which may optionally be substituted by at least one substituent selected from the group consisting of amino groups, hydroxyl groups, carboxyl groups, ($C_1$–$C_4$ alkoxy) carbonyl groups, substituents having the formula —NH—A¹ᵃ, wherein A¹ᵃ represents a glycyl, alanyl, β-aspartyl or γ-glutamyl group, and substituents having the formula —CO—A²ᵃ, wherein A²ᵃ represents a glycino, alanino, valino, leucino, phenylglycino or phenylalanino group, and
    cyclobutyl, cyclopentyl, cyclohexyl and cycloheptyl groups;
  R⁵ and R⁶ are the same or different and each is independently selected from the group consisting of hydrogen atoms, $C_1$–$C_4$ alkyl groups, carboxyl groups, ($C_1$–$C_4$ alkoxy) carbonyl groups, carbamoyl groups, ($C_1$–$C_4$ alkyl)-carbamoyl groups and di-($C_1$–$C_4$ alkyl) carbamoyl groups; and
  X represents a sulfur atom, sulfinyl group or sulfonyl group.

13. A cyclic amino compound or a pharmacologically acceptable salt thereof according to claim 1, wherein R³ is selected from the group consisting of 4-(—S—X—R⁴)-1-piperidinyl groups and 4-(—S—X—R⁴)-3-(=CR⁵R⁶)-1-piperidinyl groups, wherein
  R⁴ is selected from the group consisting of
    phenyl groups which may optionally be substituted by at least one substituent selected from the group consisting of fluorine atoms, chlorine atoms, bromine atoms, methyl groups, methoxy groups, nitro groups and cyano groups,
straight $C_1$–$C_4$ alkyl groups which may optionally be substituted by at least one substituent selected from the group consisting of amino groups, hydroxyl groups, carboxyl groups, methoxycarbonyl groups, ethoxycarbonyl groups, substituents having the formula —NH—$A^{1b}$, wherein $A^{1b}$ represents a glycyl or γ-glutamyl group, and substituents having the formula —CO—$A^{2b}$, wherein $A^{2b}$ represents a glycino, alanino or valino group, and
cyclopentyl and cyclohexyl groups;
$R^5$ and $R^6$ are the same or different and each is independently selected from the group consisting of hydrogen atoms, methyl groups, ethyl groups, carboxyl groups, methoxycarbonyl groups, ethoxycarbonyl groups, carbamoyl groups, methylcarbamoyl groups, ethylcarbamoyl groups, N,N-dimethyl-carbamoyl groups and N,N-diethylcarbamoyl groups; and
X represents a sulfur atom, a sulfinyl group or a sulfonyl group.

14. A cyclic amino compound or a pharmacologically acceptable salt thereof according to claim 1, wherein $R^3$ is selected from the group consisting of 4-(—S—X—$R^4$)-1-piperidinyl groups and 4-(—S—X—$R^4$)-3-(=$CR^5R^6$)-1-piperidinyl
$R^4$ is selected from the group consisting of
phenyl groups which may optionally be substituted by at least one substituent selected from the group consisting of fluorine atoms, chlorine atoms, methyl groups, methoxy groups and nitro groups,
methyl, ethyl and propyl groups which may optionally be substituted by at least one substituent selected from the group consisting of amino groups, hydroxyl groups, carboxyl groups, methoxycarbonyl groups, ethoxycarbonyl groups, substituents having the formula —NH—$A^{1c}$ represents a γ-glutamyl group, and substituents having the formula —CO—$A^{2c}$, wherein $A^{2c}$ represents a glycino group, and
cyclopentyl and cyclohexyl groups;
$R^5$ represents a hydrogen atom;
$R^6$ is selected from the group consisting of hydrogen atoms, methyl groups, carboxyl groups, methoxycarbonyl groups, ethoxycarbonyl groups, carbamoyl groups, methylcarbamoyl groups and N,N-dimethylcarbamoyl group; and
X represents a sulfur atom, sulfinyl group or sulfonyl group.

15. A cyclic amino compound or a pharmacologically acceptable salt thereof according to claim 1, wherein $R^3$ is selected from the group consisting of 4-(—S—X—$R^4$)-1-piperidinyl groups and 4-(—S—X—$R^4$)-3-(=$CR^5R^6$)-1-piperidinyl groups, wherein
$R^4$ is selected from the group consisting of
phenyl groups which may optionally be substituted by at least one substituent selected from the group consisting of fluorine atoms, chlorine atoms, methyl groups, methoxy groups and nitro groups,
methyl, ethyl and propyl groups which may optionally be substituted by at least one substituent selected from the group consisting of amino groups, hydroxyl groups, carboxyl groups, methoxycarbonyl groups, ethoxycarbonyl groups, substituents having the formula —NH—$A^{1c}$ represents a γ-glutamyl group, and substituents having the formula —CO—$A^{2c}$, wherein $A^{2c}$ represents a glycino group, and
cyclopentyl and cyclohexyl groups;

$R^5$ represents a hydrogen atom;
$R^6$ is selected from the group consisting of carboxyl groups, methoxycarbonyl groups and ethoxycarbonyl groups; and
X represents a sulfur atom or sulfonyl group.

16. A cyclic amino compound or a pharmacologically acceptable salt thereof according to claim 1, wherein
$R^1$ represents a phenyl group which is substituted by from 1 to 3 substituents selected from the group consisting of halogen atoms, methyl groups, ethyl groups, difluoromethyl groups, trifluoromethyl groups, methoxy groups, ethoxy groups, difluoromethoxy groups, trifluoromethoxy groups, cyano groups and nitro groups, and
$R^2$ is selected from the group consisting of
$C_2$–$C_4$ alkanoyl group and ($C_3$–$C_6$ cycloalkyl)carbonyl groups, said groups optionally being substituted by at least one substituent selected from the group consisting of fluorine atoms, chlorine atoms, methoxy groups, ethoxy groups and cyano groups,
benzoyl groups which may optionally be substituted by at least one substituent selected from the group consisting of fluorine atoms, chlorine atoms, methyl groups, ethyl groups, methoxy groups and ethoxy groups, and
($C_1$–$C_4$ alkoxy)carbonyl groups.

17. A cyclic amino compound or a pharmacologically acceptable salt thereof according to claim 1, wherein
$R^1$ represents a phenyl group which is substituted by 1 or 2 substituents selected from the group consisting of fluorine atoms, chlorine atoms, bromine atoms, trifluoromethyl groups, difluoromethoxy groups, trifluoromethoxy groups, cyano groups and nitro groups, and
$R^2$ is selected from the group consisting of
$C_2$–$C_4$ alkanoyl groups and ($C_3$–$C_6$ cycloalkyl) carbonyl groups, said groups optionally being substited by at least one fluorine or chlorine atom,
benzoyl groups, and
($C_1$–$C_4$ alkoxy)carbonyl groups.

18. A cyclic amino compound or a pharmacologically acceptable salt thereof according to claim 1, wherein
$R^1$ represents a phenyl group which is substituted at the 2-or 4-position by a substituent selected from the group consisting of fluorine atoms, chlorine atoms, bromine atoms, trifluoromethyl groups, difluoromethoxy groups, trifluoromethoxy groups, cyano groups and nitro groups;
$R^2$ is selected from the group consisting of
$C_2$–$C_4$ alkanoyl groups and ($C_3$–$C_6$ cycloalkyl) carbonyl groups, said groups optionally being substituted by at least one fluorine or chlorine atom,
benzoyl groups, and
($C_2$–$C_4$ alkoxy) carbonyl groups;
$R^3$ is selected from the group consisting of 3- or 4-(—S—X—$R^4$)-1-piperidinyl groups and 4-(—S—X—$R^4$)-3-(=$CR^5R^6$) 1-piperidinyl groups, wherein
$R^4$ is selected from the group consisting of
phenyl groups which may optionally be substituted by at least one substituent selected from the group consisting of halogen atoms, methyl groups, ethyl groups, methoxy groups, ethoxy groups, nitro groups and cyano groups,
straight $C_1$–$C_6$ alkyl groups which may optionally be substituted by at least one substituent selected from the group consisting of amino groups, hydroxyl groups, carboxyl groups, ($C_1$–$C_4$ alkoxy) carbonyl groups, substituents having the formula —NH—$A^{1a}$, wherein $A^{1a}$ represents a glycyl, alanyl, β-aspartyl or γ-glutamyl group, and substituents having the formula —CO—$A^{2a}$, wherein $A^{2a}$ represents a glycino, alanino, valino, leucino, phenylglycino or phenylalanino group, and cyclobutyl group, cyclopentyl groups, cyclohexyl groups and cycloheptyl groups;

$R^5$ and $R^6$ are the same or different and each is independently selected from the group consisting of hydrogen atoms, $C_1$–$C_4$ alkyl groups, carboxyl groups, ($C_1$–$C_4$ alkoxy) carbonyl groups, carbamoyl groups, ($C_1$–$C_4$ alkyl)-carbamoyl groups and di-($C_1$–$C_4$ alkyl) carbamoyl groups; and X represents a sulfur atom, sulfinyl group or sulfonyl group.

19. A cyclic amino compound or a pharmacologically acceptable salt thereof according to claim 1, wherein $R^1$ represents a phenyl group which is substituted at the 2- or 4- position by a fluorine atom or chlorine atom;

$R^2$ is selected from the group consisting of
acetyl, propionyl, isobutyryl, cyclopropylcarbonyl, and cyclobutyl-carbonyl groups which are optionally substituted by at least one fluorine atom,
methoxycarbonyl groups, and
ethoxycarbonyl groups;

$R^3$ is selected from the group consisting of 4-(—S—X—$R^4$)-1-piperidinyl groups, wherein $R^4$ is selected from the group consisting of
phenyl groups which may optionally be substituted by at least one substituent selected from the group consisting of fluorine atoms, chlorine atoms, bromine atoms, methyl groups, methoxy groups, nitro groups and cyano groups,
straight $C_1$–$C_4$ alkyl groups which may optionally be substituted by at least one substituent selected from the group consisting of amino groups, hydroxyl groups, carboxyl groups, methoxycarbonyl groups, ethoxycarbonyl groups, substituents having the formula —NH—$A^{1b}$, wherein $A^{1b}$ represents a glycyl or γ-glutamyl group, and substituents having the formula —CO—$A^{2b}$, wherein $A^{2b}$ represents a glycino, alanino or valino group,
cyclopentyl groups, and
cyclohexyl groups;

$R^5$ and $R^6$ are the same or different and each is independently selected from the group consisting of hydrogen atoms, methyl groups, ethyl groups, carboxyl groups, methoxycarbonyl groups, ethoxycarbonyl groups, carbamoyl groups, methylcarbamoyl groups, ethylcarbamoyl groups, N,N-dimethylcarbamoyl groups and N,N-diethylcarbamoyl groups; and X represents a sulfur atom, sulfinyl groups or sulfonyl group.

20. A cyclic amino compound or a pharmacologically acceptable salt thereof according to claim 1, wherein $R^1$ represents a phenyl group which is substituted at the 2- or 4-position by a fluorine atom or chlorine atom;

$R^2$ represents a propionyl, cyclopropylcarbonyl, methoxycarbonyl or ethoxycarbonyl group;

$R^3$ is selected from the group consisting of 4-(—S—X—$R^4$)-1-piperidinyl groups, wherein $R^4$ is selected from the group consisting of
phenyl groups which may optionally be substituted by at least one substituent selected from the group consisting of fluorine atoms, chlorine atoms, methyl groups, methoxy groups and nitro groups,
methyl, ethyl and propyl groups which may optionally be substituted by at least on substituent selected from the group consisting of amino groups, hydroxyl groups, carboxyl groups, methoxycarbonyl groups, ethoxycarbonyl groups, substituents having the formula —NH—$A^{1c}$, wherein $A^{1c}$ represents a γ-glutamyl group, and substituents having the formula —CO—$A^{2c}$, wherein $A^{2c}$ represents a glycino group,
cyclopentyl groups, and
cyclohexyl groups;

$R^5$ represents a hydrogen atom;

$R^6$ is selected from the group consisting of hydrogen atoms, methyl groups, carboxyl groups, methoxycarbonyl groups, ethoxycarbonyl groups,carbamoyl groups, methylcarbamoyl groups and N,N-dimethylcarbamoyl groups; and X represents a sulfur atom, sulfinyl group or sulfonyl group.

21. A cyclic amino compound or a pharmacologically acceptable salt thereof according to claim 1, wherein $R^1$ represents a phenyl group which is substituted at the 2- or 4- position by a fluorine atom or chlorine atom;

$R^2$ represents a propionyl, cyclopropylcarbonyl, methoxycarbonyl or ethoxycarbonyl group;

$R^3$ is selected from the group consisting of 4-(—S—X—$R^4$)-1-piperidinyl groups and 4-(—S—X—$R^4$)-3-(=$CR^5R^6$)-1-piperidinyl groups, wherein $R^4$ is selected from the group consisting of
phenyl groups which may optionally be substituted by at least one substituent selected from the group consisting of fluorine atoms, chlorine atoms, methyl groups, methoxy groups and nitro groups,
methyl, ethyl and propyl groups which may optionally be substituted by at least on substituent selected from the group consisting of amino groups, hydroxyl groups, carboxyl groups, methoxycarbonyl groups, ethoxycarbonyl groups, substituents having the formula —NH—$A^{1c}$, wherein $A^{1c}$ represents a γ-glutamyl group, and substituents having the formula —CO—$A^{2c}$, wherein $A^{2c}$ represents a glycino group,
cyclopentyl groups, and
cyclohexyl groups;

$R^5$ represents a hydrogen atom;

$R^6$ represents a carboxyl, methoxycarbonyl or ethoxycarbonyl group; and

X represents a sulfur atom sulfonyl group.

22. A cyclic amino compound or a pharmacologically acceptable salt thereof according to claim 1, which is selected from the group consisting of 1-(α-cyclopropylcarbonyl-2-fluorobenzyl)-4-(4-methylphenylsulfonylthio) piperidine, 1-(2-fluoro-α-methoxycarbonylbenzyl)-4-(4-methylphenylsulfonylthio) piperidine, 1-(2-chloro-α-methoxycarbonylbenzyl)-4-(4-methylphenylsulfonylthio) piperidine, 1-(α-cyclopropylcarbonyl-2-fluorobenzyl)-4-(4-methylphenylsulfinylthio) piperidine, 1-(α-cyclopropylcarbonyl-2-fluorobenzyl)-4-(4-methylphenyldisulfanyl) piperidine, 4-(4-chlorophenylsulfonylthio)-1-(α-cyclopropylcarbonyl-2-fluorobenzyl) piperidine, 1-(α-cyclopropylcarbonyl-2-fluorobenzyl)-4-(4-fluorophenylsulfonylthio) piperidine, 1-(α-cyclopropylcarbonyl-2-fluorobenzyl)-4-(4-methoxyphenylsulfonylthio) piperidine, 1-(α-cyclopropylcarbonyl-2-fluorobenzyl)-4-phenylsulfonylthiopiperidine, 1-(α-cyclopropylcarbonyl-2-fluorobenzyl)-4-(2-nitrophenyldisulfanyl) piperidine, 1-(α-cyclopropylcarbonyl-2-fluorobenzyl)-4-(2,4-dinitrophenyldisulfanyl) piperidine, 1-(α-cyclopropylcarbonyl-2-fluorobenzyl)-4-methylsulfonylthiopiperidine, 1-(α-cyclopropylcarbonyl-2-fluorobenzyl)-4-methylsulfonylthiopiperidine, 1-(α-cyclopropylcarbonyl-2-fluorobenzyl)-4-(2-methoxycarbonylethyldisulfany) piperidine, (E)-1-(2-chloro-α-methoxycarbonylbenzyl)-3-methoxycarbonylmethylidene-4-(4-methylphenylsulfonylthio) piperidine, (E)-1-(α-cuclopropylcarbonyl-2-fluorobenzyl)-3-ethoxycarbonylmethylidene-4-(4-methylphenylsulfonylthio) piperidine, (E)-1-(2-chloro-α-methoxycarbonylbenzyl)-3-ethoxycarbonylmethylidene-4-(4-methylphenylsulfonylthio) piperidine and (Z)-4-[(R)-2-amino-2-carboxyethyldisulfanyl]-3-carboxymethylidene-1-(α-cyclopropylcarbonyl-2-fluorobenzyl) piperidine.

23. 1-(α-Cyclopropylcarbonyl-2-fluorobenzyl)-4-(4-methylphenylsulfonylthio)-piperidine.

24. 1-(2-Fluoro-α-methoxycarbonylbenzyl)-4-(4-methylphenylsulfonylthio)-piperidine.

25. 1-(α-Cyclopropylcarbonyl-2-fluorobenzyl)-4-(4-methoxyphenl-sulfonylthio)piperidine.

26. (Z)-4-[(R)-2-amino-2-carboxyethyldisulfanyl]-3-carboxymethylidene-1-(α-cyclopropylcarbonyl-2-fluorobenzyl)piperidine.

27. A pharmaceutical composition comprising a pharmaceutically effective amount of a pharmacologically active compound together with a carrier therefor, wherein said pharmacologically active compound is a cyclic amino compound of formula (I) or a pharmacologically acceptable salt thereof according to any one of claims 1–26.

28. A method of treating a warm-blooded animal suffering from a disease condition resulting from platelet aggregation which comprises administering to said animal a pharmaceutically effective amount of a platelet aggregation inhibitory agent, said agent being a cyclic amino compound of the formula (I) or a pharmacologically acceptable salt thereof according to claim 1.

29. The method of claim 28 wherein said animal is a human.

30. A method for the prevention or treatment of an embolism in a warm-blooded animal, which comprises administering to said animal a pharmaceutically effective amount of a cyclic amino compound of formula (I) or a pharmacologically acceptable salt thereof according to claim 1.

31. A method for the prevention or treatment of an embolism in a human, which comprises administering to said human a pharmaceutically effective amount of a cyclic amino compound of formula (I) or a pharmacologically acceptable salt thereof according to any one of claim 1–26.

32. A method for the prevention or treatment of a thrombosis in a warm-blooded animal, which comprises administering to said animal a pharmaceutically effective amount of a cyclic amino compound of formula (I) or a pharmacologically acceptable salt according to claim 1.

33. A method for the prevention of a thrombosis in a human, which comprises administering to said human a pharmaceutically effective amount of a cyclic amino compound of formula (I) or a pharmacologically acceptable salt according to any one of claims 1–26.

34. A method for the prevention or treatment of arteriosclerosis in a warm-blooded animal, which comprises administering to said animal a pharmaceutically effective amount of a cyclic amino compound of formula (I) or a pharmacologically acceptable salt thereof according to claim 1.

35. A method for the prevention or treatment of arteriosclerosis in a human, which comprises administering to said human a pharmaceutically effective amount of a cyclic amino compound of formula (I) or a pharmacologically acceptable salt thereof according to any one of claims 1–26.

36. A method according to claim 30, wherein the method is for the treatment of a human.

37. A method according to claim 32, wherein the method is for the treatment of a human.

38. A method according to claim 34, wherein the method is for the treatment of a human.

* * * * *

UNITED STATES PATENT AND TRADEMARK OFFICE
CERTIFICATE OF CORRECTION

PATENT NO.   : 6,610,708 B1
DATED        : August 26, 2003
INVENTOR(S)  : Asai et al.

It is certified that error appears in the above-identified patent and that said Letters Patent is hereby corrected as shown below:

Column 81,
Line 29, "200" should begin a new paragraph.

Column 91,
Line 60, delete "where".

Column 92,
Lines 7, 16 and 26, delete "where".

Column 97,
Lines 14 and 15, delete "1– (α–cyclopropylcarbonyl-2-fluorobenzyl) -4-methylsulfonylthiopiperidine" and replace with -- 1- (α-cyclopropylcarbonyl-2-fluorobenzyl) -4-methylsulfinylthiopiperidine --.

Signed and Sealed this

Third Day of May, 2005

JON W. DUDAS
*Director of the United States Patent and Trademark Office*